(12) United States Patent
Fu et al.

(10) Patent No.: US 12,152,035 B2
(45) Date of Patent: Nov. 26, 2024

(54) ANDROGEN RECEPTOR BINDING MOLECULE AND USE THEREOF

(71) Applicant: Industrial Technology Research Institute, Hsinchu (TW)

(72) Inventors: Chih-Wei Fu, Taoyuan (TW); Hao-Hsuan Liu, Taichung (TW); Chiu-Lien Hung, Kaohsiung (TW); Yu-Chin Lin, Taichung (TW); Tsan-Lin Hu, Jhubei (TW); Chien-Chin Huang, Yizhu Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/561,055

(22) Filed: Dec. 23, 2021

(65) Prior Publication Data
US 2022/0227771 A1 Jul. 21, 2022

Related U.S. Application Data

(60) Provisional application No. 63/131,984, filed on Dec. 30, 2020.

(51) Int. Cl.
| | | |
|---|---|---|
| *C07D 487/04* | (2006.01) | |
| *A61P 35/00* | (2006.01) | |
| *C07D 401/04* | (2006.01) | |
| *C07D 401/14* | (2006.01) | |
| *C07D 417/12* | (2006.01) | |
| *C07D 417/14* | (2006.01) | |

(52) U.S. Cl.
CPC ............ *C07D 487/04* (2013.01); *A61P 35/00* (2018.01); *C07D 401/04* (2013.01); *C07D 417/12* (2013.01); *C07D 417/14* (2013.01)

(58) Field of Classification Search
CPC ... C07D 487/04; C07D 401/14; C07D 417/14
See application file for complete search history.

(56) References Cited

U.S. PATENT DOCUMENTS

| | | |
|---|---|---|
| 10,584,101 B2 | 3/2020 | Crew et al. |
| 10,660,968 B2 | 5/2020 | Phillips et al. |
| 10,730,870 B2 | 8/2020 | Crew et al. |

(Continued)

FOREIGN PATENT DOCUMENTS

| | | |
|---|---|---|
| CN | 101952286 A | 1/2011 |
| CN | 102388048 A | 3/2012 |

(Continued)

OTHER PUBLICATIONS

Taiwanese Office Action and Search Report for Taiwanese Application No. 110148478, dated Nov. 24, 2022.
(Continued)

*Primary Examiner* — Kamal A Saeed
*Assistant Examiner* — Karen Cheng
(74) *Attorney, Agent, or Firm* — Birch, Stewart, Kolasch & Birch, LLP

(57) ABSTRACT

An androgen receptor (AR) binding molecule has the structure of Formula (I) shown in the following:

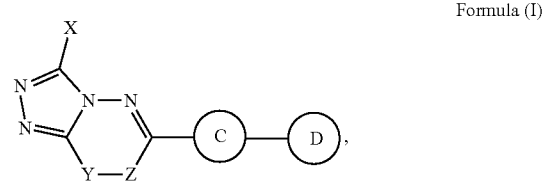

Formula (I)

wherein

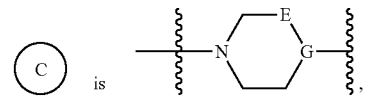

E is $CH_2$, G is CH,

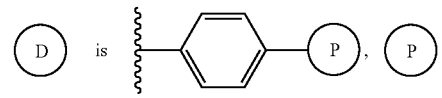

is OH, $NH_2$, OTf or C≡C, X is $CF_3$ or trifluoromethylphenyl, == is a single bond, and Y and Z are $CH_2$; or

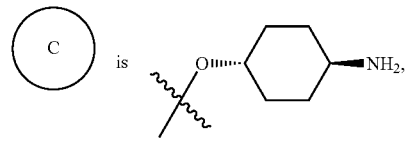

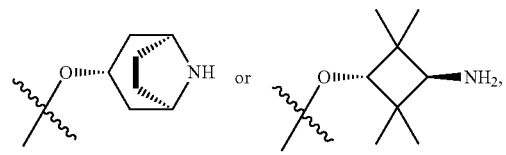

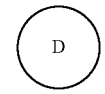

is absent, X is $CF_3$, == is a double bond, and Y and Z are CH.

3 Claims, 14 Drawing Sheets

(56) References Cited

U.S. PATENT DOCUMENTS

| | | |
|---|---|---|
| 2015/0291562 A1 | 10/2015 | Crew et al. |
| 2017/0298033 A1 | 10/2017 | Andersen et al. |
| 2017/0327469 A1 | 11/2017 | Crew et al. |
| 2018/0346461 A1 | 12/2018 | Crew et al. |
| 2020/0039924 A1 | 2/2020 | Narayanan et al. |

FOREIGN PATENT DOCUMENTS

| | | | |
|---|---|---|---|
| CN | 102482280 | A | 5/2012 |
| CN | 169422737 | A | 3/2019 |
| JP | 2011-507824 | A | 3/2011 |
| JP | 2012-517462 | A | 8/2012 |
| JP | 2012-526790 | A | 11/2012 |
| JP | 2017-513862 | A | 6/2017 |
| JP | 2017-178941 | A | 10/2017 |
| JP | 2018-502925 | A | 2/2018 |
| TW | 200301117 | A | 7/2003 |
| WO | WO 2009/081197 | A1 | 7/2009 |
| WO | WO 2010/092371 | A1 | 8/2010 |
| WO | WO 2011/106570 | A1 | 9/2011 |
| WO | WO 2017/041040 | A1 | 3/2017 |
| WO | WO 2017/176708 | A1 | 10/2017 |
| WO | WO 2017/210771 | A1 | 12/2017 |
| WO | WO 2018/136792 | A1 | 7/2018 |
| WO | WO 2020/198711 | A1 | 10/2020 |

OTHER PUBLICATIONS

Extended European Search Report for European Application No. 21217408.0, dated May 11, 2022.

Scott et al., "Systematic Investigation of the Permeability of Androgen Receptor PROTACs," American Chemical Society Medicinal Chemistry Letters, vol. 11, Jun. 8, 2020, pp. 1539-1547 (9 pages total).

Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, vol. 62, Jan. 10, 2019, pp. 941-964 (24 pages total).

Japanese Office Action for corresponding Japanese Application No. 2021-209993, dated May 17, 2023.

Chinese Office Action and Search Report dated Sep. 13, 2023 for Application No. 202111594426.0.

ANDROGEN RECEPTOR BINDING MOLECULE AND USE THEREOF

CROSS REFERENCE TO RELATED APPLICATION

This application claims the benefit of U.S. Provisional Application No. 63/131,984, filed on Dec. 30, 2020, the entirety of which is incorporated by reference herein.

TECHNICAL FIELD

The present disclosure relates to an androgen receptor binding molecule and the use thereof, and in particular it relates to the related applications of a proteolysis targeting chimera (PROTAC) prepared therefrom.

BACKGROUND

Prostate cancer is the second-most-prevalent cancer for men worldwide and the second-leading cause of cancer death for men in the United States.

The five-year survival rate for initial therapy after being diagnosed with prostate cancer can reach over 90%. However, in 90% of prostate patients treated with first-line androgen-deprivation therapy (ADT), prostate cancer recurs and evolves into castration-resistant prostate cancer (CRPC) only 2-5 years later. Once the change to castration-resistant prostate cancer occurs, the five-year survival rate drops to 30%, with 50% of patients having androgen mutation (AR mutation), androgen amplification (AR amplification) or the formation of androgen variants (AR-variants), and thus it causes abnormal activation of androgens and resistance to current medications, especially in patients with androgen receptor splice variant 7 (AR-V7).

Therefore, there is a need for novel therapeutic drugs to solve the dilemma of under treatment of castration-resistant prostate cancer.

SUMMARY

The present disclosure provides an androgen receptor (AR) binding molecule having the structure of Formula (I) as shown below:

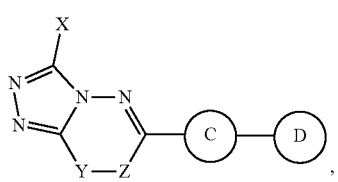

Formula (I)

wherein

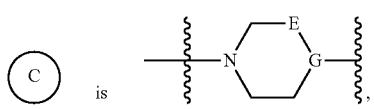 is 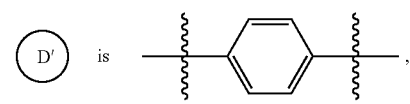,

E is $CH_2$, G is CH,

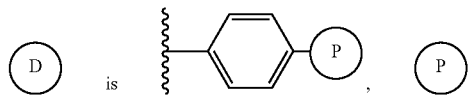 is 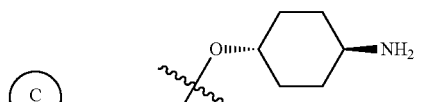,

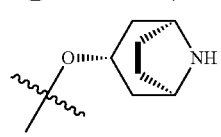 is OH, $NH_2$, OTf or C≡C, X is $CF_3$ or trifluoromethylphenyl, == is a single bond, and Y and Z are $CH_2$; or

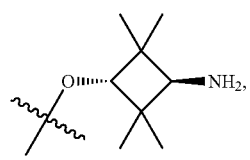

is absent, X is $CF_3$, == is a double bond, and Y and Z are CH.

The present disclosure also provides a compound having the structure of Formula (a) as shown below: A-R1-L-R2-E Formula (a). A is an androgen receptor binding moiety having the structure of Formula (I') as shown below:

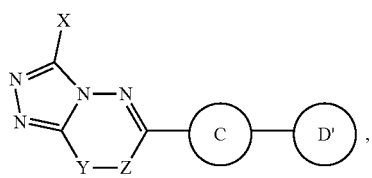

Formula (I')

wherein

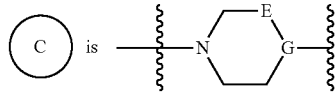 is 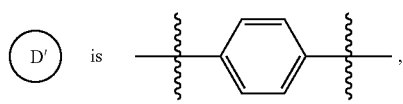,

E is $CH_2$, G is CH,

X is CF$_3$ or trifluoromethylphenyl, == is a single bond, and Y and Z are CH$_2$; or

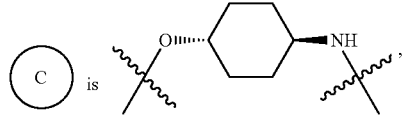

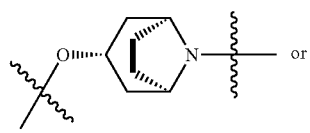

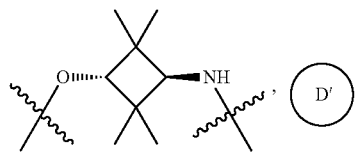

is absent, X is CF$_3$, == is a double bond, and Y and Z are CH. R1 and R2 are junction points, wherein R1 is O, N, C—C triple bond or C≡C, and wherein when

is absent, R1 is absent and

is directly linked to L, and R2 is NH, COO, C≡C or C—C single bond. L is a linker, comprising at least one of the following: polyethylene glycol (PEG), polypropylene glycol (PPG), a saturated carbon chain, a saccharide, an aromatic ring and a heterocycle with a total number of atoms of 7-17. E is an E3 ubiquitin ligase binding moiety which comprises one of the structures as shown below:

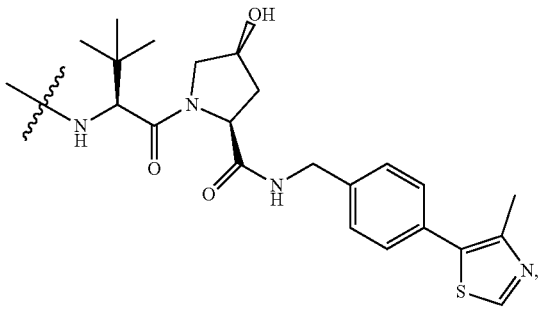

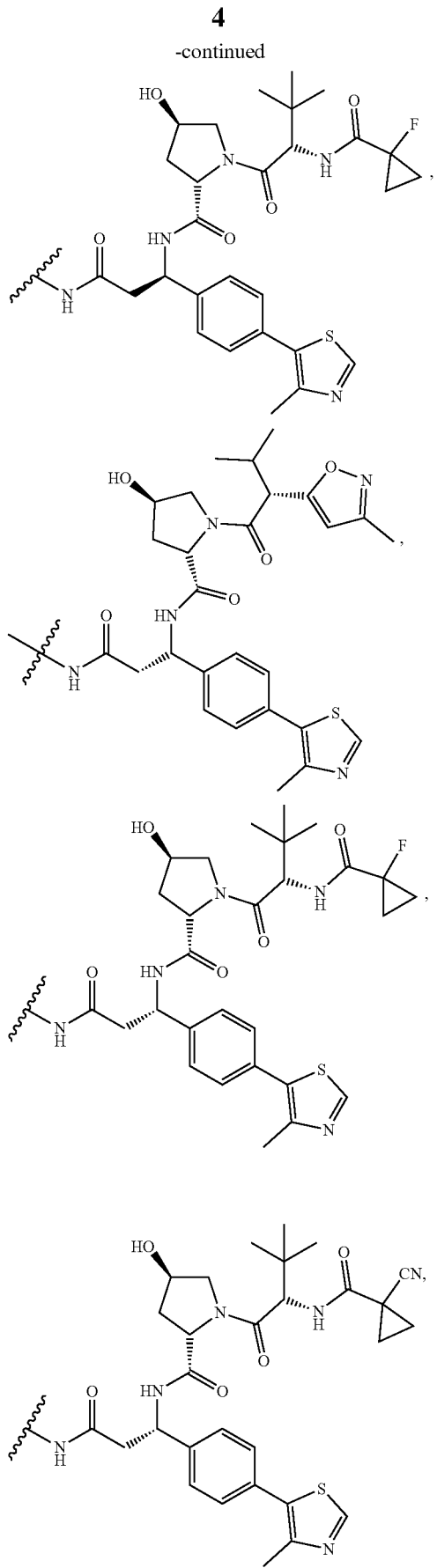

-continued

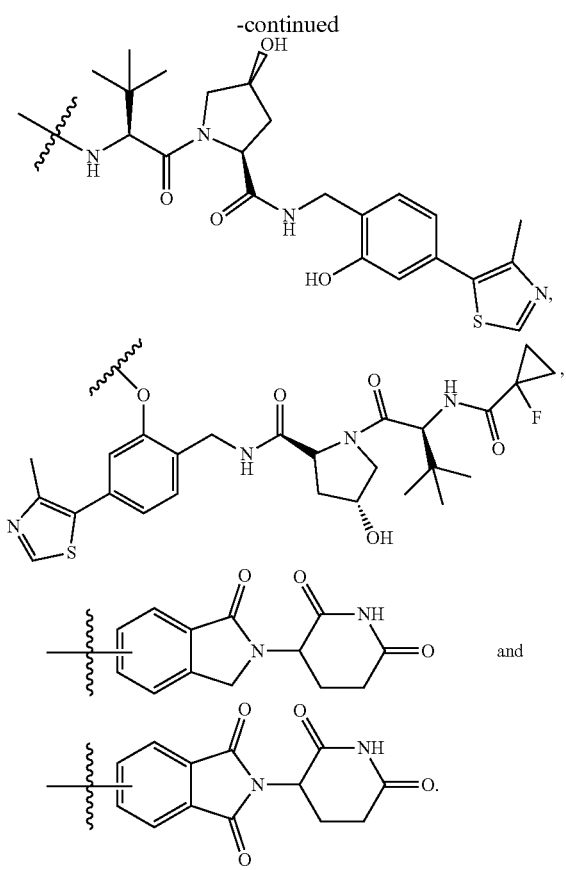

and

The present disclosure also provides a pharmaceutical composition comprising a compound and a pharmaceutically acceptable carrier and salts. The compound has the structure of Formula (a) as shown below: A-R1-L-R2-E Formula (a). A is an androgen receptor binding moiety having the structure of Formula (I') as shown below:

Formula (I')

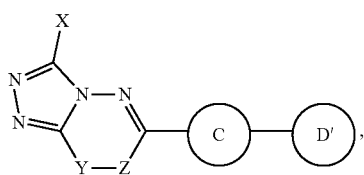

wherein

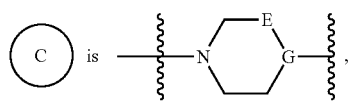

E is $CH_2$, G is CH,

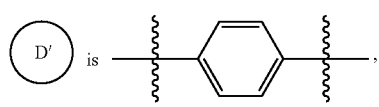

X is $CF_3$ or trifluoromethylphenyl, == is a single bond, and Y and Z are $CH_2$; or

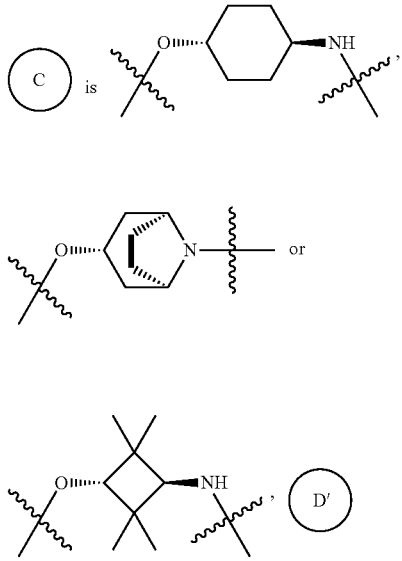

is absent, X is $CF_3$, == is a double bond, and Y and Z are CH. R1 and R2 are junction points, wherein R1 is O, N, C≡C or C—C single bond, and wherein when

is absent, R1 is absent and

C is directly linked to L, and R2 is NH, COO, C≡C or C—C single bond. L is a linker, comprising at least one of the following: polyethylene glycol (PEG), polypropylene glycol (PPG), a saturated carbon chain, a saccharide, an aromatic ring and a heterocycle with a total number of atoms of 7-17. E is an E3 ubiquitin ligase binding moiety which comprises one of the structures as shown below:

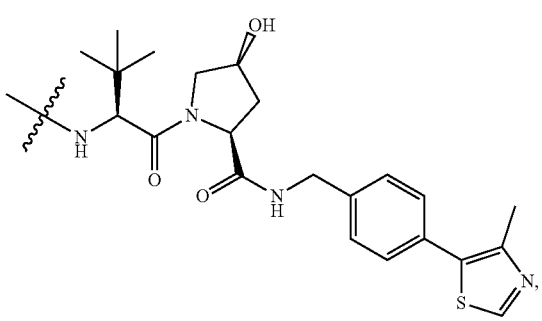

-continued

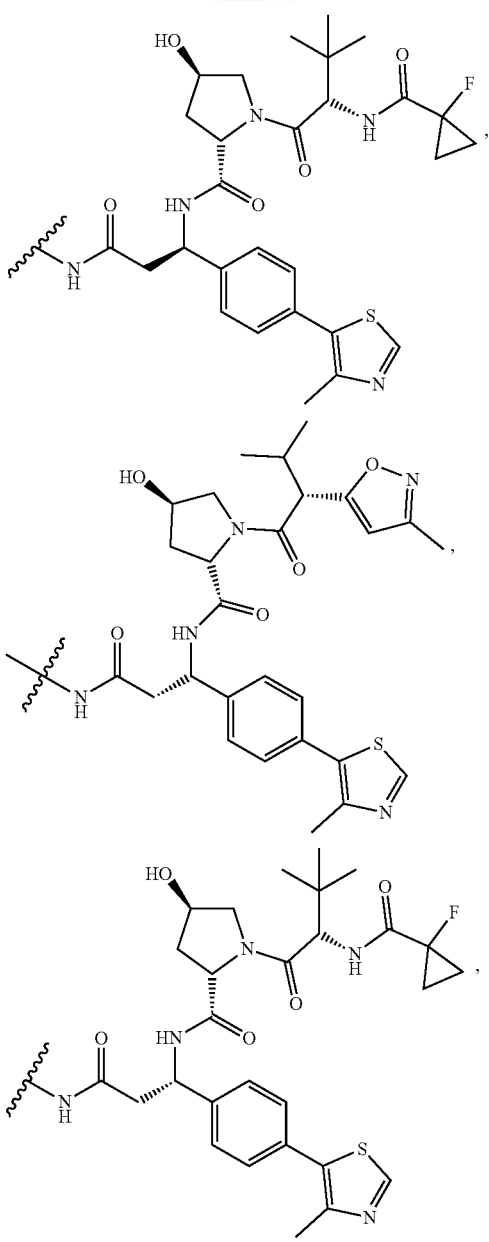

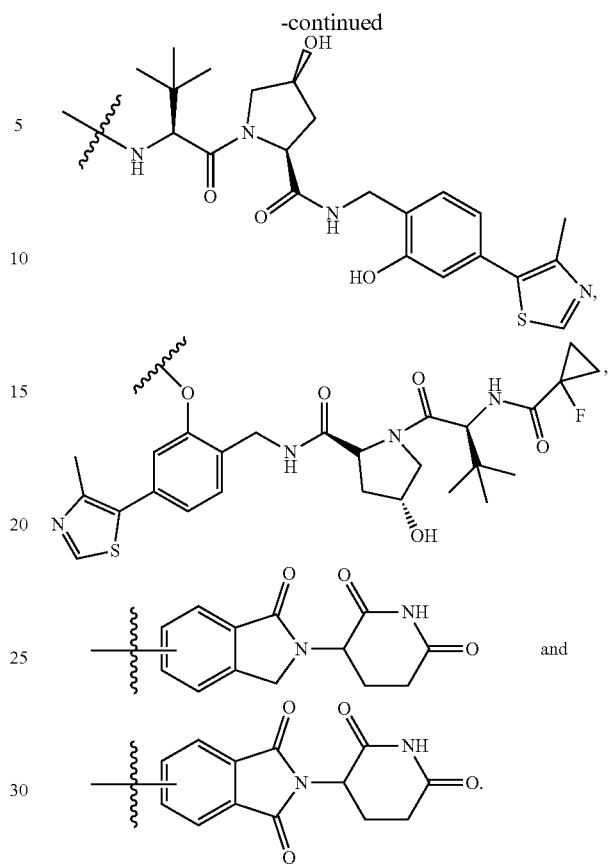

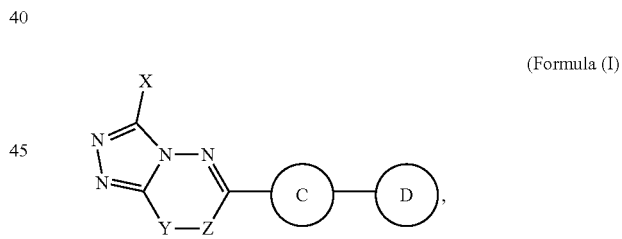

The present disclosure further provides the use of an androgen receptor binding molecule in the manufacture of a reagent for inhibiting androgen receptor. The androgen receptor binding molecule has the structure of Formula (I) as shown below

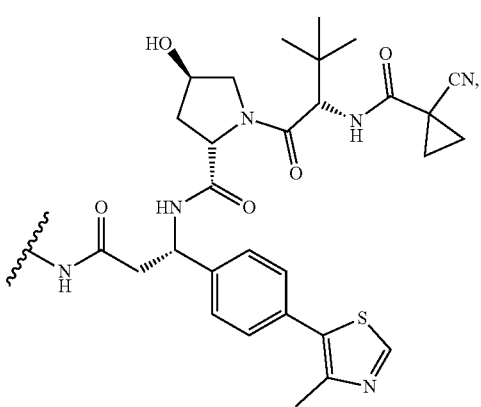

wherein

C is
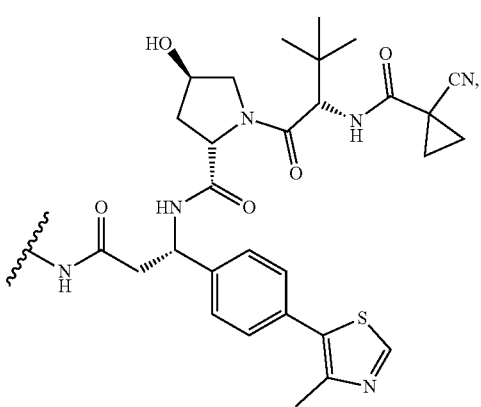

E is CH$_2$, G is CH,

D is is OH, NH$_2$, OTf or C≡C, X is CF$_3$ or trifluoromethylphenyl, === is a single bond, and Y and Z are CH$_2$; or

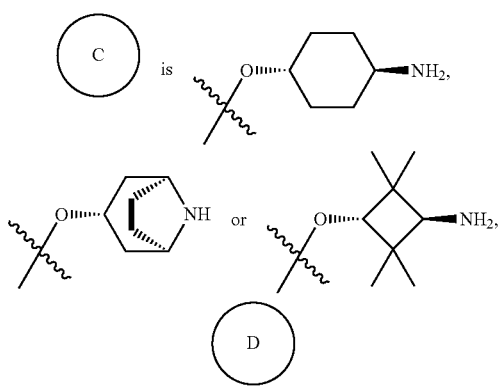

is absent, X is CF$_3$, === is a double bond, and Y and Z are CH.

The present disclosure further provides the use of an androgen receptor binding molecule in the manufacture of proteolysis targeting chimera (PROTAC). The androgen receptor binding molecule has the structure of Formula (I) as shown below:

Formula (I)

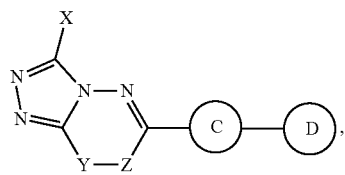

wherein

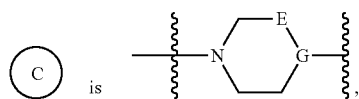

E is CH$_2$, G is CH,

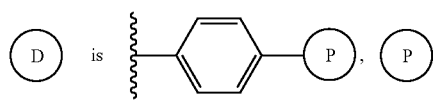

is OH, NH$_2$, OTf or C≡C, X is CF$_3$ or trifluoromethylphenyl, === is a single bond, and Y and Z are CH$_2$; or

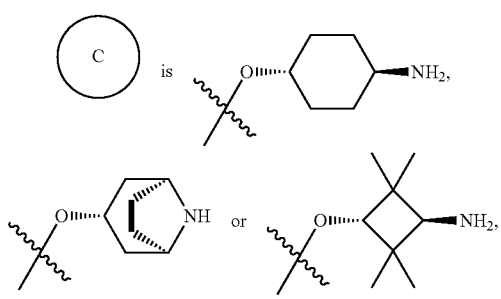

is absent, X is CF$_3$, === is a double bond, and Y and Z are CH.

Moreover, the present disclosure provides the use of an androgen receptor binding molecule in the manufacture of a drug for treating prostate cancer. The androgen receptor binding molecule has the structure of Formula (I) as shown below:

Formula (I)

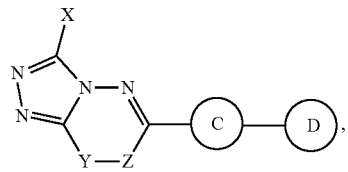

wherein

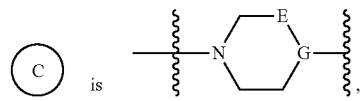

E is CH$_2$, G is CH,

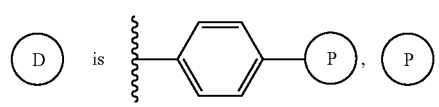

is OH, NH$_2$, OTf or C≡C, X is CF$_3$ or trifluoromethylphenyl, === is a single bond, and Y and Z are CH$_2$; or

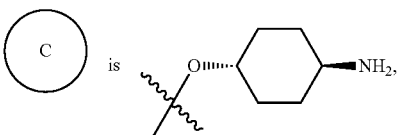

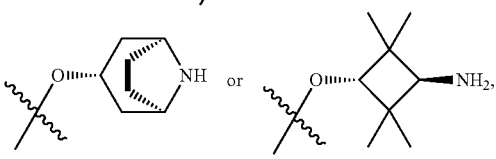

is absent, X is CF$_3$, === is a double bond, and Y and Z are CH.

Furthermore, the present disclosure further provides the use of a compound in the manufacture of a drug for treating prostate cancer. The compound has the structure of Formula (α) as shown below: A-R1-L-R2-E Formula (α). A is an androgen receptor binding moiety having the structure of Formula (I') as shown below:

Formula (I')

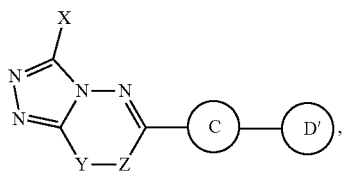

wherein

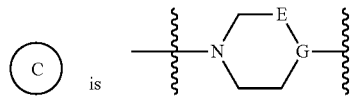 is 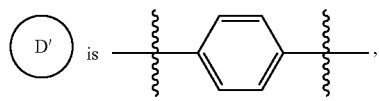

E is CH$_2$, G is CH,

X is CF$_3$ or trifluoromethylphenyl, == is a single bond, and Y and Z are CH$_2$; or

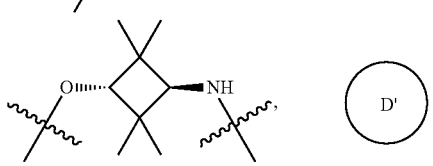 

is absent, X is CF$_3$, == is a double bond, and Y and Z are CH. R1 and R2 are junction points, wherein R1 is O, N, C≡C or C—C single bond, and wherein when

is absent, R1 is absent and

is directly linked to L, and R2 is NH, COO, C≡C or C—C single bond. L is a linker, comprising at least one of the following: polyethylene glycol (PEG), polypropylene glycol (PPG), a saturated carbon chain, a saccharide, an aromatic ring and a heterocycle with a total number of atoms of 7-17. E is an E3 ubiquitin ligase binding moiety which comprises one of the structures as shown below:

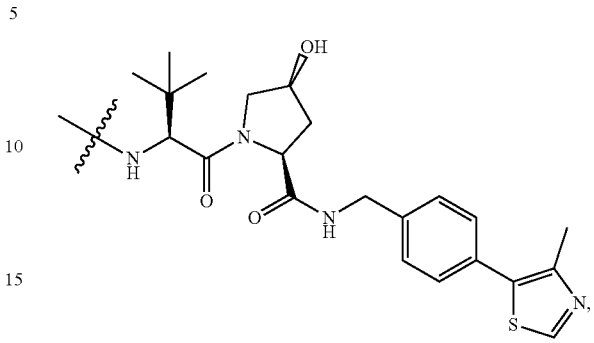

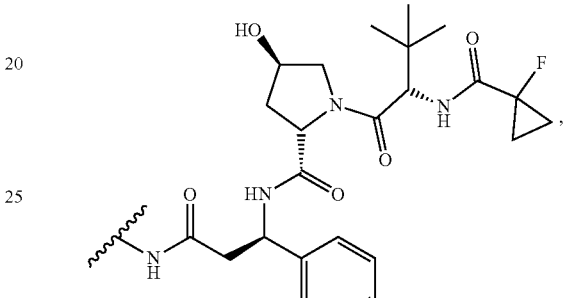

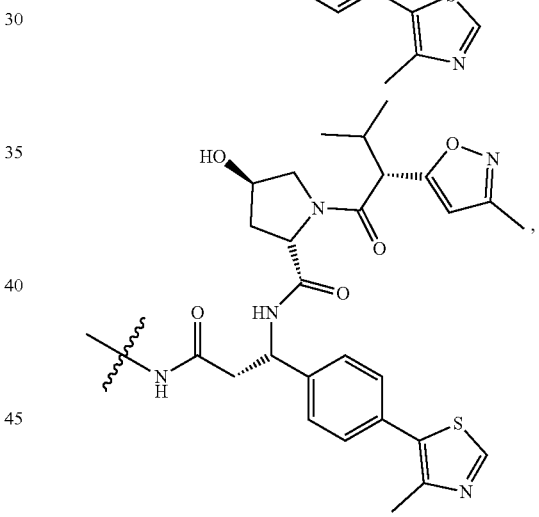

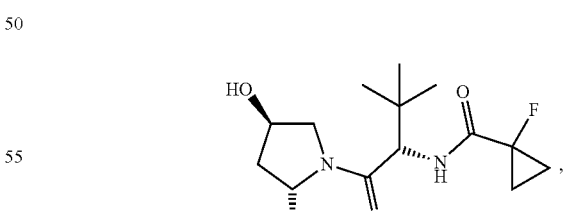

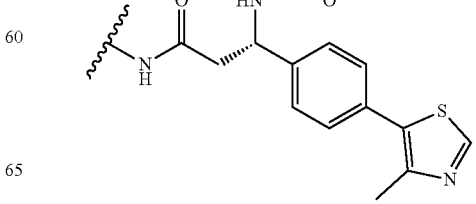

-continued

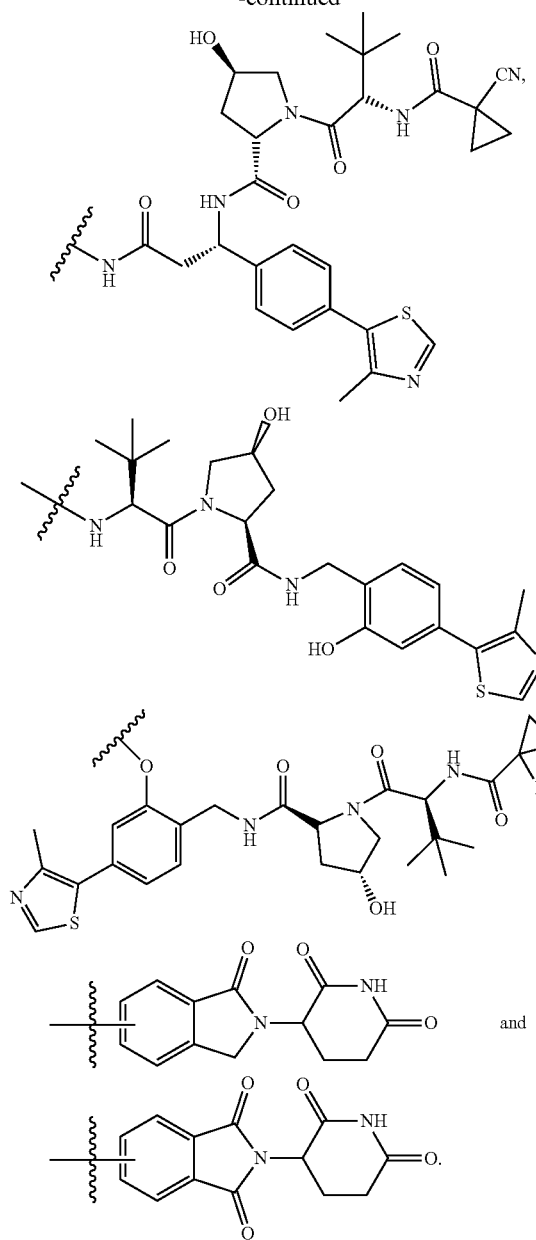

A method for treating prostate cancer, comprising: administering a compound to a subject in need thereof to treat prostate cancer in the subject. The compound has the structure of Formula (α) as shown below: A-R1-L-R2-E Formula (α). A is an androgen receptor binding moiety having the structure of Formula (I') as shown below:

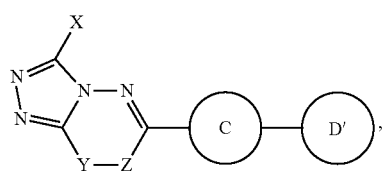

Formula (I')

wherein

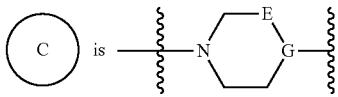

E is $CH_2$, G is CH,

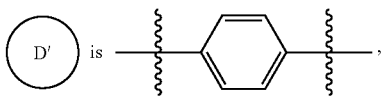

X is $CF_3$ or trifluoromethylphenyl, == is a single bond, and Y and Z are $CH_2$; or

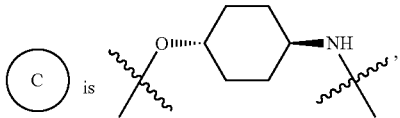

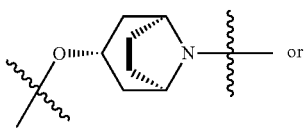

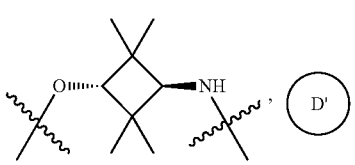

is absent, X is $CF_3$, == is a double bond, and Y and Z are CH. R1 and R2 are junction points, wherein R1 is O, N, or C—C single bond, and wherein when

is absent, R1 is absent and

is directly linked to L, and R2 is NH, COO, or C—C single bond. L is a linker, comprising at least one of the following: polyethylene glycol (PEG), polypropylene glycol (PPG), a saturated carbon chain, a saccharide, an aromatic ring and a heterocycle with a total number of atoms of 7-17. E is an E3 ubiquitin ligase binding moiety which comprises one of the structures as shown below:

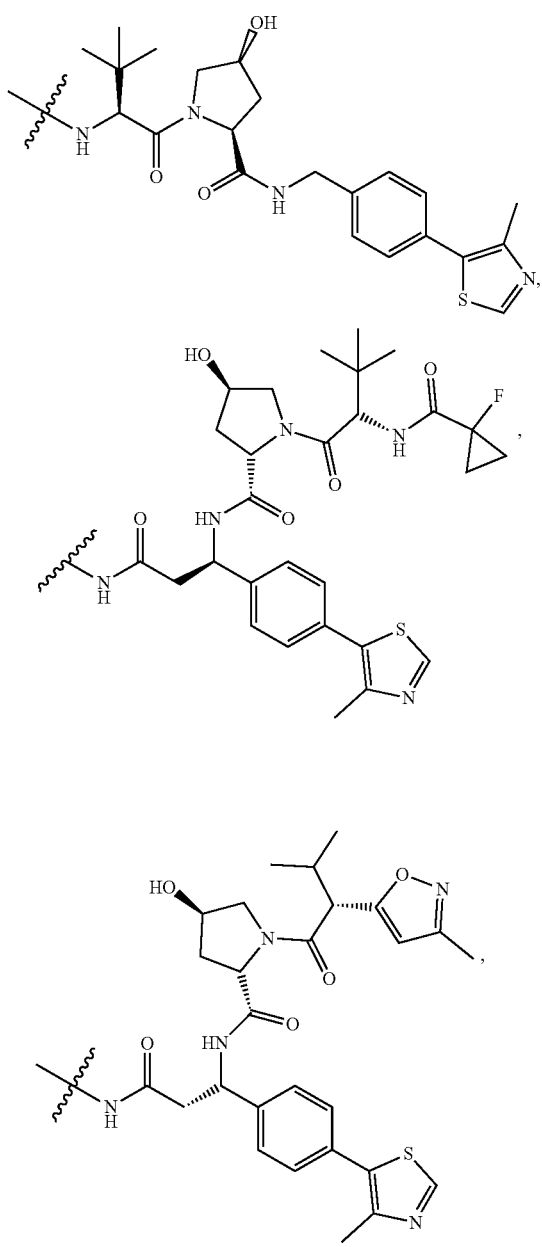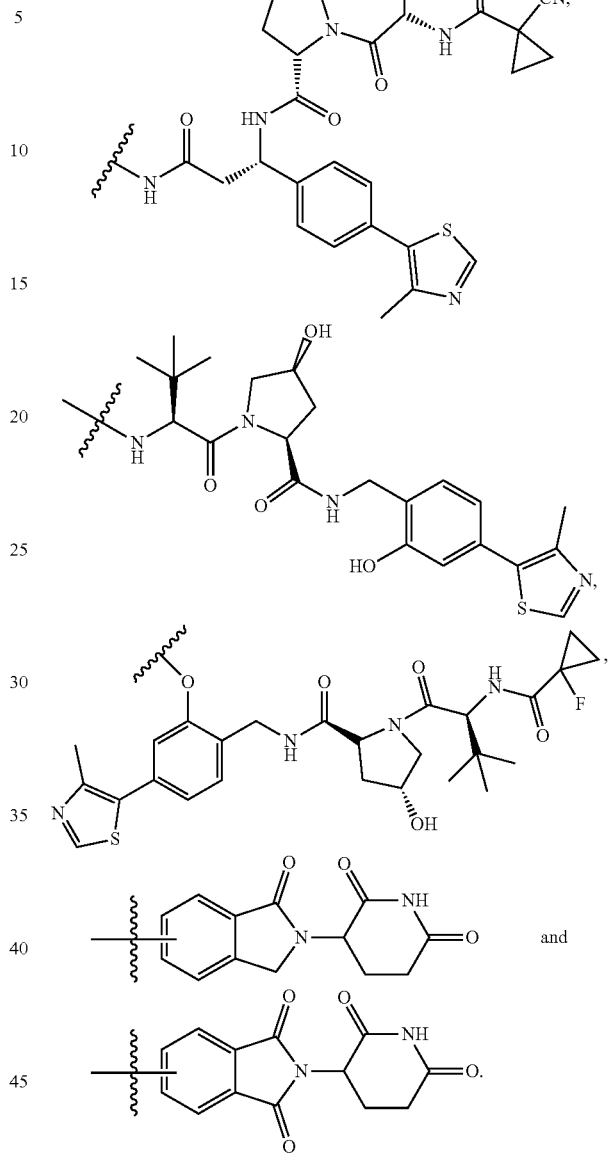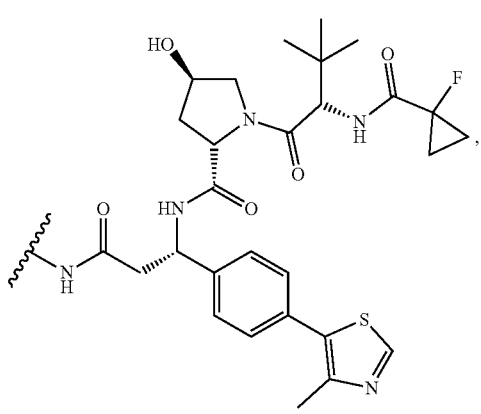

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1A:
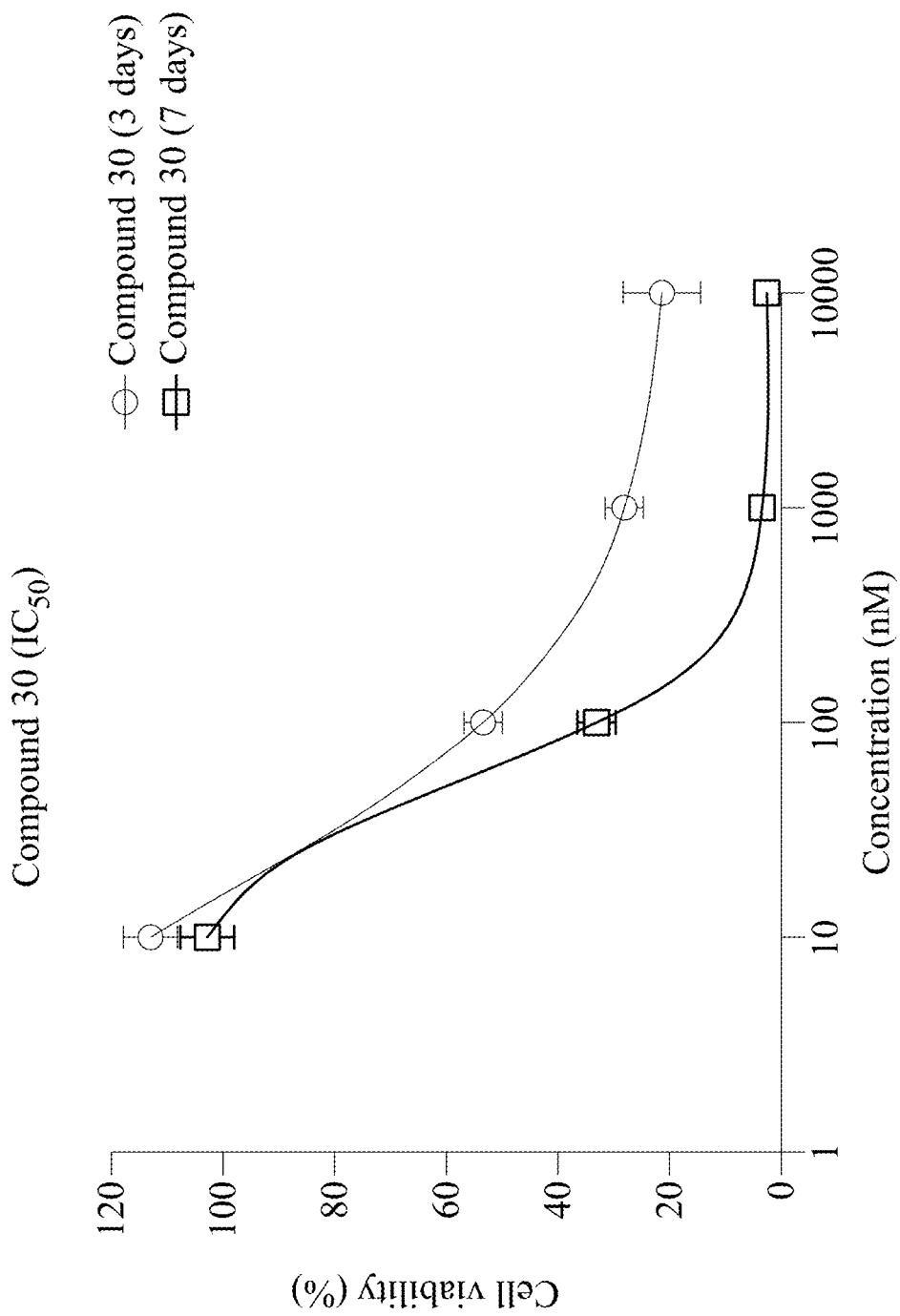
FIG. 1A shows the cell viability of cells treated with Compound 30.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Androgen receptor (AR) belongs to nuclear receptors, which is generally a protein with a molecular weight of 100,000 Daltons, and consists of an N-terminal transcription promoter region (N-terminal domain, NTD), a DNA-binding moiety (DBD), hinge region and ligand-binding moiety (ligand-binding moiety, LBD) of four domains.

The signal transductions of recurrence and metastasis of prostate cancer are mainly through androgen receptors. For the recurrence and metastasis of prostate cancer, the current treatment methods mainly use drugs to inhibit the production of androgen receptors or block the binding of androgen receptors to androgen receptors. However, after several months of treatment, patients with recurrence are prone to drug resistance occurs and the tumor recurs again, which makes subsequent treatment more difficult.

The present disclosure can provide a novel androgen receptor binding molecule.

A "binding molecule" as used in the present disclosure refers to a molecule which is capable of binding to another molecule or compound. For example, an androgen receptor binding molecule refers to a molecule which is capable of binding to an androgen receptor.

The androgen receptor binding molecule of the present disclosure mentioned above can effectively bind to the androgen receptor, thereby inhibiting the activity of the androgen receptor and/or blocking the binding of the androgen receptor to the androgen receptor, and it can also be effectively applied to various drugs related to the inhibition or degradation of androgen receptors, such as the preparation of related uses of proteolysis targeting chimera (PROTAC) for androgen receptors, but it is not limited thereto.

Proteolysis targeting chimeras are small molecule drugs with two different functional ligands, one with the ability to bind to a protein of interest (POI) and the other to recruit an E3 ubiquitin ligase. Through binding the proteolysis targeting chimera to the target protein, the E3 ubiquitin ligase will be able to get close to the target protein and label it with ubiquitin. The target protein which is labeled by ubiquitin will be recognized and cleaved by the proteasome and degraded into small fragments of peptides, so that the proteolysis targeting chimera is separated from the target protein and can be recycled in cells.

According to the foregoing, the androgen receptor binding molecule of the present disclosure can be used as a ligand having the ability to bind to the target protein in a proteolysis targeting chimera which aims the androgen receptor as the target protein.

The androgen receptor (AR) binding molecule of the present disclosure may have the structure of Formula (I) as shown below, but it is not limited thereto:

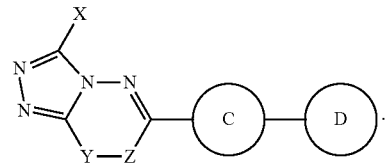

Formula (I)

In one embodiment, for the Formula (I) shown above

may be

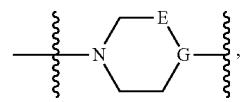

wherein E may be CH$_2$, G may be CH,

may be

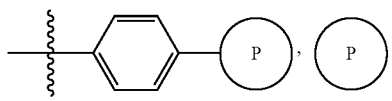

may be OH, NH$_2$, OTf or, X is CF$_3$ or trifluoromethylphenyl, == is a single bond, and Y and Z may be CH$_2$, but they are not limited thereto.

In another embodiment, for the Formula (I) shown above,

may be

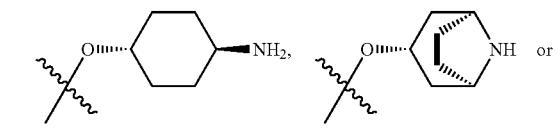

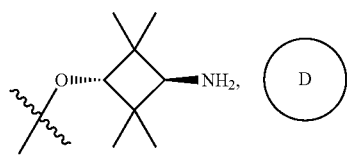

is absent, X may be CF$_3$, == is a double bond, and Y and Z may be CH, but they are not limited thereto.

In one specific embodiment, the androgen receptor binding molecule having the structure of Formula (I) of the present disclosure mentioned above may include, but is not limited to, compounds having any of the structures of Formulas (II) to (VI) shown in Table 1 below:

TABLE 1

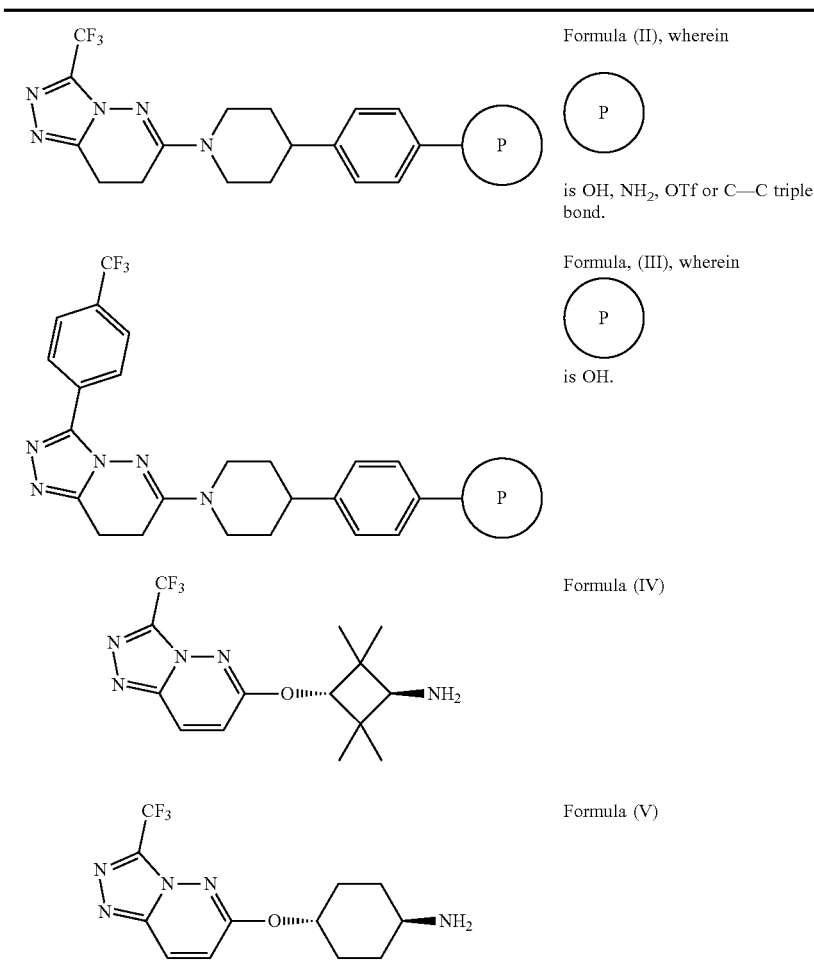

| | |
|---|---|
| | Formula (II), wherein P is OH, NH$_2$, OTf or C—C triple bond. |
| | Formula, (III), wherein P is OH. |
| | Formula (IV) |
| | Formula (V) |

TABLE 1-continued

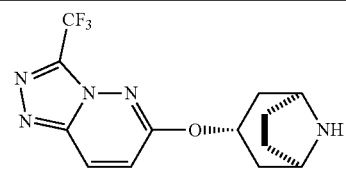
Formula (VI)

The androgen receptor binding molecule of the present disclosure mentioned above can bind to general full-length androgen receptors, as well as to various androgen mutations (AR mutation), androgen amplification (AR amplification), androgen receptor splice variant (androgen receptor splice variant), etc., without any specific limitation.

In one embodiment, the binding targets of the androgen receptor binding molecule of the present disclosure mentioned above may include, but is not limited to, at least one of the following: full-length androgen receptors, androgen receptor splice variant 7 (AR-V7), etc.

Based on the foregoing, the present disclosure may also provide a use of any of the androgen receptor binding molecules of the present disclosure mentioned above in the manufacture of an agent for inhibiting androgen receptor.

Also, based on the foregoing, the present disclosure may also provide a use of any of the androgen receptor binding molecules of the present disclosure mentioned above in the manufacture of a proteolysis targeting chimera.

In addition, based on the foregoing, the present disclosure may also provide a use of any of the androgen receptor binding molecules of the present disclosure mentioned above in the manufacture of a drug for treating prostate cancer. The prostate cancer mentioned above is not particularly limited, and may be general prostate cancer, castration-resistant prostate cancer (CRPC), etc., or may be prostate cancer with androgen mutation (AR mutation), androgen amplification (AR amplification), androgen variants (AR-variants), etc., such as androgen receptor splice variant 7.

The present disclosure may also provide a compound. The compound of the present disclosure can be used in the manufacture of a drug or pharmaceutical composition that can be used to treat a disease associated with androgen receptor over-expression, or a disease that can be attenuated and/or treated by inhibition of androgen receptor activity and/or degradation of androgen receptor, or a cancer (e.g., prostate cancer), but it is not limited thereto. Alternatively, the compound of the present disclosure may be used in the treatment of a disease which may be a disease associated with androgen receptor over-expression, or a disease that can be attenuated and/or treated by inhibition of androgen receptor activity and/or degradation of androgen receptor, or a cancer (e.g., prostate cancer), but it is not limited thereto.

The compound of the present disclosure mentioned above may have the structure of Formula ($\alpha$) as shown below, but it is not limited thereto:

A-R1-L-R2-E    Formula ($\alpha$).

In Formula ($\alpha$) shown above, A is an androgen receptor binding moiety.

As mentioned in the present disclosure, "binding moiety" means a specific region in a molecule or compound, which is capable of binding to another molecule or compound. For example, an androgen receptor binding moiety refers to a specific region in a molecule or compound, which is capable of binding to androgen receptor.

According to the definition of the term "binding moiety" in the present disclosure described in the above paragraph, it is understood that the "androgen receptor binding moiety" in the compound of the present disclosure refers to a specific region in the compound of the present disclosure, which is capable of binding to androgen receptor.

In the Formula (A) shown above, A, which is an androgen receptor binding moiety, may have the structure of Formula (I') as shown below, but it is not limited to thereto.

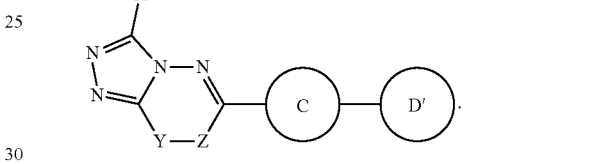
Formula (I')

In one embodiment, for the Formula (I') shown above,

may be

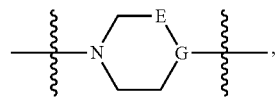

wherein E may be $CH_2$, G may be CH,

may be

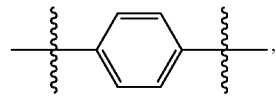

X may be CF$_3$ or trifluoromethylphenyl, ═══ is a single bond, and Y and Z may be CH$_2$, but it is not limited thereto.

In another embodiment, for the Formula (I') shown above,

may be

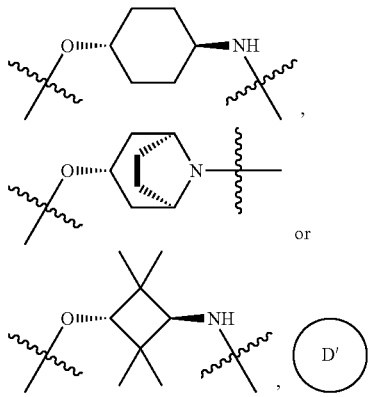

may be absent, X may be CF$_3$, ═══ is a double bond, and Y and Z may be CH, but it is not limited thereto.

In one specific embodiment, the androgen receptor binding moiety (A) having the structure of Formula (I') in the compound of the present disclosure mentioned above may include, but not limited to, any structure of Formula (II') to Formula (VI') shown in Table 2 below:

TABLE 2

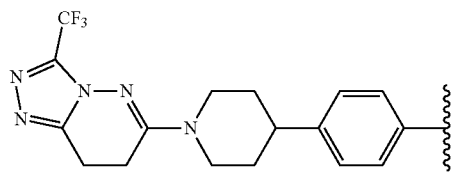 [SMILES: *c1ccc(C2CCN(C3=Nn4c(nnc4C(F)(F)F)CC3)CC2)cc1]
Formula (II')

Formula (III')

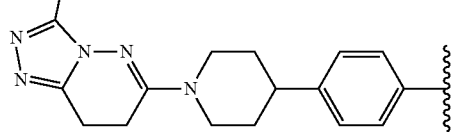
Formula (IV')

TABLE 2-continued

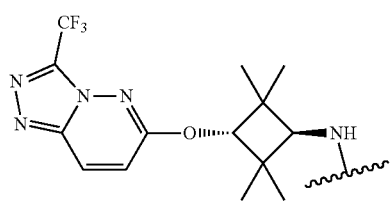 [SMILES: *N[C@H]1C(C)(C)[C@H](Oc2ccc3nnc(C(F)(F)F)n3n2)C1(C)C]
Formula (V')

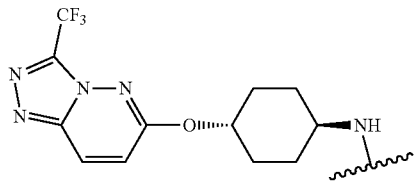 [SMILES: *N[C@H]1CC[C@H](Oc2ccc3nnc(C(F)(F)F)n3n2)CC1]
Formula (VI')

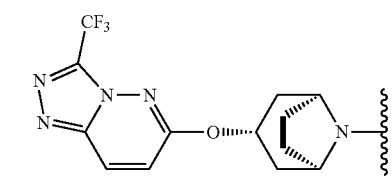

In Formula (α) shown above, R1 and R2 may be junction points. R1 may be O, N, C≡C, C—C single bond, etc., but it is not limited thereto. When

is absent, R1 is absent and

is directly linked to L. R2 may be NH, COO, C≡C, C—C single bond, etc., but it is also not limited thereto.

In Formula (α) shown above, L is a linker. The L which can be a linker mentioned above may comprise at least one of the following, but it is not limited thereto: Polyethylene glycol (PEG), polypropylene glycol (PPG), a saturated carbon chain, a saccharide, an aromatic ring, a heterocycle, etc., with a total number of atoms of 7-17.

The polyethylene glycol mentioned above may have following structure, but is not limited thereto:

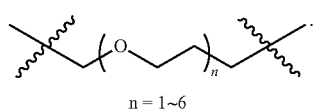

n = 1~6

The polypropylene glycol mentioned above may have following structure, but is not limited thereto:

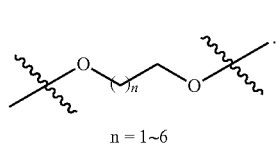

n = 1~6

The saturated carbon chain mentioned above may have one of following structures, but is also not limited thereto:

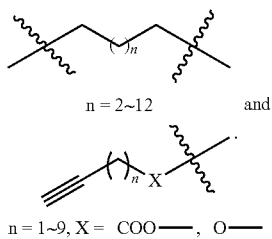

n = 2~12    and n = 1~9, X = COO——, O——

The saccharide mentioned above may have one of following structures, but is also not limited thereto:

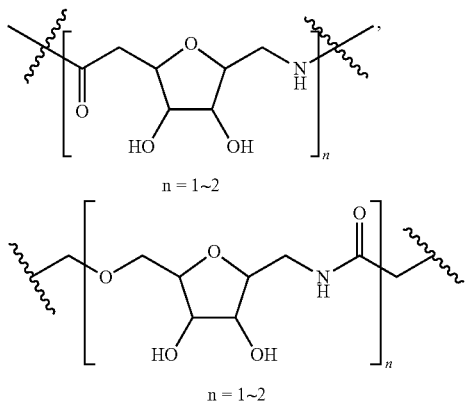

n = 1~2 n = 1~2 etc.

The aromatic hydrocarbon mentioned above may have one of following structures, but is also not limited thereto:

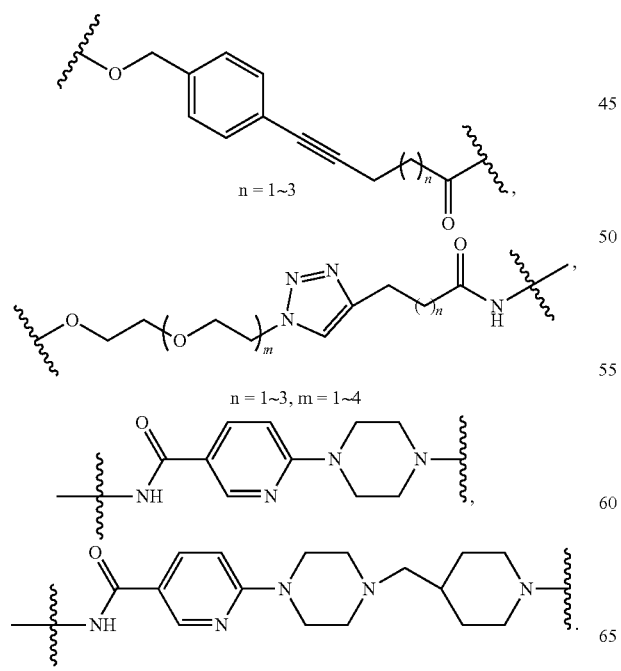

n = 1~3, n = 1~3, m = 1~4,

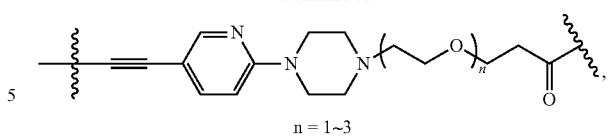

n = 1~3 etc.

The heterocycle mentioned above may comprise, but is not limited to one of following structures:

m = 3~7, n = 1~3, X = O, NH etc.

Furthermore, in Formula (α) shown above, E may be an E3 ubiquitin ligase binding moiety. The E mentioned above, which can be an E3 ubiquitin ligase binding moiety, may include, but is not limited to, one of the following structures:

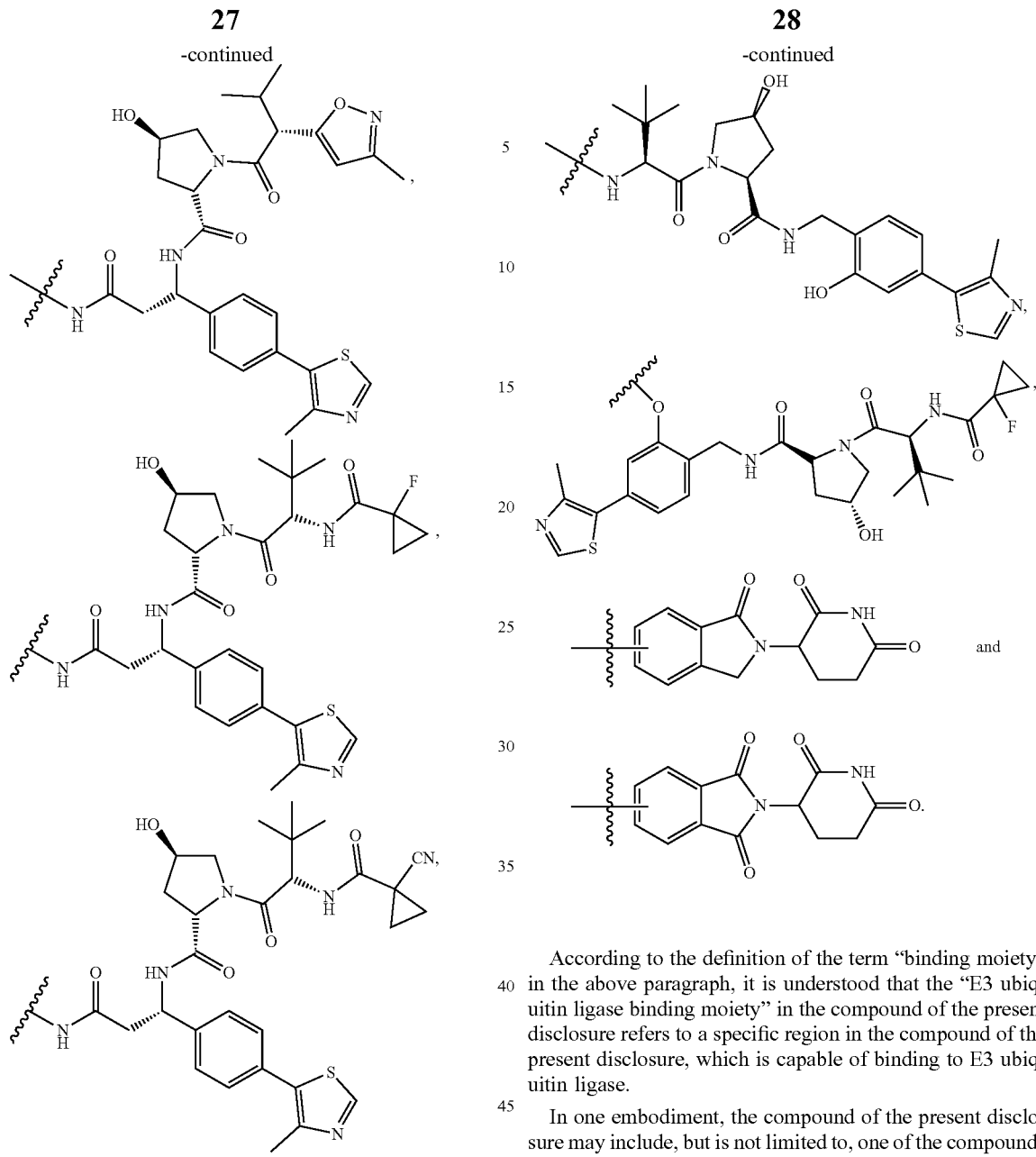

According to the definition of the term "binding moiety" in the above paragraph, it is understood that the "E3 ubiquitin ligase binding moiety" in the compound of the present disclosure refers to a specific region in the compound of the present disclosure, which is capable of binding to E3 ubiquitin ligase.

In one embodiment, the compound of the present disclosure may include, but is not limited to, one of the compounds shown in Table 3 below.

TABLE 3

| Compound number | Structure |
|---|---|
| 1 | 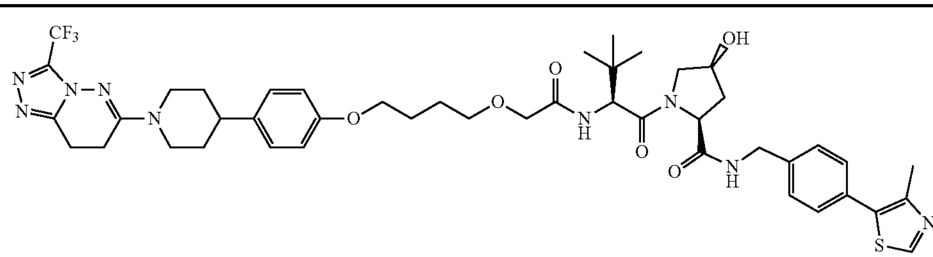 |

TABLE 3-continued

| Compound number | Structure |
| --- | --- |
| 2 | (structure 2) |
| 3 | (structure 3) |
| 4 | (structure 4) |
| 5 | (structure 5) |

TABLE 3-continued

| Compound number | Structure |
| --- | --- |
| 6 | 6 |
| 7 | 7 |
| 8 | 8 |
| 9 | 9 |

TABLE 3-continued

| Compound number | Structure |
|---|---|
| 10 | 10 |
| 11 | 11 |
| 12 | 12 |
| 13 | 13 |
| 14 | 14 |

TABLE 3-continued

| Compound number | Structure |
| --- | --- |
| 15 | *structure 15* |
| 16 | *structure 16* |
| 17 | *structure 17* |
| 18 | *structure 18* |
| 19 | *structure 19* |

TABLE 3-continued

| Compound number | Structure |
|---|---|
| 20 | (structure 20) |
| 21 | (structure 21) |
| 22 | (structure 22) |
| 23 | (structure 23) |
| 24 | (structure 24) |

TABLE 3-continued

| Compound number | Structure |
| --- | --- |
| 25 | 25 |
| 26 | 26 |
| 27 | 27 |
| 28 | 28 |

TABLE 3-continued

| Compound number | Structure |
| --- | --- |
| 29 | (structure 29) |
| 30 | (structure 30) |
| 31 | (structure 31) |
| 32 | (structure 32) |
| 33 | (structure 33) |

TABLE 3-continued

| Compound number | Structure |
|---|---|
| 34 | 34 |
| 35 | 35 |
| 36 | 36 |
| 37 | 37 |
| 38 | 38 |

TABLE 3-continued
| Compound number | Structure |
|---|---|
| 39 | 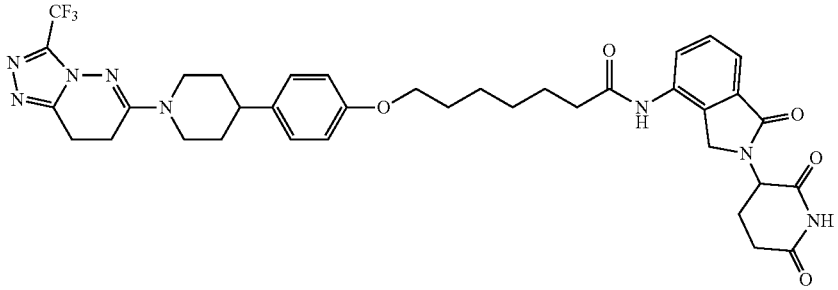 [SMILES: O=C1CCC(N2Cc3c(NC(=O)CCCCCCOc4ccc(C5CCN(C6=Nn7c(nnc7C(F)(F)F)CC6)CC5)cc4)cccc3C2=O)C(=O)N1] |
| 40 | 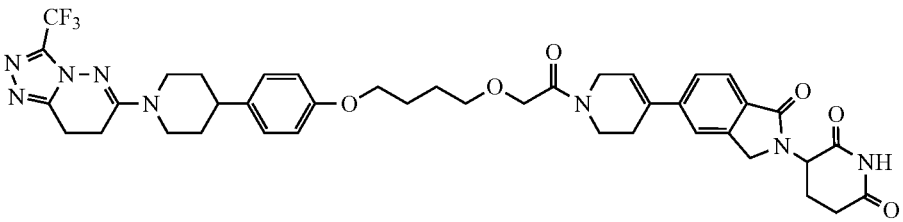 [SMILES: O=C1CCC(N2Cc3cc(C4=CCN(C(=O)COCCCCOc5ccc(C6CCN(C7=Nn8c(nnc8C(F)(F)F)CC7)CC6)cc5)CC4)ccc3C2=O)C(=O)N1] |
| 41 | 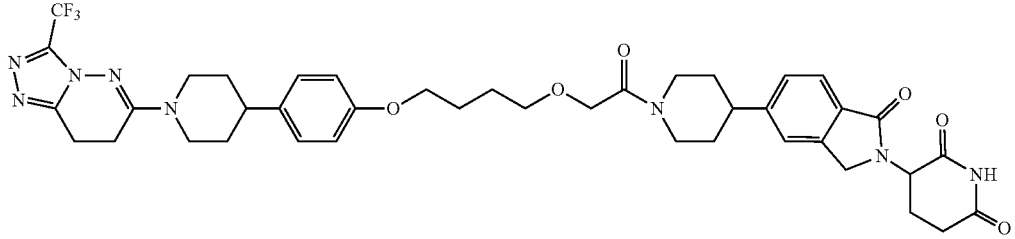 [SMILES: O=C1CCC(N2Cc3cc(C4CCN(C(=O)COCCCCOc5ccc(C6CCN(C7=Nn8c(nnc8C(F)(F)F)CC7)CC6)cc5)CC4)ccc3C2=O)C(=O)N1] |
| 42 | 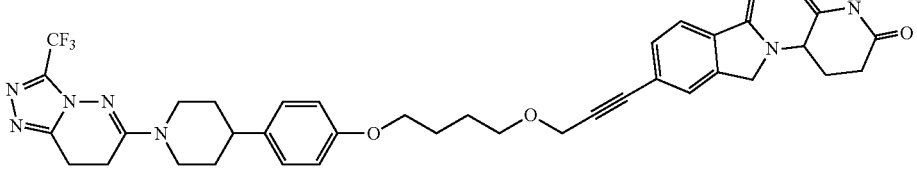 |
| 43 | 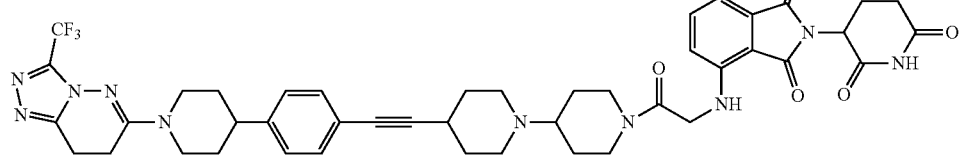 |

TABLE 3-continued

| Compound number | Structure |
|---|---|
| 44 | 44 |
| 45 | 45 |
| 46 | 46 |

TABLE 3-continued

| Compound number | Structure |
| --- | --- |
| 47 | 47 |
| 48 | 48 |
| 49 | 49 |

TABLE 3-continued

| Compound number | Structure |
|---|---|
| 50 | *(structure 50)* |
| 51 | *(structure 51)* |
| 52 | *(structure 52)* |
| 53 | *(structure 53)* |

In one specific embodiment, the compound of the present disclosure may be Compound 1 shown above. In another specific embodiment, the compound of the present disclosure may be Compound 30 shown above. In yet another specific embodiment, the compound of the present disclosure may be Compound 30 shown above.

According to the structure of the compound of the present disclosure shown above, the compound of the present disclosure may be a proteolysis targeting chimera for androgen receptor, which can effectively bind to the androgen receptor and thus cause the androgen receptor to be recognized by the proteasome for cleavage and degradation.

The above-mentioned compound of the present disclosure may bind to general full-length androgen receptors, and may also bind to various androgen mutations, androgen amplifications, androgen receptor splice variant, etc., without particular limitations.

In one embodiment, the binding target of the compound of the present disclosure may include, but is not limited to, at least one of the following: full-length androgen receptor, androgen receptor splice variant 7, etc.

Based on the above, the present disclosure may also provide a pharmaceutical composition, which may include, but is not limited to, any compound of the present disclosure mentioned above and a pharmaceutically acceptable carrier or salt.

The pharmaceutical composition of the present disclosure may be used for the treatment of a disease, and the above-mentioned disease may be a disease associated with androgen receptor over-expression, or a disease can be attenuated and/or treated by inhibition of androgen receptor activity and/or degradation of androgen receptor, or a cancer (e.g., prostate cancer), but it is not limited thereto. In one embodiment, the pharmaceutical composition of the present disclosure can be used for the treatment of prostate cancer, and the above-mentioned prostate cancer is not particularly limited, and may be general prostate cancer, castration-resistant prostate cancer (CRPC), etc., or may be prostate cancer with androgen mutation (AR mutation), androgen amplification (AR amplification), androgen variants (AR-variants), etc., such as androgen receptor splice variant 7.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Moreover, the pharmaceutically acceptable salt mentioned above may comprise, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

Furthermore, the pharmaceutical composition of the present disclosure can be administered to a subject in need thereof, but is not limited thereto. The administration route of the pharmaceutical composition of the present disclosure may include parenteral manner, oral manner, via inhalation spray, or by implanted reservoir, but is not limited thereto. The parenteral methods may comprise, but is not limited to, subcutaneous, intracutaneous, intravenous, intramuscular, intra-articular, intra-arterial, intrasynovial, intrasternal, intrathecal, intraleaional injection, external ophthalmic use, and intraocular injection, as well as infusion techniques, etc.

In addition, the subject in need to be administrated the pharmaceutical composition mentioned above may comprise, but is not limited to, a vertebrate. Moreover, the vertebrate mentioned above may comprise a fish, an amphibian, a reptile, a bird or a mammal, but it is not limited thereto. Examples of the mammal may comprise, but are not limited to a human, an orangutan, a monkey, a horse, a donkey, a dog, a cat, a rabbit, a guinea pig, a rat and a mouse. In one embodiment, the subject mentioned above may be a human.

Also, based on the above, the present disclosure can also provide a method for treating prostate cancer. The method mentioned above may include, but is not limited to, administering any compound of the present disclosure mentioned above to a subject in need thereof for the treatment of prostate cancer in the subject.

The prostate cancer mentioned above is not particularly limited, and may be general prostate cancer, castration-resistant prostate cancer (CRPC), etc., or may be prostate cancer with androgen mutation (AR mutation), androgen amplification (AR amplification), androgen variants (AR-variants), etc., such as androgen receptor splice variant 7.

In addition, the subject mentioned above may comprise, but is not limited to, a vertebrate. Moreover, the vertebrate mentioned above may comprise a fish, an amphibian, a reptile, a bird or a mammal, but it is not limited thereto. Examples of the mammal may comprise, but are not limited to a human, an orangutan, a monkey, a horse, a donkey, a dog, a cat, a rabbit, a guinea pig, a rat and a mouse. In one embodiment, the subject mentioned above may be a human.

EXAMPLES

1. Preparation of Compound 1

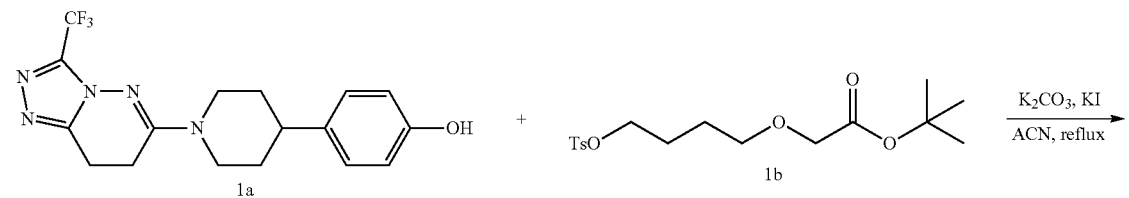

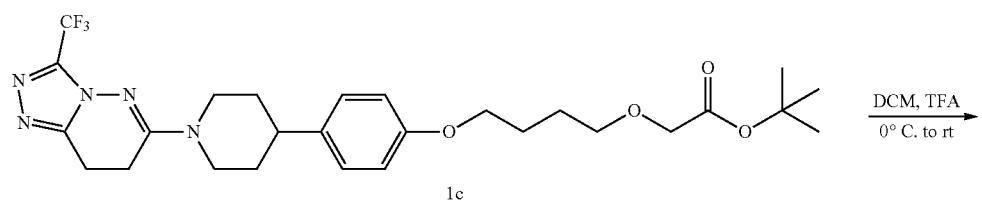

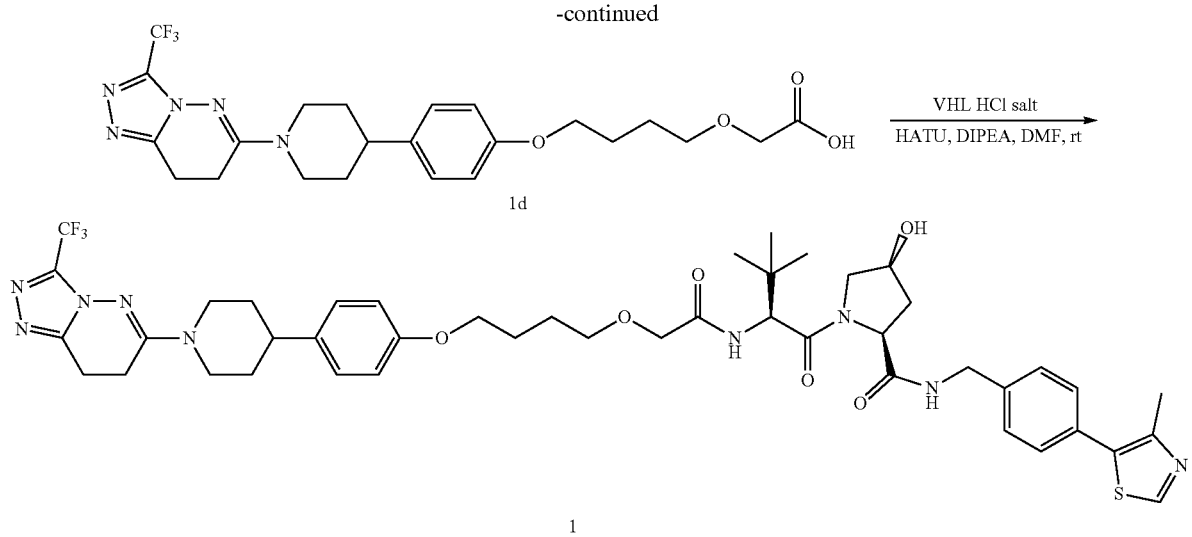

Preparation of tert-butyl 2-(4-(4-(1-(3-(trifluoromethyl)-7,8-dihydro-[1,2,4]triazolo[4,3-b]pyridazin-6-yl)piperidin-4-yl)phenoxy)butoxy)acetate (1c)

4-(1-(3-(trifluoromethyl)-7,8-dihydro-[1,2,4]triazolo[4,3-b]pyridazin-6-yl)piperidin-4-yl)phenol (1a) (150 mg, 0.41 mmol) and tert-butyl 2-(4-(tosyloxy)butoxy)acetate (1b) (162 mg, 0.45 mmol) were placed in a 25 mL round bottom flask, and ACN (4.1 mL) was added to the round bottom flask mentioned above at room temperature, followed by sequentially adding $K_2CO_3$ (113 mg, 0.82 mmol) and KI (17 mg, 0.20 mmol). The system was heated to reflux for 8 hours. After the reaction was complete, the solid was filtered off, and the filtrate was concentrated to obtain a crude product. The crude product was purified via column chromatography (MeOH/DCM=1/50) to give tert-butyl 2-(4-(4-(1-(3-(trifluoromethyl)-7,8-dihydro-[1,2,4]triazolo[4,3-b]pyridazin-6-yl)piperidin-4-yl)phenoxy)butoxy)acetate (1c) (150 mg, 66%)

1-2. Preparation of 2-(4-(4-(1-(3-(trifluoromethyl)-7,8-dihydro-[1,2,4]triazolo[4,3-b]pyridazin-6-yl)piperidin-4-yl)phenoxy)butoxy)acetic acid (1d)

Tert-butyl 2-(4-(4-(1-(3-(trifluoromethyl)-7,8-dihydro-[1,2,4]triazolo[4,3-b]pyridazin-6-yl)piperidin-4-yl)phenoxy)butoxy)acetate (1c) (146 mg, 0.26 mmol) was dissolved in DCM (8.8 mL) at room temperature. After the system was moved to an ice bath and stirred for 5 minutes, TFA (4.4 mL) was slowly added dropwise. After stirring continued for 5 minutes, the ice bath was removed and the system was allowed to react at room temperature for 2 hours. After the reaction was complete, the reactant was concentrated under reduced pressure to dry, and azeotroped with toluene three times (3 mL×3), and then lyophilized to obtain 2-(4-(4-(1-(3-(trifluoromethyl)-7,8-dihydro-[1,2,4]triazolo[4,3-b]pyridazin-6-yl)piperidin-4-yl)phenoxy)butoxy)acetic acid (1d) (129 mg, 99%).

1-3. Preparation of (2S,4S)-1-((S)-3,3-dimethyl-2-(2-(4-(4-(1-(3-(trifluoromethyl)-7,8-dihydro-[1,2,4]triazolo[4,3-b]pyridazin-6-yl)piperidin-4-yl)phenoxy)butoxy)acetamido)butanoyl)-4-hydroxy-N-(4-(4-methylthiazol-5-yl)benzyl)pyrrolidine-2-carboxamide (1)

2-(4-(4-(1-(3-(trifluoromethyl)-7,8-dihydro-[1,2,4]triazolo[4,3-b]pyridazin-6-yl)piperidin-4-yl)phenoxy)butoxy)acetic acid (1d) (145 mg, 0.29 mmol) and VHL HCl salt (150 mg, 0.32 mmol) were injected in DMF (2.9 mL) at room temperature, and HATU (122 mg, 0.32 mmol) and DIPEA (0.15 mL, 0.88 mmol) were sequentially added, and stirred at room temperature for 10 minutes, and then left to react at room temperature for 5 hours. After completion of the reaction, the reactant was neutralized by adding water, and extracted with ethyl acetate and saturated brine. The obtained organic layer was dried with anhydrous sodium sulfate and was filtered and concentrated to obtain a crude product. The crude product was purified by column chromatography (methanol/DCM=1/50→1/20) to obtain (2S,4S)-1-((S)-3,3-dimethyl-2-(2-(4-(4-(1-(3-(trifluoromethyl)-7,8-dihydro-[1,2,4]triazolo[4,3-b]pyridazin-6-yl)piperidin-4-yl)phenoxy)butoxy)acetamido)butanoyl)-4-hydroxy-N-(4-(4-methylthiazol-5-yl)benzyl)pyrrolidine-2-carboxamide (1) (157 mg, 59%).

$^1$H-NMR (500 MHz, CDCl$_3$): δ 8.66 (s, 1H), 7.36-7.32 (m, 5H), 7.18 (d, J=9.0 Hz, 1H), 7.10 (d, J=8.0 Hz, 2H), 6.83 (d, J=8.0 Hz, 2H), 4.72 (t, J=7.5, 8.5 Hz, 1H), 4.57-4.53 (m, 2H), 4.49 (d, J=9.0 Hz, 1H), 4.34 (dd, J=5.5, 15.3 Hz, 2H), 4.09 (d, J=11.0 Hz, 1H), 3.97-3.89 (m, 4H), 3.62-3.56 (m, 3H), 3.21 (t, J=8.0, 8.0 Hz, 2H), 3.02-2.95 (m, 2H), 2.79 (t, J=7.0, 8.5 Hz, 2H), 2.50 (s, 3H), 2.14-2.09 (m, 1H), 2.00-1.92 (m, 3H), 1.86-1.78 (m, 7H), 1.71-1.63 (m, 3H), 1.25 (s, 1H), 0.94 (s, 9H). LCMS [M+H]$^+$=908.3.

2. Preparation of Compound 2
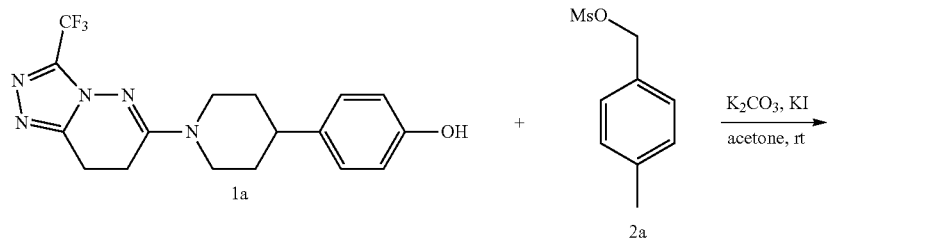
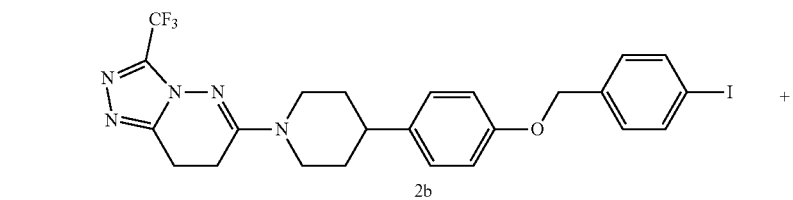
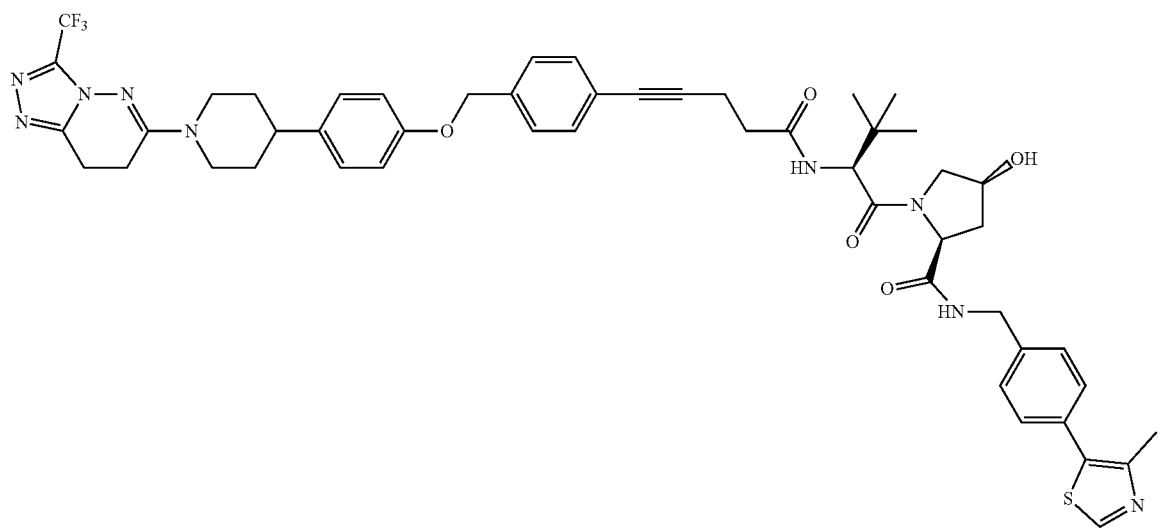
2

2-1. Preparation of 6-(4-(4-(4-iodobenzyloxy)phenyl)piperidin-1-yl)-3-(trifluoromethyl)-7,8-dihydro-[1,2,4]triazolo[4,3-b]pyridazine (2b)

This compound was prepared using a method similar to that used to prepare compound 1c. The crude product was purified by flash chromatography (MeOH/DCM=1/100) to give the title compound 2b (174 mg, 73%).

2-2. Preparation of (2S,4S)-1-((S)-3,3-dimethyl-2-(5-(4-((4-(1-(3-(trifluoromethyl)-7,8-dihydro-[1,2,4]triazolo[4,3-b]pyridazin-6-yl)piperidin-4-yl)phenoxy)methyl)phenyl)pent-4-ynamido)butanoyl)-4-hydroxy-N-(4-(4-methylthiazol-5-yl)benzyl)pyrrolidine-2-carboxamide (2)

6-(4-(4-(4-iodobenzyloxy)phenyl)piperidin-1-yl)-3-(trifluoromethyl)-7,8-dihydro-[1,2,4]triazolo[4,3-b]pyridazine (2b) (80 mg, 0.14 mmol), (2S,4S)-1-((S)-3,3-dimethyl-2-pent-4-ynamidobutanoyl)-4-hydroxy-N-(4-(4-methylthiazol-5-yl)benzyl)pyrrolidine-2-carboxamide (2c) (77 mg, 0.15 mmol), CuI (5 mg, 0.03 mmol) and PdCl$_2$(PPh$_3$)$_2$ (10 mg, 0.01 mmol) were placed in a high pressure tube, and DMF (0.7 mL) and Et$_3$N (0.7 mL) were added under argon. The reaction was heated to 90° C. and reacted for 2 hours. After the reaction was complete, the solvent was removed to obtain a crude product. The crude product was initially purified by column chromatography (MeOH/DCM=4/25→1/19→1/15), and then purified by reverse phase preparative HPLC to obtain (2S,4S)-1-((S)-3,3-dimethyl-2-(5-(4-((4-(1-(3-(trifluoromethyl)-7,8-dihydro-[1,2,4]triazolo[4,3-b]pyridazin-6-yl)piperidin-4-yl)phenoxy)methyl)phenyl)pent-4-ynamido)butanoyl)-4-hydroxy-N-(4-(4-methylthiazol-5-yl)benzyl)pyrrolidine-2-carboxamide (2) (60 mg, 45%).

$^1$H-NMR (500 MHz, CDCl$_3$): δ 8.68 (s, 1H), 7.40-7.30 (m, 8H), 7.26 (s, 1H), 7.11 (d, J=7.0 Hz, 2H), 6.89 (d, J=7.5 Hz, 2H), 6.42 (d, J=8.5 Hz, 1H), 5.00 (s, 2H), 4.65 (t, J=8.0, 7.5 Hz, 1H), 4.60-4.53 (m, 3H), 4.33 (ABq, J=4.5, 5.0 Hz, 2H), 4.10 (d, J=10.5 Hz, 1H), 3.60 (d, J=10.0 Hz, 1H), 3.21 (s, 2H), 3.00 (t, J=13.5, 13.0 Hz, 2H), 2.80-2.73 (m, 5H), 2.55-2.52 (m, 2H), 2.50 (s, 3H), 2.12-2.07 (m, 1H), 1.94 (d, J=13.0 Hz, 2H), 1.69-1.67 (m, 4H), 1.25 (s, 1H), 0.92 (s, 9H). LCMS [M+H]$^+$=964.4.

3. Preparation of Compound 3

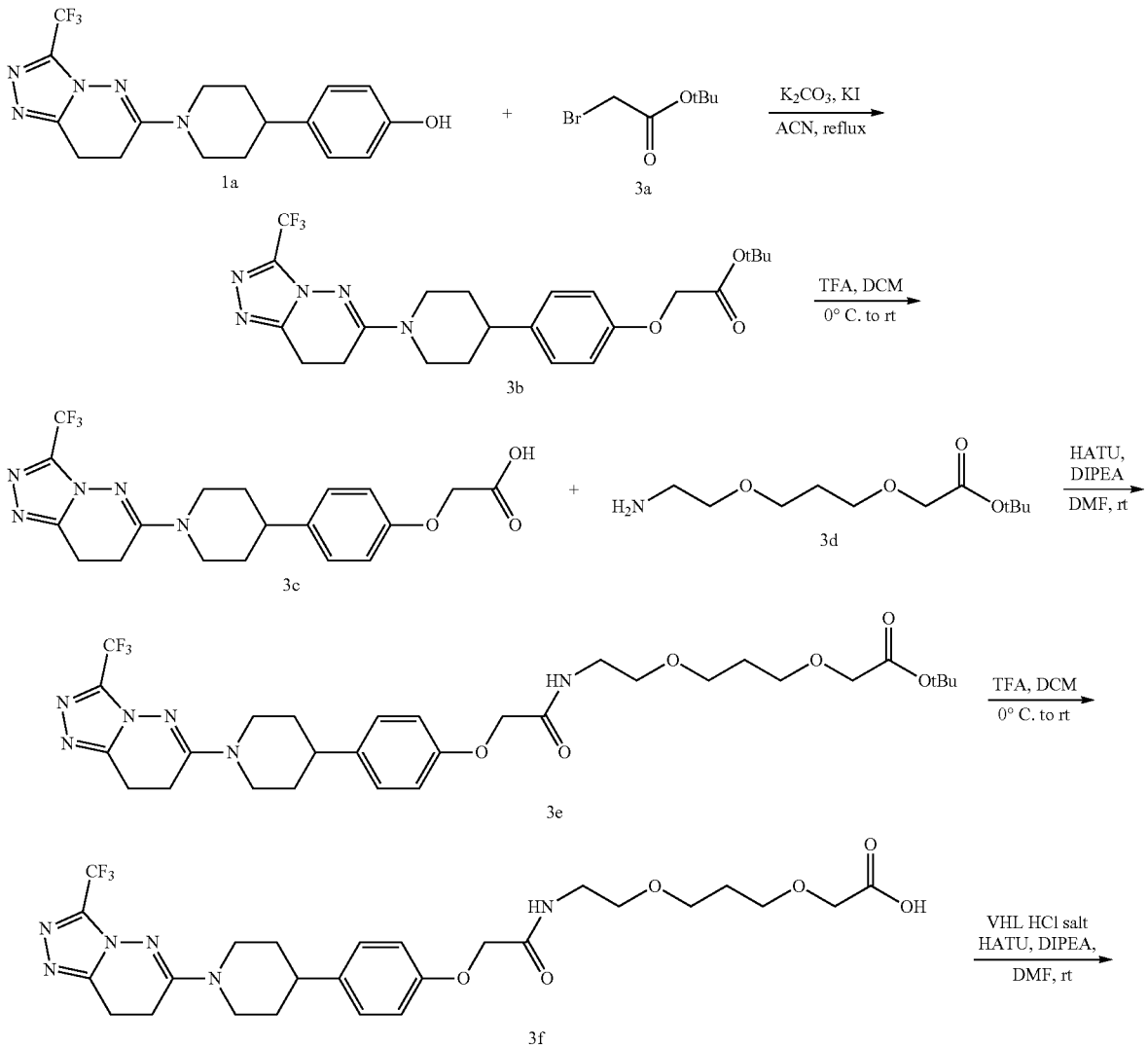

-continued

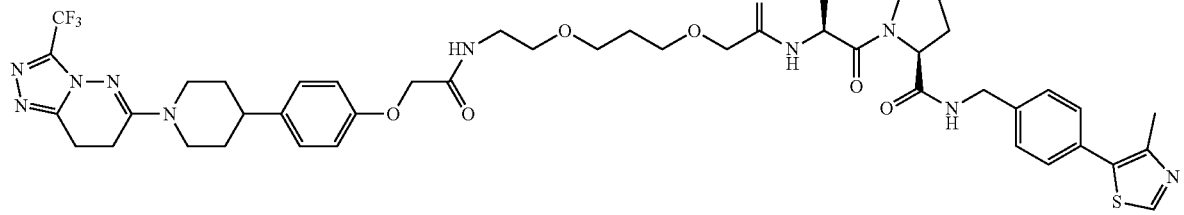

3

3-1. Preparation of tert-butyl 2-(4-(1-(3-(trifluoromethyl)-7,8-dihydro-[1,2,4]triazolo[4,3-b]pyridazin-6-yl)piperidin-4-yl)phenoxy)acetate (3b)

This compound was prepared using a method similar to that used to prepare compound 1c. The crude was purified by flash chromatography (Ethyl acetate/hexane=1/1→Ethyl acetate) to give the title compound 3b (394 mg, 100%).

3-2. Preparation of 2-(4-(1-(3-(trifluoromethyl)-7,8-dihydro-[1,2,4]triazolo[4,3-b]pyridazin-6-yl)piperidin-4-yl)phenoxy)acetic acid (3c)

This compound was prepared using a method similar to that used to prepare compound 1d. (347 mg, 99%).

3-3. Preparation of tert-butyl 2-(3-(2-(2-(4-(1-(3-(trifluoromethyl)-7,8-dihydro-[1,2,4]triazolo[4,3-b]pyridazin-6-yl)piperidin-4-yl)phenoxy)acetamido)ethoxy)propoxy)acetate (3e)

This compound was prepared using a method similar to that used to prepare compound 1. The crude product was purified by flash chromatography (DCM→MeOH/DCM=1/100→1/80→1/50→1/30) to give the title compound 3e (103 mg, 71%).

3-4. Preparation of 2-(3-(2-(2-(4-(1-(3-(trifluoromethyl)-7,8-dihydro-[1,2,4]triazolo[4,3-b]pyridazin-6-yl)piperidin-4-yl)phenoxy)acetamido)ethoxy)propoxy)acetic acid (3f)

This compound was prepared using a method similar to that used to prepare compound 1d (93 mg, 99%).

3-5. Preparation of (2S,4S)-1-((S)-2-tert-butyl-4,14-dioxo-15-(4-(1-(3-(trifluoromethyl)-7,8-dihydro-[1,2,4]triazolo[4,3-b]pyridazin-6-yl)piperidin-4-yl)phenoxy)-6,10-dioxa-3,13-diazapentadecane)-4-hydroxy-N-(4-(4-methylthiazol-5-yl)benzyl)pyrrolidine-2-carboxamide (3)

This compound was prepared using a method similar to that used to prepare compound 1. The crude product was purified by reverse phase preparative HPLC to give the title compound 3 (12 mg, 7%).

$^1$H-NMR (500 MHz, CD$_3$OD): δ 8.88 (s, 1H), 7.54 (d, J=10.0 Hz, 1H), 7.45 (ABq, J=8.0, 8.5 Hz, 4H), 7.18 (d, J=9.0 Hz, 2H), 6.91 (d, J=8.5 Hz, 2H), 4.69 (d, J=9.5 Hz, 1H), 4.60-4.55 (m, 2H), 4.55-4.46 (m, 2H), 4.43 (s, 4H), 4.36-4.33 (m, 2H), 3.95 (s, 1H), 3.93 (s, 1H), 3.88-3.85 (m, 1H), 3.80-3.79 (m, 1H), 3.63-3.51 (m, 8H), 3.47-3.43 (m, 3H), 3.35 (s, 1H), 3.20 (t, J=7.5, 8.0 Hz, 3H), 3.04 (t, J=13.0, 11.5 Hz, 2H), 2.93 (t, J=8.0, 7.5 Hz, 3H), 2.83-2.78 (m, 1H), 2.46 (s, 3H), 2.25-2.21 (m, 1H), 2.11-2.06 (m, 1H), 2.03 (s, 2H), 1.89-1.81 (m, 5H), 1.72-1.65 (m, 2H). LCMS [M+H]$^+$=995.4.

4. Preparation of Compound 4

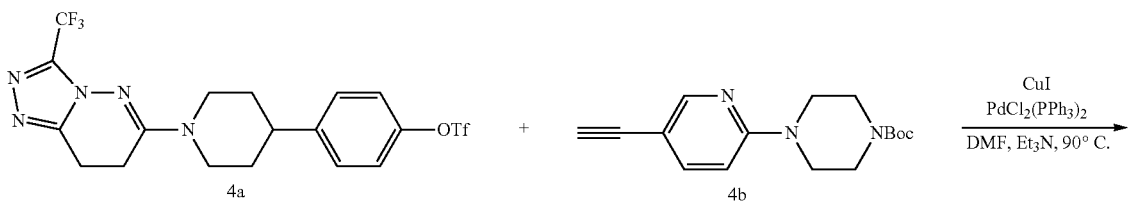

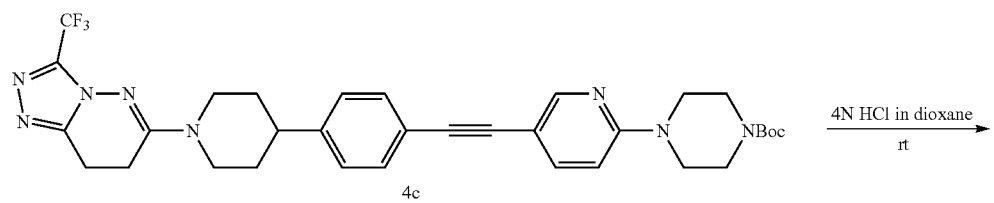

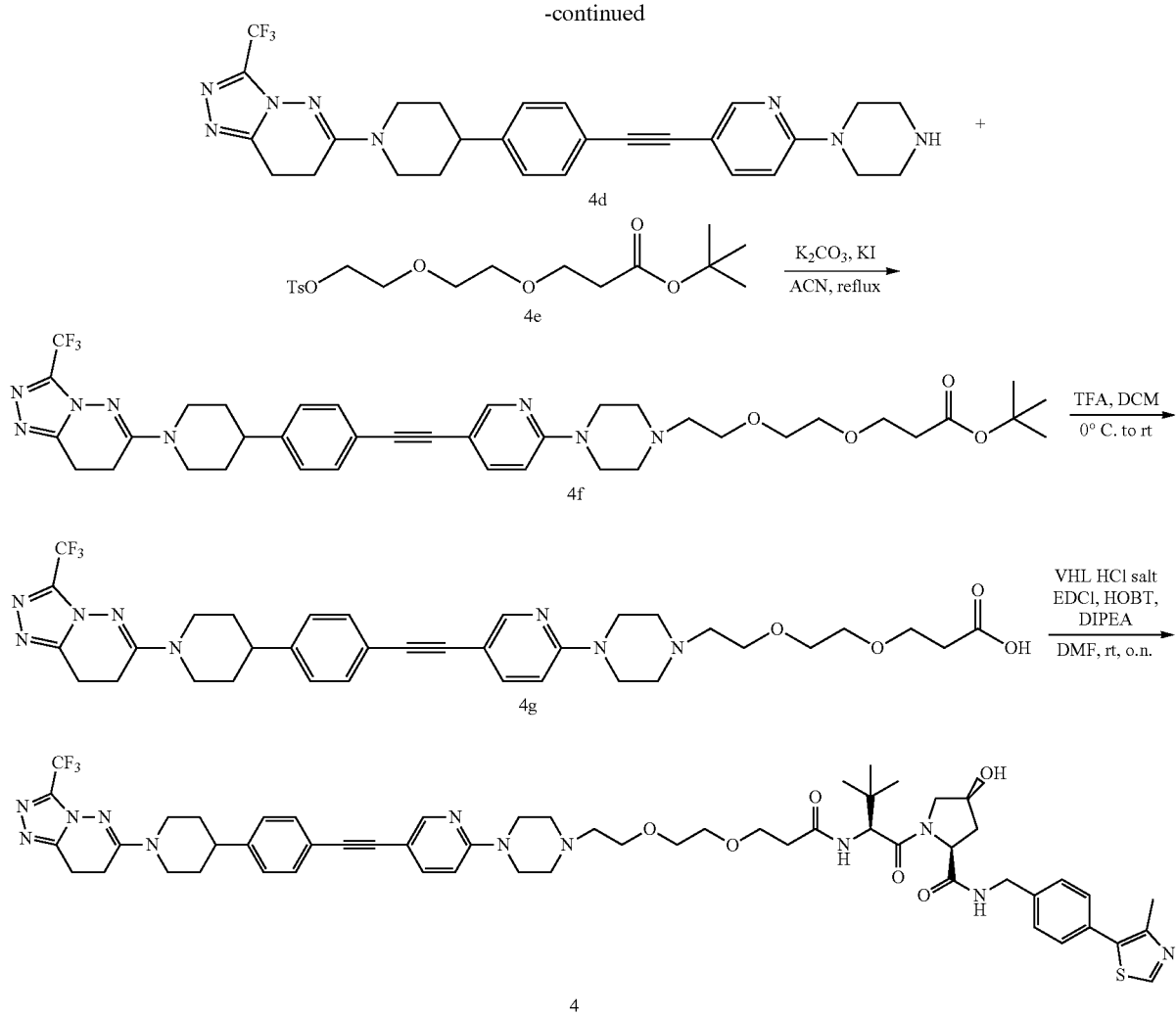

4-1. Preparation of tert-butyl 4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazine-1-carboxylate (4c)

This compound was prepared using a method similar to that used to prepare compound 2. The crude was purified by flash chromatography (Ethyl acetate/hexane=1/1→Ethyl acetate) to give the title compound 4c (149 mg, 86%).

4-2. Preparation of 6-(4-(4-((6-(piperazin-1-yl)pyridin-3-yl)ethynyl)phenyl)piperidin-1-yl)-3-(trifluoromethyl)-7,8-dihydro-[1,2,4]triazolo[4,3-b]pyridazine (4d)

4N HCl (2.3 mL) in dioxane was poured into a round-bottomed flask containing tert-butyl 4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazine-t-carboxylate (4c) (149 mg, 0.23 mmol), and after stirring, it was found that the compound could not be completely dissolved, and thus about 1 mL of MeOH was added to increase the solubility of the compound. The reactant was stirred at room temperature for 3 hours, concentrated and drained after the reaction was complete, and then azeotroped 3 times with toluene (3 mL) to remove residual HCl, and finally lyophilized by a lyophilizer to obtain 6-(4-(4-((6-(piperazin-1-yl)pyridin-3-yl)ethynyl)phenyl)piperidin-1-yl)-3-(trifluoromethyl)-7,8-dihydro-[1,2,4]triazolo[4,3-b]pyridazine (4d) (124 mg, 99%).

4-3. Preparation of tert-butyl 3-(2-(2-(4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazin-1-yl)ethoxy)ethoxy)propanoate (4f)

This compound was prepared using a method similar to that used to prepare compound 1c. The crude was purified by flash chromatography (MeOH/DCM=1/50→1/30→1/20) to give the title compound 4f (50 mg, 23%).

$^1$H-NMR (500 MHz, CDCl$_3$): δ 8.32 (s, 1H), 7.55 (d, J=8.5 Hz, 1H), 7.44 (d, J=8.5 Hz, 2H), 7.16 (d, J=8.5 Hz, 2H), 6.58 (d, J=9 Hz, 1H), 3.70 (t, J=6.5, 7.0 Hz, 2H), 3.66 (t, J=7.5, 6.0 Hz, 2H), 3.57 (s, 7H), 3.20 (t, J=8.0, 7.5 Hz, 2H), 3.00 (t, J=12.5, 12.5 Hz, 2H), 2.78 (t, J=7.0, 8.0 Hz, 2H), 2.65-2.61 (m, 5H), 2.49 (t, J=6.5, 7.0 Hz, 2H), 1.96 (d, J=13.5 Hz, 2H), 1.75-1.66 (m, 2H), 1.43 (s, 9H).

4.4. Preparation of 3-(2-(2-(4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazin-1-yl)ethoxy)ethoxy)propanoic acid (4g)

This compound was prepared using a method similar to that used to prepare compound 1d. (46 mg, 99%).

4-5. Preparation of (2S,4S)-1-((S)-3,3-dimethyl-2-(3-(2-(2-(4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazin-1-yl)ethoxy)ethoxy)propanamido)butanoyl)-4-hydroxy-N-(4-(4-methylthiazol-5-yl)benzyl)pyrrolidine-2-carboxamide (4)

DMF (2.4 mL) was added to 3-(2-(2-(4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazin-1-yl)ethoxy)ethoxy)propanoic acid (4g) (83 mg, 0.12 mmol) and VHL HCl salt (84 mg, 0.18 mmol) was injected, followed by sequentially adding EDCI (46 mg, 0.24 mmol), HOBT (32 mg, 0.24 mmol) and DIPEA (0.09 mL, 0.54 mmol), and reacted at room temperature for 8 hours. After the completion of the reaction, water was added to the reactant for neutralization, and the neutralized reactant was extracted with ethyl acetate and saturated brine. The obtained organic layer was dehydrated and filtered with anhydrous sodium sulfate and concentrated to obtain a crude product. Purification was performed by column chromatography (MeOH/DCM=1/20→1/15→1/13→1/10→1/8→1/5) to obtain the product (2S,4S)-1-((S)-3,3-dimethyl-2-(3-(2-(2-(4-(5-((4-(1-(3-(trifluoromethyl)-7,8-dihydro-[1,2,4]triazolo[4,3-b]pyridazin-6-yl)piperidin-4-yl)phenyl)ethynyl)pyridin-2-yl)piperazin-1-yl)ethoxy)ethoxy)propanamido)butanoyl)-4-hydroxy-N-(4-(4-methylthiazol-5-yl)benzyl)pyrrolidine-2-carboxamide (4) (31 mg, 23%).

$^1$H-NMR (500 MHz, CD$_3$OD): δ 8.85 (s, 1H), 8.27 (s, 1H), 7.65 (d, J=10 Hz, 1H), 7.44-7.41 (m, 8H), 7.26 (d, J=10 Hz, 2H), 6.87 (d, J=10 Hz, 1H), 4.66 (s, 1H), 4.49 (s, 2H), 4.36 (d, J=15 Hz, 2H), 3.88 (d, J=15 Hz, 1H), 3.85-3.70 (m, 11H), 3.65-3.60 (m, 5H), 3.25-3.19 (m, 5H), 3.12-3.04 (m, 7H), 2.95 (t, J=10, 10 Hz, 3H), 2.57-2.52 (m, 2H), 2.49 (s, 3H), 2.24-2.20 (m, 1H), 2.10-2.06 (s, 1H), 1.9 (d, J=15 Hz, 2H), 1.74 (dd, J=15, 22.5 Hz, 2H), 1.04 (s, 9H). LCMS: [M+H]$^+$=1107.0.

5. Preparation of Compound 5

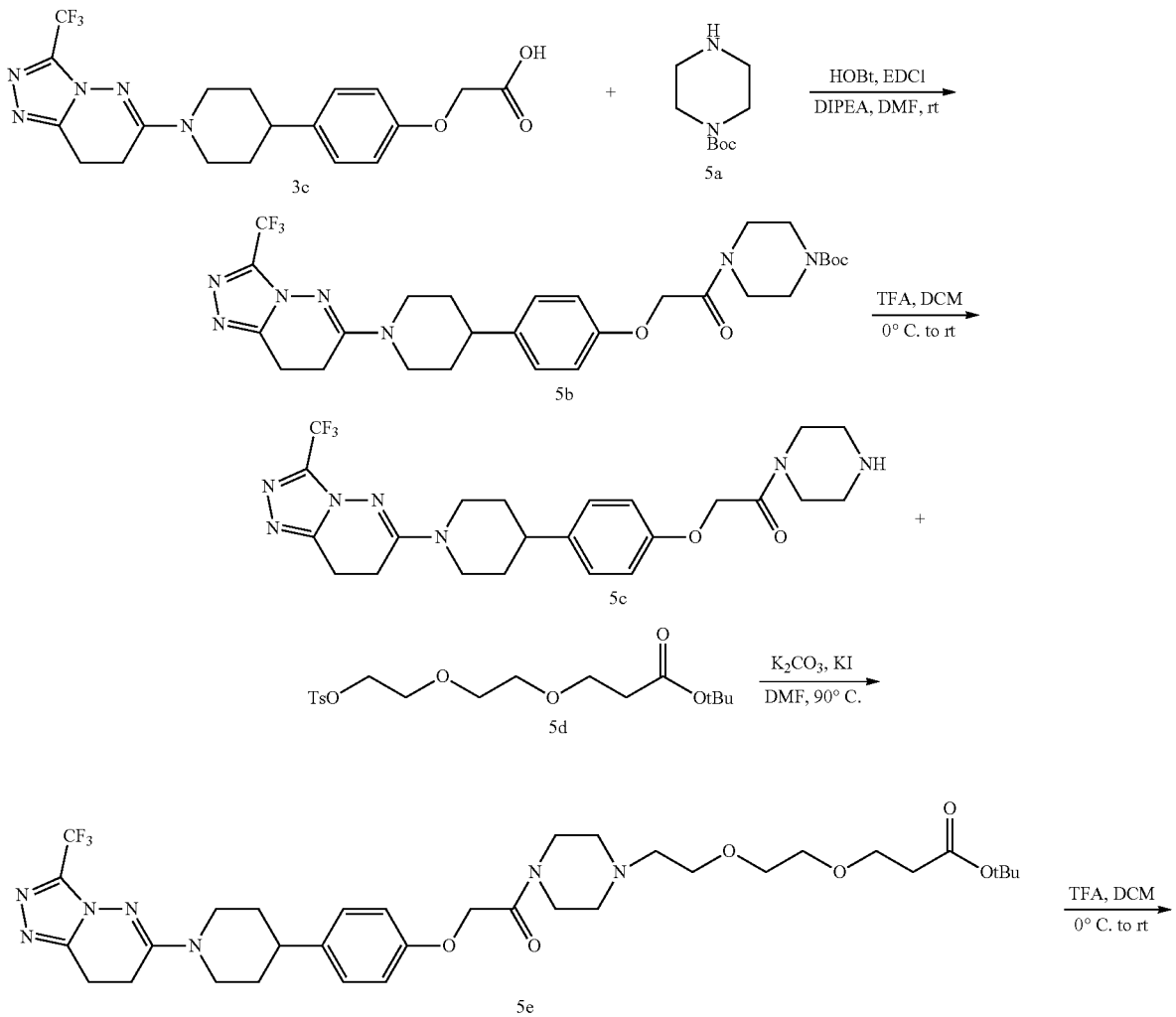

-continued

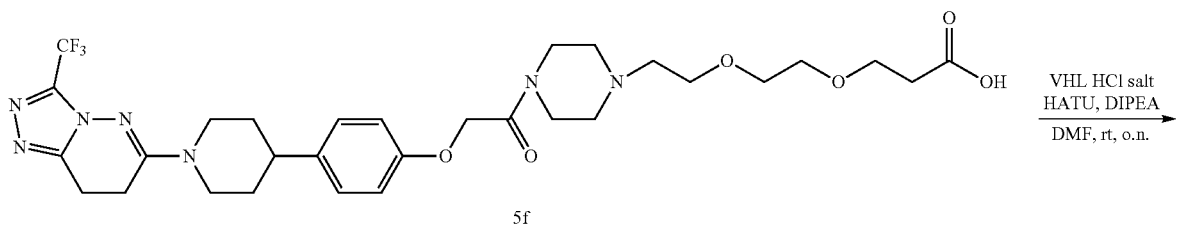

5f

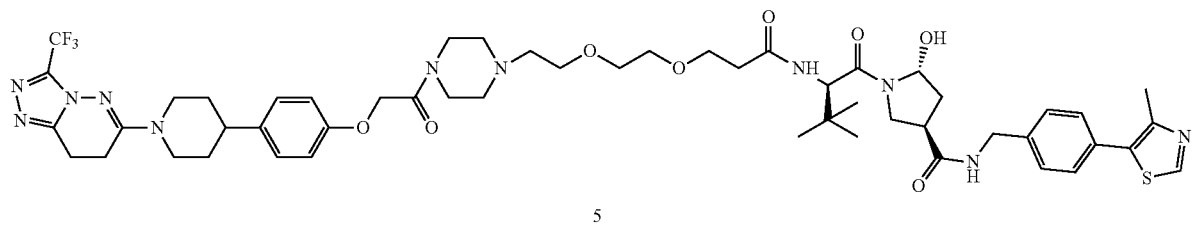

5

5-1. Preparation of tert-butyl 4-(2-(4-(1-(3-(trifluoromethyl)-7,8-dihydro-[1,2,4]triazolo[4,3-b]pyridazin-6-yl)piperidin-4-yl)phenoxy)acetyl)piperazine-1-carboxylate (5b)

This compound was prepared using a method similar to that used to prepare compound 4. The crude product was purified by flash chromatography (MeOH/Ethyl acetate=1/100) to give the title compound 5b (193 mg, 83%).

5-2. Preparation of 1-(piperazin-1-yl)-2-(4-(1-(3-(trifluoromethyl)-7,8-dihydro-[1,2,4]triazolo[4,3-b]pyridazin-6-yl)piperidin-4-yl)phenoxy)ethanone (5c)

This compound was prepared using a method similar to that used to prepare compound 1d. (159 mg, 99%).

5-3. Preparation of tert-butyl 3-(2-(2-(4-(2-(4-(1-(3-(trifluoromethyl)-7,8-dihydro-[1,2,4]triazolo[4,3-b]pyridazin-6-yl)piperidin-4-yl)phenoxy)acetyl)piperazin-1-yl)ethoxy)ethoxy)propanoate (5e)

This compound was prepared using a method similar to that used to prepare compound 1c. The crude product was purified by flash chromatography (MeOH/DCM=1/30→1/15) to give the title compound 5e (130 mg, 48%).

5-4. Preparation of 3-(2-(2-(4-(2-(4-(1-(3-(trifluoromethyl)-7,8-dihydro-[1,2,4]triazolo[4,3-b]pyridazin-6-yl)piperidin-4-yl)phenoxy)acetyl)piperazin-1-yl)ethoxy)ethoxy)propanoic acid (5f)

This compound was prepared using a method similar to that used to prepare compound 1d. (118 mg, 99%).

5-5. Preparation of (3R,5R)-1-((R)-3,3-dimethyl-2-(3-(2-(2-(4-(2-(4-(1-(3-(trifluoromethyl)-7,8-dihydro-[1,2,4]triazolo[4,3-b]pyridazin-6-yl)piperidin-4-yl)phenoxy)acetyl)piperazin-1-yl)ethoxy)ethoxy)propanamido)butanoyl)-5-hydroxy-N-(4-(4-methylthiazol-5-yl)benzyl)pyrrolidine-3-carboxamide (5)

This compound was prepared using a method similar to that used to prepare compound 1. The crude product was purified by flash chromatography (MeOH/DCM=1/20→1/10→1/8) to give the title compound 5 (80 mg, 27%).
$^1$H-NMR (500 MHz, CD$_3$OD): δ 8.86 (s, 1H), 7.42 (ABq, $J_{AB}$=10 Hz, 4H), 7.16 (d, J=10 Hz, 2H), 6.89 (d, J=10 Hz, 2H), 4.76 (s, 2H), 4.65 (t, J=5, 5 Hz, 1H), 4.57-4.48 (m, 3H), 4.34 (d, J=15 Hz, 2H), 3.88 (d, J=10 Hz, 1H), 3.8 (dd, J=2.5, 6 Hz, 1H), 3.74-3.70 (m, 3H), 3.68-3.61 (m, 10H), 3.04 (t, J=11.5, 12 Hz, 3H), 2.95-2.92 (m, 3H), 2.66 (t, J=4.5, 9 Hz, 2H), 2.61-2.54 (m, 4H), 2.46 (s, 3H), 1.87 (d, J=12.5 Hz, 3H), 1.72-1.70 (m, 3H), 1.33 (d, J=28 Hz, 2H), 0.90 (s, 9H). LCMS [M+H]$^+$=1065.0.

6. Preparation of Compound 6

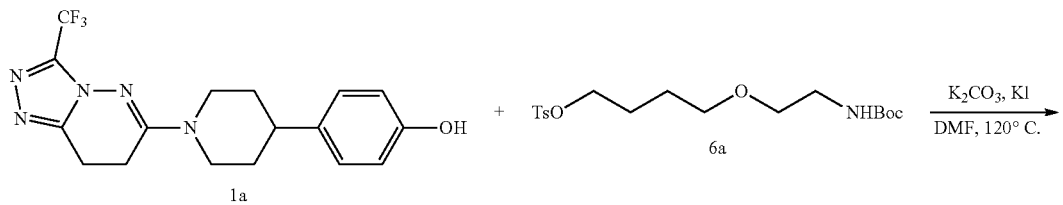

-continued
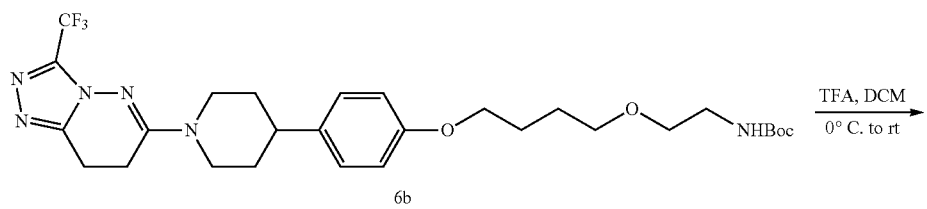
6b
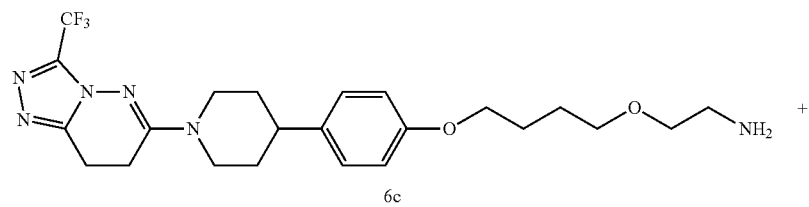
6c
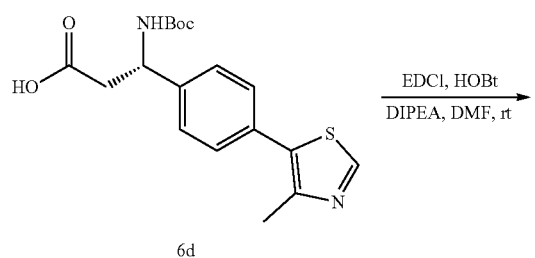
6d
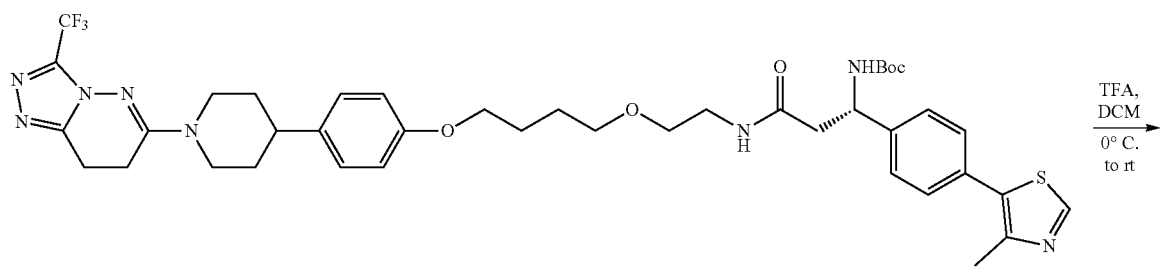
6e
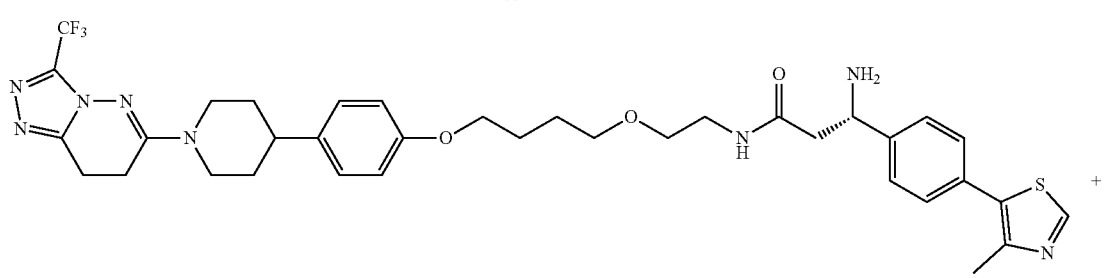
6f
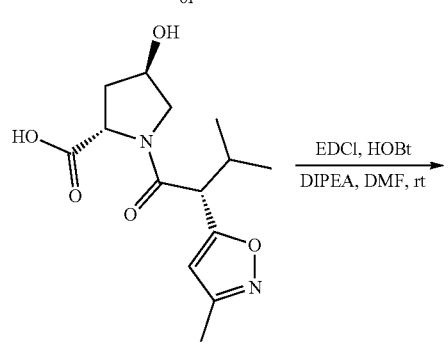
6g

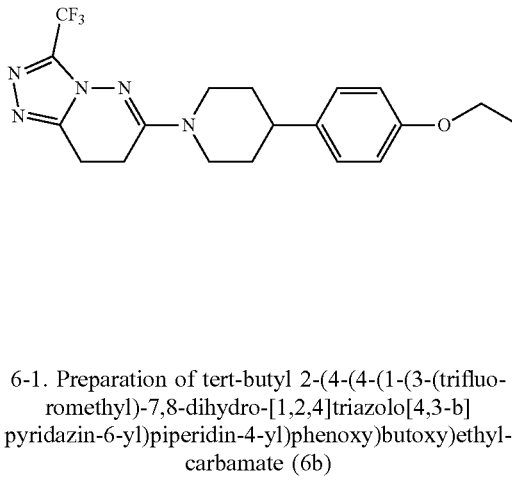
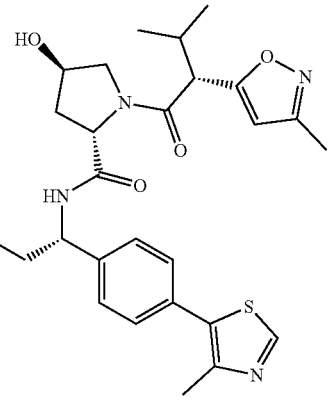

6

6-1. Preparation of tert-butyl 2-(4-(4-(1-(3-(trifluoromethyl)-7,8-dihydro-[1,2,4]triazolo[4,3-b]pyridazin-6-yl)piperidin-4-yl)phenoxy)butoxy)ethylcarbamate (6b)

This compound was prepared using a method similar to that used to prepare compound 1c. The crude was purified by flash chromatography (MeOH/DCM=1/60) to give the title compound 6b (152 mg, 45%).

$^1$H-NMR (500 MHz, CDCl$_3$): δ 7.06 (d, J=8.0 Hz, 2H), 6.80 (d, J=8.0 Hz, 2H), 3.91 (t, J=5.5, 5.5 Hz, 2H), 3.59-3.58 (m, 2H), 3.46-3.43 (m, 6H), 3.15 (t, J=8.0, 7.0 Hz, 2H), 2.77-2.70 (m, 2H), 1.89 (d, J=13.0 Hz, 2H), 1.80-1.78 (m, 2H), 1.71-1.59 (m, 7H).

6-2. Preparation of 2-(4-(4-(1-(3-(trifluoromethyl)-7,8-dihydro-[1,2,4]triazolo[4,3-b]pyridazin-6-yl)piperidin-4-yl)phenoxy)butoxy)ethanamine (6c)

This compound was prepared using a method similar to that used to prepare compound 1d (125 mg, 99%).

6-3. Preparation of (S)-tert-butyl 1-(4-(4-methylthiazol-5-yl)phenyl)-3-oxo-3-(2-(4-(4-(1-(3-(trifluoromethyl)-7,8-dihydro-[1,2,4]triazolo[4,3-b]pyridazin-6-yl)piperidin-4-yl)phenoxy)butoxy)ethylamino)propylcarbamate (6e)

This compound was prepared using a method similar to that used to prepare compound 4. The crude was purified by flash chromatography (MeOH/DCM=1/60→1/50→1/40→1/25) to give the title compound 6e (84 mg, 39%).

$^1$H-NMR (500 MHz, CDCl$_3$): δ 8.63 (s, 1H), 7.34 (ABq, J=10.0, 5.0 Hz, 4H), 7.09 (d, J=8.5 Hz, 2H), 6.81 (d, J=8.5 Hz, 2H), 5.28 (s, 1H), 3.90 (t, J=5.5, 6.5 Hz, 2H), 3.41-3.32 (m, 6H), 3.19 (t, J=7.5, 8.0 Hz, 2H), 2.98 (t, J=12.5, 12.5 Hz, 2H), 2.77 (t, J=8.0, 8.5 Hz, 3H), 2.72 (s, 2H), 2.49 (s, 3H), 1.95-1.91 (m, 3H), 1.77-1.72 (m, 3H), 1.67-1.60 (m, 5H), 1.40 (s, 9H).

6-4. Preparation of (S)-3-amino-3-(4-(4-methylthiazol-5-yl)phenyl)-N-(2-(4-(4-(1-(3-(trifluoromethyl)-7,8-dihydro-[1,2,4]triazolo[4,3-b]pyridazin-6-yl)piperidin-4-yl)phenoxy)butoxy)ethyl)propanamide (6f)

This compound was prepared using a method similar to that used to prepare compound 1d. (73 mg, 99%).

6-5. Preparation of (2S,4R)-4-hydroxy-1-((R)-3-methyl-2-(3-methylisoxazol-5-yl)butanoyl)-N—((S)-1-(4-(4-methylthiazol-5-yl)phenyl)-3-oxo-3-(2-(4-(4-(1-(3-(trifluoromethyl)-7,8-dihydro-[1,2,4]triazolo[4,3-b]pyridazin-6-yl)piperidin-4-yl)phenoxy)butoxy)ethylamino)propyl)pyrrolidine-2-carboxamide (6)

This compound was prepared using a method similar to that used to prepare compound 4. The crude product was purified by reverse phase preparative HPLC to give the title compound 6 (10 mg, 6%).

$^1$H-NMR (500 MHz, CD$_3$OD): δ 8.82 (s, 1H), 7.46-7.36 (m, 4H), 7.13 (d, J=9.0 Hz, 2H0, 6.81 (d, J=8.5 Hz, 2H), 6.24-6.21 (m, 1H), 4.59-4.31 (m, 5H), 3.95-3.92 (m, 2H), 3.86 (d, J=8.5 Hz, 1H), 3.77-3.57 (m, 2H), 3.43-3.41 (m, 2H), 3.37-3.34 (m, 2H), 3.29-3.28 (m, 1H), 3.21 (t, J=15.5, 8.0 Hz, 2H), 3.04 (t, J=12.5, 12.0 Hz, 2H), 2.93 (t, J=8.0, 7.5 Hz, 2H), 2.86-2.84 (m, 1H), 2.80-2.69 (m, 3H), 2.46 (s, 3H), 2.44-2.39 (m, 1H), 2.23 (d, J=14.5 Hz, 3H), 2.00-1.95 (m, 1H), 1.89 (d, J=13.0, 2H), 1.77-1.72 (m, 2H), 1.69-1.65 (m, 4H), 1.31 (s, 2H), 1.05 (d, J=7.0 Hz, 3H), 0.94-0.80 (m, 3H). LCMS [M+H]$^+$=1002.9.

7. Preparation of Compound 7

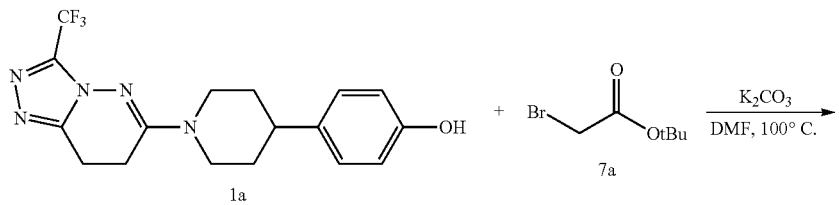

-continued

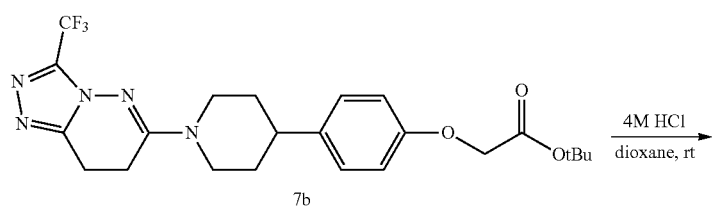

7b

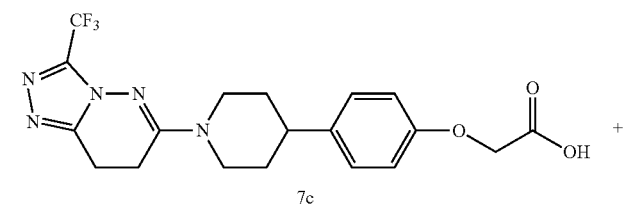

7c

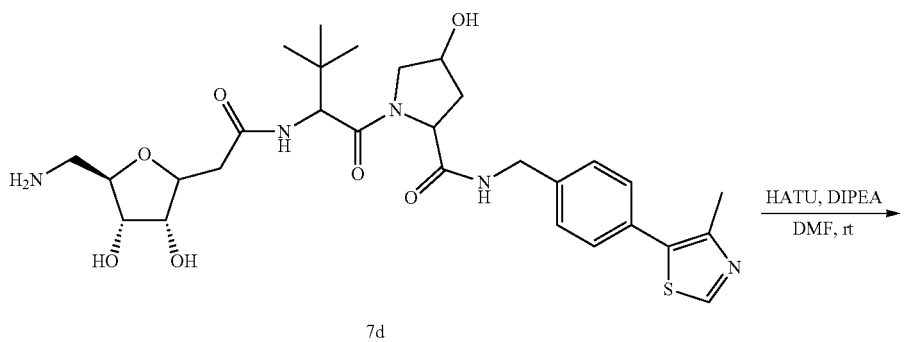

7d

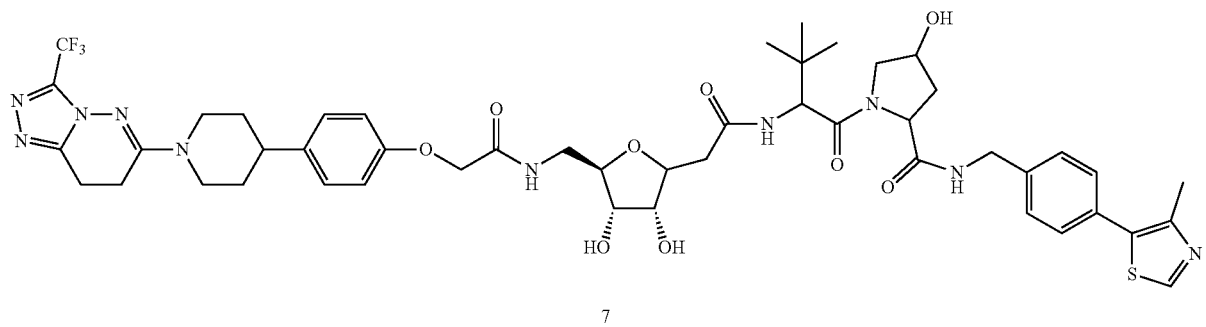

7

7-1. Preparation of tert-butyl 2-(4-(1-(3-(trifluoromethyl)-7,8-dihydro-[1,2,4]triazolo[4,3-b]pyridazin-6-yl)piperidin-4-yl)phenoxy)acetate (7b)

This compound was prepared using a method similar to that used to prepare compound 1c. The crude product was purified by flash chromatography (MeOH/DCM=1/99→5/95) to give the title compound 7b (72 mg, 27%).

7-2. Preparation of 2-(4-(1-(3-(trifluoromethyl)-7,8-dihydro-[1,2,4]triazolo[4,3-b]pyridazin-6-yl)piperidin-4-yl)phenoxy)acetic acid (7c)

This compound was prepared using a method similar to that used to prepare compound 4d (66 mg, 95%).

7-3. Preparation of 1-(2-(2-(((3R,4S,5R)-3,4-dihydroxy-5-((2-(4-(1-(3-(trifluoromethyl)-7,8-dihydro-[1,2,4]triazolo[4,3-b]pyridazin-6-yl)piperidin-4-yl)phenoxy)acetamido)methyl)tetrahydrofuran-2-yl)acetamido)-3,3-dimethylbutanoyl)-4-hydroxy-N-(4-(4-methylthiazol-5-yl)benzyl)pyrrolidine-2-carboxamide (7)

This compound was prepared using a method similar to that used to prepare compound 1. The crude product was purified by reverse phase preparative HPLC to give the title compound 7 (13 mg, 9%). LCMS [M+H]$^+$=1010.6.

8. Preparation of Compound 8
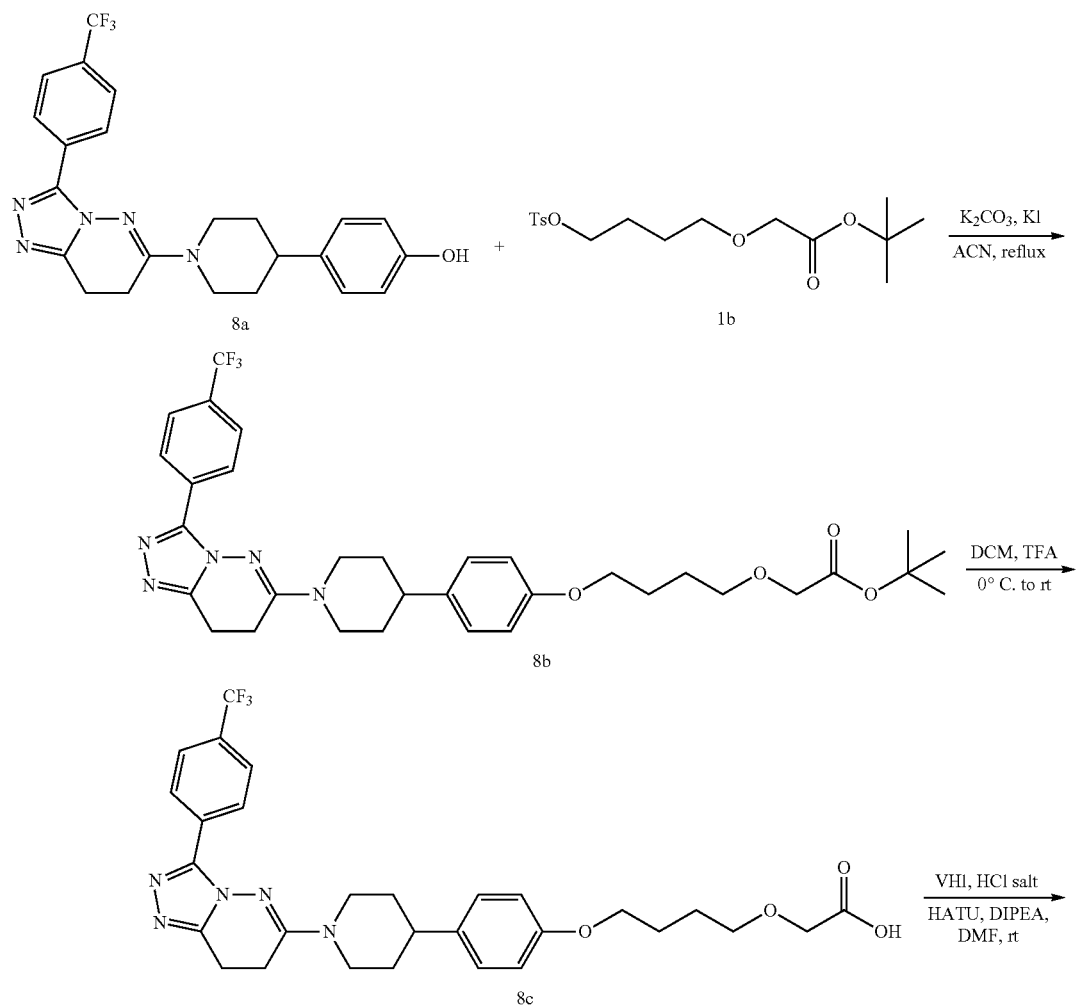
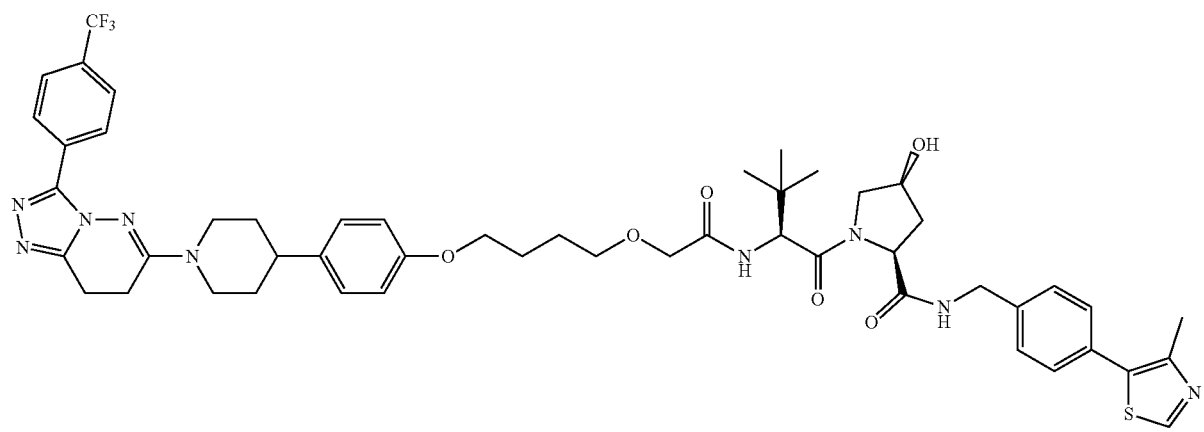

8-1. Preparation of tert-butyl 2-(4-(4-(1-(3-(4-(trifluoromethyl)phenyl)-7,8-dihydro-[1,2,4]triazolo[4,3-b]pyridazin-6-yl)piperidin-4-yl)phenoxy)butoxy)acetate (8b)

This compound was prepared using a method similar to that used to prepare compound 1c. The crude product was purified by flash chromatography (MeOH/DCM=1/50→1/40) to give the title compound 8b (32 mg, 23%).

$^1$H-NMR (500 MHz, CDCl$_3$): δ 8.42 (d, J=8.5 Hz, 2H), 7.70 (d, J=8.5 Hz, 2H), 7.11 (d, J=8.5 Hz, 2H), 6.85 (d, J=8.5 Hz, 2H), 4.29 (d, J=12.0 Hz, 2H), 3.97 (dd, J=6.0, 12.0 Hz, 4H), 3.57 (t, J=6.5, 6.5 Hz, 2H), 3.23 (t, J=7.0, 7.5 Hz, 2H), 3.02 (t, J=13.0, 12.5 Hz, 1H), 2.80-2.73 (m, 2H), 1.97 (d, J=13.0, 2H), 1.91-1.85 (m, 3H), 1.81-1.67 (m, 5H), 1.46 (s, 9H).

8-2. Preparation of 2-(4-(4-(1-(3-(4-(trifluoromethyl)phenyl)-7,8-dihydro-[1,2,4]triazolo[4,3-b]pyridazin-6-yl)piperidin-4-yl)phenoxy)butoxy)acetic acid (8c)

This compound was prepared using a method similar to that used to prepare compound 1d (29 mg, 100%).

8-3. Preparation of (2S,4S)-1-((S)-3,3-dimethyl-2-(2-(4-(4-(1-(3-(4-(trifluoromethyl)phenyl)-7,8-dihydro-[1,2,4]triazolo[4,3-b]pyridazin-6-yl)piperidin-4-yl)phenoxy)butoxy)acetamido)butanoyl)-4-hydroxy-N-(4-(4-methylthiazol-5-yl)benzyl)pyrrolidine-2-carboxamide (8)

This compound was prepared using a method similar to that used to prepare compound 1. The crude product was purified by reverse phase preparative HPLC to give the title compound 8 (27 mg, 54%).

$^1$H-NMR (500 MHz, CDCl$_3$): δ 8.66 (s, 1H), 8.42 (d, J=8.0 Hz, 2H), 7.70 (d, J=8.5 Hz, 2H), 7.37-7.30 (m, 5H), 7.18 (d, J=9.0 Hz, 1H), 7.12 (d, J=8.5 Hz, 2H), 6.84 (d, J=8.5 Hz, 2H), 4.72 (t, J=8.5, 9.0 Hz, 1H), 4.58-4.55 (m, 2H), 4.50 (d, J=8.5 Hz, 1H), 4.35-4.28 (m, 3H), 4.11 (d, J=11.5 Hz, 1H), 3.96-3.89 (m, 4H), 3.62-3.56 (m, 3H), 3.24 (t, J=7.5, 7.5 Hz, 2H), 3.02 (t, J=13.0, 12.0 Hz, 2H), 2.80-2.73 (m, 3H), 2.59-2.53 (m, 1H), 2.50 (s, 3H), 2.14-2.10 (m, 1H), 1.98-1.75 (m, 10H). LCMS [M+H]$^+$=983.9.

9. Preparation of Compound 9

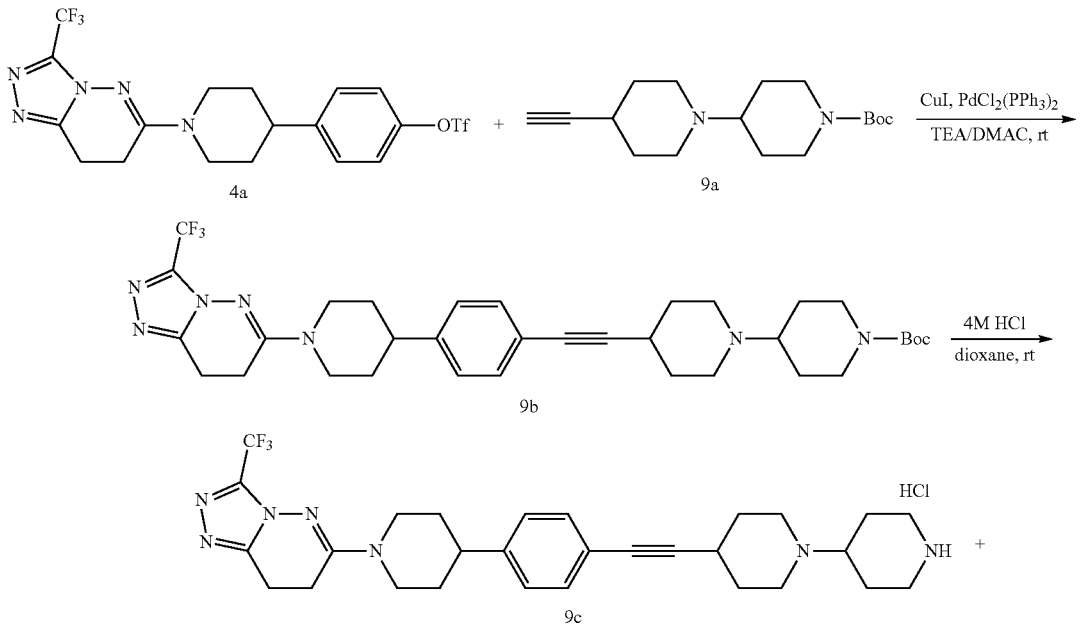

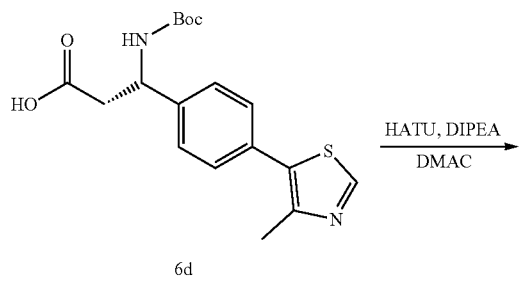

-continued

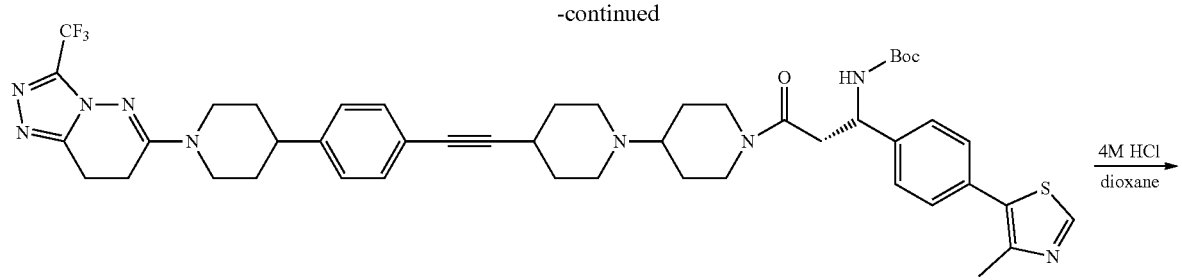

9d

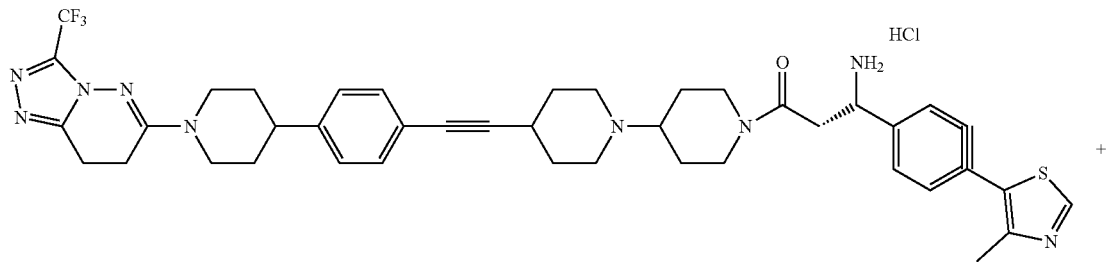

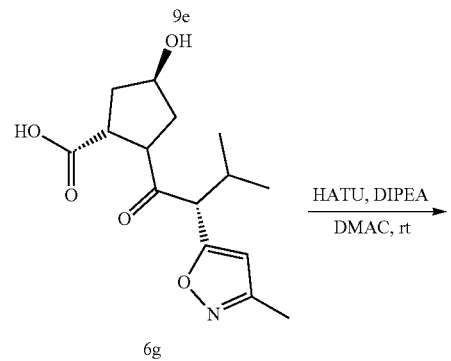

6g

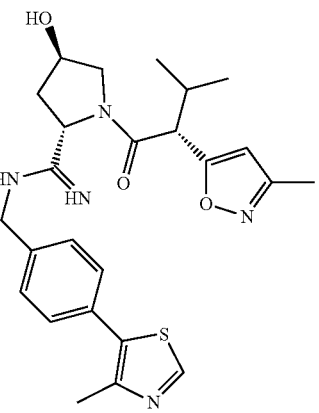

9

9-1. Preparation of tert-butyl 4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidine]-1'-carboxylate (9b)

This compound was prepared using a method similar to that used to prepare compound 2. The crude product was purified by flash chromatography (MeOH/DCM=1/99→5/95) to give the title compound 9b (92 mg, 37%).

9-2. Preparation of 6-(4-(4-([1,4'-bipiperidin]-4-ylethynyl)phenyl)piperidin-1-yl)-3-(trifluoromethyl)-7,8-dihydro-[1,2,4]triazolo[4,3-b]pyridazine (9c)

This compound was prepared using a method similar to that used to prepare compound 4d (90 mg, 98%).

9-3. Preparation of tert-butyl(S)-(1-(4-(4-methylthiazol-5-yl)phenyl)-3-oxo-3-(4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidin]-1'-yl)propyl)carbamate (9d)

This compound was prepared using a method similar to that used to prepare compound 1. The crude product was purified by reverse phase preparative HPLC to give the title compound 9d.

9-4. Preparation of (S)-3-amino-3-((4-methylthiazol-5-yl)-417,515-cyclohexa-1,3,5-trien-4-yn-1-yl)-1-(4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidin]-1'-yl)propan-1-one (9e)

This compound was prepared using a method similar to that used to prepare compound 4d (35 mg, 27%, 2 steps).

9-5. Preparation of (2S,4R)-4-hydroxy-1-((R)-3-methyl-2-(3-methylisoxazol-5-yl)butanoyl)-N—((S)-1-(4-(4-methylthiazol-5-yl)phenyl)-3-oxo-3-(4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidin]-1'-yl)propyl)pyrrolidine-2-carboxamide (9)

This compound was prepared using a method similar to that used to prepare compound 1. The crude product was purified by reverse phase preparative HPLC to give the title compound 9 (22 mg, 49%). LCMS [M+H]$^+$=1063.5.

10. Preparation of Compound 10 and Compound 11

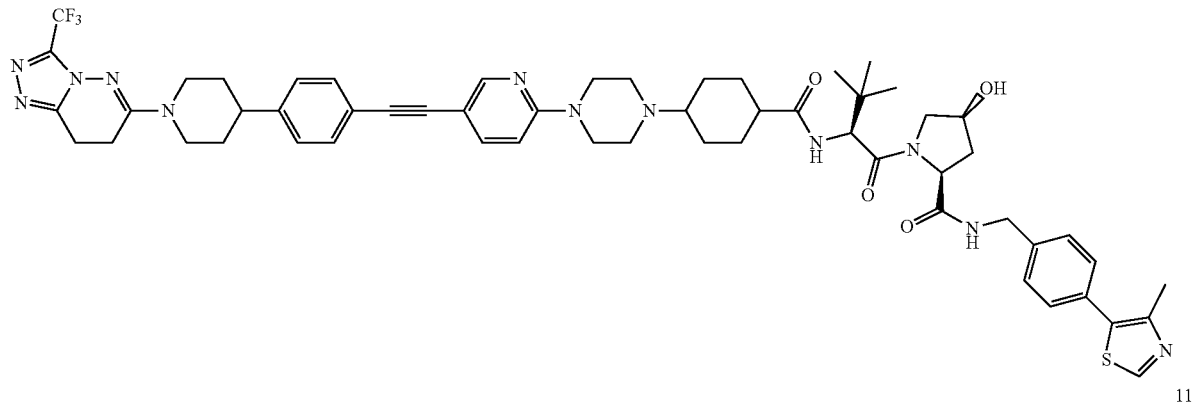

The preparation scheme of Compound 10 and Compound 11 shown above can be deduced from the preparation scheme of Compound 4 shown above.

11. Preparation of Compound 12

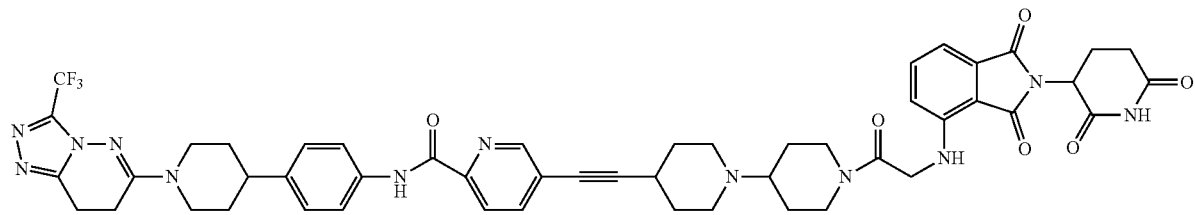

The preparation scheme of Compound 12 shown above can be deduced from the preparation scheme of Compound 51 as shown below.
12. Preparation of Compound 13
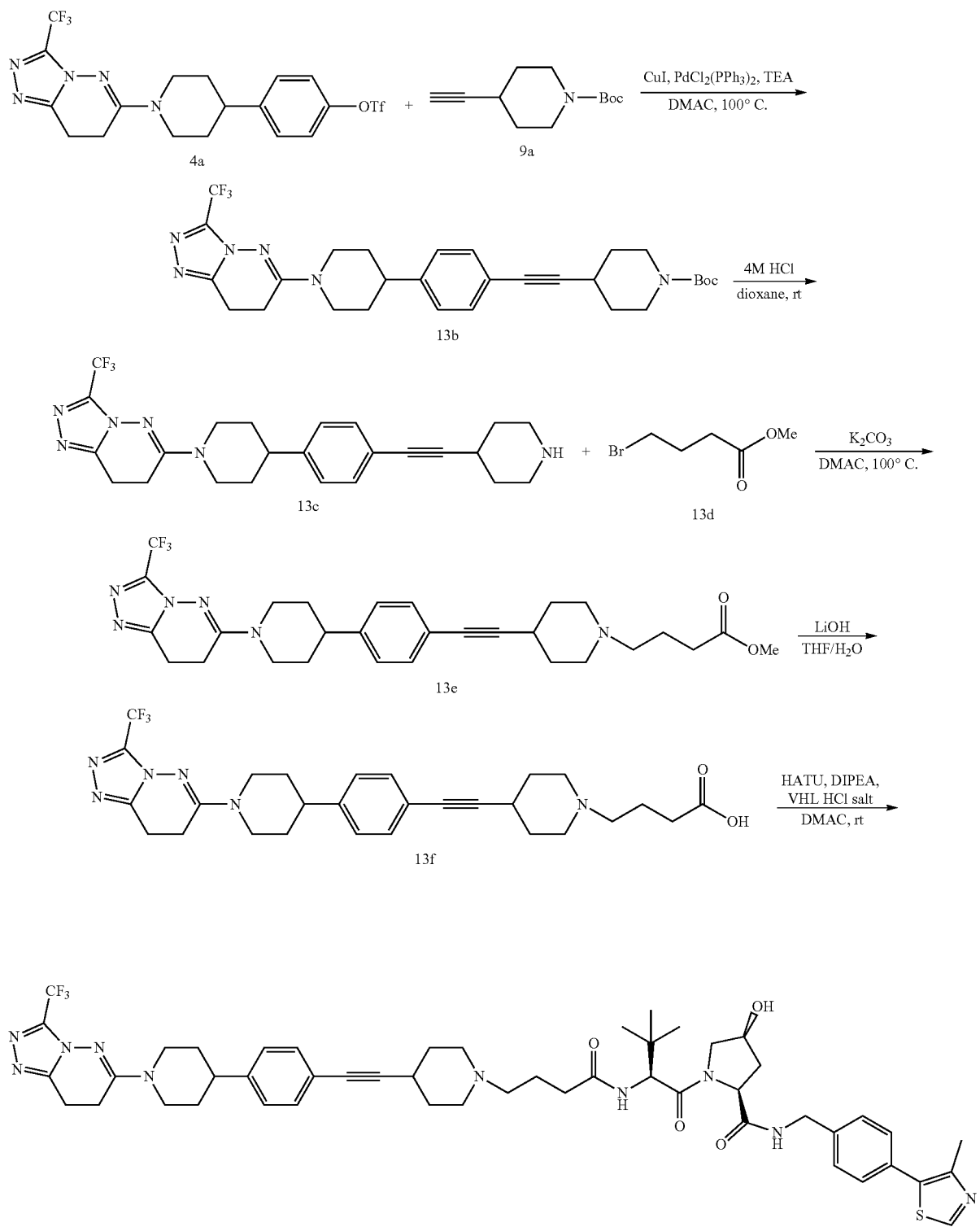

12-1. Preparation of tert-butyl 4-((4-(1-(3-(trifluoromethyl)-7,8-dihydro-[1,2,4]triazolo[4,3-b]pyridazin-6-yl)piperidin-4-yl)phenyl)ethynyl)piperidine-1-carboxylate (13b)

This compound was prepared using a method similar to that used to prepare compound 2. The crude product was purified by flash chromatography (MeOH/DCM=1/99→5/95) to give the title compound 13b (155 mg, 69%).

12-2. Preparation of 6-(4-(4-(piperidin-4-ylethynyl)phenyl)piperidin-1-yl)-3-(trifluoromethyl)-7,8-dihydro-[1,2,4]triazolo[4,3-b]pyridazine (13c)

This compound was prepared using a method similar to that used to prepare compound 4d (130 mg, 95%).

12-3. Preparation of methyl 4-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)butanoate (13e)

This compound was prepared using a method similar to that used to prepare compound 1c. The crude product was purified by flash chromatography (MeOH/DCM=1/99→1/95) to give the title compound 13e (70 mg, 56%).

12-4. Preparation of 4-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)butanoic acid (13f)

Methyl 4-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)butanoate (13e) (70.4 mg, 0.126 mmol) was dissolved in $H_2O$/THF (1 mL/1 mL) and stirred, then LiOH (6 mg, 0.25 mmol) was added and reacted at room temperature. After 2 hours of reaction, THF was removed from the reactant and some water was added to the reactant. Afterwards, the reactant was acidified with 1N citric acid and extracted with DCM. The obtained organic layer was dehydrated with anhydrous magnesium sulfate, filtered, and then concentrated under reduced pressure to obtain 4-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)butanoic acid (13f) (40.9 mg, 60%).

12-5. Preparation of (2S,4S)-1-((S)-3,3-dimethyl-2-(4-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)butanamido)butanoyl)-4-hydroxy-N-(4-(4-methylthiazol-5-yl)benzyl)pyrrolidine-2-carboxamide (13)

This compound was prepared using a method similar to that used to prepare compound 1. The crude product was purified by reverse phase preparative HPLC to give the title compound 13 (11 mg, 16%).

$^1$H-NMR (CD$_3$OD, 500 MHz) δ 8.95 (s, 1H), 7.47 (d, J=8.0 Hz, 2H), 7.42-7.28 (m, 4H), 7.32 (d, J=7.5 Hz, 1H), 7.23 (dd, J=8.0, 8.0 Hz, 2H), 4.6-4.3 (m, 8H), 3.92 (t, J=10.0 Hz, 1H), 3.85-3.75 (m, 1H), 3.70-3.49 (m, 3H), 3.30-2.80 (m, 16H), 2.60-2.40 (m, 6H), 2.3-2.0 (m, 10H), 1.9-1.8 (m, 4H), 1.8-1.6 (m, 2H), 1.06 (s, 9H). LCMS [M+H]$^+$=956.6.

13. Preparation of Compound 14

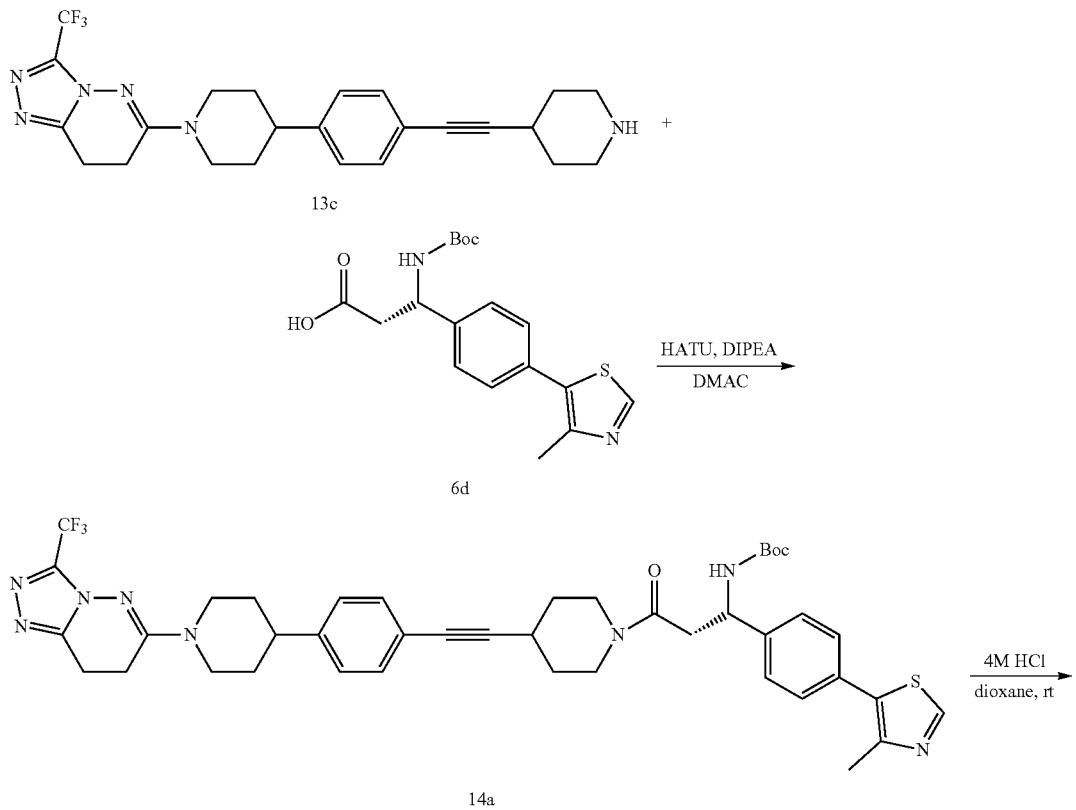

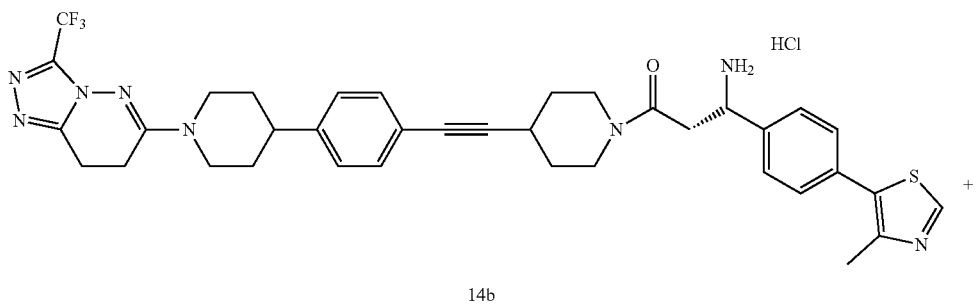

14b

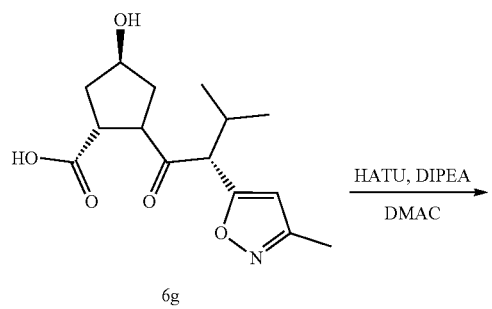

6g

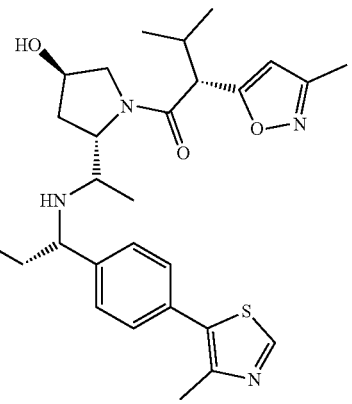

14

13-1. Preparation of tert-butyl (S)-(1-(4-(4-methyl-thiazol-5-yl)phenyl)-3-oxo-3-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)propyl)carbamate (14a)

This compound was prepared using a method similar to that used to prepare compound 1. The crude product was purified by flash chromatography (MeOH/DCM=1/99→5/95) to give the title compound 14a (37 mg, 29%).

13-2. Preparation of (S)-3-amino-3-(4-(4-methylthiazol-5-yl)phenyl)-1-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)propan-1-one (14b)

This compound was prepared using a method similar to that used to prepare compound 4d (31 mg, 89%).

13-3. Preparation of (2S,4R)-4-hydroxy-1-((R)-3-methyl-2-(3-methylisoxazol-5-yl)butanoyl)-N—((S)-1-(4-(4-methylthiazol-5-yl)phenyl)-3-oxo-3-(4-((4-(1-(3-(trifluoromethyl)-7,8-dihydro-[1,2,4]triazolo[4,3-b]pyridazin-6-yl)piperidin-4-yl)phenyl)ethynyl)piperidin-1-yl)propyl)pyrrolidine-2-carboxamide (14)

This compound was prepared using a method similar to that used to prepare compound 1. The crude product was purified by reverse phase preparative HPLC to give the title compound 14 (10 mg, 25%). LCMS [M+H]$^+$=980.6.

14. Preparation of Compounds 19-23
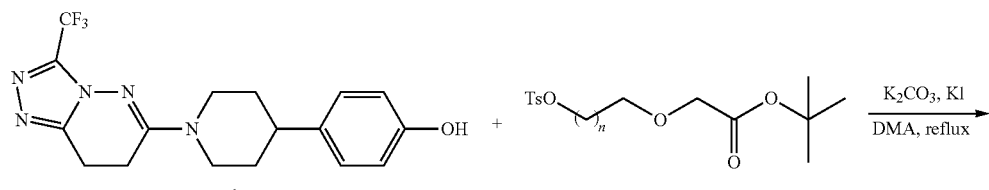
19a: n = 1
20a: n = 2
21a: n = 4
22a: n = 5
23a: n = 6
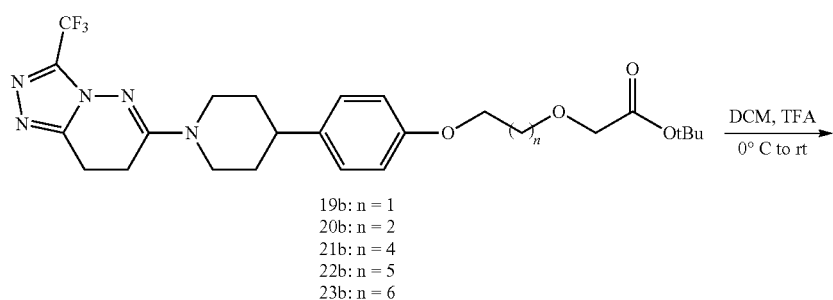
19b: n = 1
20b: n = 2
21b: n = 4
22b: n = 5
23b: n = 6
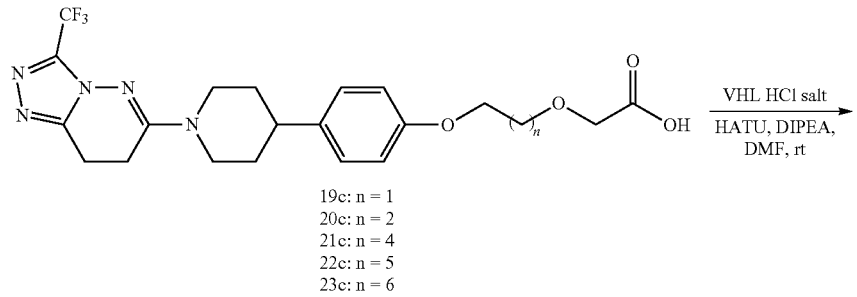
19c: n = 1
20c: n = 2
21c: n = 4
22c: n = 5
23c: n = 6
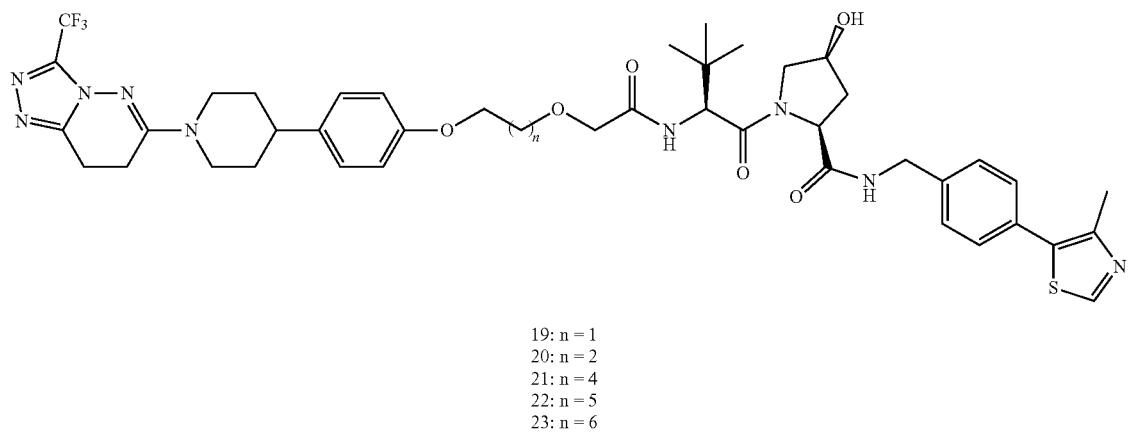
19: n = 1
20: n = 2
21: n = 4
22: n = 5
23: n = 6

These compounds were prepared using a method similar to that used to prepare compound 1.

14-1. (2S,4S)-1-((S)-3,3-dimethyl-2-(2-(2-(4-(1-(3-(trifluoromethyl)-7,8-dihydro-[1,2,4]triazolo[4,3-b]pyridazin-6-yl)piperidin-4-yl)phenoxy)ethoxy)acetamido)butanoyl)-4-hydroxy-N-(4-(4-methylthiazol-5-yl)benzyl)pyrrolidine-2-carboxamide (19)

$^1$H-NMR (500 MHz, CD$_3$OD): δ 8.86 (1H, s), 7.47 (2H, d, J=6.5 Hz), 7.40 (2H, d, J=7.5 Hz), 7.09 (2H, d, J=7.5 Hz), 6.95 (2H, d, J=6.5 HZ), 4.72 (1H, s), 4.59 (2H, d, J=14.0 Hz), 4.51 (I H, s), 4.42-4.31 (2H, m), 4.16 (2H, s), 4.11 (2H, s), 3.91-3.80 (4H, m), 3.19 (2H, d, J=7.5 Hz), 3.01 (2H, t, J=11.5, 13.0 Hz), 2.93 (2H, d, J=7.0 Hz), 2.81-2.70 (1H, s), 2.43 (3H, s), 2.24-2.08 (2H, m), 1.82 (2H, d, J=13.0 Hz), 1.66-1.59 (2H, m), 1.03 (9H, s). LCMS [M+H]$^+$=879.9.

14-2. (2S,4S)-1-((S)-3,3-dimethyl-2-(2-(3-(4-(1-(3-(trifluoromethyl)-7,8-dihydro-[1,2,4]triazolo[4,3-b]pyridazin-6-yl)piperidin-4-yl)phenoxy)propoxy)acetamido)butanoyl)-4-hydroxy-N-(4-(4-methylthiazol-5-yl)benzyl)pyrrolidine-2-carboxamide (20)

$^1$H-NMR (500 MHz, CDCl$_3$): δ 8.67 (s, 1H), 7.35 (ABX, J=8.5, 7.5 Hz, 4H), 7.30 (t, J=6.0, 6.0 Hz, 1H), 7.15 (d, J=8.0 Hz, 1H), 7.10 (d, J=8.0 Hz, 2H), 6.85 (d, J=8.5 Hz, 2H), 4.72 (t, J=8.0, 7.5 Hz, 1H), 4.58-4.54 (m, 2H), 4.48 (d, J=9.0 Hz, 1H), 4.34 (dd, J=5.0, 15.25 Hz, 2H), 4.10 (d, J=11.0 Hz, 1H), 4.04 (t, J=5.5, 6.5 Hz, 2H), 3.94 (d, J=4.5 Hz, 2H), 3.73-3.68 (m, 2H), 3.61 (dd, J=3.0, 11.25 Hz, 1H), 3.21 (t, J=8.0, 8.0 Hz, 2H), 3.06-2.94 (m, 2H), 2.78 (t, J=7.5, 8.0 Hz, 2H), 2.73-2.71 (m, 1H), 2.59-2.53 (m, 1H), 2.51 (s, 3H), 2.14-2.05 (m, 3H), 1.92 (d, J=12.5 Hz, 2H), 1.69-1.63 (m, 10H), 0.93 (s, 9H). LCMS [M+H]$^+$=895.0.

14-3. 5-(4-(1-(3-(trifluoromethyl)-7,8-dihydro-[1,2,4]triazolo[4,3-b]pyridazin-6-yl)piperidin-4-yl)phenoxy)pentyl((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)carbamate (21)

$^1$H-NMR (500 MHz, CD$_3$OD): δ 8.84 (1H, s), 7.44 (2H, s), 7.40 (2H, d, J=6.5 Hz), 7.10 (2H, d, J=7.0 Hz), 6.81 (2H, d, J=7.5 Hz), 4.69 (1H, s), 4.56 (2H, d, J=9.0 Hz), 4.51 (1H, d, J=6.0 Hz), 4.35-4.32 (2H, m), 4.01-3.96 (4H, m), 3.87 (1H, d, J=10.5 Hz), 3.80 (1H, d, J=11.0 Hz), 3.58 (2H, s), 3.18 (2H, d, J=7.0 Hz), 3.03 (2H, s), 2.93 (2H, s), 2.76 (1H, t, J=11.5, 10.0 Hz), 2.45 (3H, s), 2.25-2.21 (1H, m), 2.11-2.07 (1H, m), 1.87-1.80 (4H, m), 1.71-1.60 (6H, m). LCMS [M+H]$^+$=921.9.

14-4. 6-(4-(1-(3-(trifluoromethyl)-7,8-dihydro-[1,2,4]triazolo[4,3-b]pyridazin-6-yl)piperidin-4-yl)phenoxy)hexyl((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)carbamate (22)

$^1$H-NMR (500 MHz, CD$_3$OD): δ 8.83 (1H, s), 7.44 (2H, s), 7.40 (2H, d, J=6.5 Hz), 7.11 (2H, d, J=7.5 Hz), 6.80 (2H, d, J=7.5 Hz), 4.68 (1H, s), 4.56 (2H, d, J=13.5 Hz), 4.51 (1H, s), 4.00-3.92 (4H, m), 3.87 (1H, d, J=10.5 Hz), 3.80 (1H, d, J=11.0 Hz), 3.56 (2H, s), 3.19 (2H, s), 3.03 (2H, t, J=12.0, 11.5 Hz), 2.95 (2H, s), 2.77 (1H, t, J=11.0, 9.5 Hz), 2.45 (3H, s), 2.25-2.20 (1H, m), 2.11-2.07 (1H, m), 1.87 (2H, d, J=12.5 Hz), 1.76 (2H, s), 1.68 (4H, d, J=8.0 Hz), 1.51 (4H, s), 0.96 (9H, s). LCMS [M+H]$^+$=935.9.

14-5. (2S,4S)-1-((S)-3,3-dimethyl-2-(2-((7-(4-(1-(3-(trifluoromethyl)-7,8-dihydro-[1,2,4]triazolo[4,3-b]pyridazin-6-yl)piperidin-4-yl)phenoxy)heptyl)oxy)acetamido)butanoyl)-4-hydroxy-N-(4-(4-methylthiazol-5-yl)benzyl)pyrrolidine-2-carboxamide (23)

$^1$H-NMR (500 MHz, CDCl$_3$): δ 8.66 (s, 1H), 7.36 (ABX, J=8.0, 7.5 Hz, 5H), 7.18 (d, J=8.5 Hz, 1H), 7.10 (d, J=7.5 Hz, 2H), 6.84 (d, J=7.5 Hz, 2H), 4.74 (t, J=8.0, 7.5 Hz, 1H), 4.58-4.53 (m, 2H), 4.47 (d, J=8.5 Hz, 1H), 4.33 (dd, J=5.0, 15.0, 2H), 4.11 (d, J=11.5 Hz, 1H), 3.93-3.87 (m, 4H), 3.61 (dd, J=2.5, 11.25 Hz, 1H), 3.51-3.47 (m, 2H), 3.21 (t, J=8.0, 8.0 Hz, 2H), 3.00 (t, J=12.5, 13.0 Hz, 2H), 2.79 (t, J=7.5, 8.0 Hz, 2H), 2.73 (d, J=12.0 Hz, 1H), 2.58-2.53 (m, 1H), 2.51 (s, 3H), 2.12 (dd, J=9.0, 12.25 Hz, 1H), 1.94 (d, J=12.5 Hz, 2H), 1.79-1.60 (m, 14H), 1.45-1.38 (m, 3H), 0.82 (s, 9H). LCMS [M+H]$^+$=950.0.

15. Preparation of Compounds 24-27

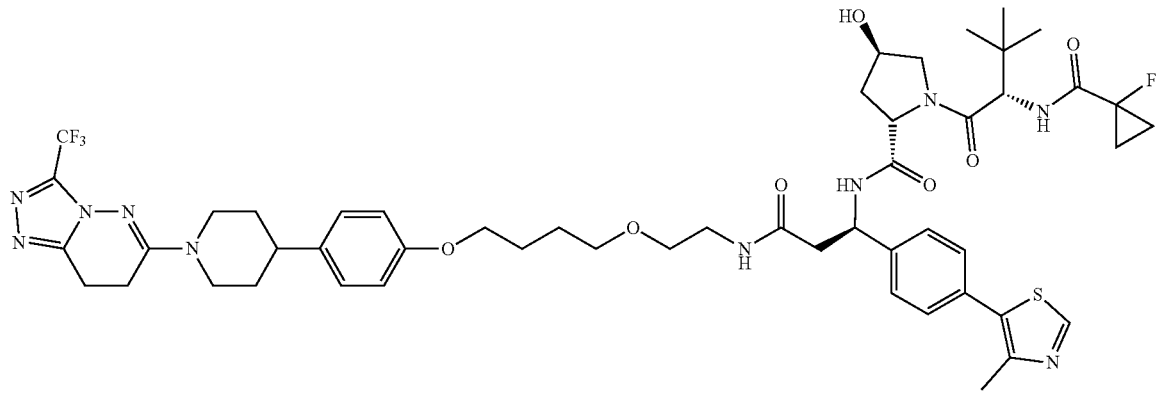

24

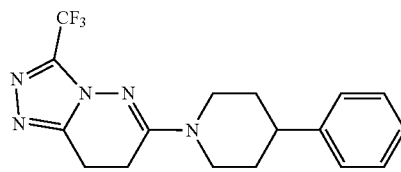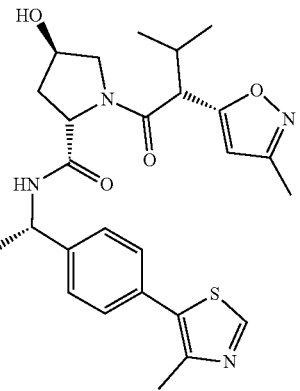
25
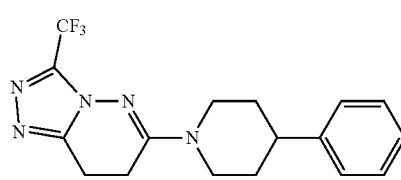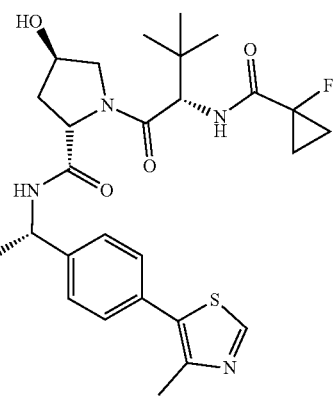
26
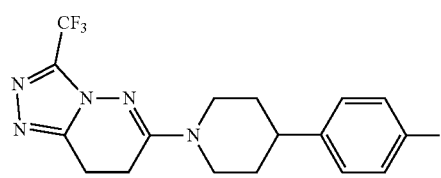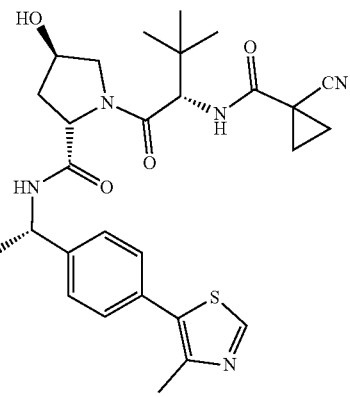
27

The preparation scheme of Compounds 24-27 shown above can be deduced from the preparation scheme of Compound 6 shown above.
16. Preparation of Compound 28
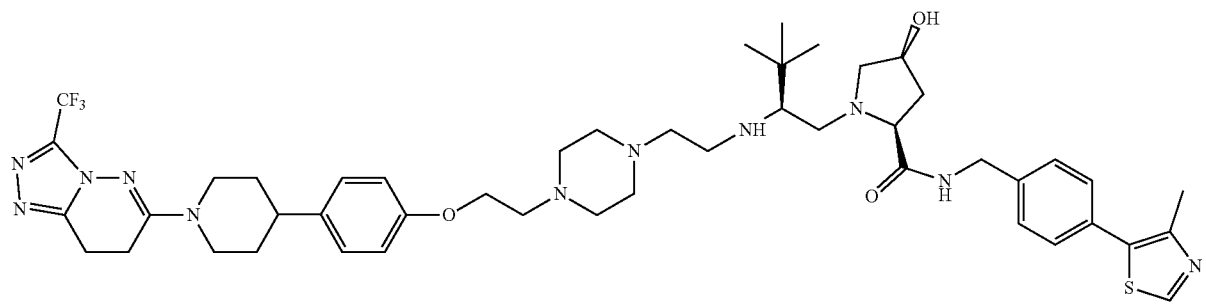
28
The preparation scheme of Compound 28 shown above can be deduced from the preparation scheme of Compound 1 shown above.
17. Preparation of Compound 29
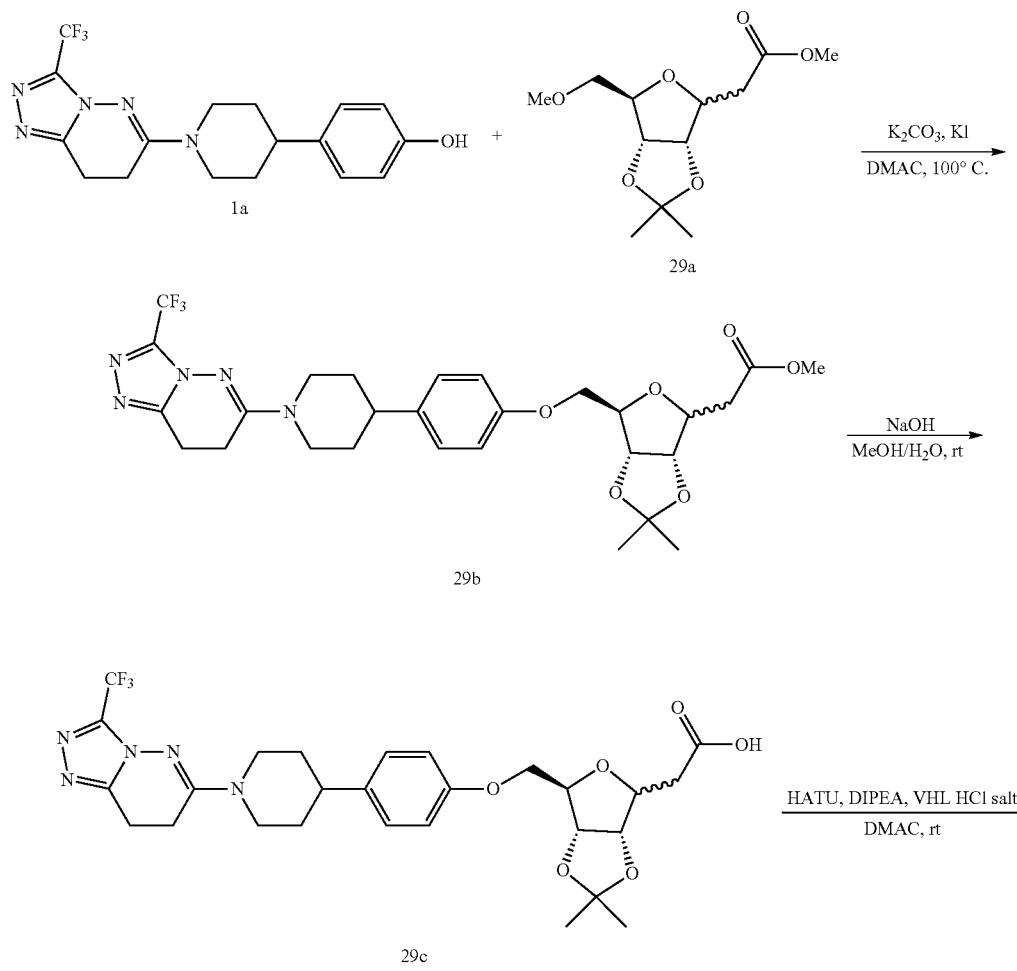

-continued

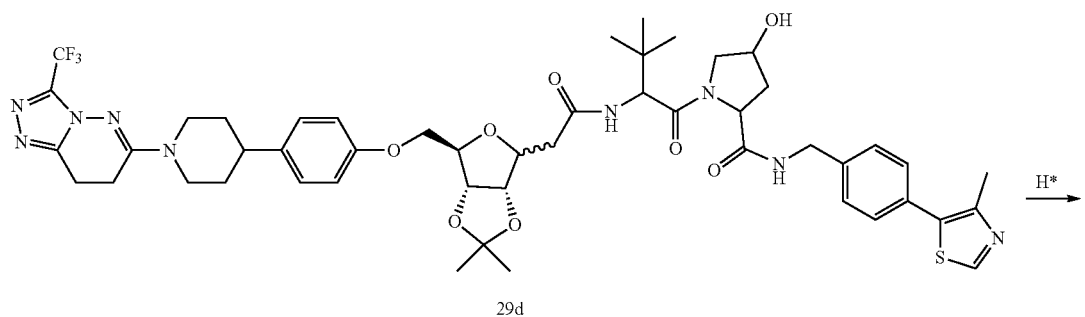

29d

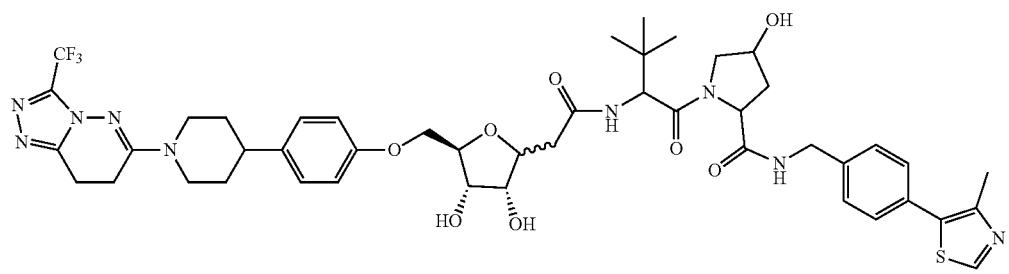

29

17-1. Preparation of methyl 2-((3aS,6R,6aR)-2,2-dimethyl-6-((4-(1-(3-(trifluoromethyl)-7,8-dihydro-[1,2,4]triazolo[4,3-b]pyridazin-6-yl)piperidin-4-yl)phenoxy)methyl)tetrahydrofuro[3,4-d][1,3]dioxol-4-yl)acetate (29b)

These compounds were prepared using a method similar to that used to prepare compound 1c. The crude product was purified by flash chromatography (MeOH/DCM=1/99→1/95) to give the title compound 29b (305 mg, 55%).

17-2. Preparation of 2-((3aS,6R,6aR)-2,2-dimethyl-6-((4-(1-(3-(trifluoromethyl)-7,8-dihydro-[1,2,4]triazolo[4,3-b]pyridazin-6-yl)piperidin-4-yl)phenoxy)methyl)tetrahydrofuro[3,4-d][1,3]dioxol-4-yl)acetic acid (29c)

Methyl 2-((3aS,6R,6aR)-2,2-dimethyl-6-((4-(1-(3-(trifluoromethyl)-7,8-dihydro-[1,2,4]triazolo[4,3-b]pyridazin-6-yl)piperidin-4-yl)phenoxy)methyl)tetrahydrofuro[3,4-d][1,3]dioxol-4-yl)acetate (29b) (305.2 mg, 0.51 mmol) was dissolved in MeOH/H$_2$O (1/1) and stirred, and NaOH (41 mg, 1.02 mol) was added to react at room temperature for 2 hours. MeOH was then removed from the reactant by concentration under reduced pressure. The reactant was acidified to pH 4-5 with 1 M citric acid and extracted with ethyl acetate. The obtained organic layer was dehydrated with anhydrous magnesium sulfate, filtered, and concentrated under reduced pressure to obtain 2-((3aS,6R,6aR)-2,2-dimethyl-6-((4-(1-(3-(trifluoromethyl)-7,8-dihydro-[1,2,4]triazolo[4,3-b]pyridazin-6-yl)piperidin-4-yl)phenoxy)methyl)tetrahydrofuro[3,4-d][1,3]dioxol-4-yl)acetic acid (29c) (275 mg, 92%).

17-3. Preparation of 1-(2-(2-((3R,4S,5R)-3,4-dihydroxy-5-((4-(1-(3-(trifluoromethyl)-7,8-dihydro-[1,2,4]triazolo[4,3-b]pyridazin-6-yl)piperidin-4-yl)phenoxy)methyl)tetrahydrofuran-2-yl)acetamido)-3,3-dimethylbutanoyl)-4-hydroxy-N-(4-(4-methylthiazol-5-yl)benzyl)pyrrolidine-2-carboxamide (29)

2-((3aS,6R,6aR)-2,2-dimethyl-6-((4-(1-(3-(trifluoromethyl)-7,8-dihydro-[1,2,4]triazolo[4,3-b]pyridazin-6-yl)piperidin-4-yl)phenoxy)methyl)tetrahydrofuro[3,4-d][1,3]dioxol-4-yl)acetic acid (29c) (275 mg, 0.471 mmol) was dissolved in DMAC and stirred, then HATU (216 mg, 0.856 mmol) and DIPEA (0.15 mL, 0.856 mmol) were added and stirred at room temperature for 10 minutes. Then VHL-HCl (200 mg, 0.428 mmol) was added to the reactant and reacted at room temperature for 4 hours. After that, reverse-phase preparative HPLC purification (50% ACN/50% H2O+0.1% TFA, 24 mL/min, 210 nm) was performed, followed by concentration under reduced pressure to remove ACN from the reactant. The remaining aqueous solution was left at room temperature to remove the carbohydrate protecting groups. After the protecting group was completely removed, the aqueous solution was lyophilized to obtain 1-(2-(2-((3R,4S,5R)-3,4-dihydroxy-5-((4-(1-(3-(trifluoromethyl)-7,8-dihydro-[1,2,4]triazolo[4,3-b]pyridazin-6-yl)piperidin-4-yl)phenoxy)methyl)tetrahydrofuran-2-yl)acetamido)-3,3-dimethylbutanoyl)-4-hydroxy-N-(4-(4-methylthiazol-5-yl)benzyl)pyrrolidine-2-carboxamide (29) (252 mg, 62%). LCMS [M+H]$^+$=953.5.

18. Preparation of Compound 30
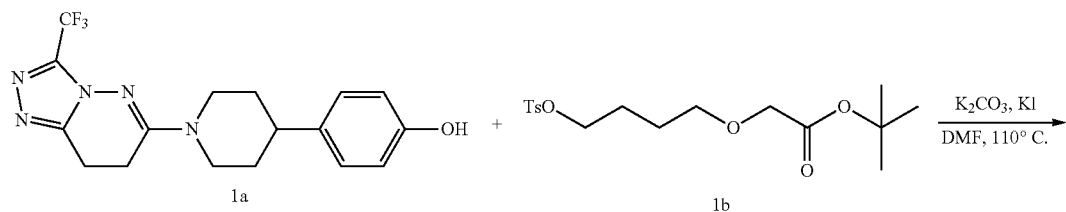
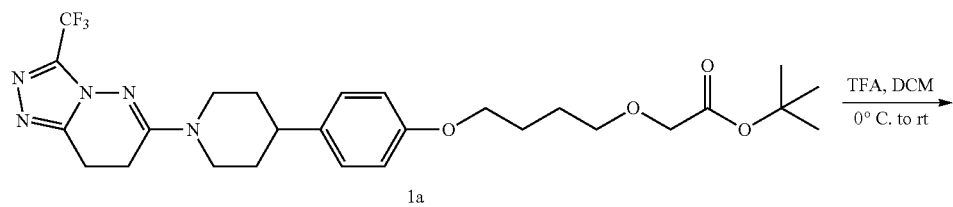
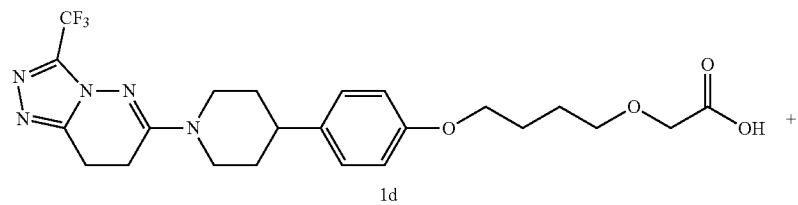
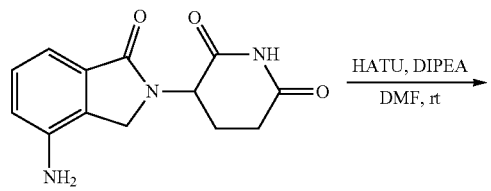
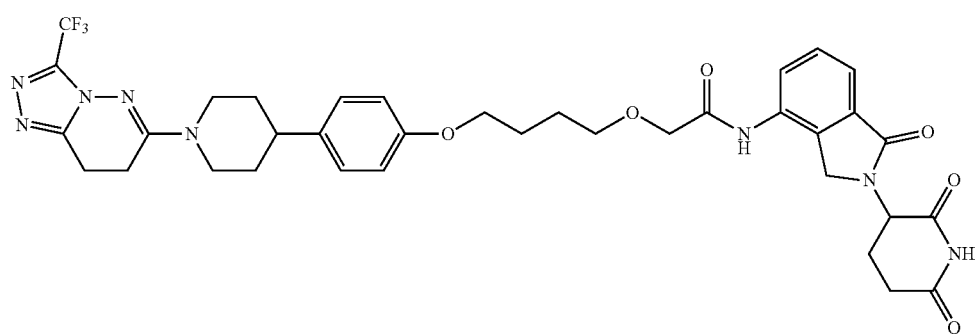

This compound was prepared using a method similar to that used to prepare compound 1.

N-(2-(2,6-dioxopiperidin-3-yl)-1-oxoisoindolin-4-yl)-2-(4-(4-(1-(3-(trifluoromethyl)-7,8-dihydro-[1,2,4]triazolo[4,3-b]pyridazin-6-yl)piperidin-4-yl)phenoxy)butoxy)acetamide (30)

¹H-NMR (500 MHz, CDCl₃): δ 8.30 (s, 1H), 8.07 (s, 1H), 7.74 (dd, J=2.5, 7.5 Hz, 2H), 7.49 (t, J=8.0, 8.0 Hz, 1H), 7.10 (d, J=8.0 Hz, 2H), 6.84 (d, J=8.5 Hz, 2H), 5.18 (dd, J=5.0, 13.25 Hz, 1H), 4.46 (d, J=8.0 Hz, 2H), 4.11 (s, 2H), 4.01 (t, J=6.0, 5.5 Hz, 2H), 3.59 (t, J=6.0, 5.5 Hz, 2H), 3.21 (t, J=8.0, 7.5 Hz, 2H), 2.99 (t, J=13.0, 12.0 Hz, 2H), 2.84-2.70 (m, 4H), 2.32 (ddd, J=5.5, 12.5, 26.0 Hz, 1H), 2.19-2.16 (m, 1H), 1.93-1.87 (m, 5H), 1.70-1.62 (m, 7H). LCMS [M+H]⁺=737.0.

19. Preparation of Compound 31

19-1. Preparation of 6-(4-(4-(hex-5-ynyloxy)phenyl)piperidin-1-yl)-3-(trifluoromethyl)-7,8-dihydro-[1,2,4]triazolo[4,3-b]pyridazine (31b)

This compound was prepared using a method similar to that used to prepare compound 1c. The crude product was purified by flash chromatography to give the title compound 31b.

19-2. Preparation of 3-(1-oxo-4-(6-(4-(1-(3-(trifluoromethyl)-7,8-dihydro-[1,2,4]triazolo[4,3-b]pyridazin-6-yl)piperidin-4-yl)phenoxy)hex-1-ynyl)isoindolin-2-yl)piperidine-2,6-dione (31)

This compound was prepared using a method similar to that used to prepare compound 2. The crude product was purified by reverse phase preparative HPLC to give the title compound 31.

¹H-NMR (500 MHz, DMSO-d6): δ 10.98 (s, 1H, NH), 7.70 (d, J=7.5 Hz, 1H), 7.62 (d, J=7.5 Hz, 1H), 7.51 (t, J=7.5

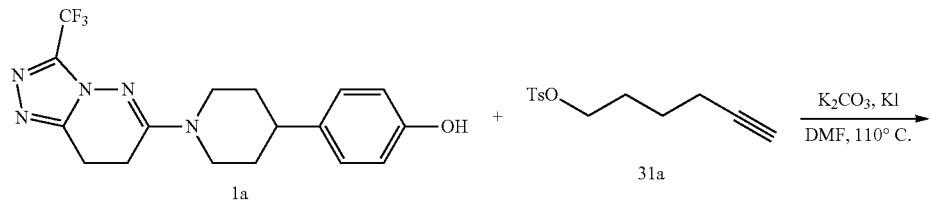

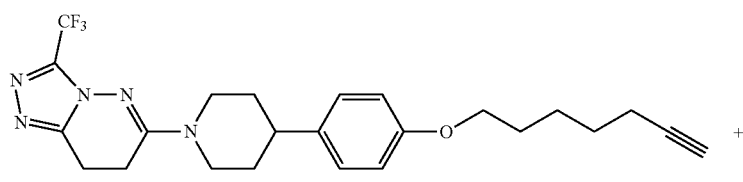

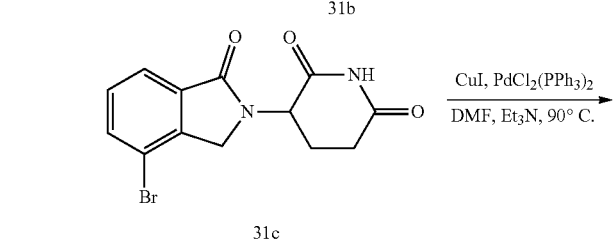

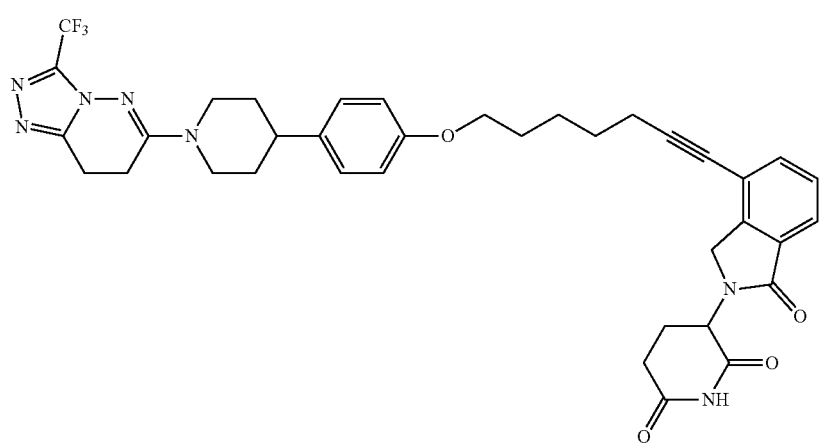

31

Hz, 1H), 7.15-7.13 (m, 2H), 6.87-6.84 (m, 2H), 5.13 (dd, J=5.5, 13.0 Hz, 1H), 4.44 (d, J=17.5 Hz, 1H), 4.33-4.27 (m, 3H), 3.99 (t, J=6.5 Hz, 2H), 3.18-3.07 (m, 4H), 2.98-2.89 (m, 4H), 2.77-2.72 (m, 1H), 2.57-2.55 (m, 2H), 2.47-2.40 (m, 1H), 2.08-1.97 (m, 1H), 1.89-1.84 (m, 2H), 1.81-1.71 (m, 3H), 1.58-1.55 (m, 3H). LCMS [M+H]$^+$=687.9.
20. Preparation of Compound 32
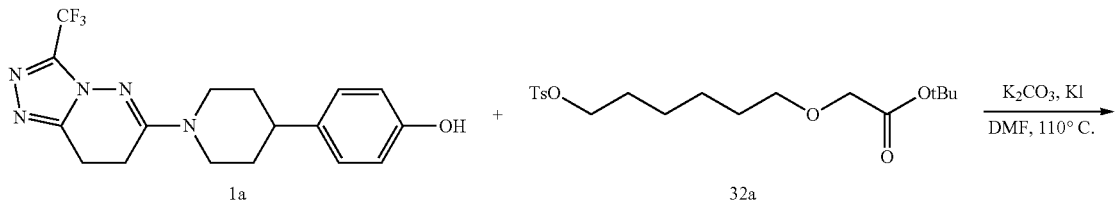
1a + 32a
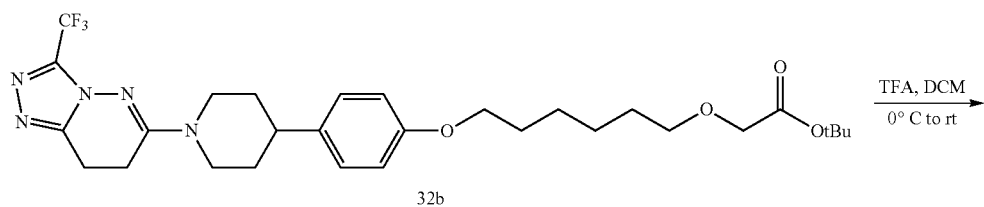
32b
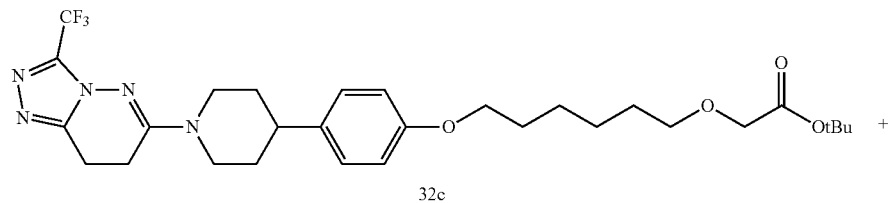
32c +
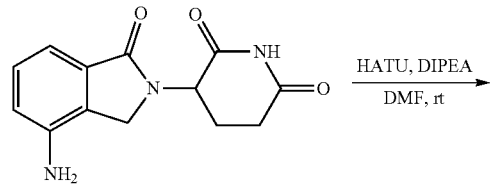
32d
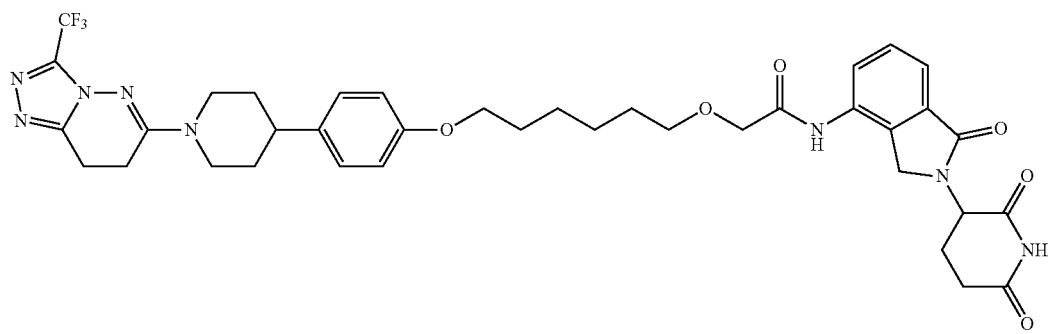
32

This compound was prepared using a method similar to that used to prepare compound 1.

N-(2-(2,6-dioxopiperidin-3-yl)-1-oxoisoindolin-4-yl)-2-((6-(4-(1-(3-(trifluoromethyl)-7,8-dihydro-[1,2,4]triazolo[4,3-b]pyridazin-6-yl)piperidin-4-yl)phenoxy)hexyl)oxy)acetamide (32)

$^1$H-NMR (500 MHz, CDCl$_3$): δ 8.28 (s, 1H), 8.06 (s, 1H), 7.74 (t, J=7.0, 7.0 Hz, 2H), 7.49 (t, J=8.0, 8.0 Hz, 2H), 7.10 (d, J=7.5 Hz, 2H), 6.84 (d, J=8.0 Hz, 2H), 5.21 (dd, J=5.0, 13.0 Hz, 1H), 4.44 (d, J=6.5 Hz, 2H), 4.30 (s, 2H), 4.09 (s, 2H), 3.97-3.93 (m, 2H), 3.66-3.62 (m, 2H), 3.22 (t, J=7.5, 7.5 Hz, 2H), 3.00 (t, J=13.0, 12.5 Hz, 2H), 2.90-2.87 (m, 2H), 2.84-2.72 (m, 5H), 2.36 (dd, J=5.0, 13.25 Hz, 1H), 2.23-2.21 (m, 1H), 1.94 (d, J=12.5 Hz, 3H), 1.80-1.79 (m, 9H), 1.74-1.60 (m, 6H), 1.57-1.44 (m, 5H). LCMS [M+H]+=765.9.

21. Preparation of Compound 33

21-1. Preparation of methyl 4-(4-((4-(1-(3-(trifluoromethyl)-7,8-dihydro-[1,2,4]triazolo[4,3-b]pyridazin-6-yl)piperidin-4-yl)phenyl)ethynyl)piperidine-1-carbonyl)benzoate (33b)

This compound was prepared using a method similar to that used to prepare compound 1. The crude product was purified by flash chromatography (MeOH/DCM=1/99→5/95) to give the title compound 33b (30 mg, 24%).

21-2. Preparation of 4-(4-((4-(1-(3-(trifluoromethyl)-7,8-dihydro-[1,2,4]triazolo[4,3-b]pyridazin-6-yl)piperidin-4-yl)phenyl)ethynyl)piperidine-1-carbonyl)benzoic acid (33c)

This compound was prepared using a method similar to that used to prepare compound 13f (12 mg, 41%).

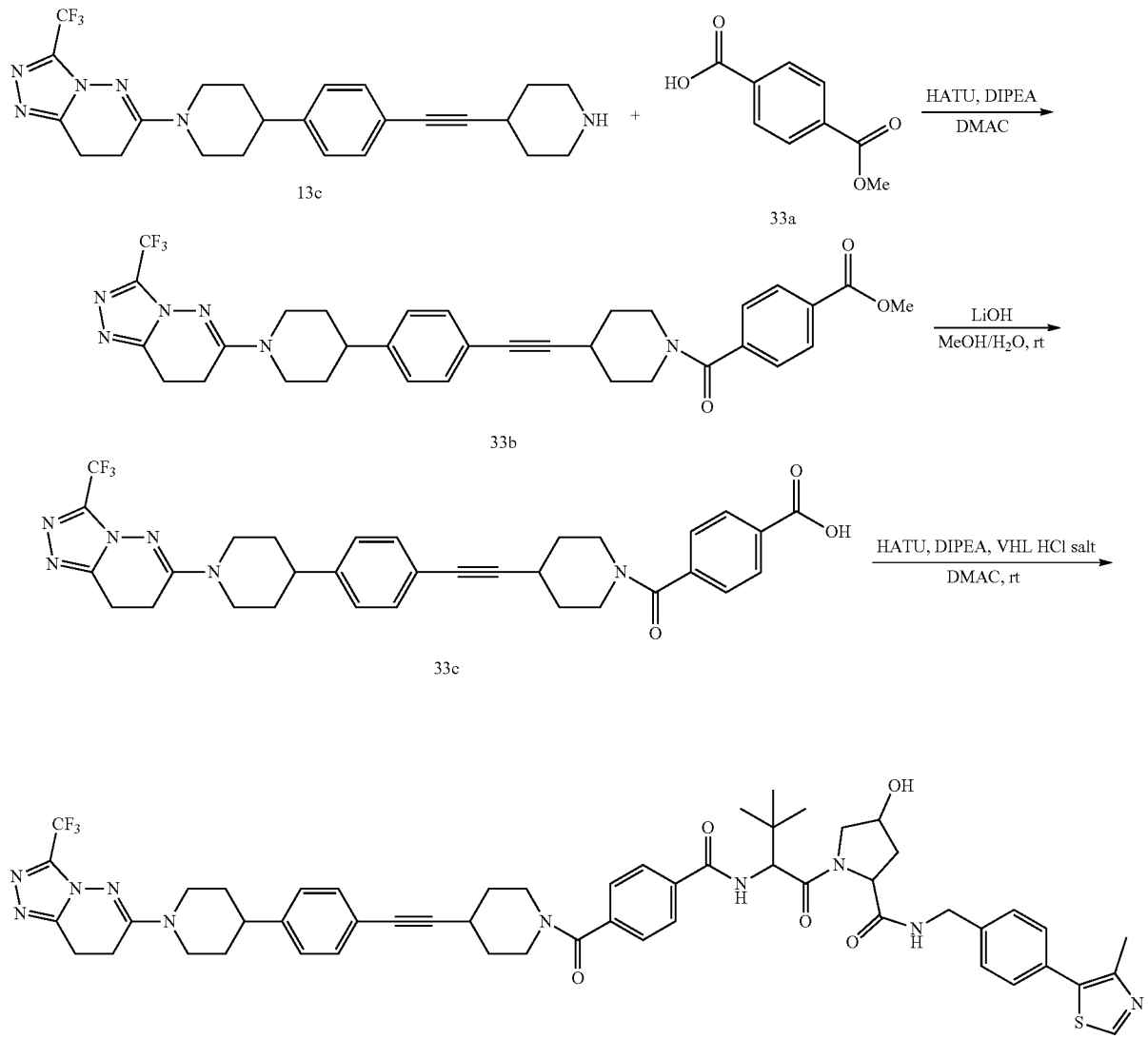

21-3. 1-(3,3-dimethyl-2-(4-(4-((4-(1-(3-(trifluoromethyl)-7,8-dihydro-[1,2,4]triazolo[4,3-b]pyridazin-6-yl)piperidin-4-yl)phenyl)ethynyl)piperidine-1-carbonyl)benzamido)butanoyl)-4-hydroxy-N-(4-(4-methylthiazol-5-yl)benzyl)pyrrolidine-2-carboxamide (33)

This compound was prepared using a method similar to that used to prepare compound 1. The crude product was purified by reverse phase preparative HPLC to give the title compound 33 (13 mg, 64%).

$^1$H-NMR (CD$_3$OD, 500 MHz) δ 8.99 (s, 1H), 7.9 (d, J=8.5 Hz, 2H), 7.52 (d, J=8.5 Hz, 2H), 7.49 (d, J=8.5 Hz, 2H), 7.44 (d, J=8.5 Hz, 2H), 7.33 (d, J=8.0 Hz, 2H), 7.21 (d, J=8.5 Hz, 2H), 5.34 (t, J=5.0 Hz, 1H), 4.92 (d, J=9.5 Hz, 1H), 4.50-4.65 (m, 4H), 4.40-4.50 (m, 3H), 3.99 (d, J=11.5 Hz, 1H), 3.80-3.90 (m, 1H), 3.21 (t, J=7.5 Hz, 2H), 2.90-3.10 (m, 7H), 2.49 (s, 3H), 2.0-2.3 (m, 6H), 1.50-1.95 (m, 10H), 1.11 (s, 9H). LCMS [M+H]$^+$=1018.6.

22. Preparation of Compound 34

This compound was prepared using a method similar to that used to prepare compound 33.

1-(3,3-dimethyl-2-(4-(4-((4-(1-(3-(trifluoromethyl)-7,8-dihydro-[1,2,4]triazolo[4,3-b]pyridazin-6-yl)piperidin-4-yl)phenyl)ethynyl)piperidine-1-carbonyl)cyclohexane-1-carboxamido)butanoyl)-4-hydroxy-N-(4-(4-methylthiazol-5-yl)benzyl)pyrrolidine-2-carboxamide (34)

$^1$H-NMR (CD$_3$OD, 500 MHz) δ 9.04 (s, 1H), 7.48 (d, J=8.0 Hz, 2H), 7.43 (d, J 8.0 Hz, 2H), 7.32 (d, J 8.5 Hz, 2H), 7.20 (d, J=8.5 Hz, 2H), 4.7-4.3 (m, 9H), 4.0-3.8 (m, 5H), 4.50-4.65 (m, 4H), 3.21 (t, J=8.0 Hz 2H), 3.06 (t, J=11 Hz, 2H), 3.0-2.8 (i, 5H), 2.75-2.65 (m, 1H), 2.50 (s, 3H), 2.45-2.3 (m, 2H), 2.25-2.15 (n, 1H), 2.15-1.5 (m, 24H), 1.11 (s, 9H). LCMS [M+H]$^+$=1024.7.

$^1$H NMR (CD$_3$OD, 500 MHz) δ 8.92 (s, 1H), 7.5-7.4 (m, 4H), 7.31 (d, J=8.0 Hz, 2H), 7.20 (d, J=8.0 Hz, 2H), 4.7-4.65 (m, 1H), 4.6-4.3 (m, 6H), 4.0-3.8 (m, 4H), 3.20 (t, J=8.0 Hz 2H), 3.06 (t, J 12.5 Hz, 2H), 3.0-2.7 (m, 6H), 2.75-2.65 (m,

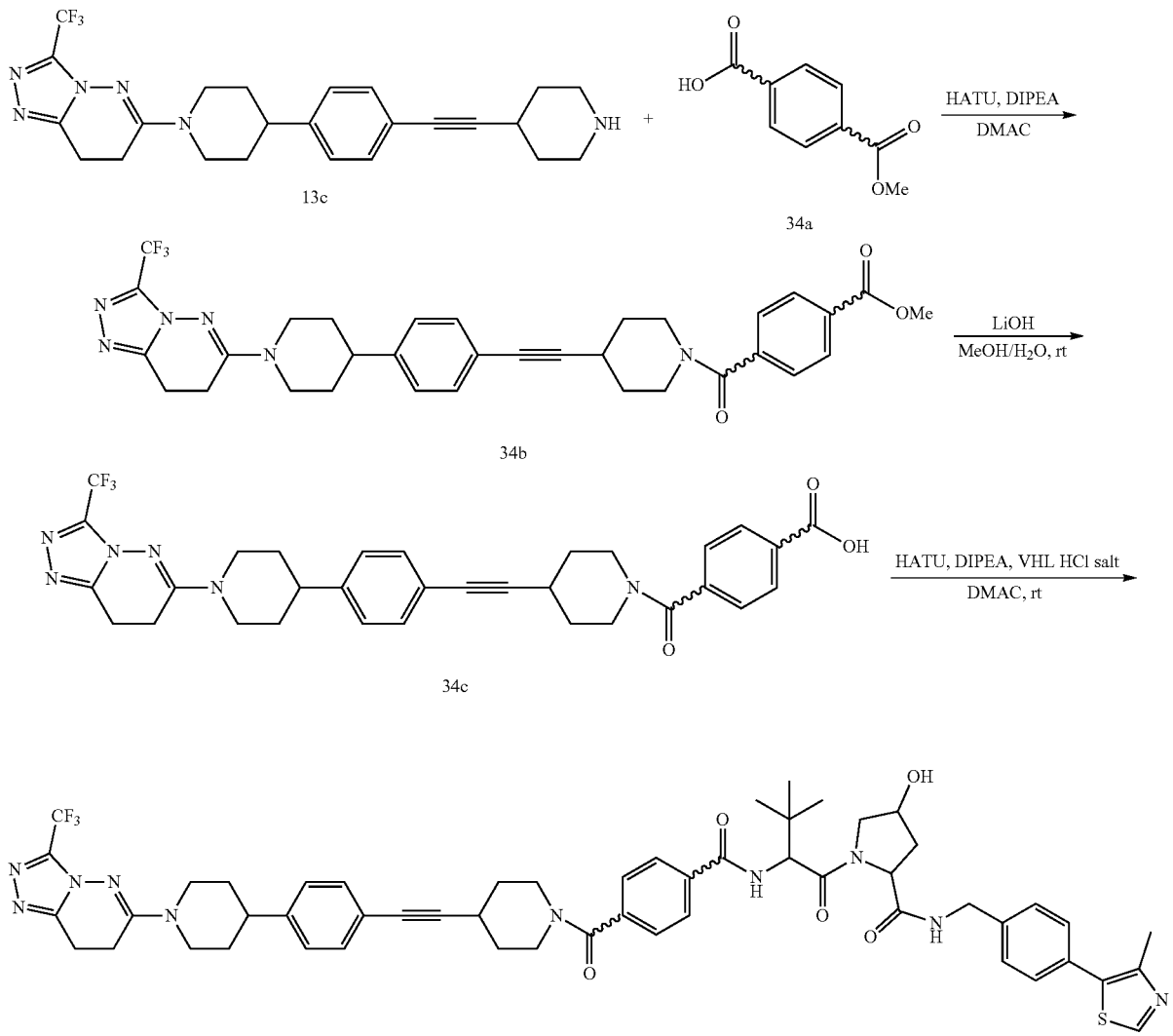

1H), 2.48 (s, 3H), 2.25-2.2 (m, 1H), 2.1-1.8 (m, 11H), 1.8-1.5 (m, 10H), 1.11 (s, 9H). LCMS [M+H]⁺=1024.7.

23. Preparation of Compound 35

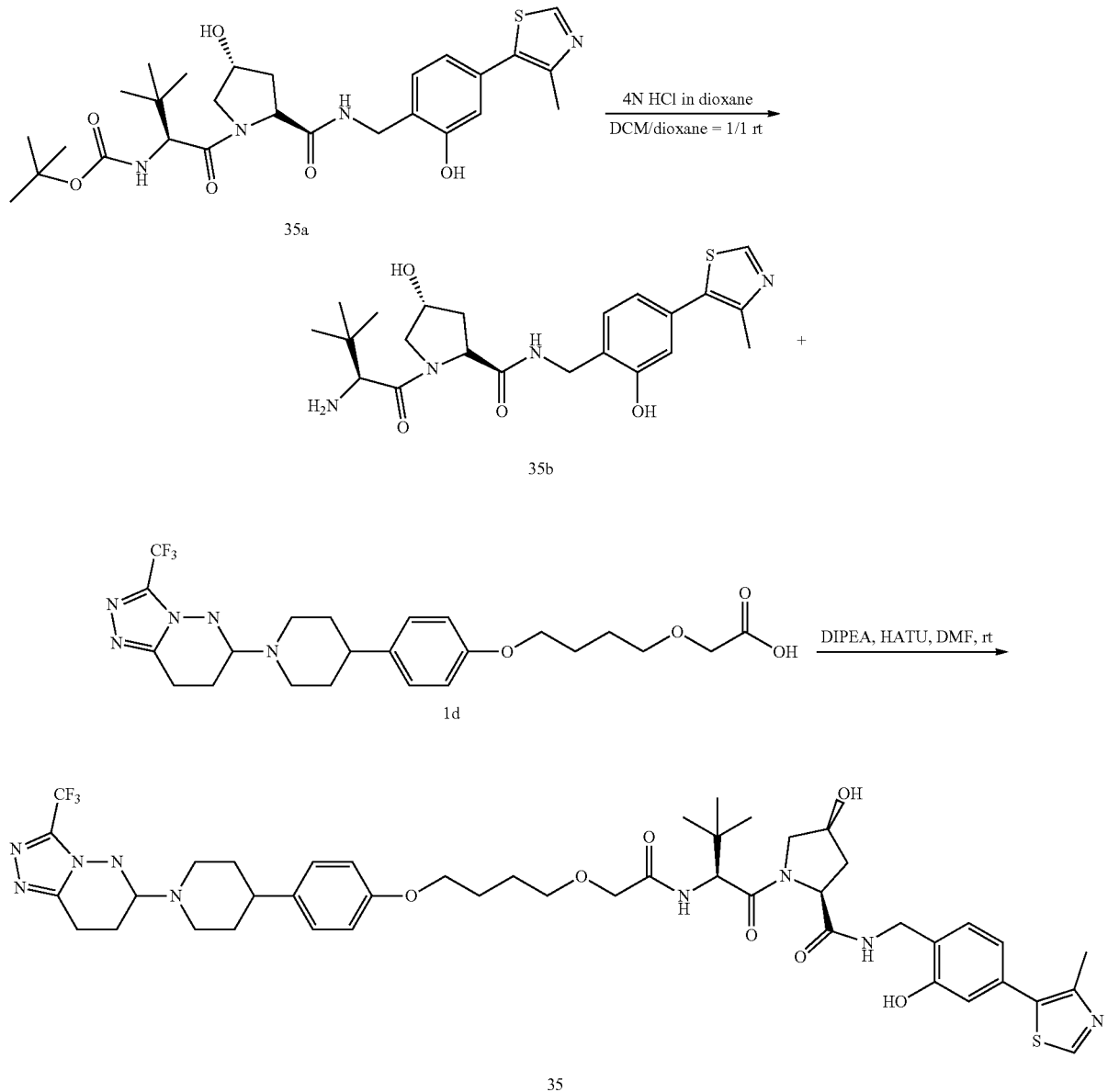

23-1. Preparation of (2R,4R)-1-((S)-2-amino-3,3-dimethylbutanoyl)-4-hydroxy-N-(2-hydroxy-4-(4-methylthiazol-5-yl)benzyl)pyrrolidine-2-carboxamide (35b)

4 N HCl in 1,4-dioxane (0.6 mL, 2.4 mmol) was added to a mixture of tert-butyl (S)-1-((2R,4R)-4-hydroxy-2-(2-hydroxy-4-(4-methylthiazol-5-yl)benzylcarbamoyl)pyrrolidin-1-yl)-3,3-dimethyl-1-oxobutan-2-ylcarbamate (35a) (100 mg, 0.2 mmol) in CH₂Cl₂ (1.2 mL) and 1,4-dioxane (1.2 mL). The reaction mixture was stirred overnight. The reaction mixture was then concentrated under reduced pressure and azeotroped with PhMe (3×3 mL). (2R,4R)-1-((S)-2-amino-3,3-dimethylbutanoyl)-4-hydroxy-N-(2-hydroxy-4-(4-methylthiazol-5-yl)benzyl)pyrrolidine-2-carboxamide (35b) was obtained as a yellow solid (80 mg, 99

23-2. Preparation of (2S,4S)-1-((S)-3,3-dimethyl-2-(2-(4-(4-(1-(3-(trifluoromethyl)-7,8-dihydro-[1,2,4]triazolo[4,3-b]pyridazin-6-yl)piperidin-4-yl)phenoxy)butoxy)acetamido)butanoyl)-4-hydroxy-N-(2-hydroxy-4-(4-methylthiazol-5-yl)benzyl)pyrrolidine-2-carboxamide (35)

This compound was using the similar method as described for Compound 1. The crude was purified by reverse phase preparative HPLC to give the title compound (66 mg, 42%).
¹H-NMR (500 MHz, CDCl₃): δ 8.64 (s, 1H), 7.12 (ABX, J=8.0, 8.0 Hz, 5H), 6.97 (s, 1H), 6.85 (t, J=8.5, 8.0 Hz, 3H), 4.72 (t, J=7.5, 8.0 Hz, 1H), 4.52-4.46 (m, 3H), 4.39 (d, J=8.5

Hz, 1H), 4.30 (s, 2H), 4.13 (dd, J=5.5, 14.5 Hz, 1H), 4.06 (d, J=11.5, 4H), 3.97-3.86 (m, 5H), 3.56-3.55 (m, 4H), 3.21 (t, J=7.5, 8.0 Hz, 2H), 3.00 (t, J=10.5, 15.0 Hz, 3H), 2.78 (t, J=7.5, 8.0 Hz, 3H), 2.74-2.72 (m, 1H), 2.51 (s, 4H), 2.09-2.05 (m, 1H), 1.93 (d, J=12.5 Hz, 3H), 1.85-1.75 (m, 10H), 1.72-1.64 (m, 5H), 0.83 (s, 9H). LCMS [M+H]⁺=925.1.
24. Preparation of Compound 36
24-1. Preparation of 7-(4-(1-(3-(trifluoromethyl)-7,8-dihydro-[1,2,4]triazolo[4,3-b]pyridazin-6-yl)piperidin-4-yl)phenoxy)heptyl 4-methylbenzenesulfonate (36b)
This compound was prepared using a method similar to that used to prepare compound 1c.
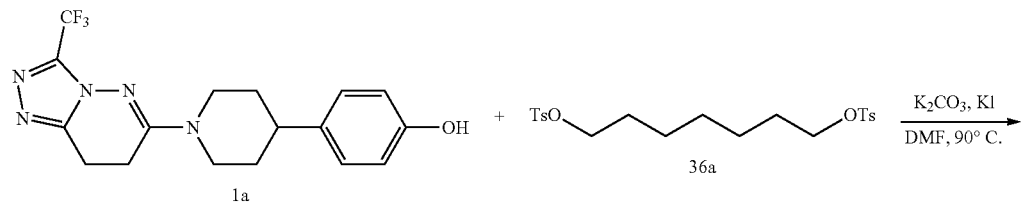
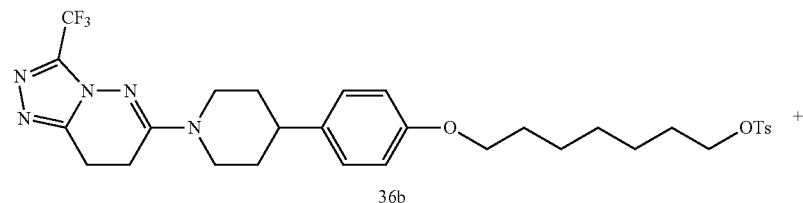
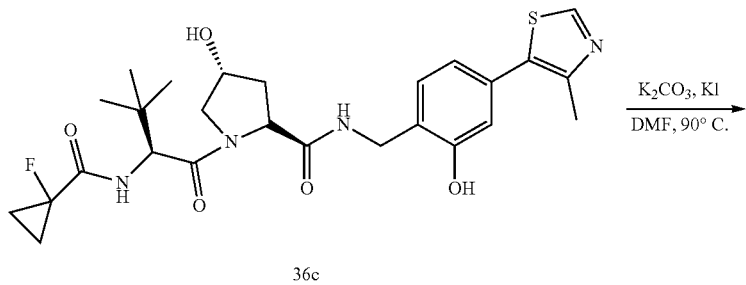
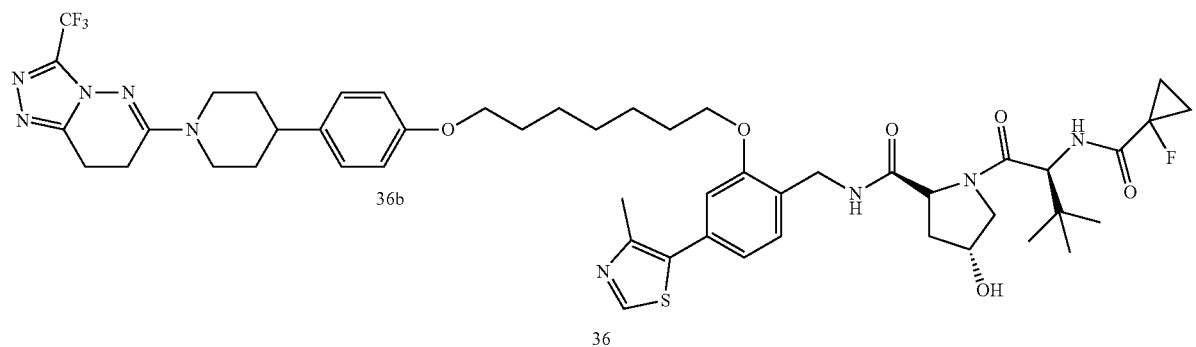

24-2. Preparation of (2R,4R)-1-((S)-2-(1-fluorocyclopropane-1-carboxamido)-3,3-dimethylbutanoyl)-4-hydroxy-N-(4-(4-methylthiazol-5-yl)-2-((7-(4-(1-(3-(trifluoromethyl)-7,8-dihydro-[1,2,4]triazolo[4,3-b]pyridazin-6-yl)piperidin-4-yl)phenoxy)heptyl)oxy)benzyl)pyrrolidine-2-carboxamide (36)

This compound was using the similar method as described for Compound 1c. The crude was purified by reverse phase preparative HPLC to give the title compound 36 (22 mg, 37%).

$^1$H-NMR (500 MHz, CDCl$_3$): δ 8.67 (s, 1H), 7.32 (d, J=8.0 Hz, 1H), 7.22 (t, J=5.5, 6.0 Hz, 1H), 7.11 (d, J=16.5 Hz, 2H), 7.17 (d, J=5.5 Hz, 1H), 6.94 (d, J=8.0 Hz, 1H), 6.85 (d, J=9.0 Hz, 3H), 4.73 (t, J=7.5, 7.5 Hz, 1H), 4.54-4.50 (m, 3H), 4.41 (dd, J=5.5, 14.75 Hz, 1H), 4.30 (s, 2H), 4.01 (d, J=6.0 Hz, 3H), 3.94 (t, J=7.0, 6.5 Hz, 2H), 3.61 (d, J=7.0 Hz, 1H), 3.21 (t, J=8.0, 8.0 Hz, 2H), 3.00 (t, J=12.0, 13.0 Hz, 1H), 2.80-2.72 (m, 3H), 2.60-2.55 (m, 1H), 2.52 (s, 3H), 2.09-2.05 (m, 1H), 1.94 (d, J=13.0 Hz, 3H), 1.89-1.82 (m, 3H), 1.80-1.76 (m, 6H), 1.72-1.65 (m, 4H), 1.56-1.45 (m, 7H), 1.37-1.24 (m, 5H), 0.93 (s, 9H). LCMS [M+H]$^+$=994.3.

25. Preparation of Compound 37

This compound was prepared using a method similar to that used to prepare compound 1.

(2S,4S)-1-((S)-3,3-dimethyl-2-(2-(4-(4-(1-(3-(trifluoromethyl)-[1,2,4]triazolo[4,3-b]pyridazin-6-yl)piperidin-4-yl)phenoxy)butoxy)acetamido)butanoyl)-4-hydroxy-N-(4-(4-methylthiazol-5-yl)benzyl)pyrrolidine-2-carboxamide (37)

$^1$H-NMR (500 MHz, CDCl$_3$): δ 8.66 (s, 1H), 7.92 (d, J=10.5 Hz, 1H), 7.34 (ABX, J=8.0, 7.5 Hz, 5H), 7.18-7.11 (m, 4H), 6.84 (d, J=8.0 Hz, 2H), 4.73 (t, J=8.0, 7.5 Hz, 1H), 4.58-4.53 (m, 2H), 4.48 (d, J=9.0 Hz, 1H), 4.38-4.31 (m, 3H), 4.12-4.06 (m, 2H), 3.97-2.92 (m, 4H), 3.62-3.51 (m, 4H), 3.11 (t, J=13.0, 12.5 Hz, 3H), 2.77 (t, J=12.0, 12.0 Hz, 1H), 2.59-2.54 (m, 1H), 2.50 (s, 3H), 2.11 (dd, J=8.0, 12.75 Hz, 1H), 1.98 (d, J=12.0 Hz, 2H), 1.86-1.76 (m, 8H), 1.74-1.70 (m, 8H), 0.94 (s, 9H). LCMS [M+H]$^+$=906.4.

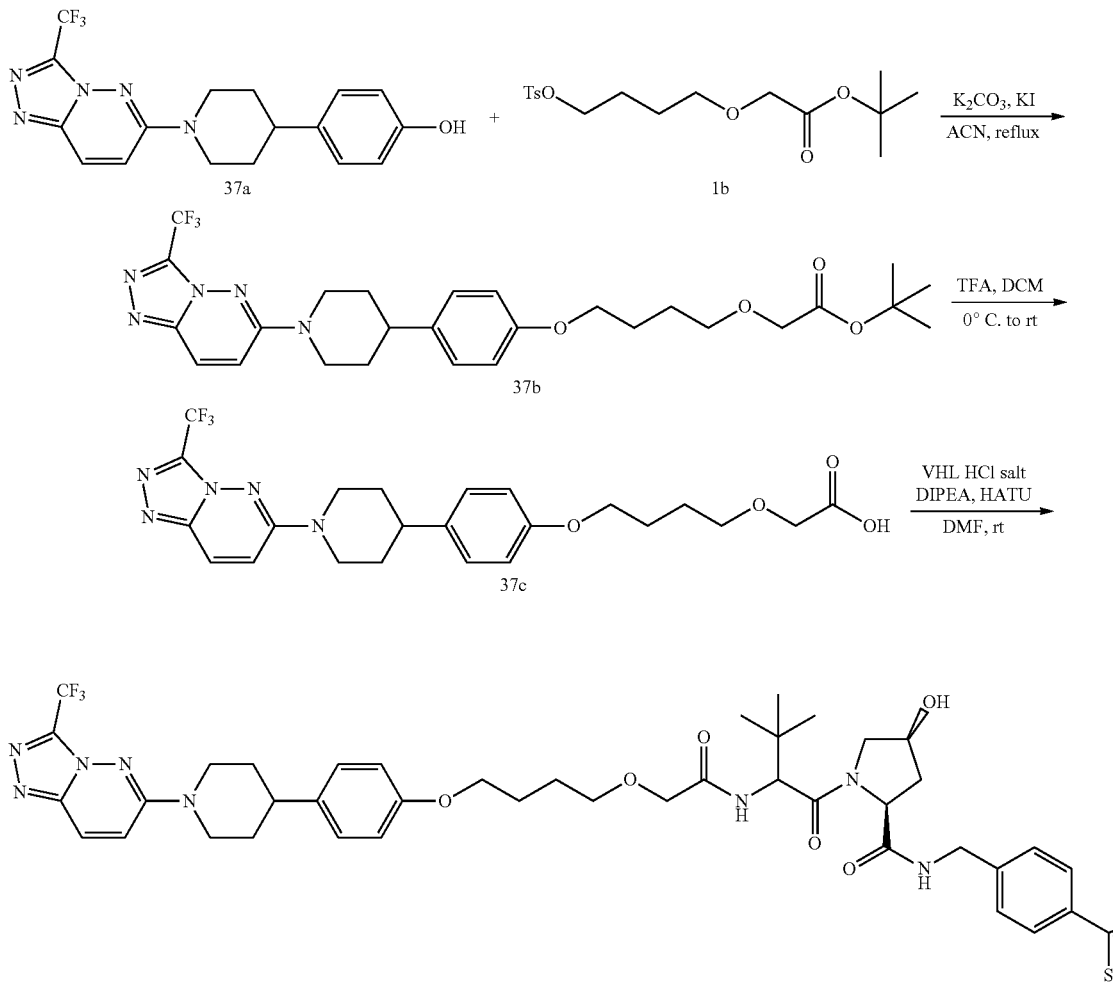

26. Preparation of Compound 38

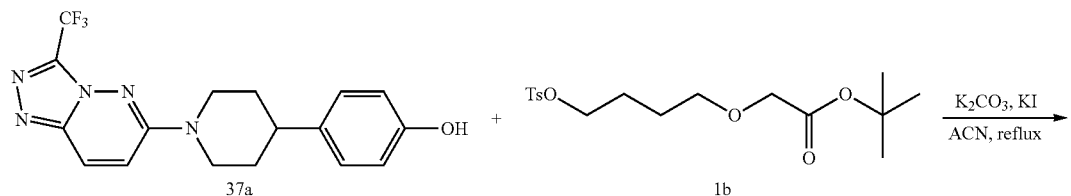

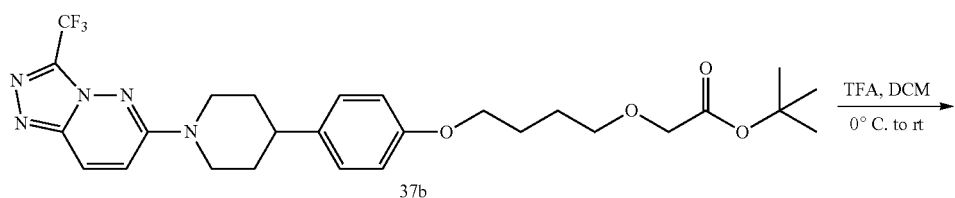

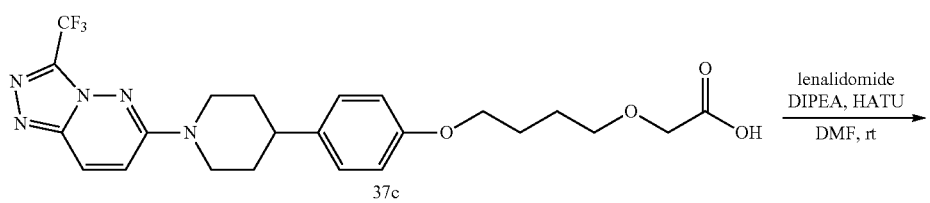

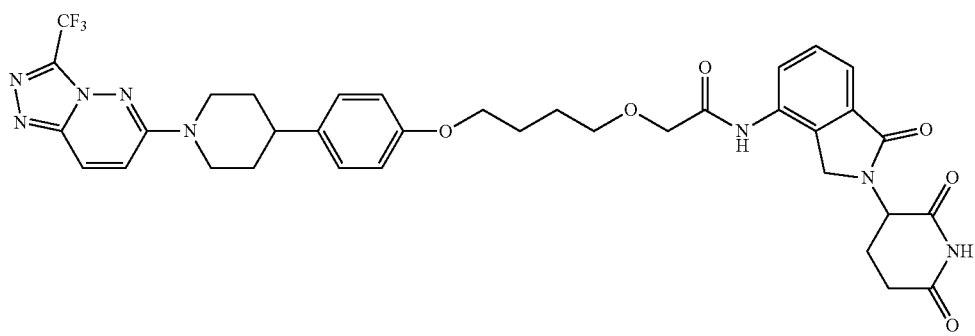

This compound was prepared using a method similar to that used to prepare compound 1.

N-(2-(2,6-dioxopiperidin-3-yl)-1-oxoisoindolin-4-yl)-2-(4-(4-(1-(3-(trifluoromethyl)-[1,2,4]triazolo[4,3-b]pyridazin-6-yl)piperidin-4-yl)phenoxy)butoxy) acetamide (38)

$^1$H-NMR (500 MHz, DMSO-d6): δ 10.99 (s, 1H), 9.72 (s, 1H), 8.23 (d, J=10.0 Hz, 1H), 7.74 (d, J=7.5 Hz, 1H), 7.64 (d, J=10.0 Hz, 1H), 7.56 (d, J=7.0 Hz, 1H), 7.51 (t, J=7.5, 7.5 Hz, 1H), 7.14 (d, J=7.5 Hz, 2H), 6.84 (d, J=8.0 Hz, 2H), 5.12 (dd, J=5.5, 13.25 Hz, 1H), 4.41-4.32 (m, 4H), 4.13 (s, 2H), 3.96 (t, J=6.5, 6.0 Hz, 2H), 3.58 (t, J=6.5, 6.0 Hz, 2H), 3.08 (t, J=12.5, 12.0 Hz, 2H), 2.93-2.86 (m, 1H), 2.78 (t, J=11.5, 12.5 Hz, 1H), 2.58 (d, J=16.0 Hz, 1H), 2.35 (ddd, J=4.0, 13.25, 26.375 Hz, 1H), 2.01-1.98 (m, 1H), 1.86 (d, J=12.0 Hz, 2H), 1.81-1.70 (m, 4H), 1.68-1.60 (m, 3H). LCMS [M+H]$^+$=735.3.

27. Preparation of Compound 39

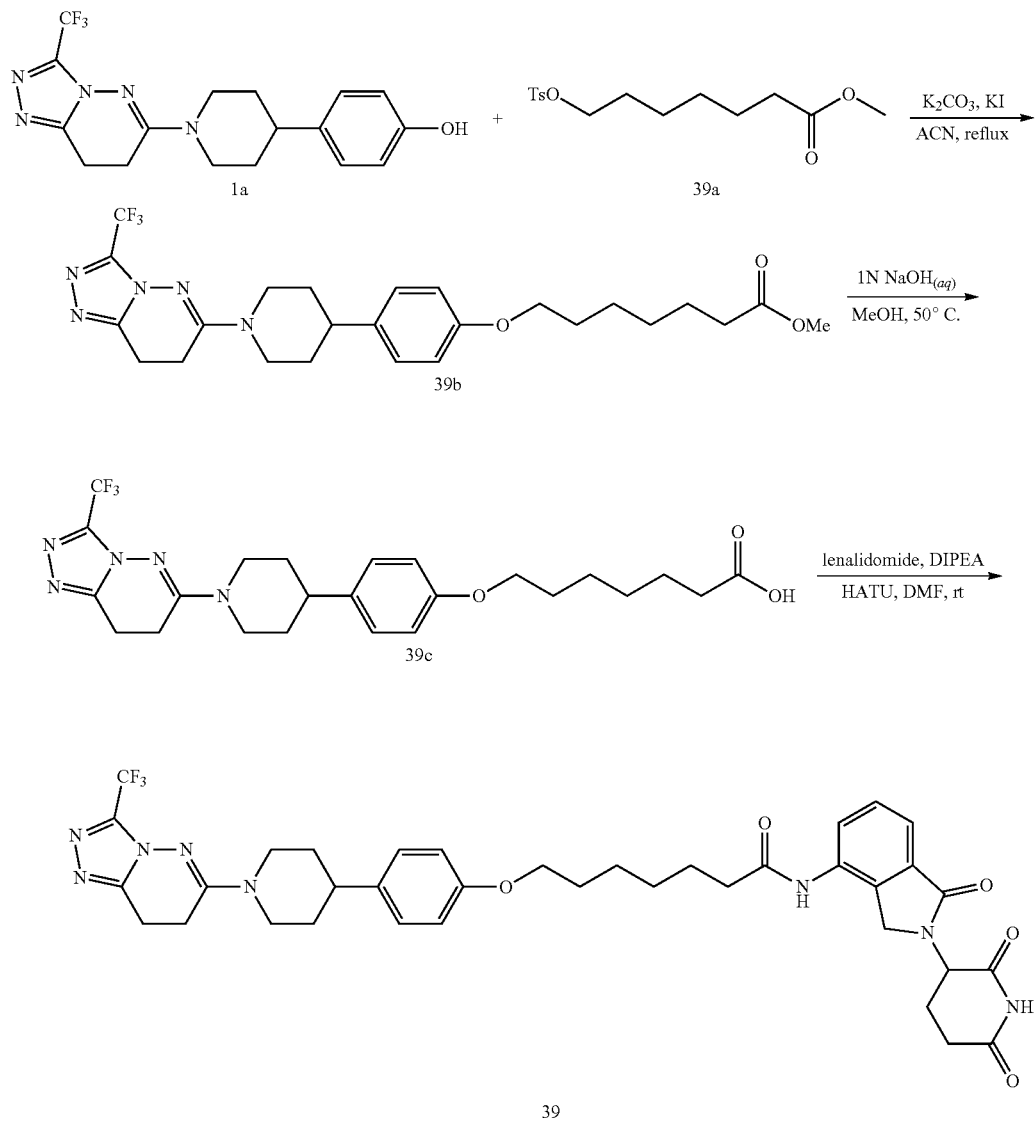

27-1. Preparation of methyl 7-(4-(1-(3-(trifluoromethyl)-7,8-dihydro-[1,2,4]triazolo[4,3-b]pyridazin-6-yl)piperidin-4-yl)phenoxy)heptanoate (39b)

This compound was prepared using a method similar to that used to prepare compound 1c. The crude product was purified by flash chromatography (MeOH/DCM=1/100→1/60) to give the title compound 39b (458 mg, 66%).

27-2. Preparation of 7-(4-(1-(3-(trifluoromethyl)-7,8-dihydro-[1,2,4]triazolo[4,3-b]pyridazin-6-yl)piperidin-4-yl)phenoxy)heptanoic acid (39c)

This compound was prepared using a method similar to that used to prepare compound 29c (97 mg, 100%).

27-3. Preparation of N-(2-(2,6-dioxopiperidin-3-yl)-1-oxoisoindolin-4-yl)-7-(4-(1-(3-(trifluoromethyl)-7,8-dihydro-[1,2,4]triazolo[4,3-b]pyridazin-6-yl)piperidin-4-yl)phenoxy)heptanamide (39)

This compound was prepared using a method similar to that used to prepare compound 1. The crude product was purified by reverse phase preparative HPLC to give the title compound 39 (16 mg, 24%).

$^1$H-NMR (500 MHz, DMSO-d6): δ 11.00 (s, 1H), 9.77 (s, 1H), 7.81 (d, J=7.0 Hz, 1H), 7.51-7.48 (m, 2H), 7.13 (d, J=8.5 Hz, 2H), 6.83 (d, J=8.0 Hz, 2H), 5.13 (dd, J=5.0, 13.25 Hz, 1H), 4.35 (ABX, J=17.5, 17.5 Hz, 2H), 4.27 (s, 1H), 3.92 (t, J=6.5, 6.0 Hz, 2H), 3.14 (t, J=7.5, 8.0 Hz, 2H), 3.00-2.87 (m, 5H), 2.75 (t, J=12.0, 11.5 Hz, 1H), 2.59 (d, J=17.5 Hz, 1H), 2.38-2.28 (m, 3H), 2.02-2.00 (m, 1H), 1.80 (d, J=12.0 Hz, 2H), 1.79-1.64 (m, 2H), 1.63-1.55 (m, 4H). LCMS [M+H]$^+$=735.3.

28. Preparation of Compound 40

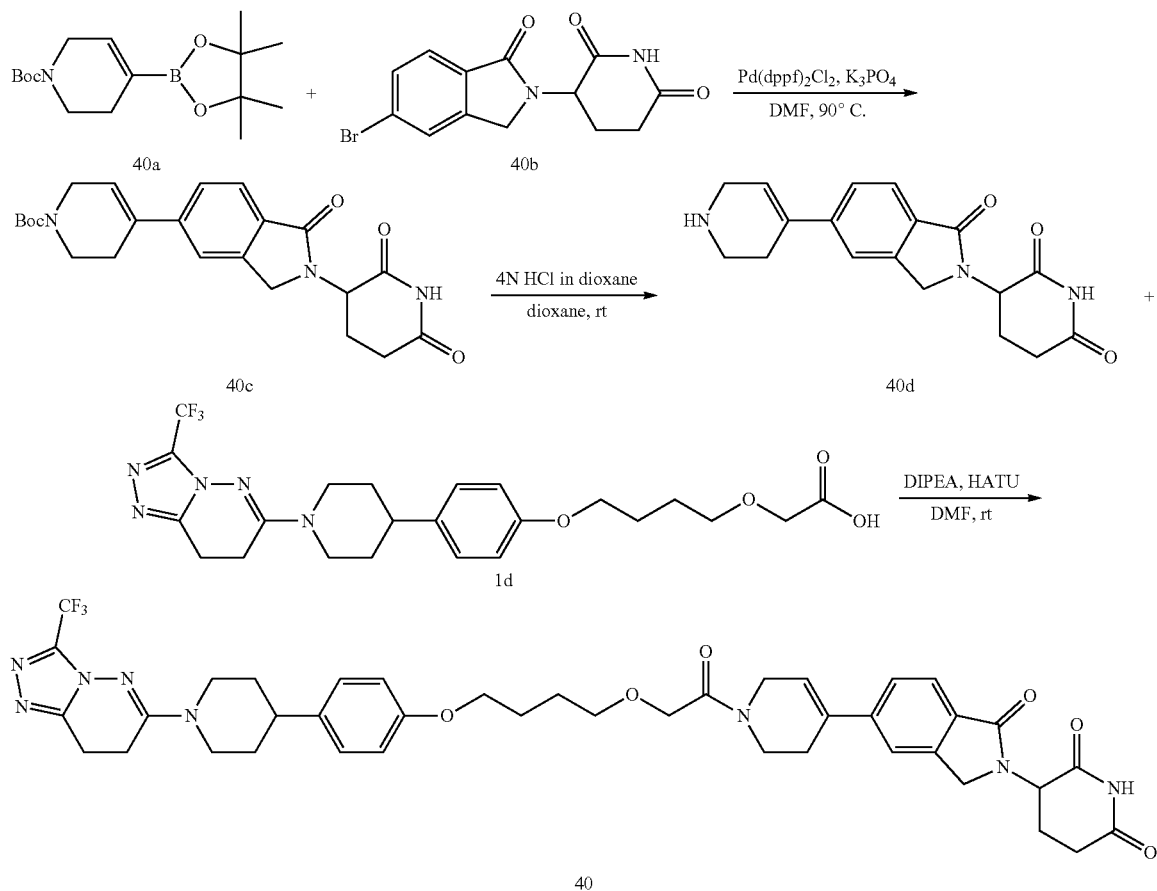

28-1. Preparation of tert-butyl 4-(2-(2,6-dioxopiperidin-3-yl)-1-oxoisoindolin-5-yl)-3,6-dihydropyridine-1(2H)-carboxylate (40c)

To a solution of tert-butyl 4-(4,4,5,5-tetramethyl-1,3,2-dioxaborolan-2-yl)-5,6-dihydropyridine-1(2H)-carboxylate (40a) (150 mg, 0.49 mmol) in DMF (2.4 mL) was added 3-(5-bromo-1-oxoisoindolin-2-yl)piperidine-2,6-dione (40b) (188 mg, 0.59 mmol), Pd(dppf)$_2$Cl$_2$ (54 mg, 0.07 mmol), and K$_3$PO$_4$ (124 mg, 0.59 mmol), and the mixture was stirred at 90° C. for 22 hours under argon. After cooled to room temperature, the reaction solution was concentrated to dryness and the residue was purified by flash chromatography (Ethyl acetate/hexane=1/1→3/1→4/1→Ethyl acetate) to get tert-butyl 4-(2-(2,6-dioxopiperidin-3-yl)-1-oxoisoindolin-5-yl)-5,6-dihydropyridine-1(2H)-carboxylate (40c) (111 mg, 54%) as a white solid.

28-2. Preparation of 3-(1-oxo-5-(1,2,3,6-tetrahydropyridin-4-yl)isoindolin-2-yl)piperidine-2,6-dione (40d)

This compound was prepared using a method similar to that used to prepare compound 35b (49 mg, 100%).

28-3. Preparation of 3-(1-oxo-5-(1-(2-(4-(4-(1-(3-(trifluoromethyl)-7,8-dihydro-[1,2,4]triazolo[4,3-b]pyridazin-6-yl)piperidin-4-yl)phenoxy)butoxy)acetyl)-1,2,3,6-tetrahydropyridin-4-yl)isoindolin-2-yl)piperidine-2,6-dione (40)

This compound was prepared using a method similar to that used to prepare compound 1. The crude product was purified by reverse phase preparative HPLC to give the title compound 40 (52 mg, 43%).

$^1$H-NMR (500 MHz, CDCl$_3$): δ 8.22 (s, 1H), 7.83 (d, J=7.5 Hz, 1H), 7.50-7.43 (m, 2H), 7.09 (d, J=8.5 Hz, 2H), 6.83 (d, J=8.0 Hz, 2H), 6.14 (d, J=37.5 Hz, 1H), 5.22 (dd, J=5.5, 13.25 Hz, 1H), 4.48 (d, J=16.5 Hz, 1H), 4.39-4.20 (m, 7H), 3.98-3.95 (m, 2H), 3.86-3.85 (m, 1H), 3.75 (t, J=5.5, 5.0 Hz, 1H), 3.61 (t, J=6.0, 5.0 Hz, 2H), 3.21 (t, J=8.0, 7.5 Hz, 2H), 3.02-2.90 (m, 3H), 2.88-2.81 (m, 2H), 2.80-2.71 (m, 4H), 2.62-2.58 (m, 2H), 2.35 (ddd, J=4.5, 12.75, 26.25 Hz, 1H), 2.23-2.20 (m, 1H), 1.94-1.80 (m, 7H), 1.71-1.63 (m, 9H). LCMS [M+H]$^+$=803.2.

29. Preparation of Compound 41

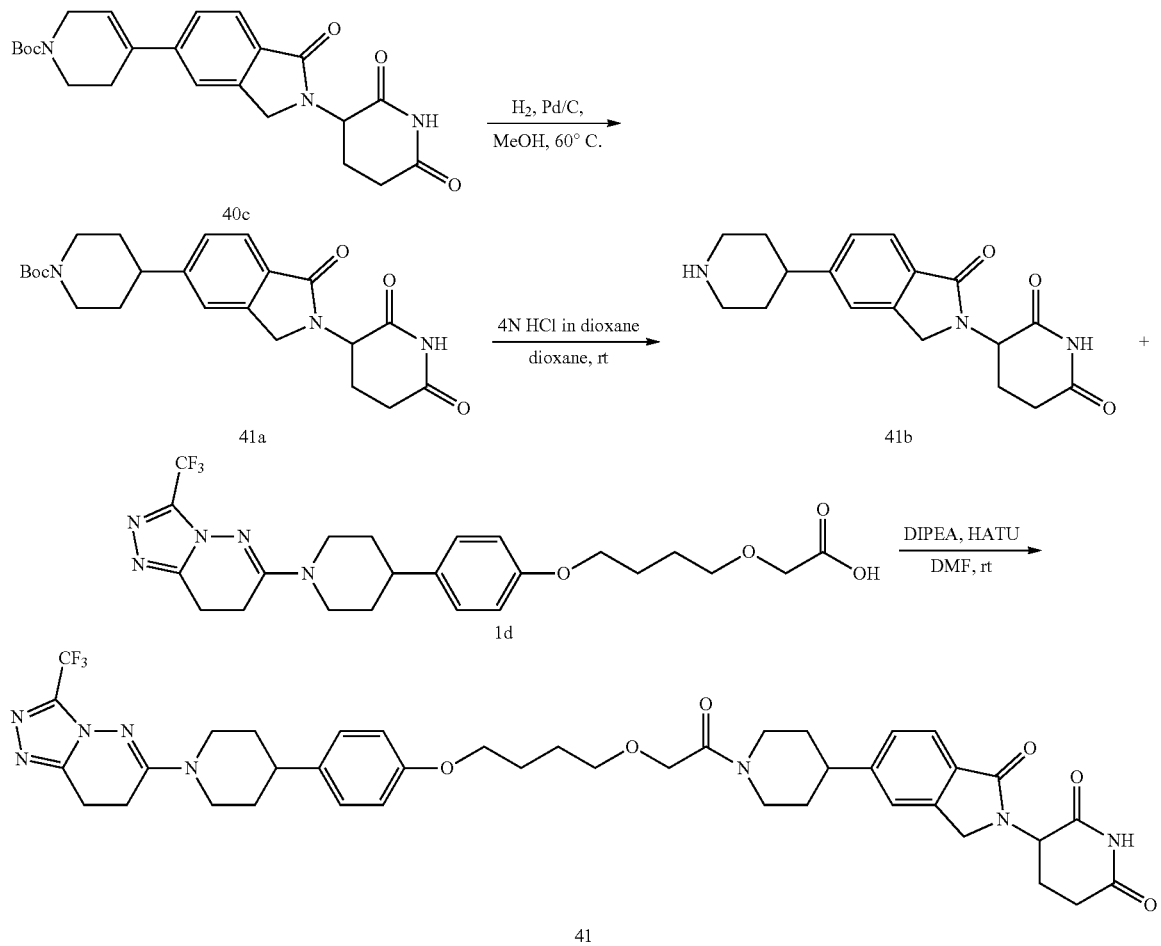

29-1. Preparation of tert-butyl 4-(2-(2,6-dioxopiperidin-3-yl)-1-oxoisoindolin-5-yl)piperidine-1-carboxylate (41a)

To a solution of tert-butyl 4-(2-(2,6-dioxopiperidin-3-yl)-1-oxoisoindolin-5-yl)-5,6-dihydropyridine-1(2H)-carboxylate (40c) (50 mg, 0.12 mmol) in MeOH (1.2 mL) was added 20% wet Pd/C (10 mg) and the mixture was stirred at 60° C. overnight under $H_2$. After cooled to room temperature, then the mixture was filtered through a Celite pad and concentrated under reduced pressure. Tert-butyl 4-(2-(2,6-dioxopiperidin-3-yl)-1-oxoisoindolin-5-yl)piperidine-1-carboxylate (41a) (45 mg, 90%) was obtained as a white solid.

29-2. Preparation of 3-(1-oxo-5-(piperidin-4-yl)isoindolin-2-yl)piperidine-2,6-dione (41b)

This compound was prepared using a method similar to that used to prepare compound 35b (34 mg, 100%)

25-3. Preparation of 3-(1-oxo-5-(1-(2-(4-(4-(1-(3-(trifluoromethyl)-7,8-dihydro-[1,2,4]triazolo[4,3-b]pyridazin-6-yl)piperidin-4-yl)phenoxy)butoxy)acetyl)piperidin-4-yl)isoindolin-2-yl)piperidine-2,6-dione (41)

This compound was prepared using a method similar to that used to prepare compound 1. The crude product was purified by reverse phase preparative HPLC to give the title compound 41 (34 mg, 27%).

$^1$H-NMR (500 MHz, CDCl$_3$): δ 8.05 (s, 1H), 7.81 (d, J=8.0 Hz, 1H), 7.32-7.26 (m, 2H), 7.10 (d, J=7.0 Hz, 2H), 6.84 (d, J=7.0 Hz, 2H), 5.20 (d, J=11.0 Hz, 1H), 4.76 (d, J=11.5 Hz, 1H), 4.46 (d, J=16.0 Hz, 1H), 4.31 (d, J=15.5 Hz, 3H), 4.23-4.08 (m, 4H), 3.97 (t, J=5.0, 6.0 Hz, 2H), 3.62-3.59 (m, 2H), 3.21 (t, J=8.0, 8.0 Hz, 2H), 3.14 (t, J=12.5, 13.0 Hz, 1H), 3.02-2.83 (m, 6H), 2.80-2.66 (m, 5H), 2.38-2.30 (m, 1H), 2.22-2.19 (m, 1H), 1.94-1.86 (m, 7H), 1.82-1.79 (m, 3H), 1.70-1.65 (m, 5H), 1.62 (s, 10H). LCMS [M+H]$^+$=805.2.

30. Preparation of Compound 42
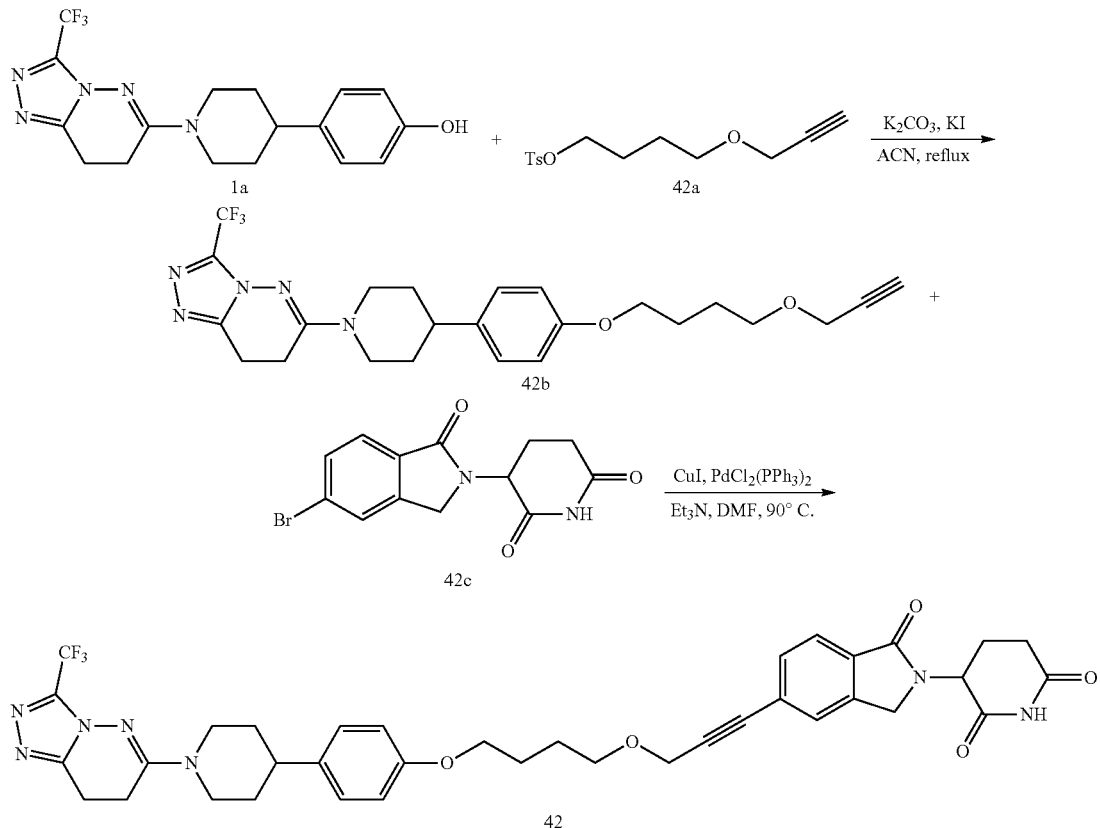
This compound was prepared using a method similar to that used to prepare compound 1.
$^1$H-NMR (500 MHz, DMSO-d6): δ 11.00 (s, 1H, NH), 7.71-7.70 (m, 2H), 7.56 (d, J=8.0 Hz, 1H), 7.12 (d, J=8.0 Hz, 2H), 6.84 (d, J=8.0 Hz, 2H), 5.12 (dd, J=5.0, 13.0 Hz, 1H), 4.47-4.42 (m, 3H), 4.35-4.27 (m, 3H), 3.96 (t, J=6.5 Hz, 2H), 3.59 (t, J=6.5 Hz, 2H), 3.16-3.06 (m, 6H), 3.00-2.87 (m, 3H), 2.78-2.74 (m, 1H), 2.61-2.58 (m, 1H), 2.41-2.37 (m, 1H), 1.80-1.76 (m, 3H), 1.71-1.68 (m, 2H), 1.60-1.56 (m, 2H). LCMS [M+H]$^+$=718.2
31. Preparation of Compound 43
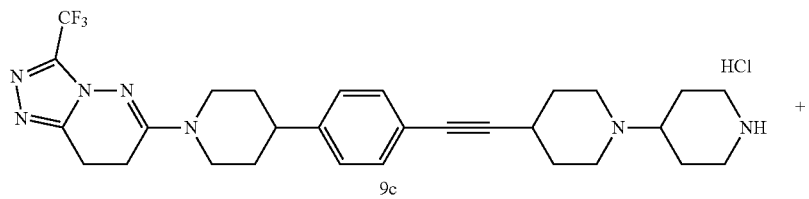
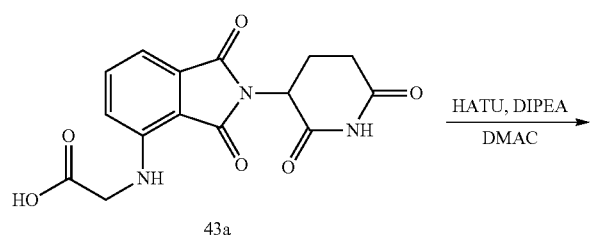

-continued

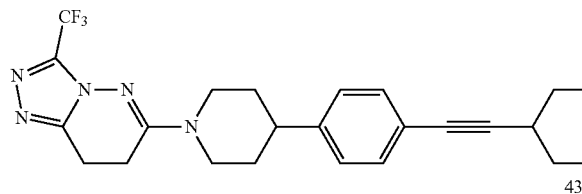

43

27-1. Preparation of 2-(2,6-dioxopiperidin-3-yl)-4-((2-oxo-2-(4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidin]-1'-yl)ethyl)amino)isoindoline-1,3-dione (43)

$^1$H-NMR (DMSO-d6, 500 MHz) δ 7.45-7.60 (m, 1H), 7.39 (d, J=8.0 Hz, 1H), 7.31 (d, J=8.0 Hz, 1H), 7.20-7.23 (m, 2H), 6.90-7.18 (m, 2H), 5.15-5.0 (m, 1 Hz), 4.6-4.15 (m, 6H), 3.8-3.4 (m, 6H), 3.4-2.6 (m, 20H), 2.4-1.6 (m, 16H). LCMS [M+H]$^+$=854.5.

32. Preparation of Compound 44

2-(2,6-dioxopiperidin-3-yl)-4-(4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidin]-1'-yl)isoindoline-1,3-dione (44)

6-(4-(4-([1,4'-bipiperidin]-4-ylethynyl)phenyl)piperidin-1-yl)-3-(trifluoromethyl)-7,8-dihydro-[1,2,4]triazolo[4,3-b]pyridazine (9c) (40.3 mg, 0.223 mmol) was dissolved in DMAC and stirred and then 2-(2,6-dioxopiperidin-3-yl)-4-fluoroisoindoline-1,3-dione (44a) (23 mg, 0.245 mmol) and K$_2$CO$_3$ (21 mg, 0.335 mmol) were added and heated to 100° C. for reaction 1 day. Next, water and DCM were added to the reactant for extraction, and the water was removed with magnesium sulfate. The crude product was then purified by

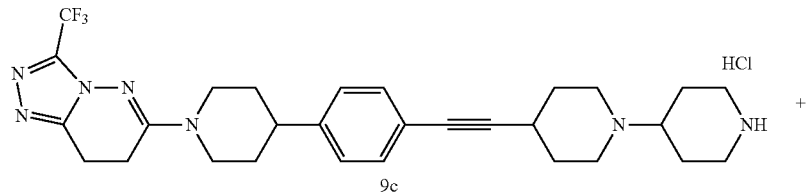

9c

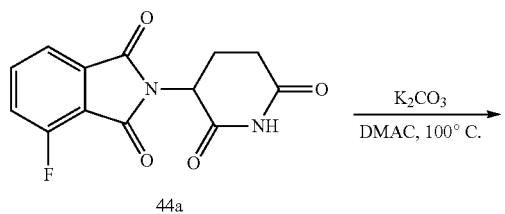

44a

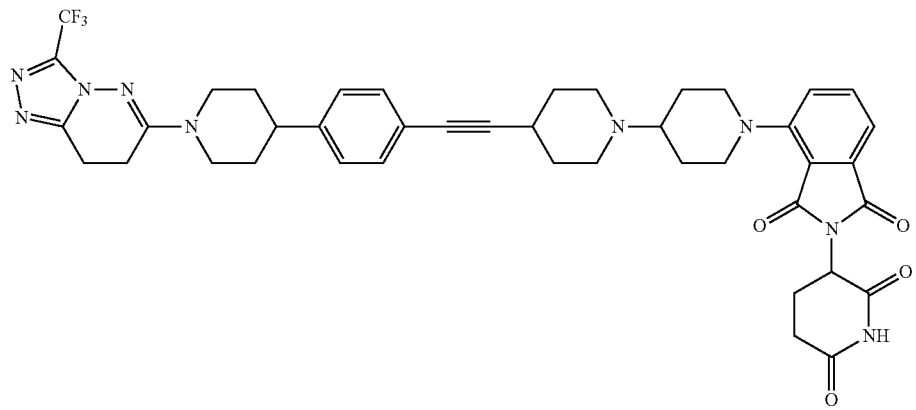

44 reverse-phase preparative HPLC (35% ACN+0.1% TFA, 24 mL/minute, 210 nm) and concentrated under reduced pressure to remove CAN, followed by lyophilization to give 2-(2,6-dioxopiperidin-3-yl)-4-(4-((4-(1-(3-(trifluoromethyl)-7,8-dihydro-[1,2,4]triazolo[4,3-b]pyridazin-6-yl)piperidin-4-yl)phenyl)ethynyl)-[1,4'-bipiperidin]-1'-yl)isoindoline-1,3-dione (44) (5.4 mg, 9%). LCMS [M+H]$^+$=797.4.

33. Preparation of Compound 45

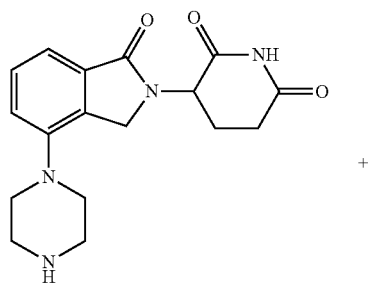

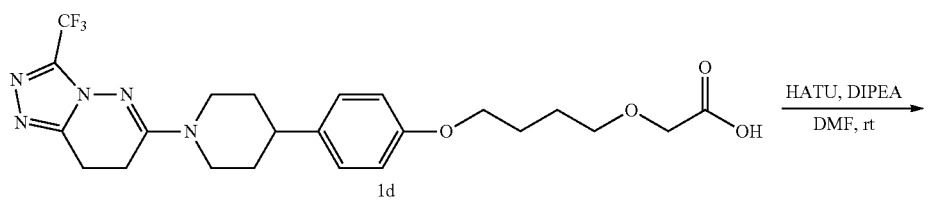

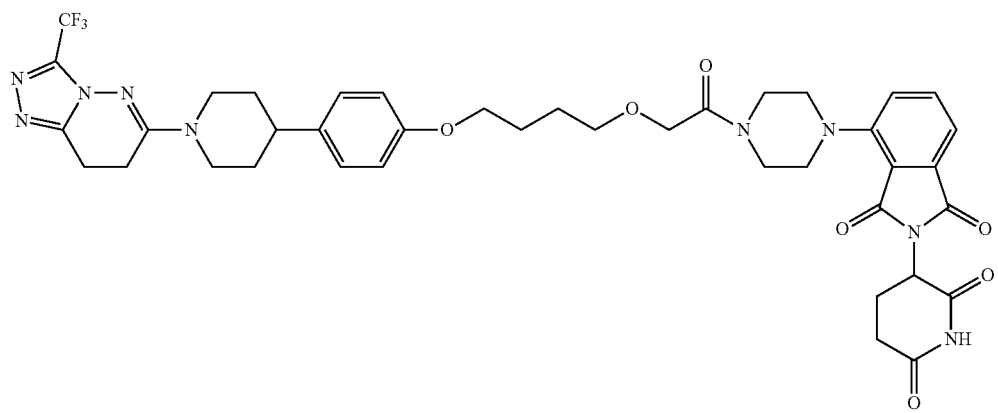

2-(2,6-dioxopiperidin-3-yl)-4-(4-(2-(4-(4-(1-(3-(trifluoromethyl)-7,8-dihydro-[1,2,4]triazolo[4,3-b]pyridazin-6-yl)piperidin-4-yl)phenoxy)butoxy)acetyl)piperazin-1-yl)isoindoline-1,3-dione (45)

This compound was prepared using a method similar to that used to prepare compound 1. The crude product was purified by reverse phase preparative HPLC to give the title compound 45 (114 mg, 26%).

$^1$H-NMR (500 MHz, CDCl$_3$): δ 7.67-7.64 (m, 2H), 7.42 (d, J=7.0 Hz, 1H), 7.24 (d, J=8.5 Hz, 1H), 7.09 (d, J=8.5 Hz, 2H), 6.82 (d, J=8.5 Hz, 2H), 5.05-5.02 (m, 1H), 4.22 (s, 2H), 3.98 (t, J=6.0, 6.0 Hz, 2H), 3.78 (s, 2H), 3.73 (s, 2H), 3.60 (t, J=6.0, 6.0 Hz, 3H), 3.35-3.33 (m, 2H), 3.23 (t, J=7.5, 8.0 Hz, 2H), 3.04-3.01 (m, 2H), 2.91 (t, J=8.0, 8.0 Hz, 2H), 2.82-2.73 (m, 4H), 2.13-2.11 (m, 1H), 1.90-1.78 (m, 7H), 1.69-1.61 (m, 2H). LCMS [M+H]$^+$=820.3.

34. Preparation of Compound 46
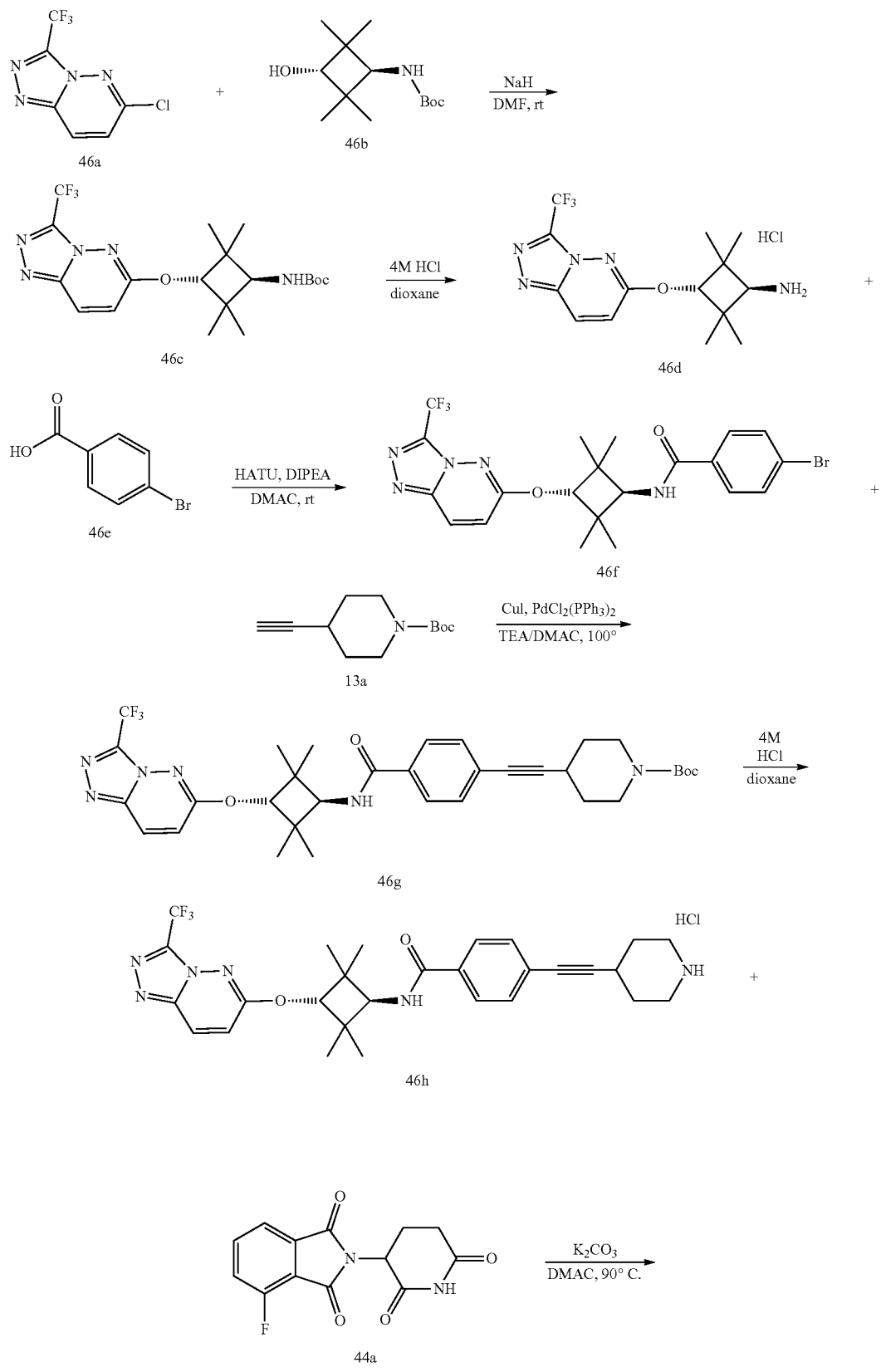

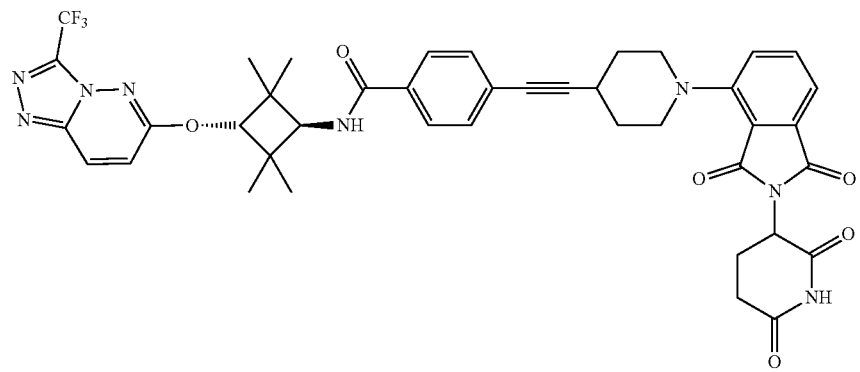

46

34-1. Preparation of tert-butyl ((1r,3r)-2,2,4,4-tetramethyl-3-((3-(trifluoromethyl)-[1,2,4]triazolo[4,3-b]pyridazin-6-yl)oxy)cyclobutyl)carbamate (46c)

A solution of tert-butyl ((1r,3r)-3-hydroxy-2,2,4,4-tetramethylcyclobutyl)carbamate (46b) (1.1 g, 4.56 mmol) in DMF at 0° C. under an atmosphere of argon was treated with sodium hydride (130 mg, 5.42 mmol, 60% dispersion in oil). The reaction was allowed to warm to room temperature over a period of 1 hour. The reaction flask was then cooled to 0° C. and to this solution 6-chloro-3-(trifluoromethyl)-[1,2,4]triazolo[4,3-b]pyridazine (46a) (1.1 g, 4.94 mmol) was added drop wise whilst the temperature was held below 0° C. The mixture was stirred at room temperature for 24 hours, and then quenched with water. The organic phase was separated and washed with brine and dried over anhydrous sodium carbonate. The sample was then concentrated in vacuo. Purification was performed by flash chromatography (MeOH/DCM=1/99→5/95) to obtain (tert-butyl ((1r,3r)-2,2,4,4-tetramethyl-3-((3-(trifluoromethyl)-[1,2,4]triazolo[4,3-b]pyridazin-6-yl)oxy)cyclobutyl)carbamate (46c) (890 mg, 46%) as a colorless oil.

34-2. Preparation of (1r,3r)-2,2,4,4-tetramethyl-3-((3-(trifluoromethyl)-[1,2,4]triazolo[4,3-b]pyridazin-6-yl)oxy)cyclobutan-1-amine (46d)

This compound was prepared using a method similar to that used to prepare compound 4d (800 mg, 98%).

30-3. Preparation of 4-bromo-N-((1r,3r)-2,2,4,4-tetramethyl-3-((3-(trifluoromethyl)-[1,2,4]triazolo[4,3-b]pyridazin-6-yl)oxy)cyclobutyl)benzamide (46f)

This compound was prepared using a method similar to that used to prepare compound 1. The crude product was purified by flash chromatography (MeOH/DCM=1/99→5/95) to obtain the title compound 46f (310 mg, 55%).

34-4. Preparation of tert-butyl 4-((4-(((1r,3r)-2,2,4,4-tetramethyl-3-((3-(trifluoromethyl)-[1,2,4]triazolo[4,3-b]pyridazin-6-yl)oxy)cyclobutyl)carbamoyl)phenyl)ethynyl)piperidine-1-carboxylate (46g)

This compound was prepared using a method similar to that used to prepare compound 2. The crude product was purified by flash chromatography (MeOH/DCM=1/99→5/95) to obtain the title compound 46g (47 mg, 38%).

34-5. Preparation of 4-(piperidin-4-ylethynyl)-N-((1r,3r)-2,2,4,4-tetramethyl-3-((3-(trifluoromethyl)-[1,2,4]triazolo[4,3-b]pyridazin-6-yl)oxy)cyclobutyl)benzamide (46h)

This compound was prepared using a method similar to that used to prepare compound 4d (50 mg, 98%).

34-6. Preparation of 4-((1-(2-(2,6-dioxopiperidin-3-yl)-1,3-dioxoisoindolin-4-yl)piperidin-4-yl)ethynyl)-N-((1r,3r)-2,2,4,4-tetramethyl-3-((3-(trifluoromethyl)-[1,2,4]triazolo[4,3-b]pyridazin-6-yl)oxy)cyclobutyl)benzamide (46)

This compound was prepared using a method similar to that used to prepare compound 44. The crude product was purified by reverse phase preparative HPLC to obtain the title compound 46 (2 mg, 3%). LCMS [M+H]$^+$=798.4.

35. Preparation of Compound 47

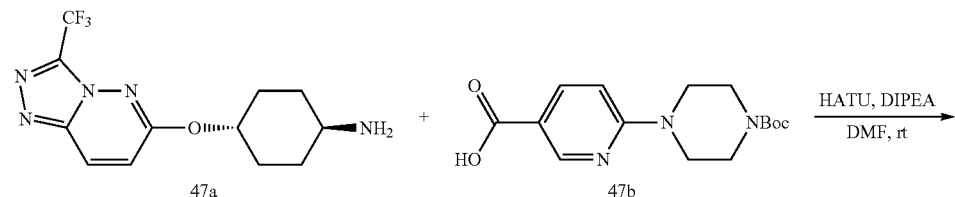

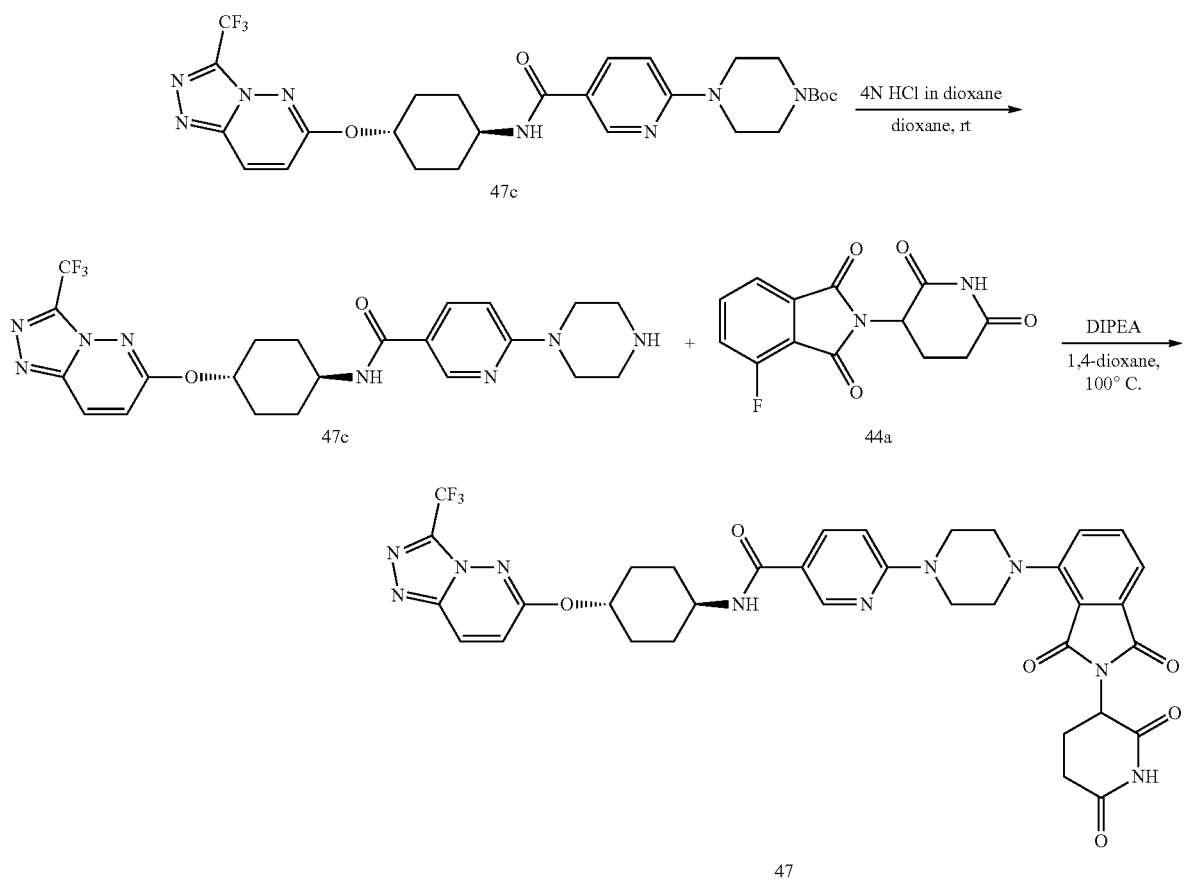

35-1. Preparation of tert-butyl 4-(5-(((1r,4r)-4-((3-(trifluoromethyl)-[1,2,4]triazolo[4,3-b]pyridazin-6-yl)oxy)cyclohexyl)carbamoyl)pyridin-2-yl)piperazine-1-carboxylate (47c)

This compound was prepared using a method similar to that used to prepare compound 1. The crude product was purified by flash chromatography (MeOH/DCM=1/100→1/80→1/40) to give the title compound 47c (396 mg, 76%).

35-2. Preparation of 6-(piperazin-1-yl)-N-((1r,4r)-4-((3-(trifluoromethyl)-[1,2,4]triazolo[4,3-b]pyridazin-6-yl)oxy)cyclohexyl)nicotinamide (47d)

This compound was prepared using a method similar to that used to prepare compound 35b (240 mg, 98%).

35-3. Preparation of 6-(4-(2-(2,6-dioxopiperidin-3-yl)-1,3-dioxoisoindolin-4-yl)piperazin-1-yl)-N-((1r,4r)-4-((3-(trifluoromethyl)-[1,2,4]triazolo[4,3-b]pyridazin-6-yl)oxy)cyclohexyl)nicotinamide (47)

A mixture of 6-(piperazin-1-yl)-N-((1r,4r)-4-((3-(trifluoromethyl)-[1,2,4]triazolo[4,3-b]pyridazin-6-yl)oxy)cyclohexyl)nicotinamide (47d) (82 mg, 0.17 mmol), 2-(2,6-dioxopiperidin-3-yl)-4-fluoroisoindoline-1,3-dione (44a) (51 mg, 0.18 mmol), and DIPEA (0.09 mL, 0.51 mmol) in 1,4-dioxane (1.7 mL) was stirred at reflux for overnight. The mixture was concentrated and purified by reverse phase preparative HPLC to obtain 6-(4-(2-(2,6-dioxopiperidin-3-yl)-1,3-dioxoisoindolin-4-yl)piperazin-1-yl)-N-((1r,4r)-4-((3-(trifluoromethyl)-[1,2,4]triazolo[4,3-b]pyridazin-6-yl)oxy)cyclohexyl)nicotinamide (47) (14 mg, 11%) as a yellow solid. LCMS [M+H]$^+$=747.3.

36. Preparation of Compound 48

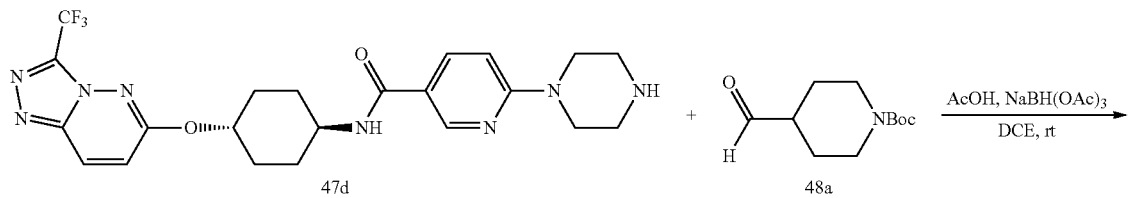

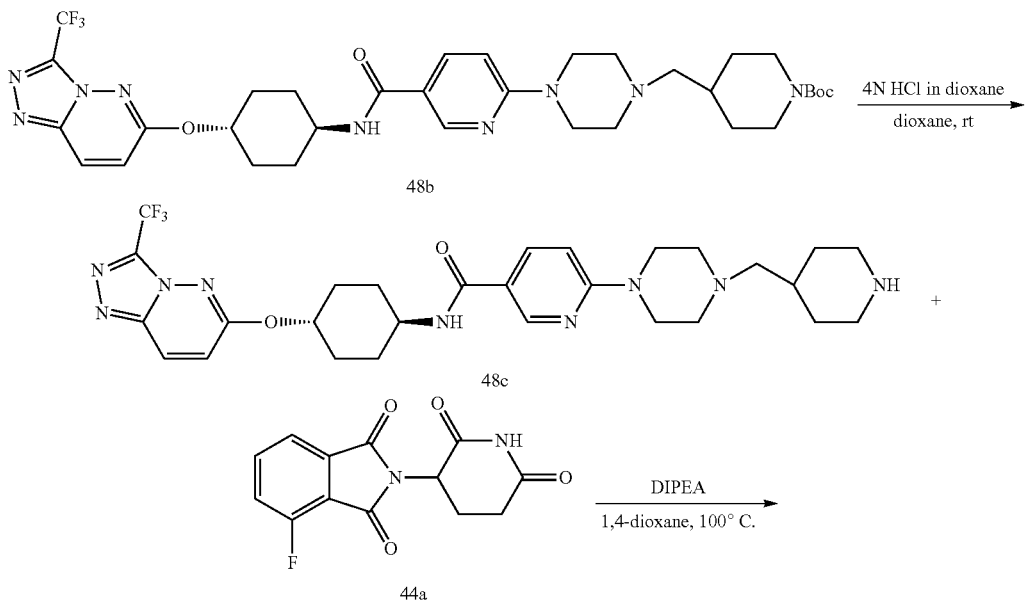

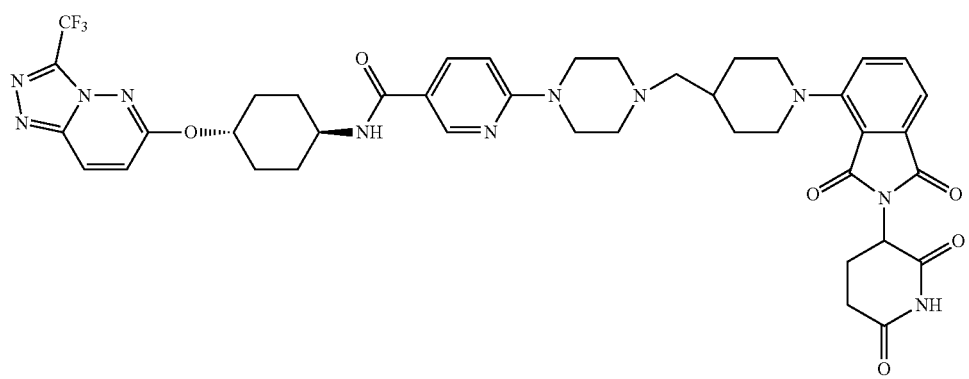 [SMILES: O=C1CCC(C2C(=O)c3cccc(N4CCC(CN5CCN(c6ccc(C(=O)N[C@H]7CC[C@H](Oc8ccc9nnc(C(F)(F)F)n9n8)CC7)cn6)CC5)CC4)c3C2=O)C(=O)N1]

36-1. Preparation of tert-butyl 4-((4-(5-(((1r,4r)-4-((3-(trifluoromethyl)-[1,2,4]triazolo[4,3-b]pyridazin-6-yl)oxy)cyclohexyl)carbamoyl)pyridin-2-yl)piperazin-1-yl)methyl)piperidine-1-carboxylate (48b)

6-(piperazin-1l-yl)-N-((1r,4r)-4-((3-(trifluoromethyl)-[1,2,4]triazolo[4,3-b]pyridazin-6-yl)oxy)cyclohexyl)nicotinamide (47d) (160 mg, 0.33 mmol) was added to a solution of the corresponding tert-butyl 4-formylpiperidine-1-carboxylate (48a) (104 mg, 0.49 mmol), acetic acid (2.0 mL), and sodium triacetoxyborohydride (207 mg, 0.98 mmol) in 2.0 mL of dry DCE. The reaction mixture was stirred for overnight at room temperature, then the crude reaction mixture was evaporated in vacuo and neutralized by NaHCO$_{3(aq)}$ to PH=8. The crude product was extracted with DCM and evaporated in vacuo without purification to obtain tert-butyl 4-((4-(5-(((1r,4r)-4-((3-(trifluoromethyl)-[1,2,4]triazolo[4,3-b]pyridazin-6-yl)oxy)cyclohexyl)carbamoyl)pyridin-2-yl)piperazin-1-yl)methyl)piperidine-1-carboxylate (48b).

32-2. Preparation of 6-(4-(piperidin-4-ylmethyl)piperazin-1-yl)-N-((1r,4r)-4-((3-(trifluoromethyl)-[1,2,4]triazolo[4,3-b]pyridazin-6-yl)oxy)cyclohexyl)nicotinamide (48c)

This compound was prepared using a method similar to that used to prepare compound 35b (34 mg, 18%, 2 steps)

32-3. Preparation of 6-(4-((1-(2-(2,6-dioxopiperidin-3-yl)-1,3-dioxoisoindolin-4-yl)piperidin-4-yl)methyl)piperazin-1-yl)-N-((1r,4r)-4-((3-(trifluoromethyl)-[1,2,4]triazolo[4,3-b]pyridazin-6-yl)oxy)cyclohexyl)nicotinamide) (48)

This compound was prepared using a method similar to that used to prepare compound 47. The crude product was purified by reverse phase preparative HPLC to obtain the title compound 48 (7 mg, 14%). LCMS [M+H]$^+$=844.5.

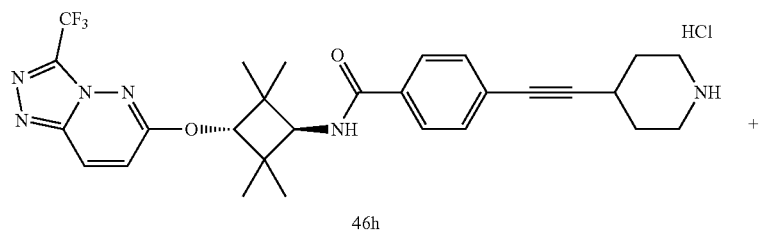

46h

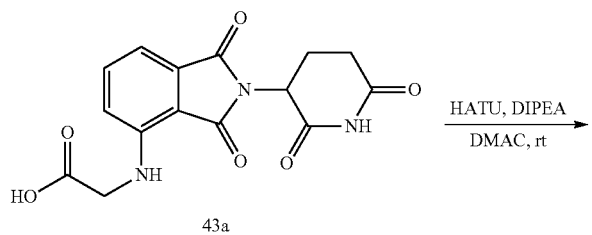

43a

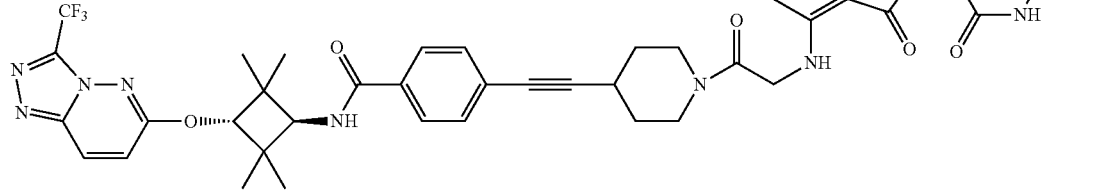

49

4-((1-((2-(2,6-dioxopiperidin-3-yl)-1,3-dioxoisoindolin-4-yl)glycyl)piperidin-4-yl)ethynyl)-N-((1r,3r)-2,2,4,4-tetramethyl-3-((3-(trifluoromethyl)-[1,2,4]triazolo[4,3-b]pyridazin-6-yl)oxy)cyclobutyl)benzamide (49)

This compound was prepared using a method similar to that used to prepare compound 1. The crude product was purified by reverse phase preparative HPLC to obtain the title compound 49 (33 mg, 38%).

$^1$H-NMR (500 MHz, DMSO-d6) δ 10.99 (s, 1H), 8.36 (d, J=10.0 Hz, 1H), 7.90 (d, J=10.0 Hz, 1H), 7.75 (d, J=8.0 Hz, 2H), 7.51 (dd, J=8.0, 8.0 Hz, 1H), 7.41 (d, J=8.5 Hz, 2H), 7.25 (d, J=9.5 Hz, 1H), 7.00 (dd, J=8.5, 8.5 Hz, 1H), 4.97 (dd, J=5.5, 5.5 Hz, 1H), 4.55 (s, 1H), 4.11 (s, 2H), 3.99 (d, J=10 Hz, 1H), 3.80-3.90 (m, 1H), 3.60-3.70 (m, 1H), 2.85-2.95 (m, 1H), 2.70-2.85 (m, 1H), 1.75-2.00 (m, 3H), 1.4-1.65 (m, 2H), 1.13 (s, 6H), 1.11 (s, 6H). LCMS [M+H]$^+$=855.4.

38. Preparation of Compound 50

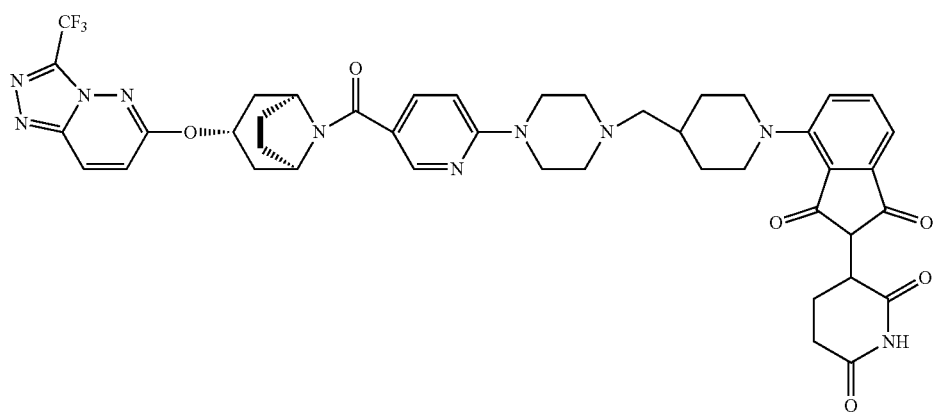

50

The preparation scheme of Compound 50 shown above can be deduced from the preparation scheme of Compound 48 shown above.
39. Preparation of Compound 51
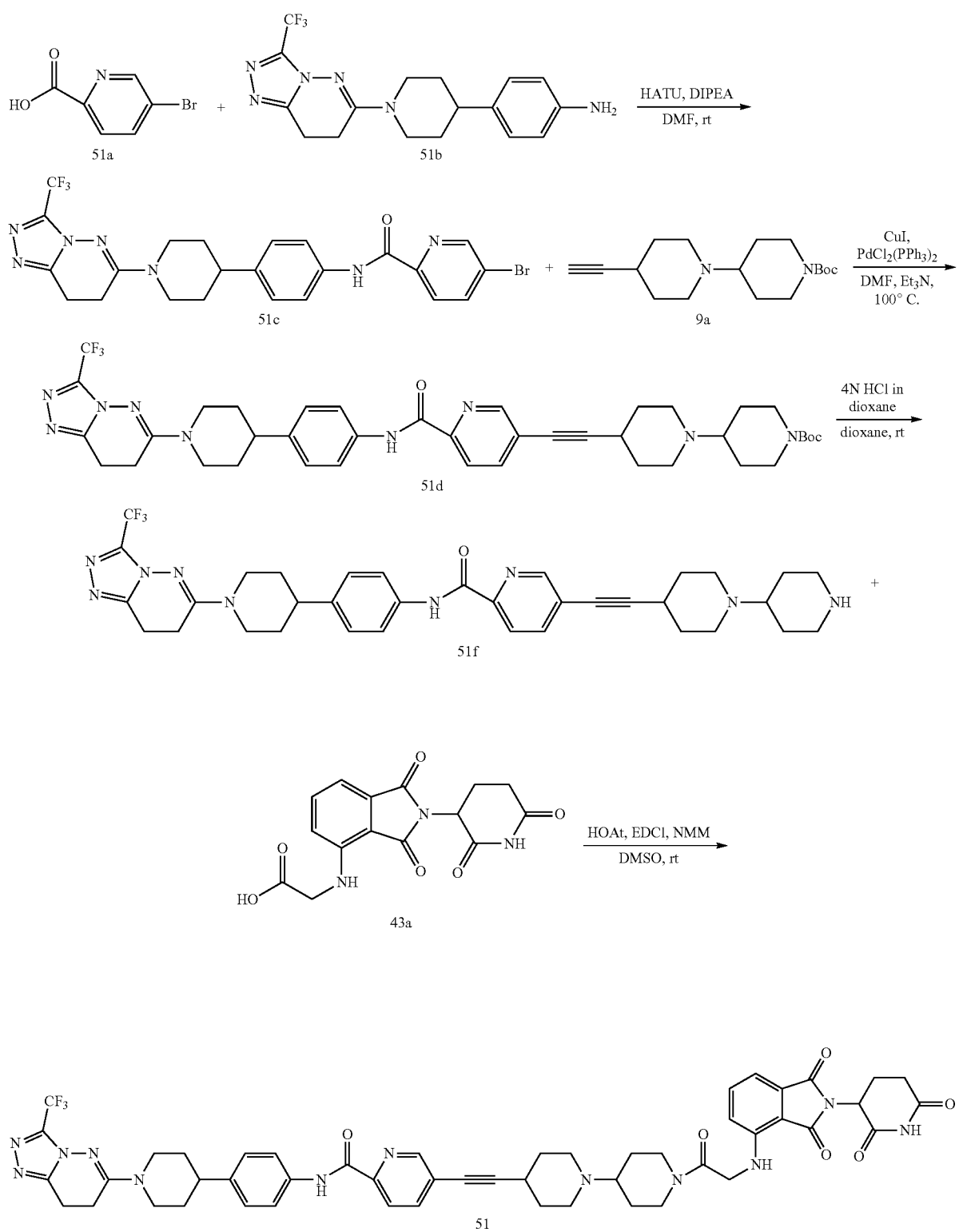

39-1. Preparation of 5-bromo-N-(4-(1-(3-(trifluoromethyl)-7,8-dihydro-[1,2,4]triazolo[4,3-b]pyridazin-6-yl)piperidin-4-yl)phenyl)picolinamide) (51c)

This compound was prepared using a method similar to that used to prepare compound 1. The crude product was purified by flash chromatography to obtain the title compound 51c (410 mg, 91%).

39-2. Preparation of tert-butyl 4-((6-((4-(1-(3-(trifluoromethyl)-7,8-dihydro-[1,2,4]triazolo[4,3-b]pyridazin-6-yl)piperidin-4-yl)phenyl)carbamoyl)pyridin-3-yl)ethynyl)-[1,4'-bipiperidine]-1'-carboxylate (51d)

This compound was prepared using a method similar to that used to prepare compound 2. The crude product was purified by flash chromatography (MeOH/DCM=1/100→1/20) to obtain the title compound 51d (400 mg, 64%).

39-3. Preparation of 5-([1,4'-bipiperidin]-4-ylethynyl)-N-(4-(1-(3-(trifluoromethyl)-7,8-dihydro-[1,2,4]triazolo[4,3-b]pyridazin-6-yl)piperidin-4-yl)phenyl)picolinamide (51f)

This compound was prepared using a method similar to that used to prepare compound 35b (345 mg, 99%).

39-4. Preparation of 5-((1'-((2-(2,6-dioxopiperidin-3-yl)-1,3-dioxoisoindolin-4-yl)glycyl)-[1,4'-bipiperidin]-4-yl)ethynyl)-N-(4-(1-(3-(trifluoromethyl)-7,8-dihydro-[1,2,4]triazolo[4,3-b]pyridazin-6-yl)piperidin-4-yl)phenyl)picolinamide (51)

A mixture of 2-(2-(2,6-dioxopiperidin-3-yl)-1,3-dioxoisoindolin-4-ylamino)acetic acid (43a) (174 mg, 0.53 mmol) in DMSO (10.5 mL) was added HOAt (143 mg, 1.05 mmol), EDCI (163 mg, 1.05 mmol), NMM (0.3 mL, 2.65 mmol) and stirred at room temperature for 15 minutes, then added 5-(1,4'-bipiperidin-4-ylethynyl)-N-(4-(1-(3-(trifluoromethyl)-7,8-dihydro-[1,2,4]triazolo[4,3-b]pyridazin-6-yl)piperidin-4-yl)phenyl)picolinamide (51f) (345 mg, 0.52 mmol). The mixture was stirred at room temperature for overnight. The mixture was diluted with $H_2O$ (10 mL) and extracted with DCM (10 mL×2). The combined organic phase was washed with brine (10 mL), dried over $Na_2SO_4$, concentrated and purified by flash column to obtain 5-((1'-((2-(2,6-dioxopiperidin-3-yl)-1,3-dioxoisoindolin-4-yl)glycyl)-[1,4'-bipiperidin]-4-yl)ethynyl)-N-(4-(1-(3-(trifluoromethyl)-7,8-dihydro-[1,2,4]triazolo[4,3-b]pyridazin-6-yl)piperidin-4-yl)phenyl)picolinamide (51) (85 mg, 17%).

$^1$H-NMR (500 MHz, DMSO-d6): δ 11.10 (s, 1H), 10.58 (s, 1H), 8.69 (s, 1H), 8.07 (dd, J=8.5, 34.25 Hz, 1H), 7.80 (d, J=8.5 Hz, 2H), 7.60 (t, J=8.0, 7.5 Hz, 1H), 7.24 (d, J=8.5 Hz, 2H), 7.11-7.06 (m, 3H), 5.06 (dd, J=5.5, 13.0 Hz, 1H), 4.43 (d, J=11.0 Hz, 1H), 4.29 (s, 1H), 4.20 (ABX, J=14.0, 6.0 Hz, 2H), 3.94 (d, J=11.0 Hz, 1H), 3.15 (t, J=7.5, 8.0 Hz, 2H), 3.06-3.02 (m, 9H), 2.93 (t, J=8.0, 7.5 Hz, 3H), 2.88-2.79 (m, 4H), 2.67-2.54 (m, 4H), 2.04-2.02 (m, 1H), 1.98-1.91 (m, 2H), 1.85-1.83 (m, 4H), 1.67-1.61 (m, 4H), 1.17 (t, J=7.0, 7.5 Hz, 7H). LCMS [M+H]$^+$=973.6.

40. Preparation of Compound 52

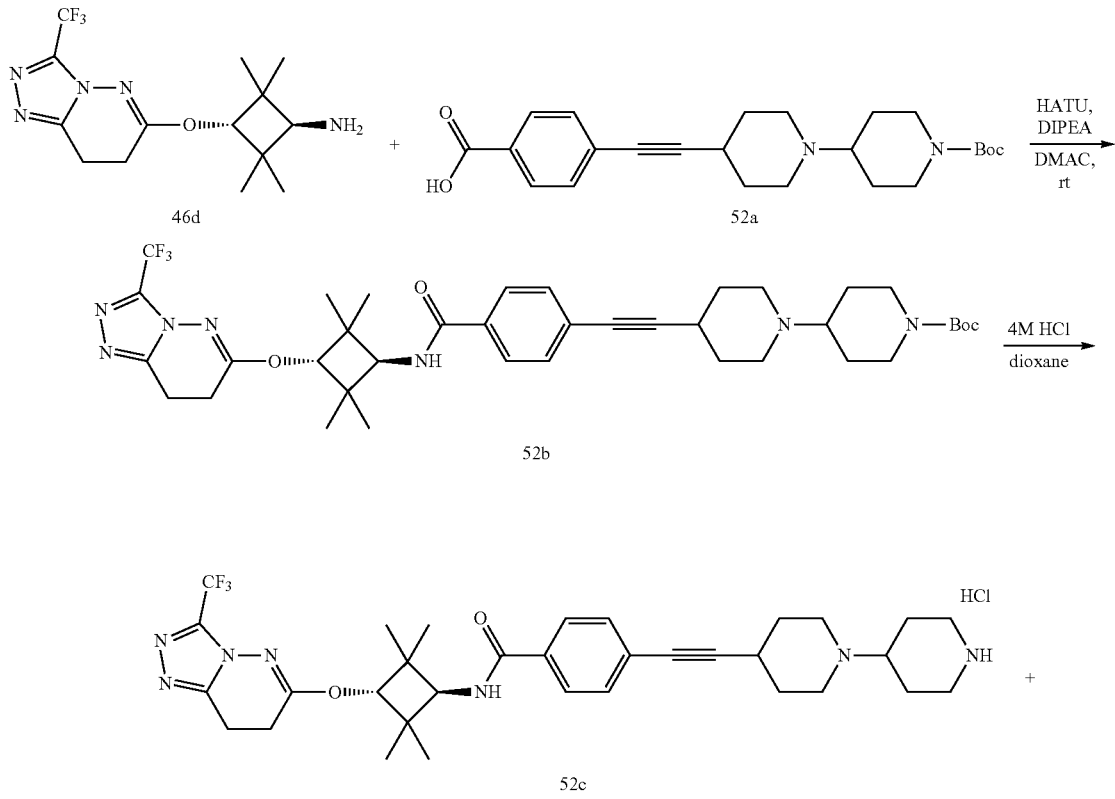

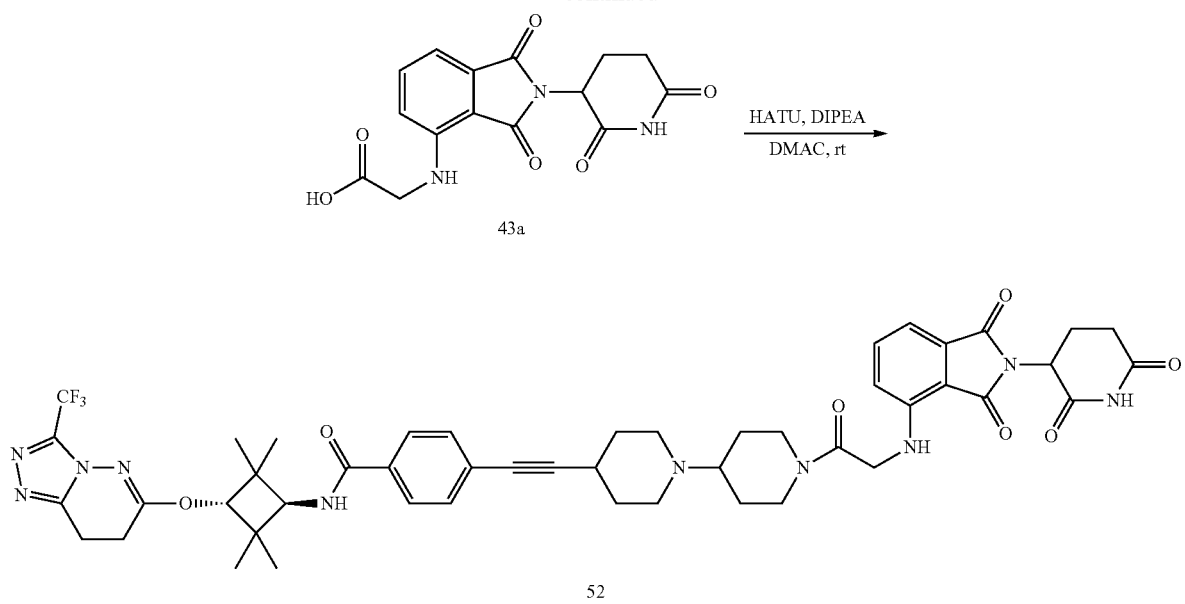

40-1. Preparation of tert-butyl 4-((4-(((1r,3r)-2,2,4,4-tetramethyl-3-((3-(trifluoromethyl)-7,8-dihydro-[1,2,4]triazolo[4,3-b]pyridazin-6-yl)oxy)cyclobutyl)carbamoyl)phenyl)ethynyl)-[1,4'-bipiperidine]-1'-carboxylate (52b)

This compound was prepared using a method similar to that used to prepare compound 1. The crude was purified by flash chromatography (MeOH/DCM=1/99→5/95) to obtain the title compound 52b (236 mg, 75%).

40-2. Preparation of 4-([1,4'-bipiperidin]-4-ylethynyl)-N-((1r,3r)-2,2,4,4-tetramethyl-3-((3-(trifluoromethyl)-7,8-dihydro-[1,2,4]triazolo[4,3-b]pyridazin-6-yl)oxy)cyclobutyl)benzamide (52c)

This compound was prepared using a method similar to that used to prepare compound 4d (238 mg, 98%).

40-3. Preparation of 4-((1'-((2-(2,6-dioxopiperidin-3-yl)-1,3-dioxoisoindolin-4-yl)glycyl)-[1,4'-bipiperidin]-4-yl)ethynyl)-N-((1r,3r)-2,2,4,4-tetramethyl-3-((3-(trifluoromethyl)-7,8-dihydro-[1,2,4]triazolo[4,3-b]pyridazin-6-yl)oxy)cyclobutyl)benzamide (52)

This compound was prepared using a method similar to that used to prepare compound 1. The crude product was purified by reverse phase preparative HPLC to obtain the title compound 52 (1 mg, 1%).

$^1$H-NMR (CD$_3$OD, 500 MHz) δ 7.8-7.65 (m, 2H), 7.6-7.4 (m, 3H), 7.1-7.0 (m, 2H), 5.2-5.0 (m, 2H), 4.63 (s, 1H), 4.4-4.1 (m, 4H), 3.6-3.4 (m, 4H), 3.2-2.6 (m, 9H), 2.4-1.6 (m, 10H), 1.26 (s, 6H), 1.25 (s, 6H).

41. Preparation of Compound 53

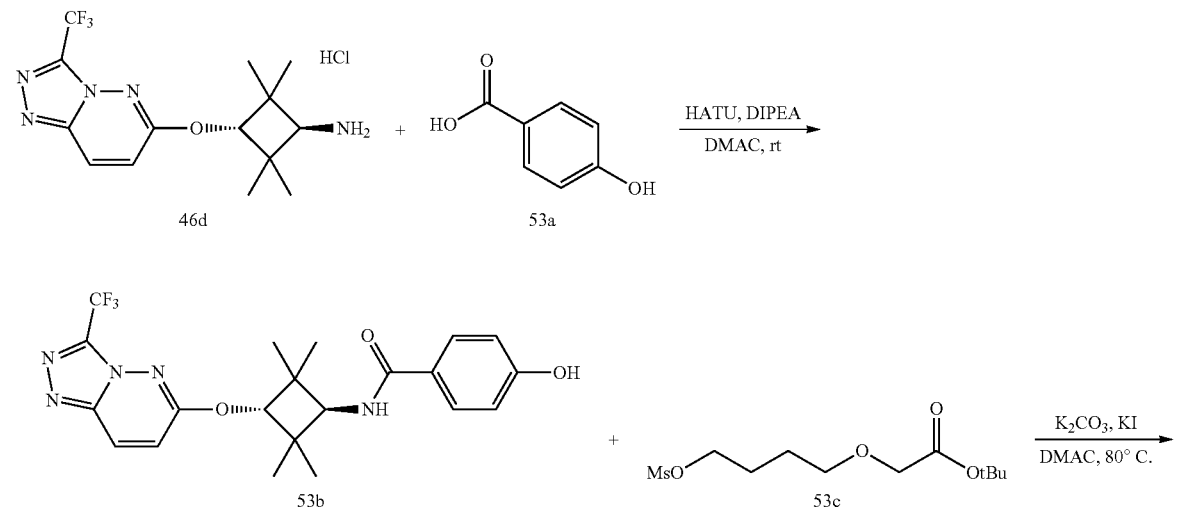

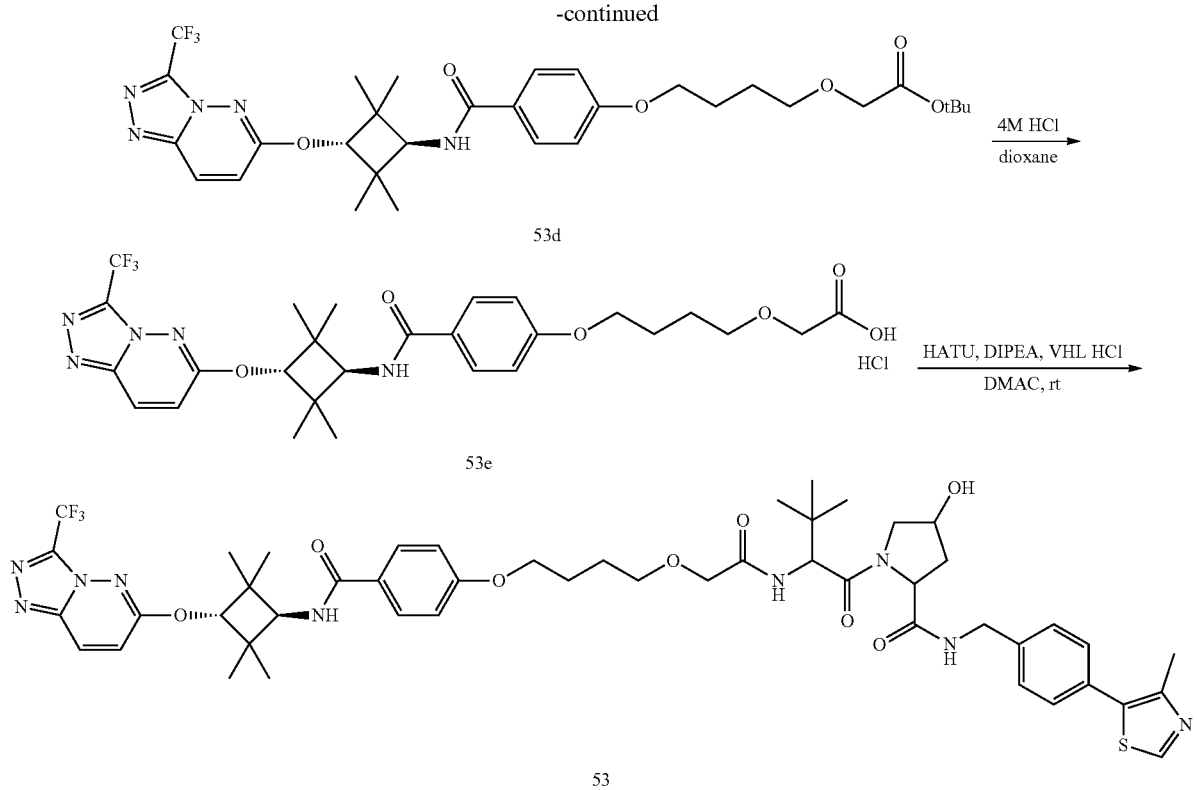

41-1. Preparation of 4-hydroxy-N-((1r,3r)-2,2,4,4-tetramethyl-3-((3-(trifluoromethyl)-[1,2,4]triazolo[4,3-b]pyridazin-6-yl)oxy)cyclobutyl)benzamide (53b)

This compound was prepared using a method similar to that used to prepare compound 1. The crude product was purified by flash chromatography (MeOH/DCM=1/99→5/95) to obtain the title compound 53b (310 mg, 55%).

41-2. Preparation of tert-butyl 2-(4-(4-(4-(((1r,3r)-2,2,4,4-tetramethyl-3-((3-(trifluoromethyl)-[1,2,4]triazolo[4,3-b]pyridazin-6-yl)oxy)cyclobutyl)carbamoyl)phenoxy)butoxy)acetate (53d)

This compound was prepared using a method similar to that used to prepare compound 44. The crude product was purified by flash chromatography (MeOH/DCM=1/99→5/95) to obtain the title compound 53d.

41-3. Preparation of 2-(4-(4-(((1r,3r)-2,2,4,4-tetramethyl-3-((3-(trifluoromethyl)-[1,2,4]triazolo[4,3-b]pyridazin-6-yl)oxy)cyclobutyl)carbamoyl)phenoxy)butoxy)acetic acid (53e)

This compound was prepared using a method similar to that used to prepare compound 4d (82 mg, 98%).

41-4. Preparation of 1-(3,3-dimethyl-2-(2-(4-(4-(((1r,3r)-2,2,4,4-tetramethyl-3-((3-(trifluoromethyl)-[1,2,4]triazolo[4,3-b]pyridazin-6-yl)oxy)cyclobutyl)carbamoyl)phenoxy)butoxy)acetamido)butanoyl)-4-hydroxy-N-(4-(4-methylthiazol-5-yl)benzyl)pyrrolidine-2-carboxamide (53)

This compound was prepared using a method similar to that used to prepare compound 1. The crude product was purified by reverse phase preparative HPLC to obtain the title compound (53 mg, 59%). LCMS [M+H]$^+$=993.6.

Example 2

In Vitro Experiment

A. Material

22Rv1 (ATCC® CRL-2505™), RPMI-1640 medium (Gibco, 11875-093), Dulbecco's Modified Eagle's Medium (DMEM), fetal bovine serum (Gibco, 10437-028), penicillin/streptomycin (Gibco, 15140-122).

B. Methods

1. Preparation of Compound Test Samples

Compound stock solutions of 10 mM were prepared with 100% DMSO and shaken for 10-15 seconds. The compound stock solutions were centrifuged at 12000 rpm (13523 rcf.) for 5 minutes and record the turbidity or precipitation state with a photo snapshot. The compound stock solutions were resuspended by shaking for 10-15 seconds, and serially diluted with 100% DMSO solution to make the compound concentration to 1000 μM, then to 100, 10, and 1 μM, and then 10-fold diluted with medium to 100, 10, 1, 0.1 μM (final 10% DMSO/medium) to complete compound test sample preparation. Compound treatment was performed by adding 10 μL of compound test sample to cells in each well of a 96-well plate (final 1% DMSO/medium).

2. Cytotoxicity Assay for Compounds

Cells (CWR22Rv1 cells or VCaP cells) were cultured in RPMI-1640 medium supplemented with 10% fetal bovine serum, 10,000 U/mL penicillin and 10,000 μg/mL streptomycin. Cells were cultured at 37° C. in a humidified 5% CO$_2$ incubator.

Cells were seeded in a 96-well plate (1×10$^4$ cells/well). 10 μL of the above compound test sample was added to each well of the 96-well plate on next day. After 72 hours of compound treatment, 10 μL of AlamaBlue reagent was added to each of 96 wells and incubated for 4 hours. The fluorescence value at Ex/Em=560/590 nm was read with a microplate reader, and the cytotoxicity (%) was calculated.

3. Analysis of Ability of Compound to Degrade Full-Length Androgen Receptor or Androgen Receptor Splice Variant 7

3-1. Western Blot

CWR22Rv1 cells were maintained in RPMI medium supplemented with 10% fetal bovine serum and 1% penicillin-streptomycin at 37° C. in a humidified environment with 5% $CO_2$.

CWR22Rv1 ($5\times10^5$ cells) were seeded in each well of a 6-well plate and incubated overnight. Before compound treatment, the medium in the wells was replaced with a new medium. Cells were treated with different concentrations of compound overnight. Subsequently, cells were harvested by adding cold PBS and scraping cells. Cells were lysed according to general procedures and Western blot assays were performed to assess the ability of compounds to degrade full-length androgen receptor or androgen receptor splice variant 7. The cells or cell lysates were kept on ice at all times.

The following reagents were used in this experiment. Phosphate buffered saline (PBS) (Hyclone, SH30028.02), fetal bovine serum (Hyclone, SH30084.23, Lot AC14563276), penicillin-streptomycin solution (Hyclone, SV30010), 0.5% Trypsin-EDTA (Gibco, 15400-054), CST Lysis Buffer (CST-9803), Halt™ Protease and Phosphatase Inhibitor (ThermoFisher, 78442), Coomassie (Bradford) Protein Assay (Coomassie (Bradford) protein assay) (ThermoFisher, 23200), androgen receptor antibody (Cell Siginaling, CST-5153S), GAPDH antibody (Cell Siginaling, CST-5174S), HRP-goat-anti-rabbit (Jackson Immuno Research, 111-035-003), skim milk, SuperSignal West Pico Maximum Sensitivity substrate (ThermoFisher, 34080).

B. Results

1. Cytotoxicity Assay for Compounds

According to the above method, the compounds prepared above were subjected to cytotoxicity test with CWR22RV1 cells and VCaP cells.

Figure 1B:
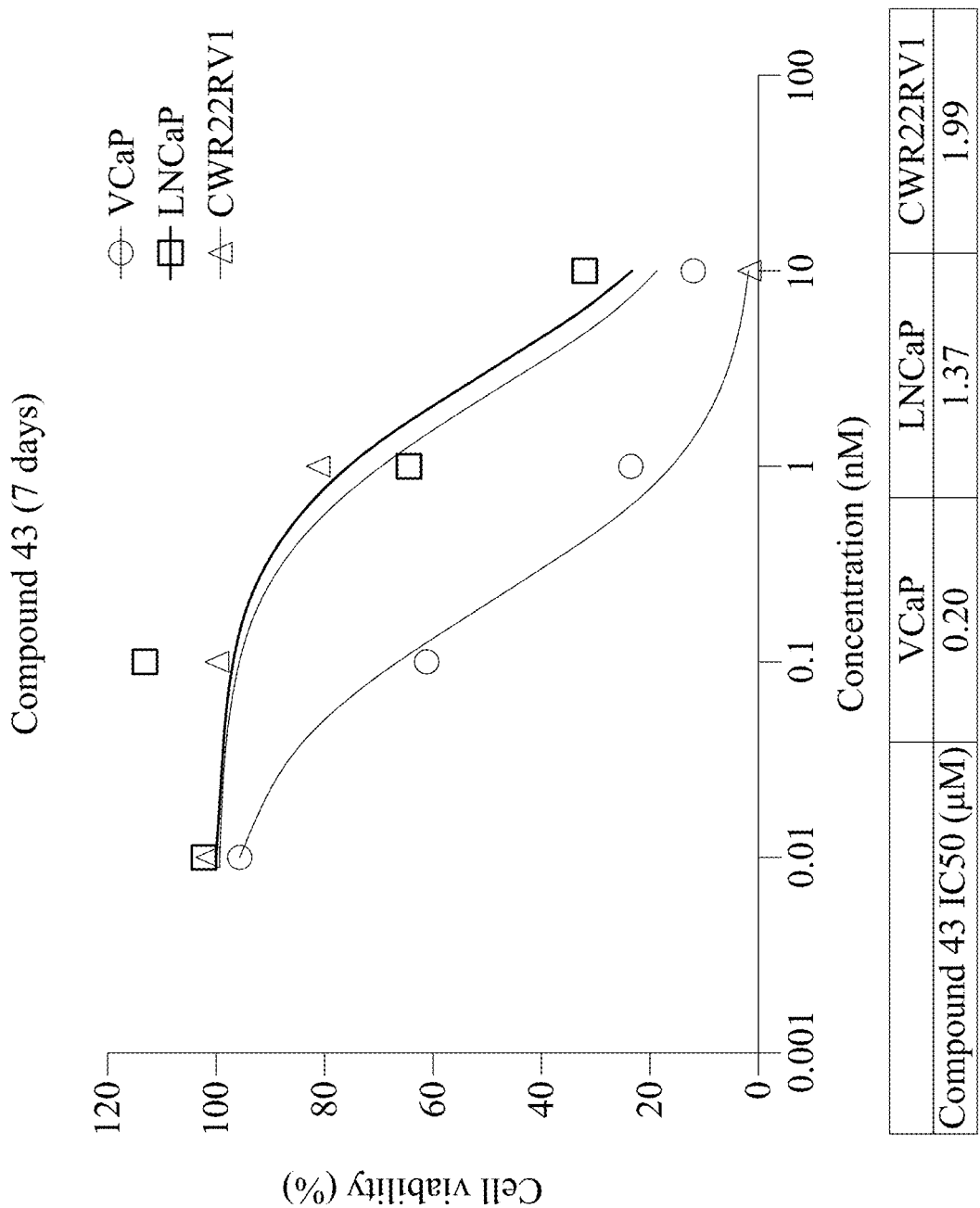
FIG. 1B shows the cell viability of cells treated with Compound 43.

The results are shown in Table 4 and FIG. 1A and FIG. 1B.

TABLE 4

Cytotoxicity of compounds

| Compound | Cytotoxicty | |
|---|---|---|
| | CWR22RV1 cells | VCaP cells |
| Compound 1 | +++ | +++ |
| Compound 2 | + | NA |
| Compound 3 | ++ | NA |
| Compound 4 | + | NA |
| Compound 5 | − | NA |
| Compound 7 | − | NA |
| Compound 6 | − | NA |
| Compound 29 | − | NA |
| Compound 8 | +++ | NA |
| Compound 19 | − | − |
| Compound 21 | +++ | + |
| Compound 22 | +++ | +++ |
| Compound 30 | +++ | +++ |
| Compound 20 | +++ | ++ |
| Compound 23 | +++ | +++ |
| Compound 13 | +++ | +++ |
| Compound 14 | +++ | +++ |
| Compound 31 | + | + |
| Compound 33 | − | +++ |
| Compound 34 | + | +++ |
| Compound 32 | + | ++ |
| Compound 9 | ++ | +++ |
| Compound 35 | +++ | +++ |
| Compound 36 | +++ | +++ |
| Compound 37 | +++ | +++ |
| Compound 38 | +++ | +++ |
| Compound 39 | +++ | +++ |
| Compound 40 | ++ | ++ |
| Compound 41 | ++ | +++ |
| Compound 42 | + | + |
| Compound 43 | +++ | +++ |
| Compound 44 | +++ | +++ |
| Compound 45 | + | +++ |
| Compound 46 | − | ++ |
| Compound 47 | − | ++ |
| Compound 48 | − | − |
| Compound 49 | ++ | +++ |
| Compound 53 | +++ | +++ |
| Compound 52 | +++ | +++ |
| Compound 51 | +++ | +++ |

Cell viability (%):
<40%: +++; 40-60%: ++; 60-80%: +; <80%: −

According to Table 4 and FIGS. 1A and 1, it is known that most of the compounds of the present disclosure have the ability to kill prostate cancer cells.

2. Analysis of Ability of Compound to Degrade Full-Length Androgen Receptor or Androgen Receptor Splice Variant 7

The compound prepared above was analyzed for its ability to degrade full-length androgen receptor and androgen receptor splice variant 7 in CWR22RV1 cells by Western blotting according to the method shown in item B.3-2 above.

Figure 2A:
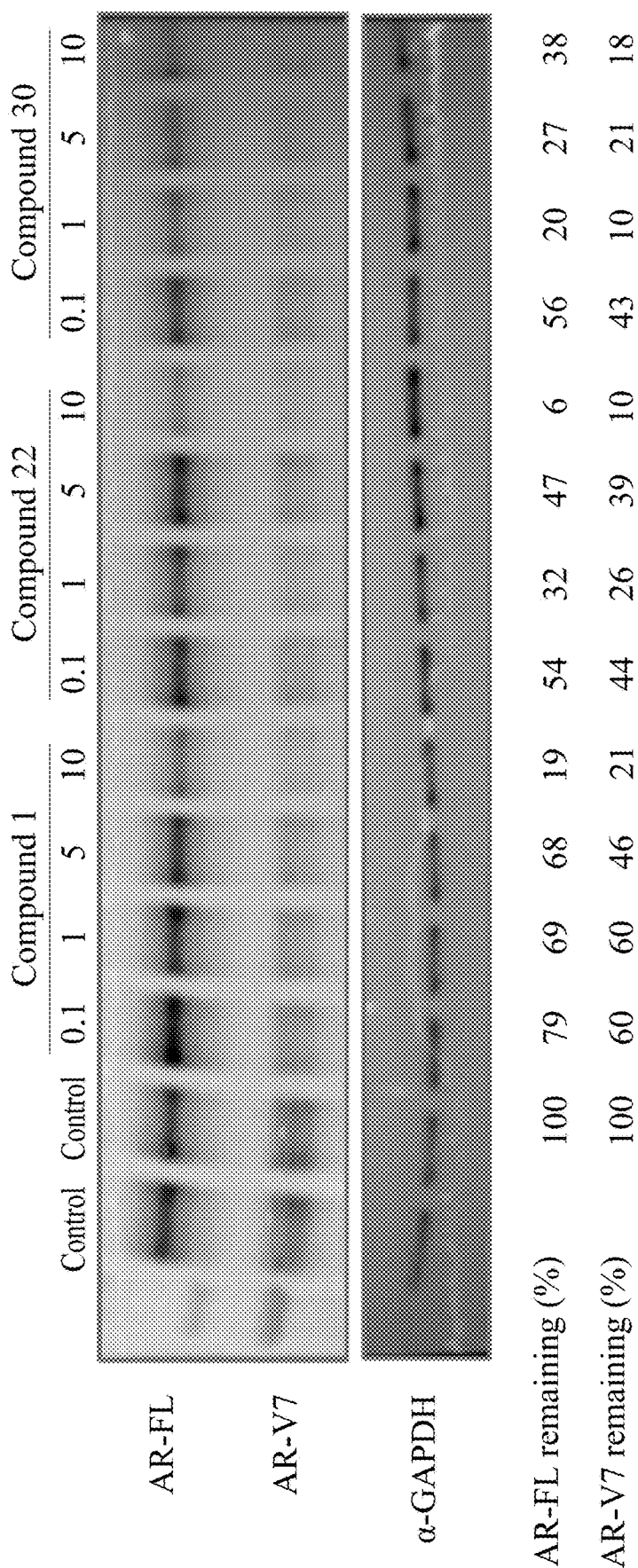
FIG. 2A shows the degradation of full-length androgen receptor and androgen receptor splice variant 7 (AR-V7) of cells respectively treated with Compound 1, Compound 22 and Compound 30.
Figure 2B:
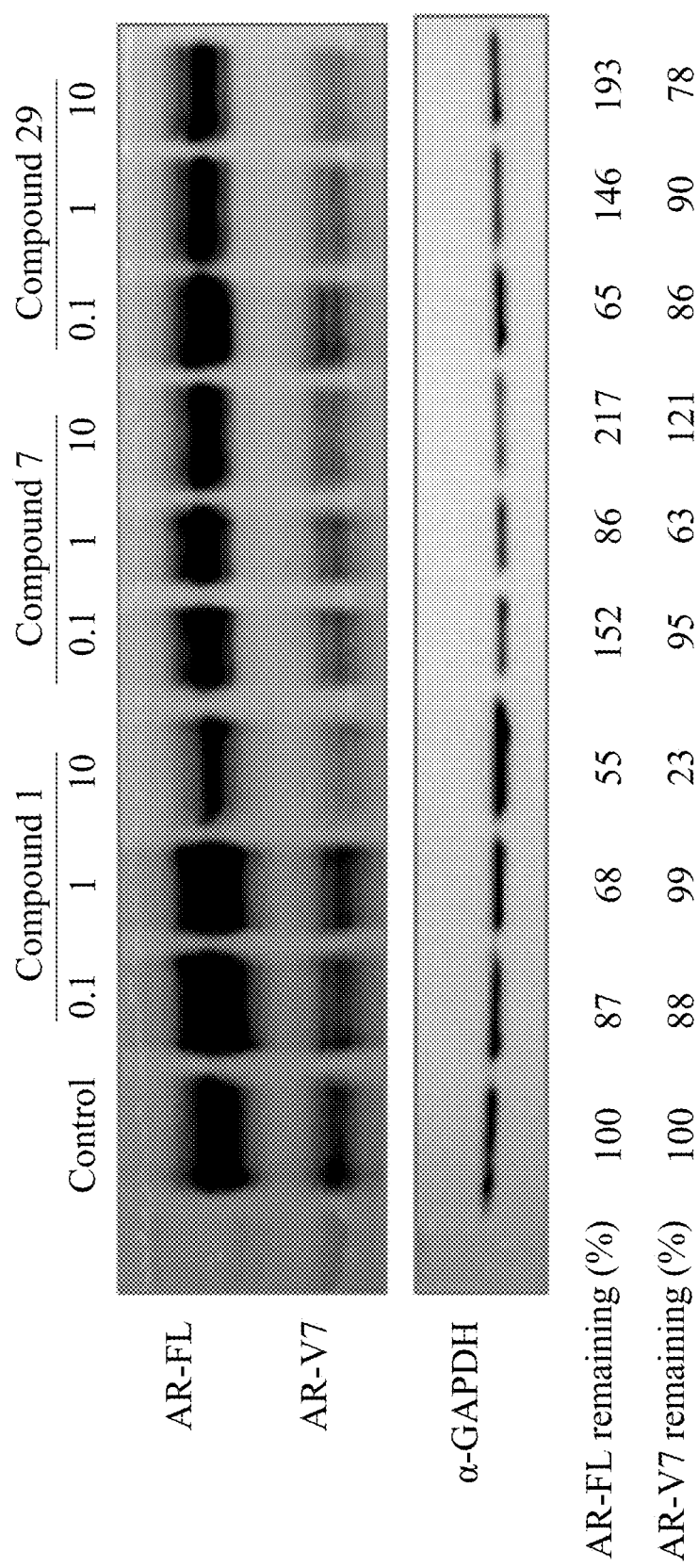
FIG. 2B shows the degradation of full-length androgen receptor and androgen receptor splice variant 7 of cells respectively treated with Compound 1, Compound 7 and Compound 29.
Figure 2C:
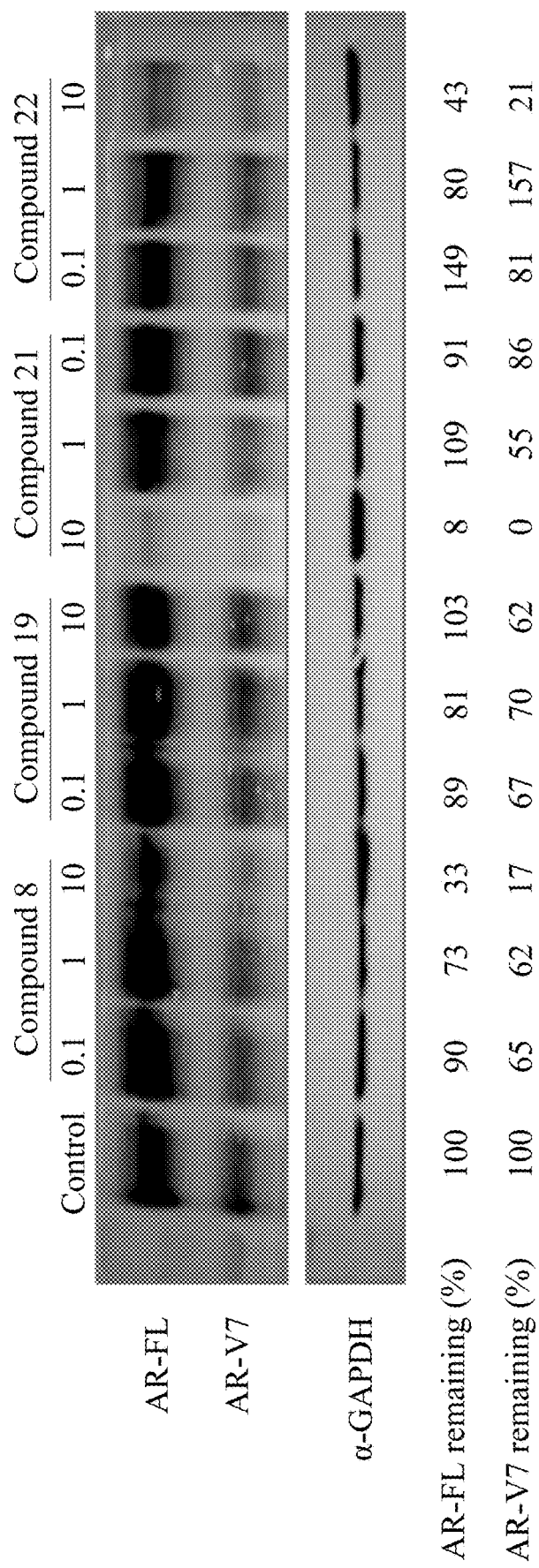
FIG. 2C shows the degradation of full-length androgen receptor and androgen receptor splice variant 7 of cells respectively treated with Compound 8, Compound 19, Compound 21 and Compound 22.
Figure 2D:
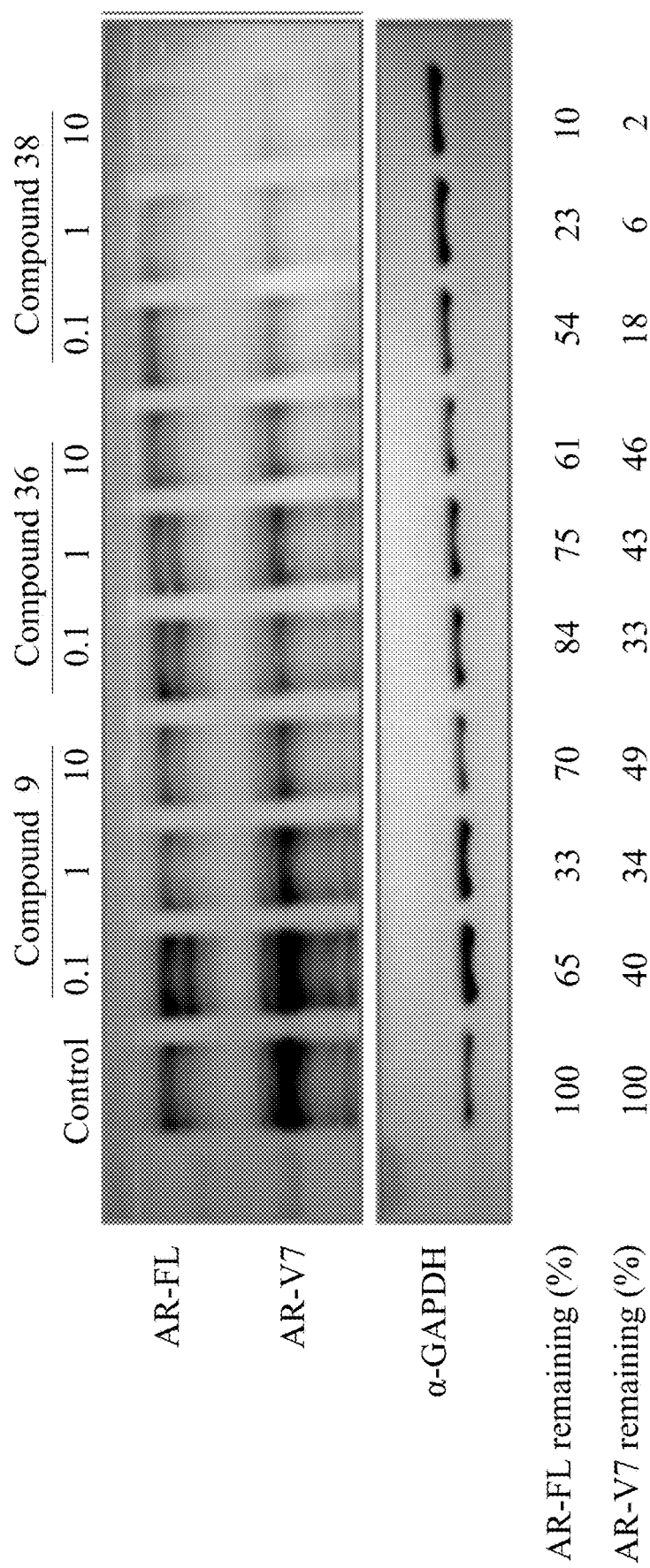
FIG. 2D shows the degradation of full-length androgen receptor and androgen receptor splice variant 7 of cells respectively treated with Compound 9, Compound 36 and Compound 38.
Figures 2E, 2F:
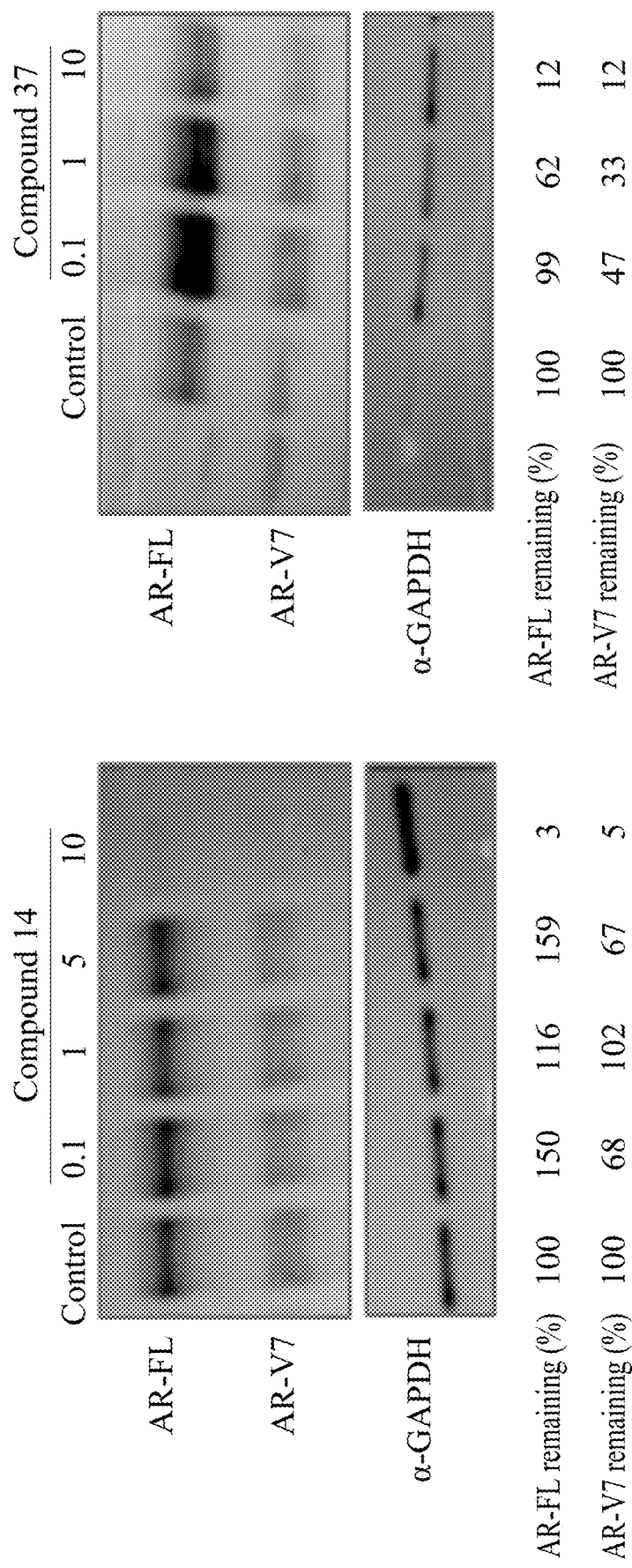
FIG. 2E shows the degradation of full-length androgen receptor and androgen receptor splice variant 7 in cells treated with Compound 14.
FIG. 2F shows the degradation of full-length androgen receptor and androgen receptor splice variant 7 in cells treated with compound 37.
Figure 2G:
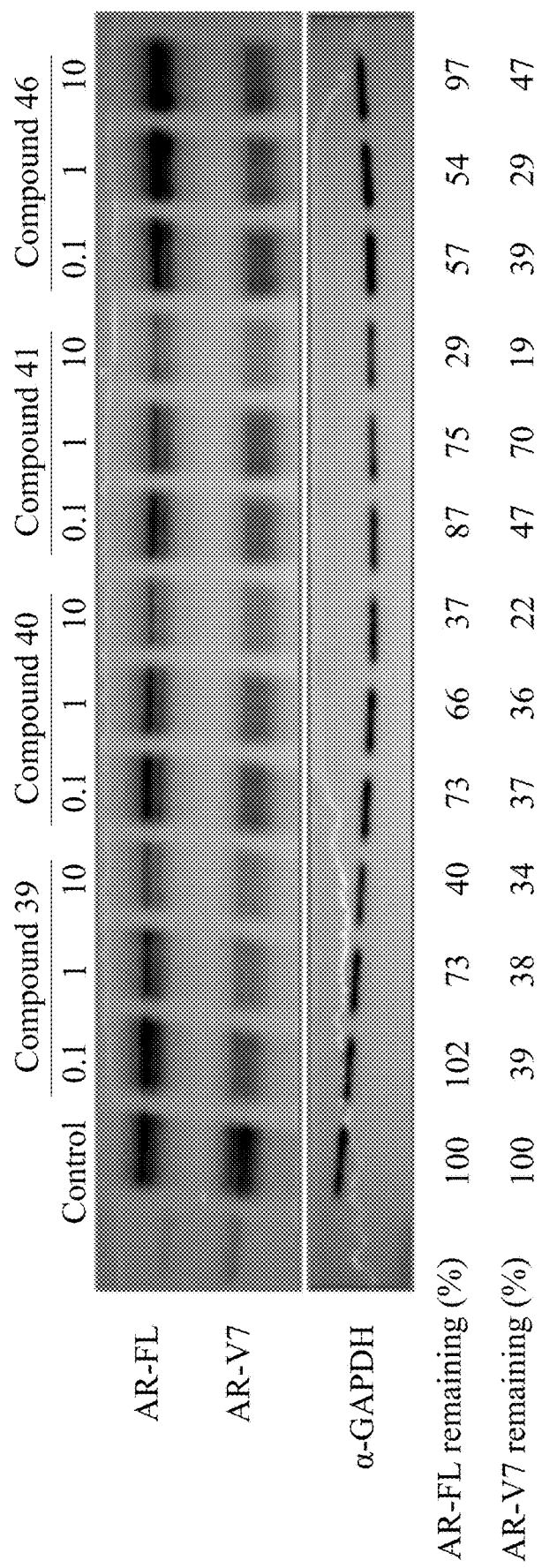
FIG. 2G shows the degradation of full-length androgen receptor and androgen receptor splice variant 7 of cells treated respectively with Compound 39, Compound 40, Compound 41 and Compound 46.
Figures 2H, 2I:
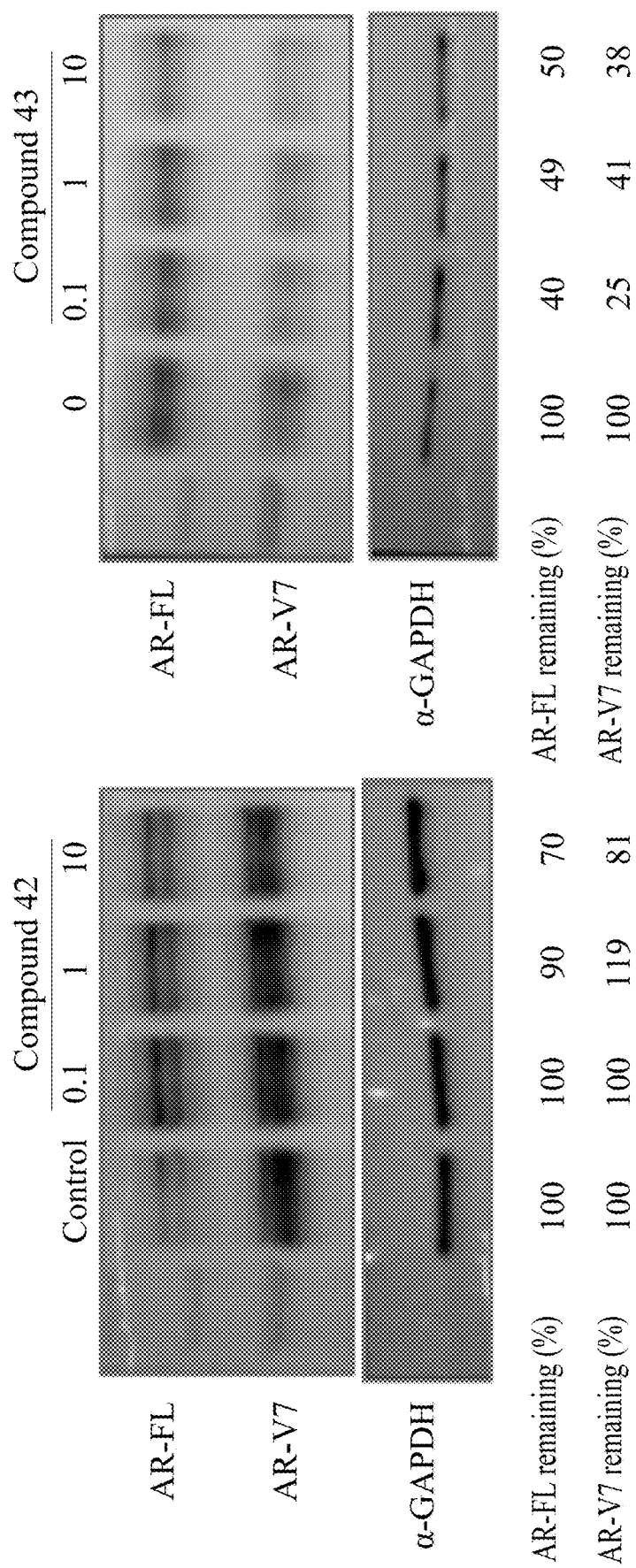
FIG. 2H shows the degradation of full-length androgen receptor and androgen receptor splice variant 7 in cells treated with Compound 42.
FIG. 2I shows the degradation of full-length androgen receptor and androgen receptor splice variant 7 in cells treated with Compound 43.
Figure 2J:
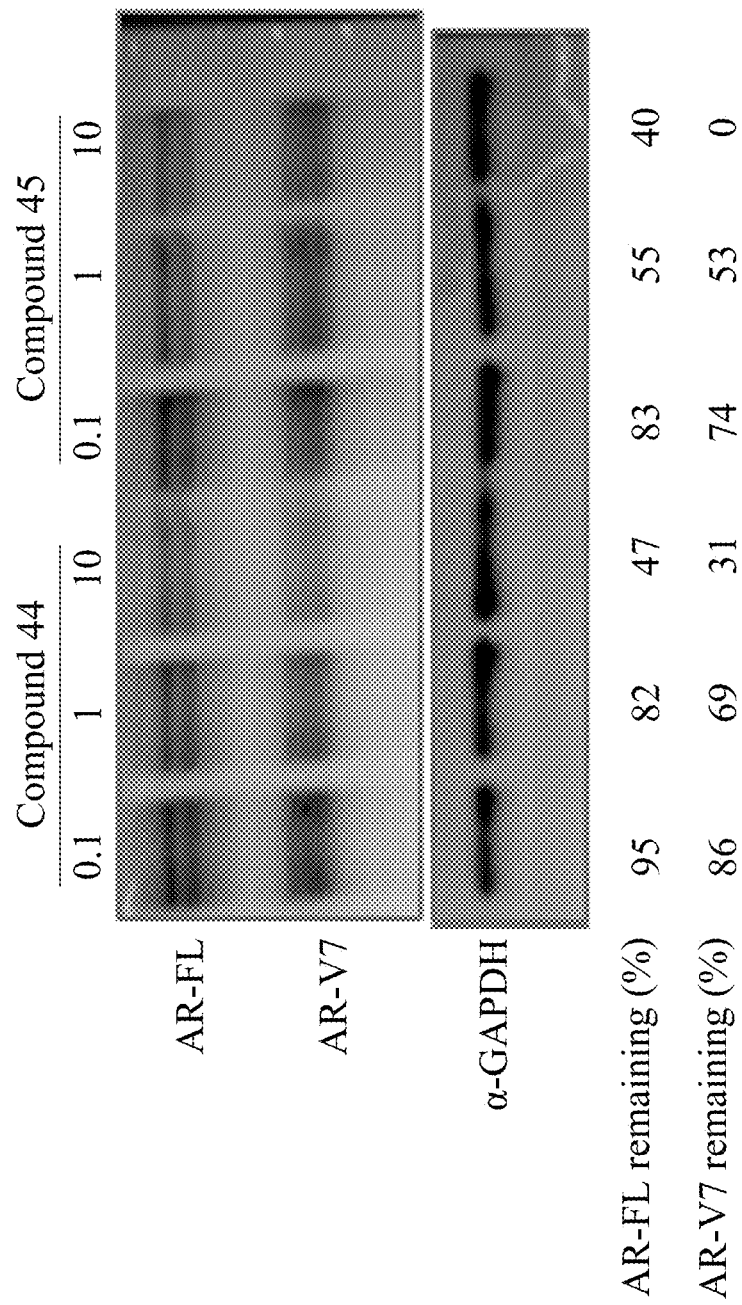
FIG. 2J shows the degradation of full-length androgen receptor and androgen receptor splice variant 7 of cells respectively treated with Compound 44 and Compound 45.
Figure 2K:
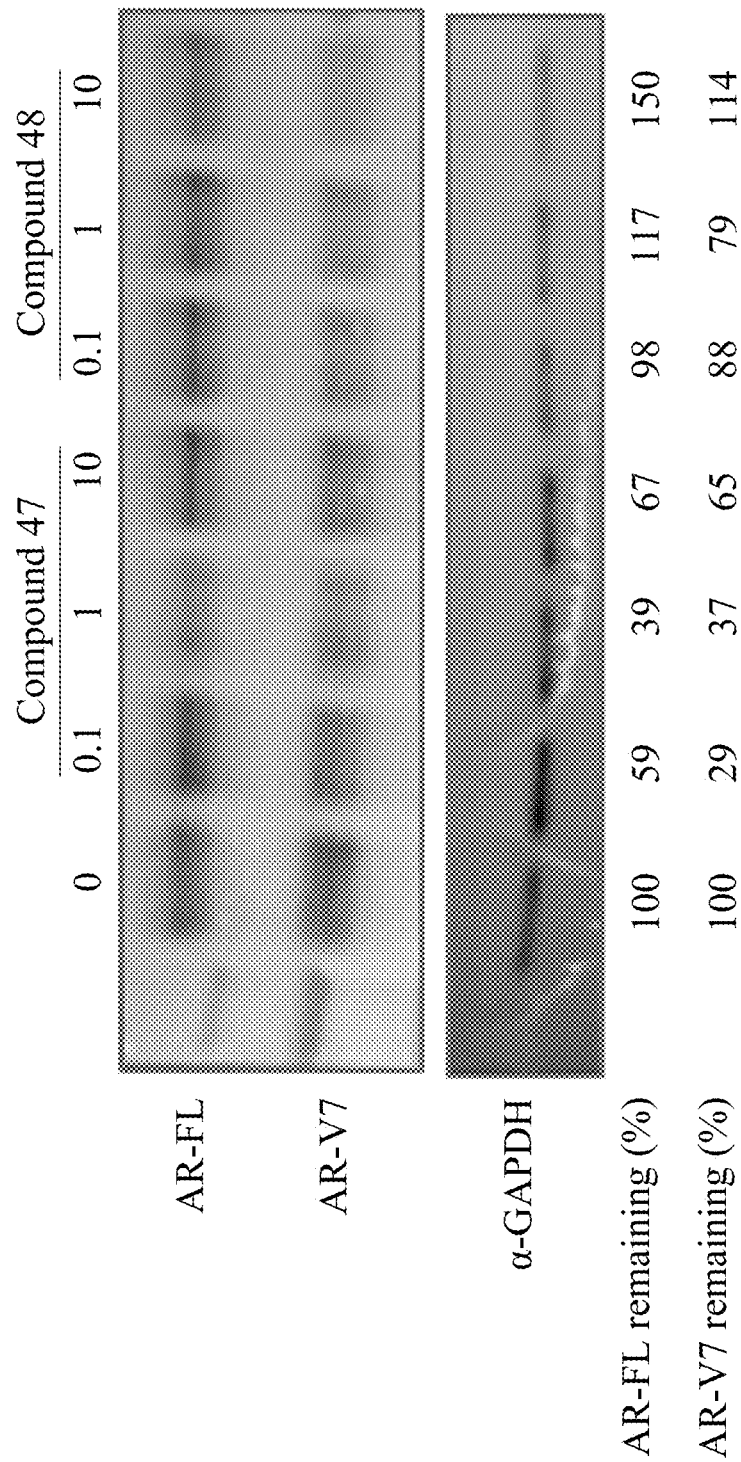
FIG. 2K shows the degradation of full-length androgen receptor and androgen receptor splice variant 7 in cells treated respectively with Compound 47 and Compound 48.
Figures 2L, 2M:
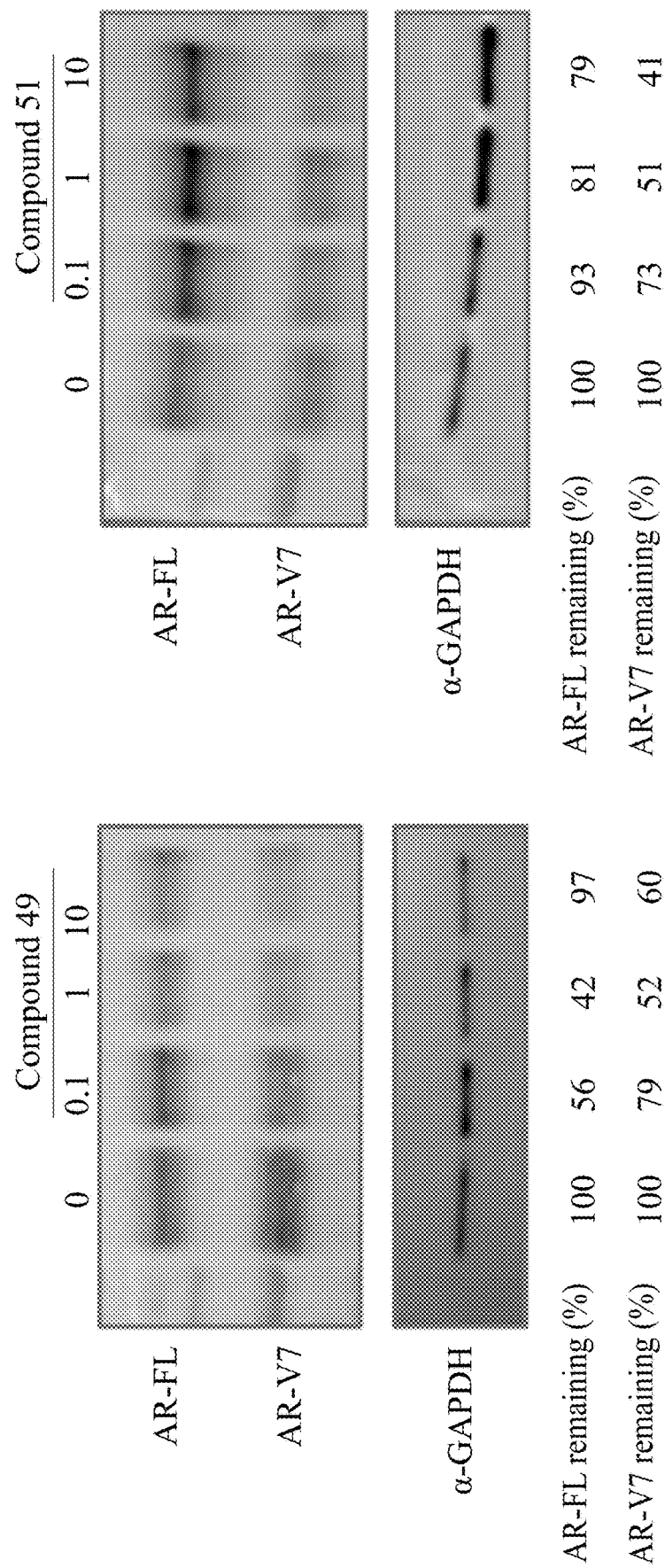
FIG. 2L shows the degradation of full-length androgen receptor and androgen receptor splice variant 7 in cells treated with Compound 49.
FIG. 2M shows the degradation of full-length androgen receptor and androgen receptor splice variant 7 in cells treated with Compound 51.
Figures 2N, 2O:
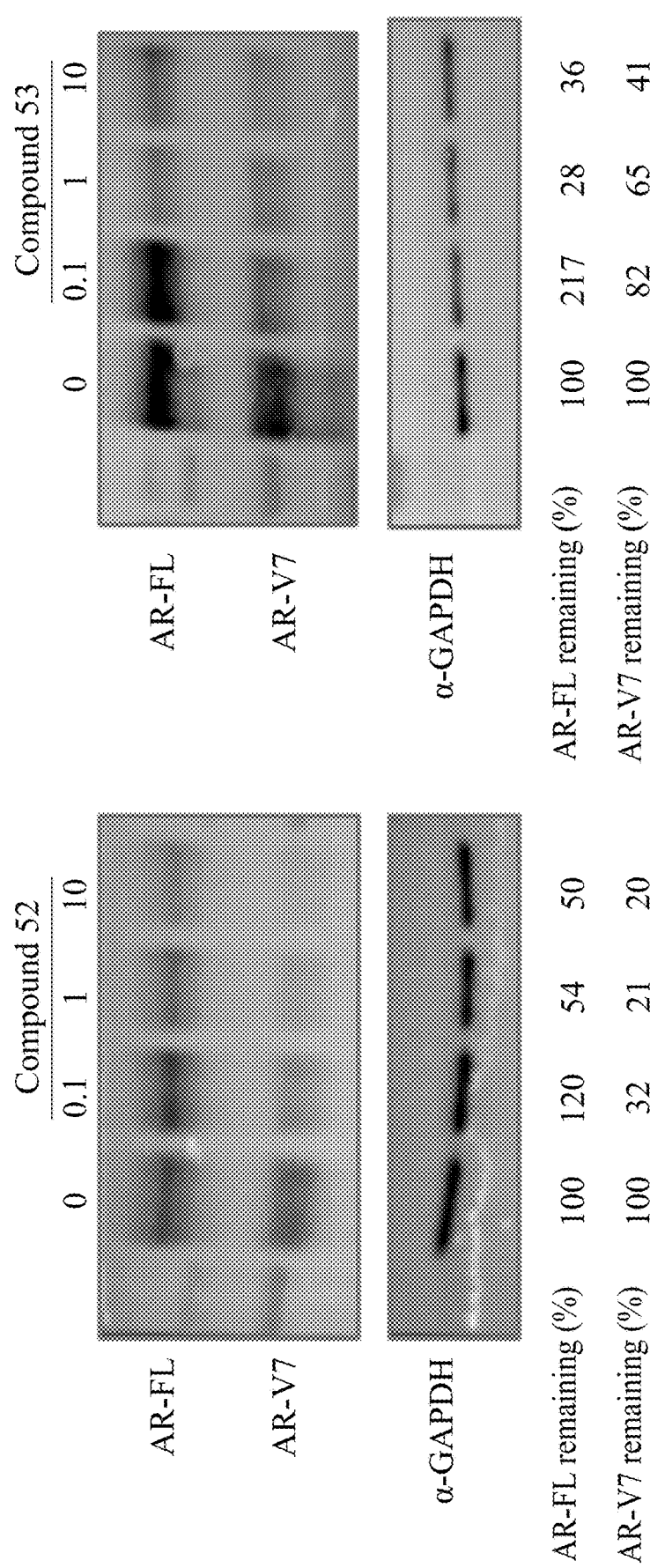
FIG. 2N shows the degradation of full-length androgen receptor and androgen receptor splice variant 7 in cells treated with Compound 52.
FIG. 2O shows the degradation of full-length androgen receptor splice variant 7 in cells treated with Compound 53.

The results are as shown in Table 5 and FIG. 2A to FIG. 2O.

TABLE 5

| Compound | Degradation ability for full-length androgen receptor | | | Degradation ability for androgen receptor alternative splicing variant 7 | | |
|---|---|---|---|---|---|---|
| concentration | 10 | 1 | 0.1 | 10 | 1 | 0.1 |
| Compound 1 | +++ | + | + | +++ | + | + |
| Compound 2 | NA | NA | NA | NA | NA | NA |
| Compound 3 | NA | NA | NA | NA | NA | NA |
| Compound 4 | NA | NA | NA | NA | NA | NA |
| Compound 5 | NA | NA | NA | NA | NA | NA |
| Compound 7 | − | − | − | − | + | − |
| Compound 6 | NA | NA | NA | NA | NA | NA |
| Compound 29 | − | − | + | + | − | − |

TABLE 5-continued

| Compound | Degradation ability for full-length androgen receptor | | | Degradation ability for androgen receptor alternative splicing variant 7 | | |
|---|---|---|---|---|---|---|
| Compound concentration | 10 | 1 | 0.1 | 10 | 1 | 0.1 |
| Compound 8 | +++ | + | − | +++ | + | + |
| Compound 19 | − | − | − | + | + | + |
| Compound 21 | +++ | − | − | +++ | ++ | − |
| Compound 22 | +++ | +++ | ++ | +++ | +++ | ++ |
| Compound 30 | +++ | +++ | ++ | +++ | +++ | ++ |
| Compound 20 | NA | NA | NA | NA | NA | NA |
| Compound 23 | NA | NA | NA | NA | NA | NA |
| Compound 13 | NA | NA | NA | NA | NA | NA |
| Compound 14 | +++ | − | − | +++ | − | + |
| Compound 31 | NA | NA | NA | NA | NA | NA |
| Compound 33 | NA | NA | NA | NA | NA | NA |
| Compound 34 | NA | NA | NA | NA | NA | NA |
| Compound 32 | NA | NA | NA | NA | NA | NA |
| Compound 9 | + | +++ | + | ++ | +++ | ++ |
| Compound 35 | NA | NA | NA | NA | NA | NA |
| Compound 36 | + | + | − | ++ | ++ | +++ |
| Compound 37 | +++ | + | − | +++ | +++ | ++ |
| Compound 38 | +++ | +++ | ++ | +++ | +++ | +++ |
| Compound 39 | ++ | + | − | +++ | +++ | +++ |
| Compound 40 | +++ | + | + | +++ | +++ | +++ |
| Compound 41 | +++ | + | − | +++ | +++ | +++ |
| Compound 42 | + | − | − | − | − | − |
| Compound 43 | ++ | ++ | ++ | +++ | ++ | +++ |
| Compound 44 | ++ | − | − | +++ | + | − |
| Compound 45 | ++ | ++ | − | +++ | ++ | + |
| Compound 46 | − | ++ | ++ | ++ | − | +++ |
| Compound 47 | + | +++ | ++ | + | − | +++ |
| Compound 48 | − | − | − | − | + | − |
| Compound 49 | − | ++ | ++ | + | ++ | + |
| Compound 53 | +++ | +++ | − | ++ | + | − |
| Compound 52 | ++ | ++ | − | +++ | +++ | +++ |
| Compound 51 | + | − | − | ++ | ++ | + |

Residual rate (%) of full-length androgen receptor or androgen receptor splice variant 7 in CWR22RV1 cells:
<40%: +++; 40-60%: ++; 60-80%: +; >80%; −

According to Table 5 and FIGS. 2A to 2O, it is known that the compounds of the present disclosure generally have the ability to degrade both the full-length androgen receptor and the androgen receptor splice variant 7.

Example 3

Animal Experiment
A. Methods
Mice: Male SCID mice (CB17/Icr-Prkdcscid/IcrIcoCrl-Bltw, 4-6 weeks old, purchased from BioLASCO Taiwan Co., Ilan, Taiwan.)

The cells were harvested when CWR22Rv1 cells or VCaP cells were cultured to exponential growth phase, and then the cells were washed twice with PBS. Then, for CWR22Rv1 cells, $5 \times 10^6$ cells were suspended in 100 μL PBS containing 33% Matrigel to form a cell suspension; for VCaP cells, $3 \times 10^6$ cells were suspended in 100 μL PBS containing 50% Matrigel to form a cell suspension cell suspension. Then, the above cell suspension was subcutaneously implanted into the right back of male SCID mice with a 25G needle.

After cell inoculation, when the average tumor volume reached 100-150 cm³ or the tumor clearly began to grow, the mice were divided into a vehicle-treated group (n=4-8), 5 mg/kg Compound 1 treated group (n=4-8) and 30 mg/kg Compound 1 treatment group (n=4-8), and administered by intraperitoneal injection (IP), twice daily (BID). The vehicle was 10% N-methylpyrrolidone (NMP, N-Methyl-2-pyrrolidone) and 20% castor oil polyoxyethylene ether (Cremophor EL) in PBS buffer solution. Tumor volume and animal body weight were determined three times a week after dosing.

Tumor size was measured with a caliper and converted to tumor volume (cm³; V) using the formula: $V=0.5 \times [Length \times (Width)^2]$ Antitumor activity was expressed as tumor growth inhibition (TGI). The calculation method is [1−(Final tumor volume of treatment group−Initial tumor volume of treatment group)/(Final tumor volume of control group−Initial tumor volume of control group)]×100%.

Data are presented as mean±standard deviation (SEM).

All relevant animal handling, care and treatment procedures in this study have been approved by the Animal Care and Use Committee (IACUC), with case numbers ITRI-IACUC-2020-011 and ITRI-IACUC-2020-014.
B. Results
The results are shown in FIG. 3.

Figure 3:
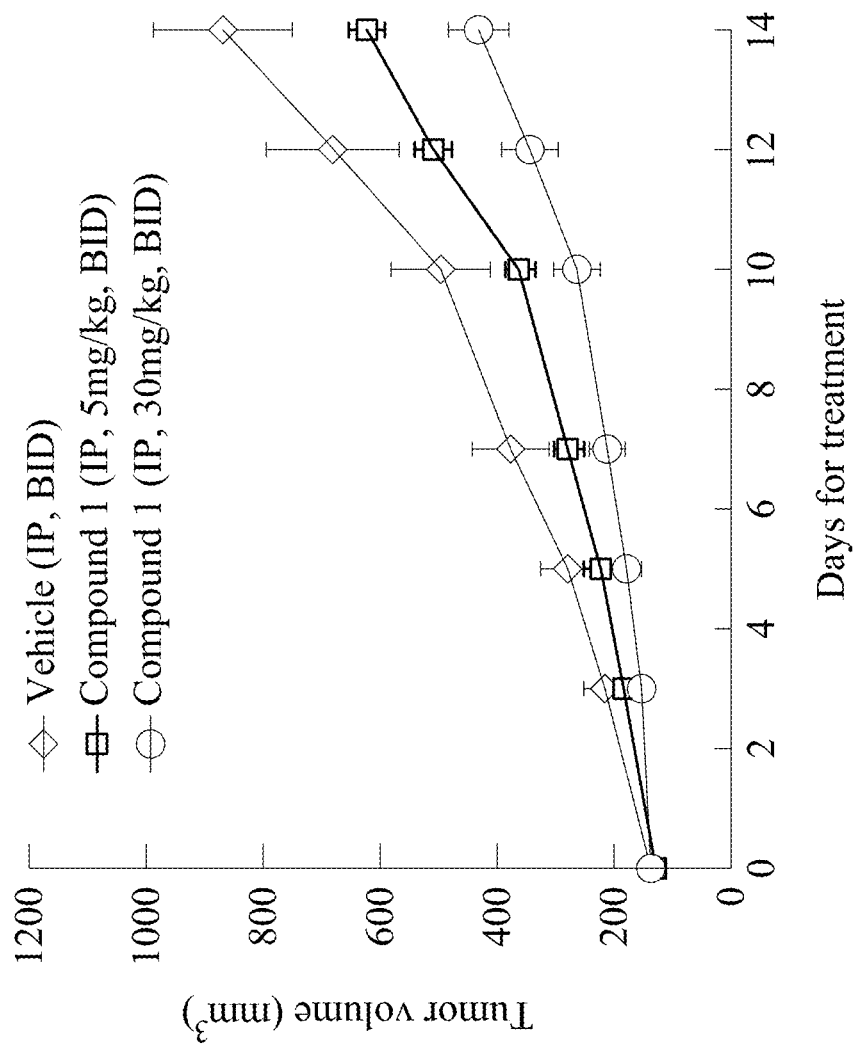
FIG. 3 shows the change in tumor size in animals treated with Compound 1.

According to FIG. 3, it is known that compared to the vehicle treatment, the increase in tumor size of the animals treated with Compound 1 of the present disclosure tends to slow down.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:
1. A compound selected from the group consisting of the compounds as shown below:
| Compound number | Structure |
|---|---|
| 1 | 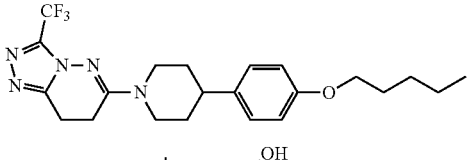 |
| 2 | 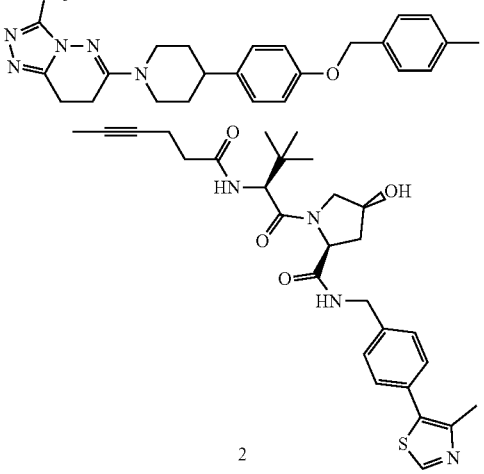 |
| 3 | 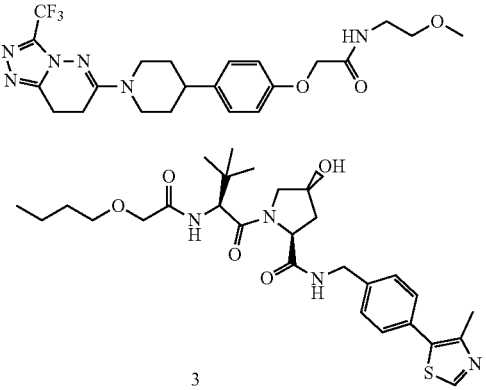 |
| 4 | 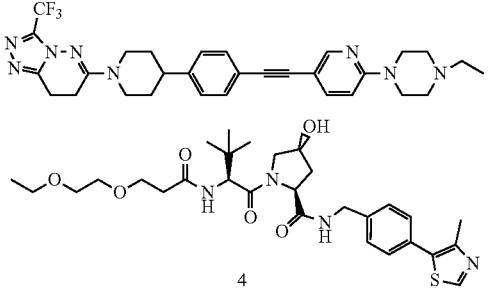 |
| 5 | 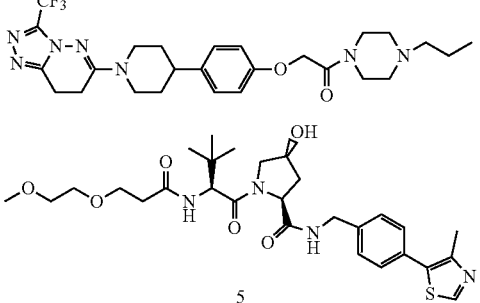 |
| 6 | 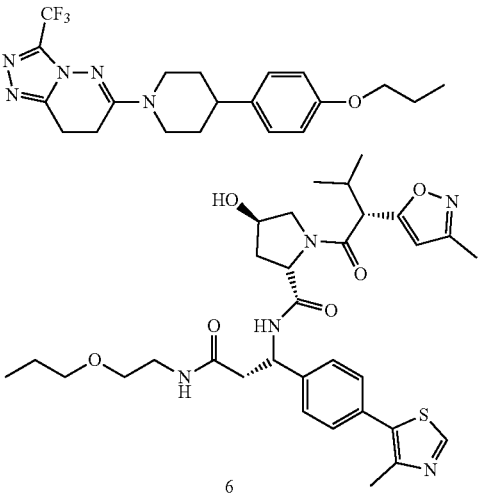 |
| 7 | 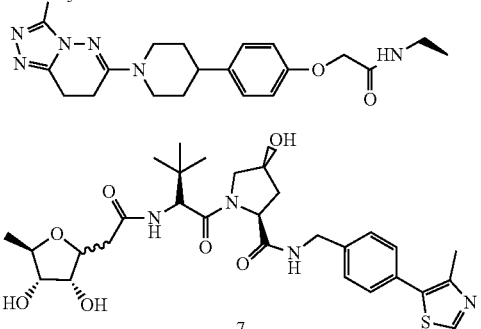 |

-continued
| Compound number | Structure |
|---|---|
| 8 | 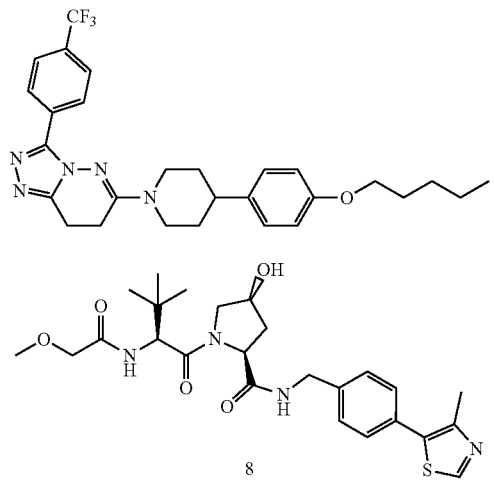 |
| 9 | 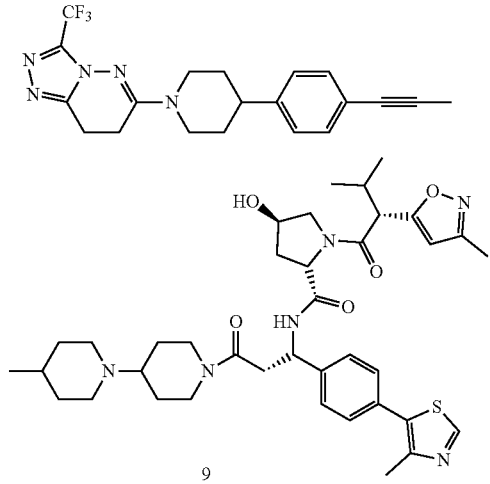 |
| 10 | 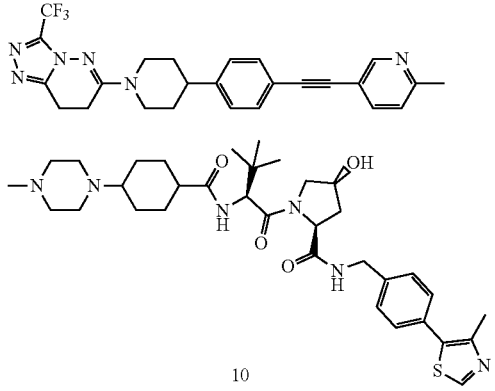 |
-continued
| Compound number | Structure |
|---|---|
| 11 | 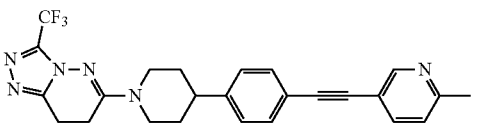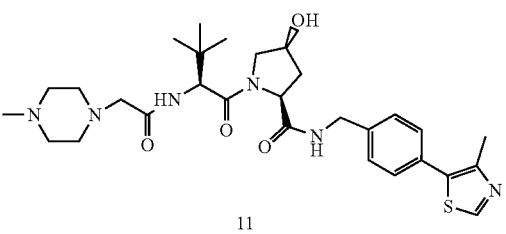 |
| 12 | 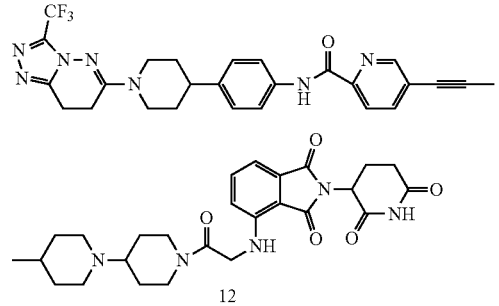 |
| 13 | 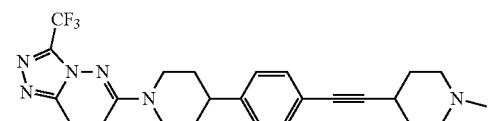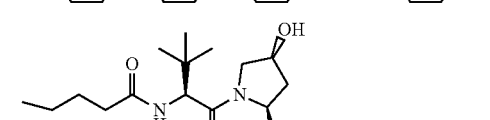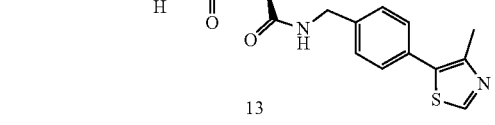 |

| Compound number | Structure |
|---|---|
| 14 | 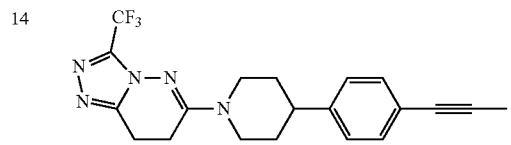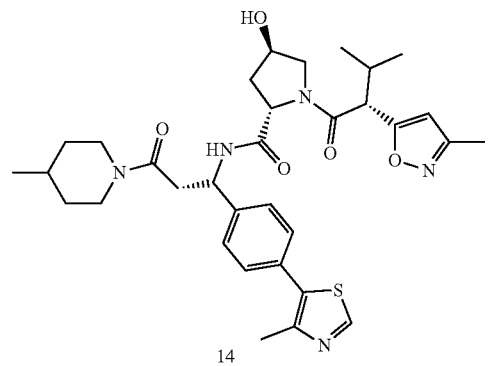 |
| 15 | 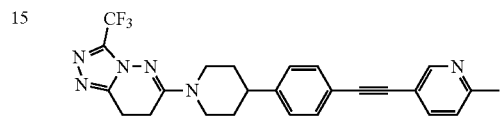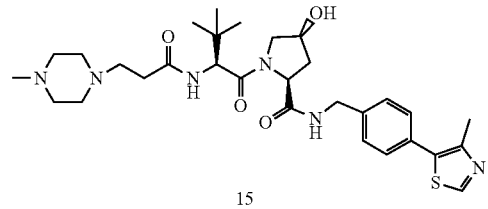 |
| 16 | 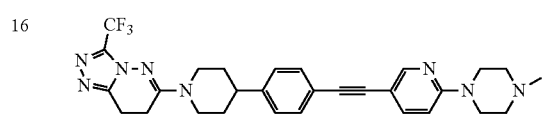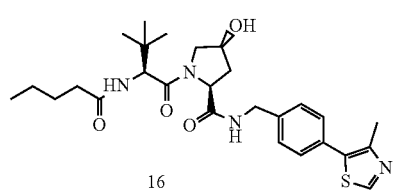 |
| 17 | 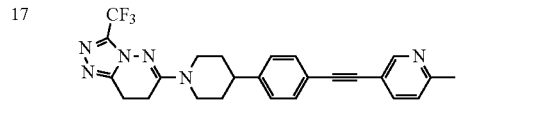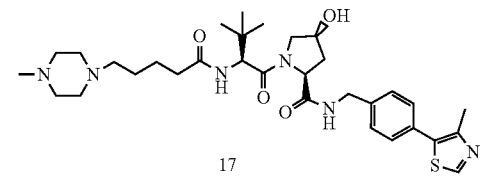 |
| Compound number | Structure |
|---|---|
| 18 | 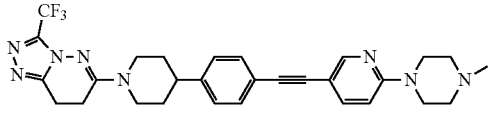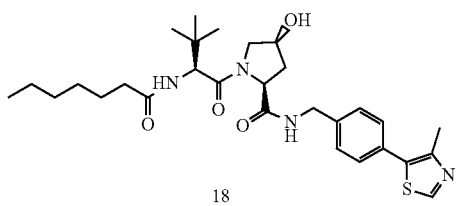 |
| 19 | 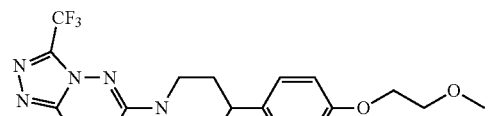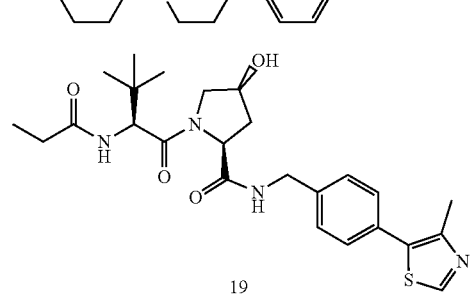 |
| 20 | 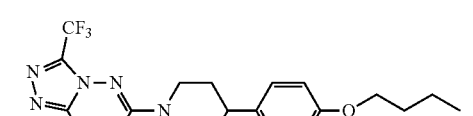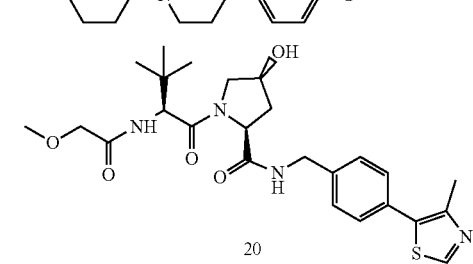 |
| 21 | 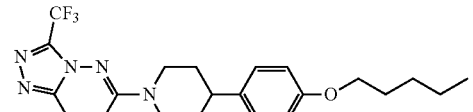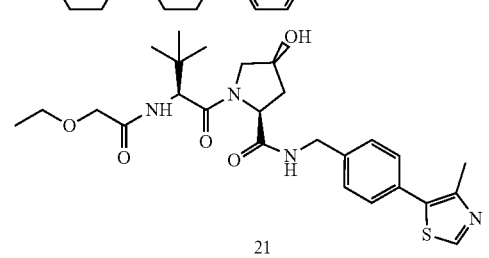 |

-continued
| Compound number | Structure |
|---|---|
| 22 | 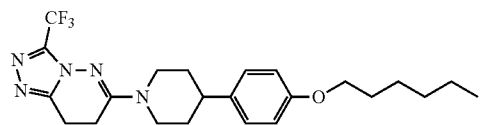 |
| 23 | 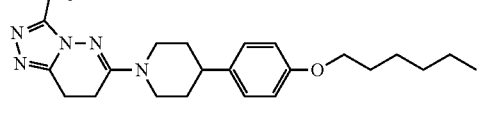 |
| 24 | 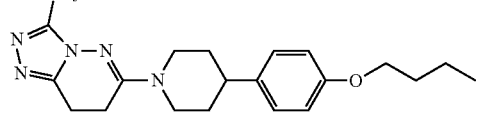 |
-continued
| Compound number | Structure |
|---|---|
| 25 | 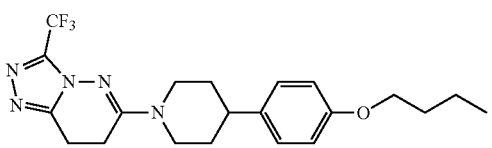 |
| 26 | 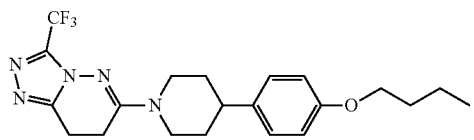 |
| 27 | 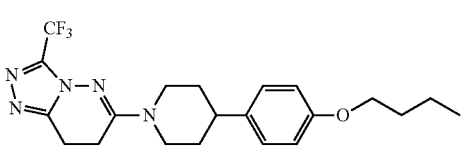 |

| Compound number | Structure |
|---|---|
| 28 | 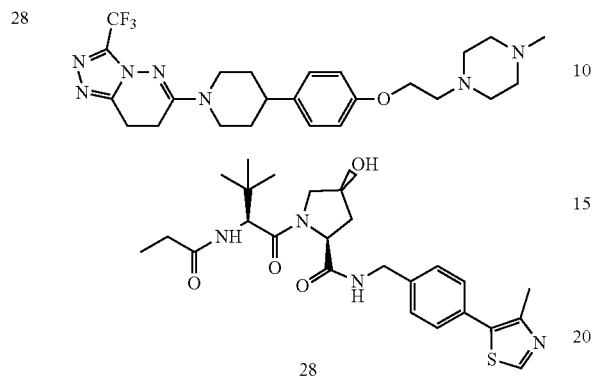 |
| 29 | 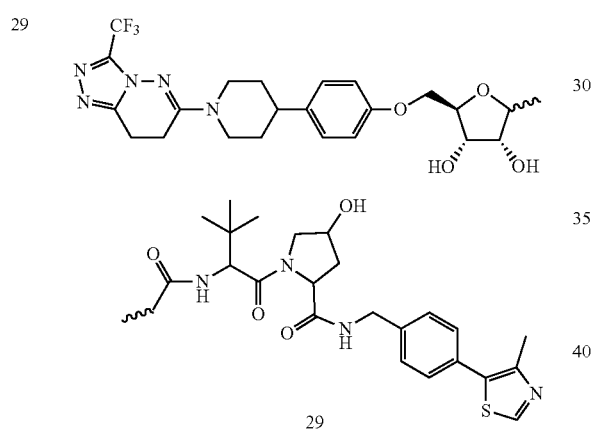 |
| 30 | 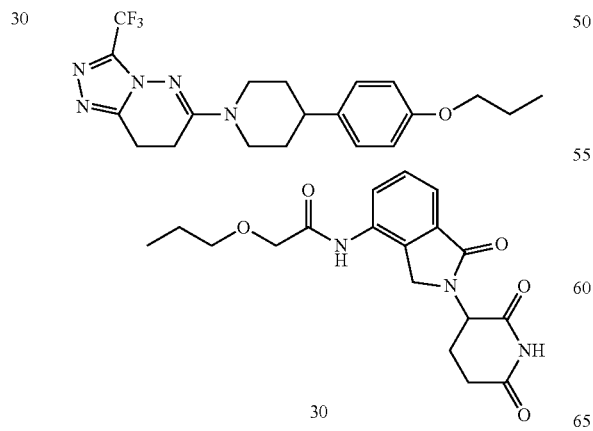 |
| Compound number | Structure |
|---|---|
| 31 | 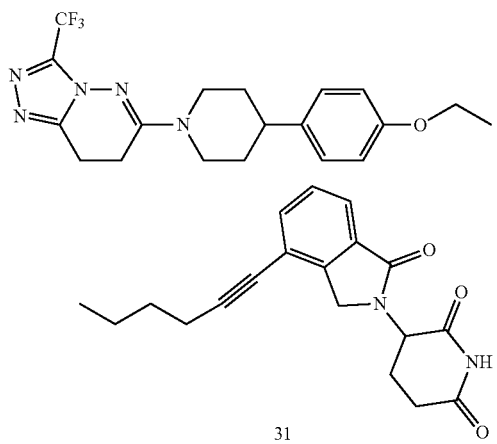 |
| 32 | 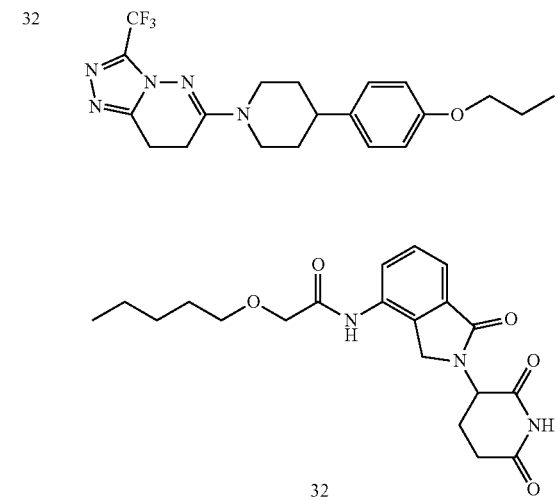 |
| 33 | 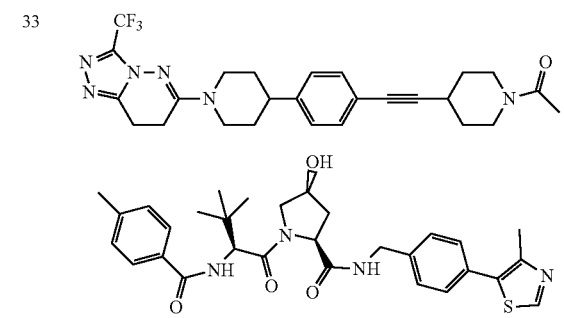 |

| Compound number | Structure |
|---|---|
| 34 | 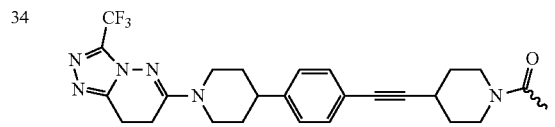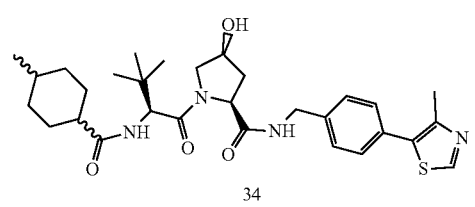34 |
| 35 | 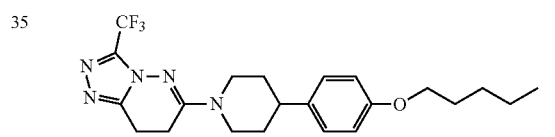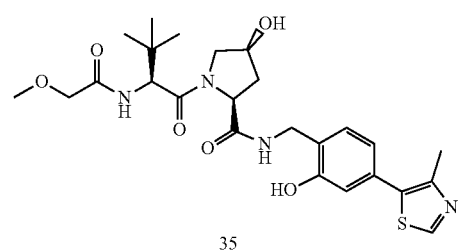35 |
| 36 | 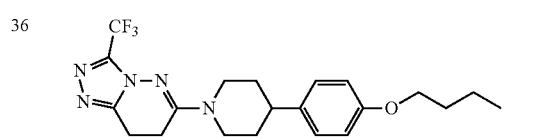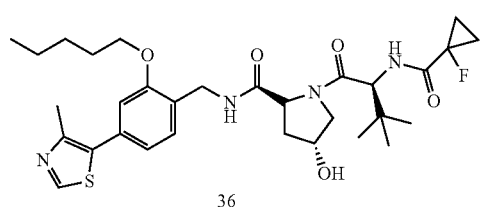36 |
| 37 | 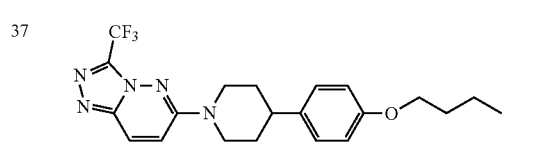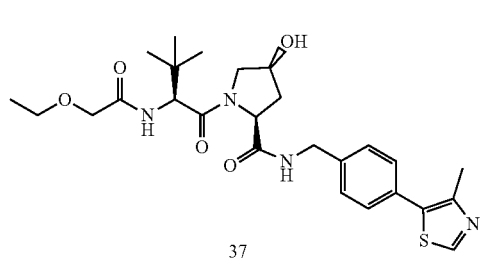37 |
| Compound number | Structure |
|---|---|
| 38 | 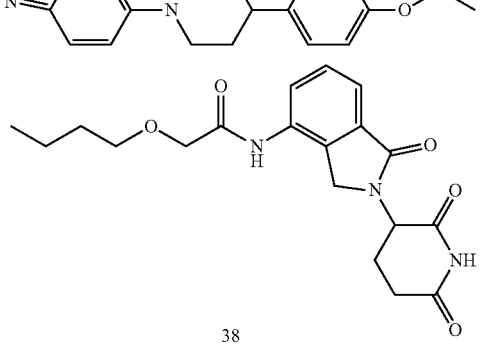38 |
| 39 | 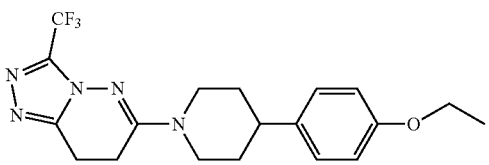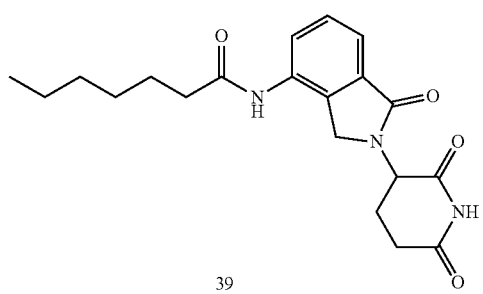39 |
| 40 | 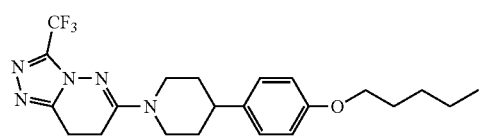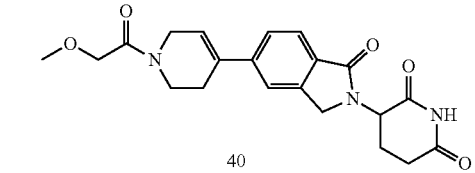40 |

| Compound number | Structure |
|---|---|
| 41 | 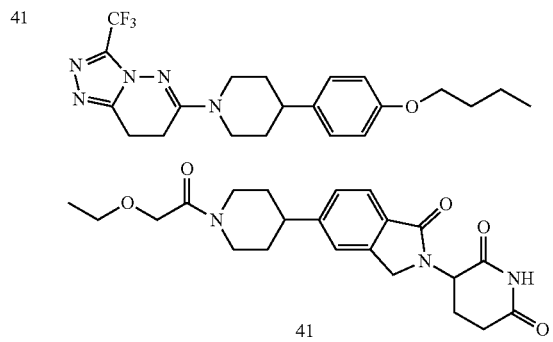 41 |
| 42 | 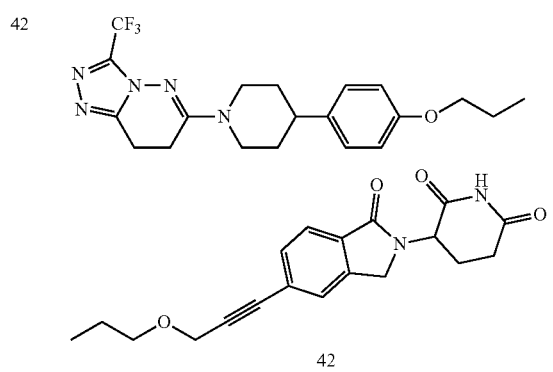 42 |
| 43 | 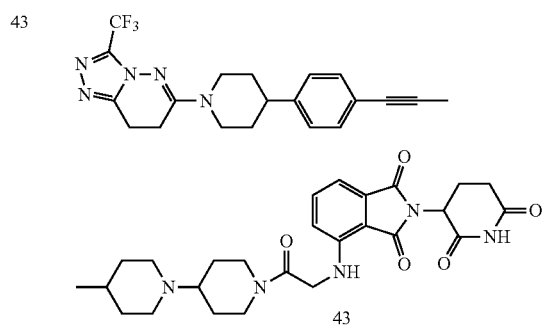 43 |
| 44 | 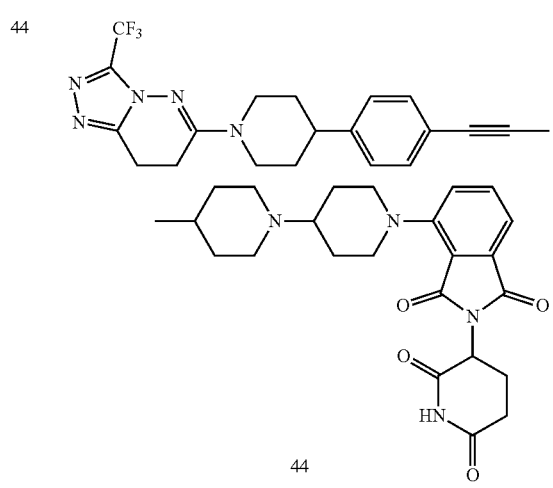 44 |
| Compound number | Structure |
|---|---|
| 45 |  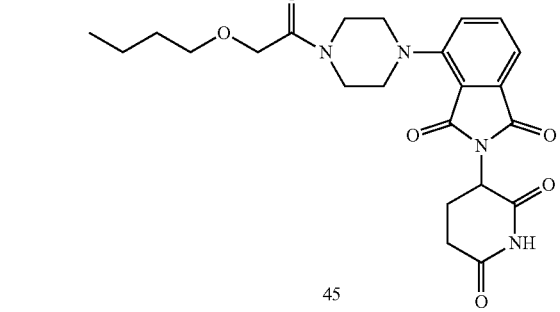 45 |
| 46 | 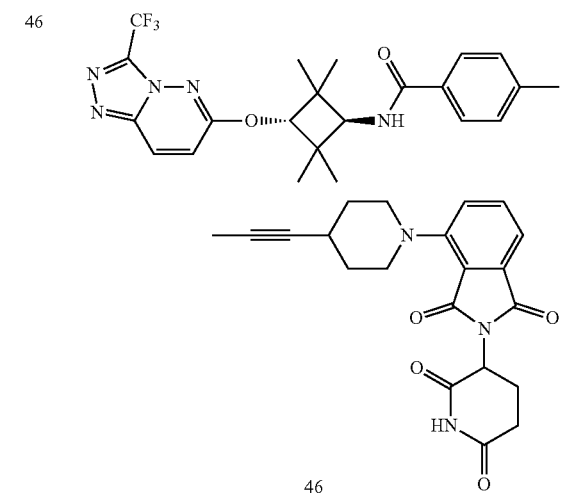 46 |
| 47 | 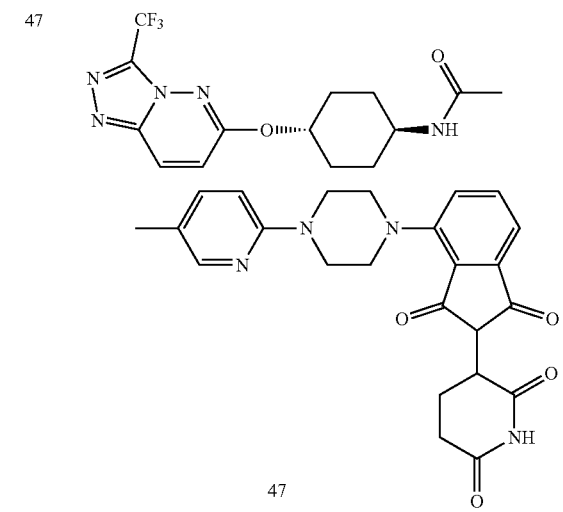 47 |

| Compound number | Structure |
|---|---|
| 48 | 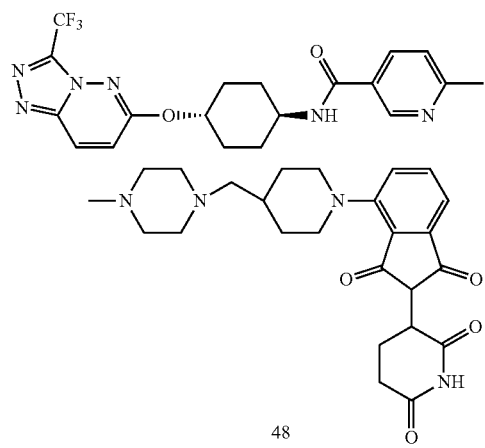 |
| 49 | 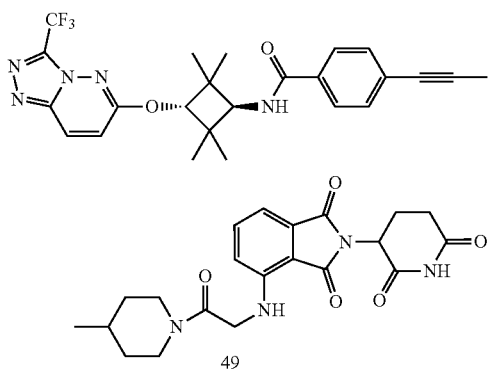 |
| 50 | 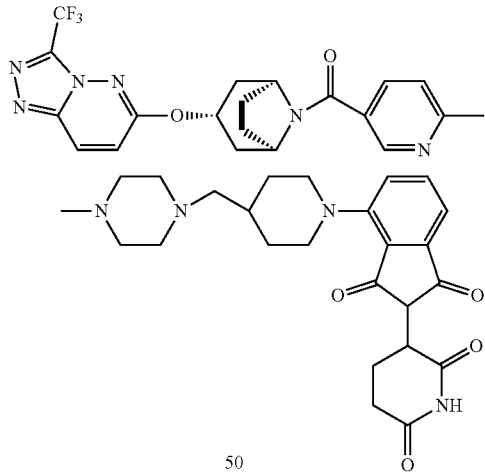 |
| Compound number | Structure |
|---|---|
| 51 | 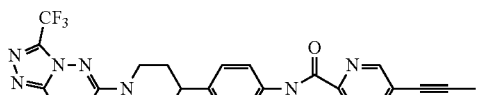 |
| 52 | 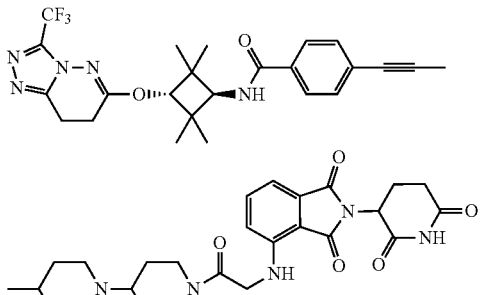 |
| 53 | 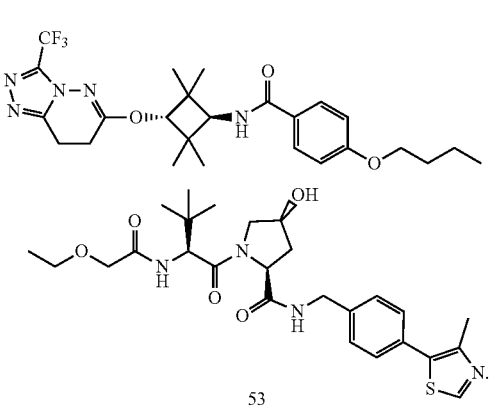 |

2. A method for treating prostate cancer comprising:
administering a compound to a subject in need thereof to treat prostate cancer in the subject,
wherein the compound is selected from the group consisting of the compounds as shown below:
| Compound number | Structure |
|---|---|
| 1 | 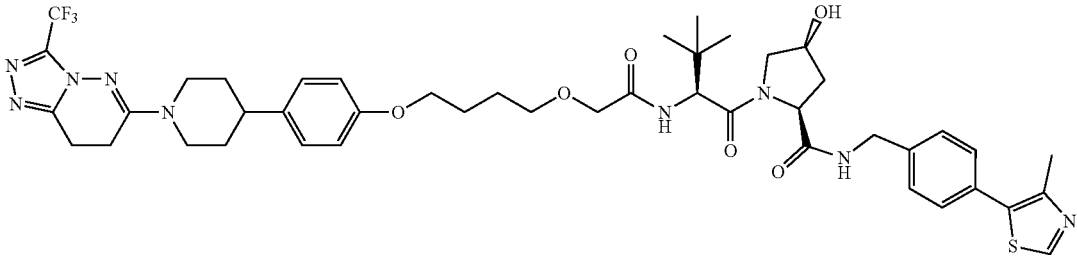 <br> 1 |
| 2 | 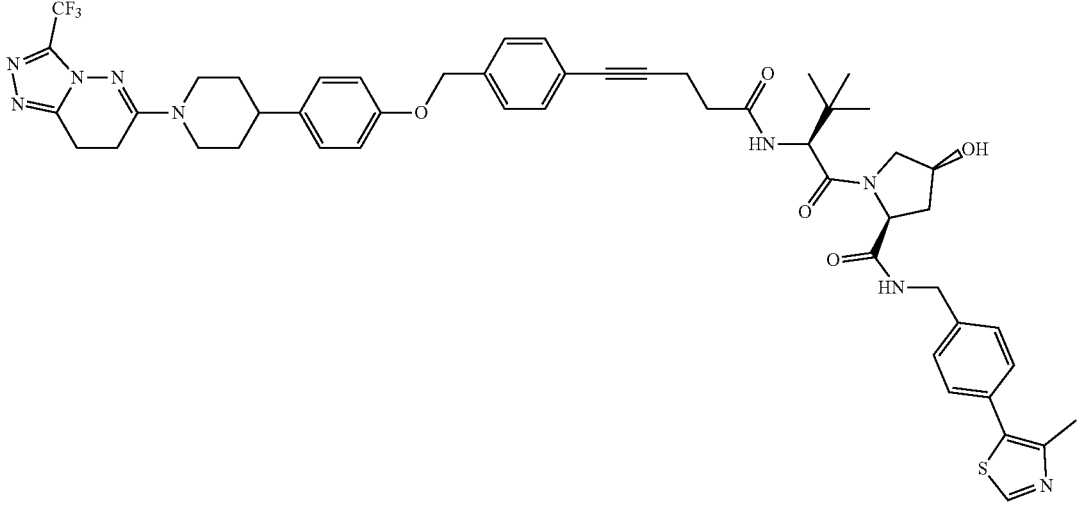 <br> 2 |
| 3 | 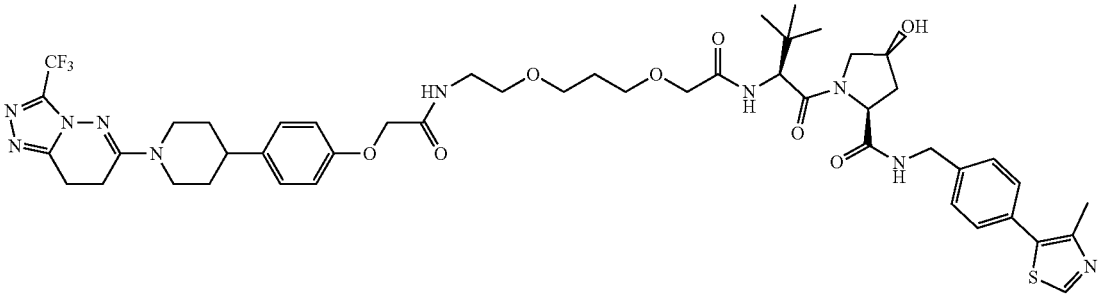 <br> 3 |
| 4 | 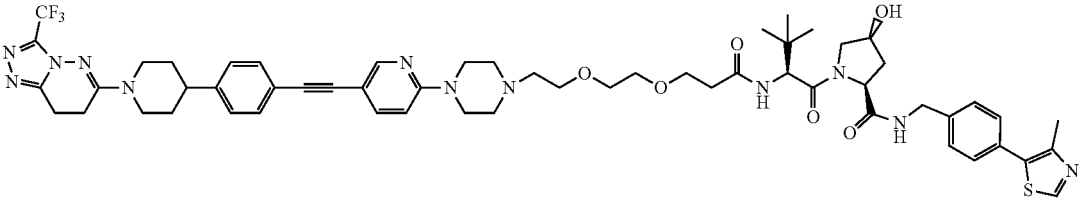 <br> 4 |

| Compound number | Structure |
|---|---|
| 5 | 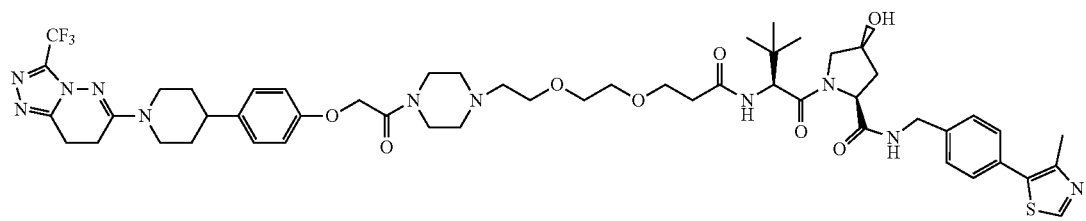<br>5 |
| 6 | 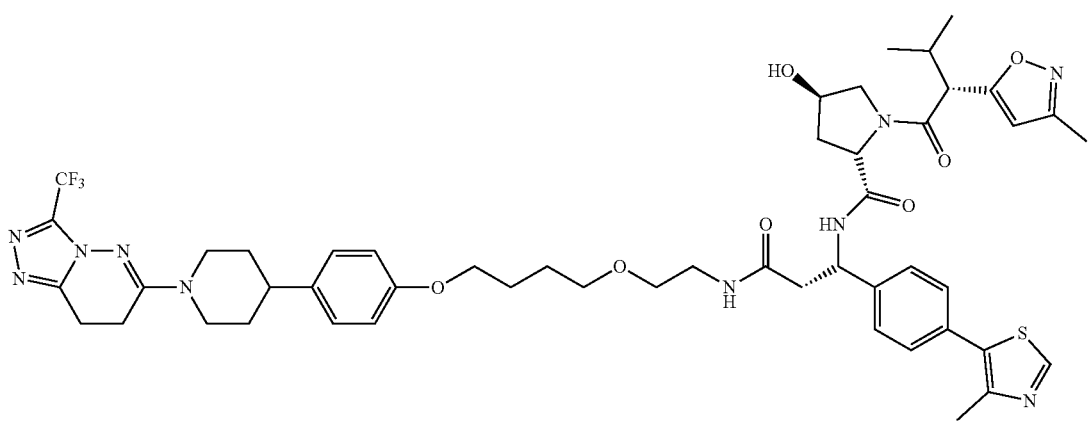<br>6 |
| 7 | 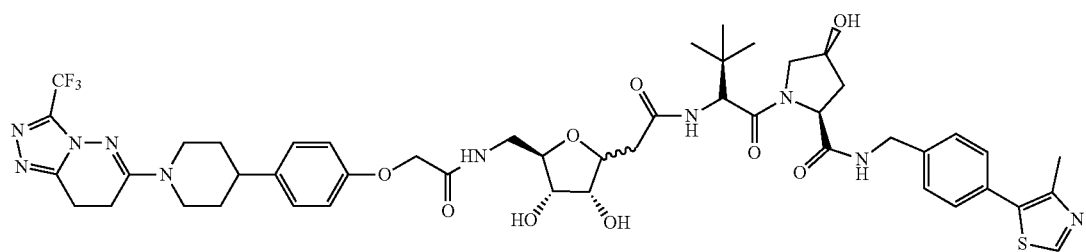<br>7 |
| 8 | 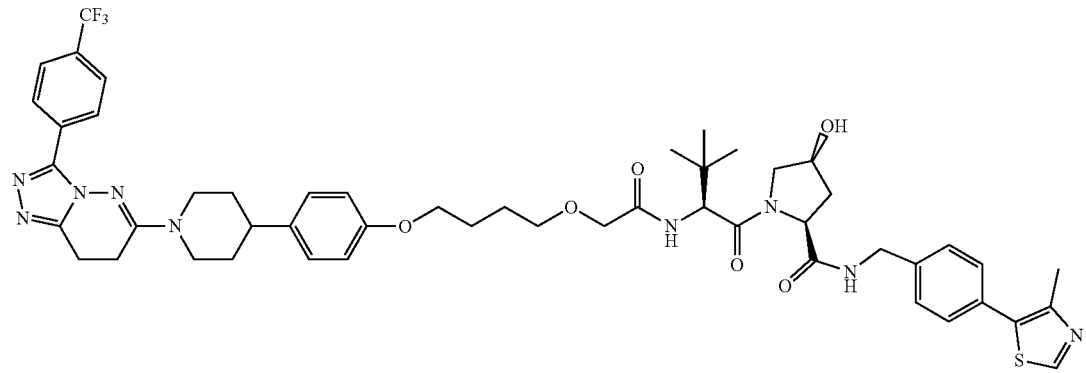<br>8 |

| Compound number | Structure |
|---|---|
| 9 | 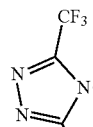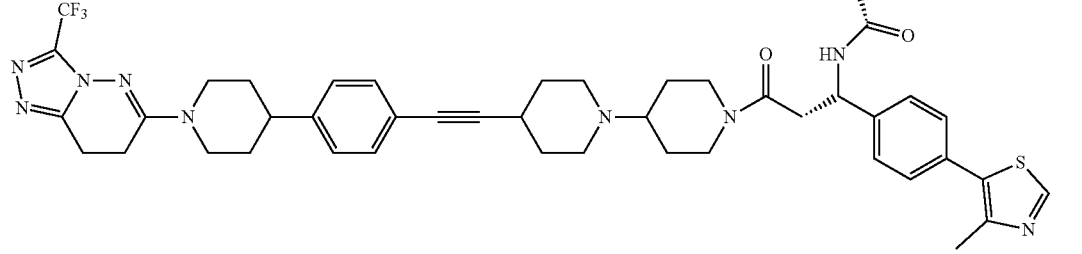 |
| 10 | 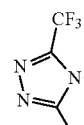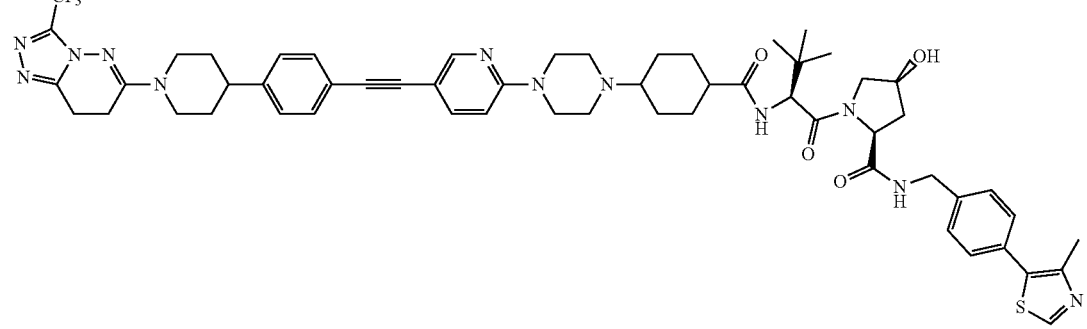 |
| 11 | 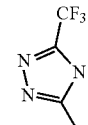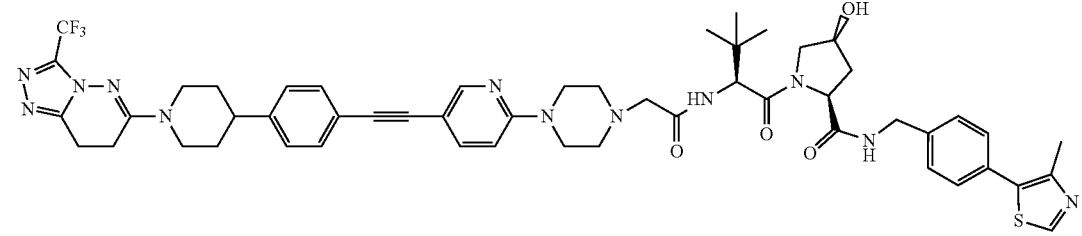 |
| 12 | 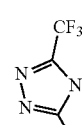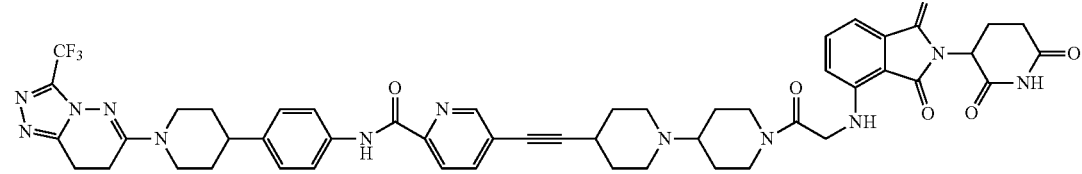 |

-continued
| Compound number | Structure |
|---|---|
| 13 | 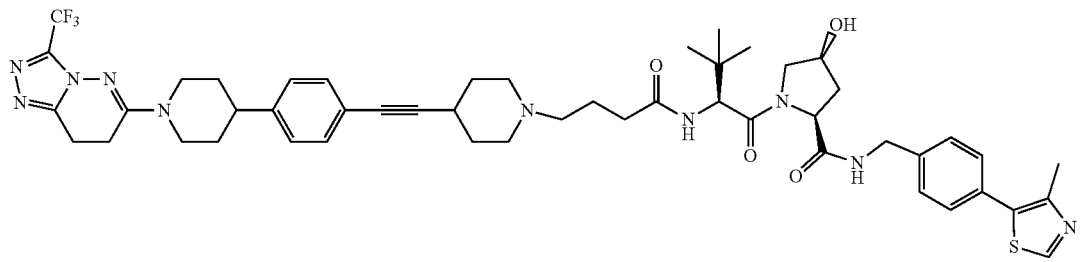<br>13 |
| 14 | 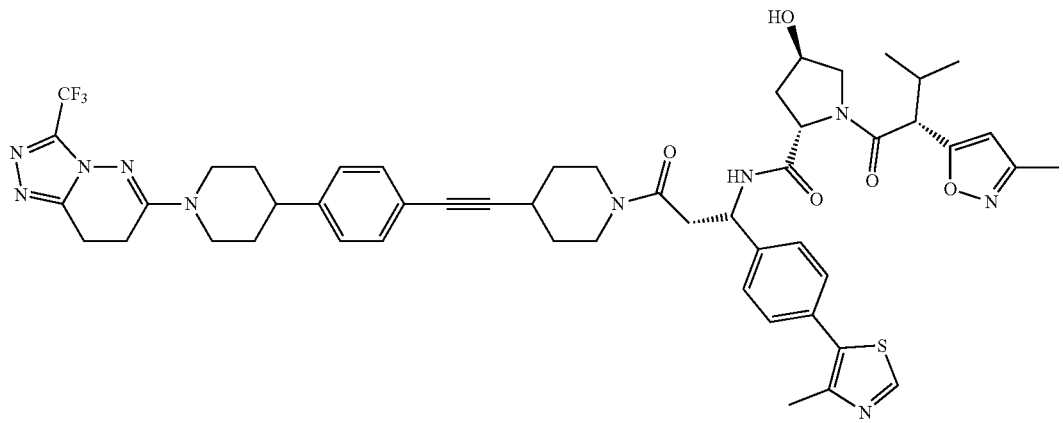<br>14 |
| 15 | 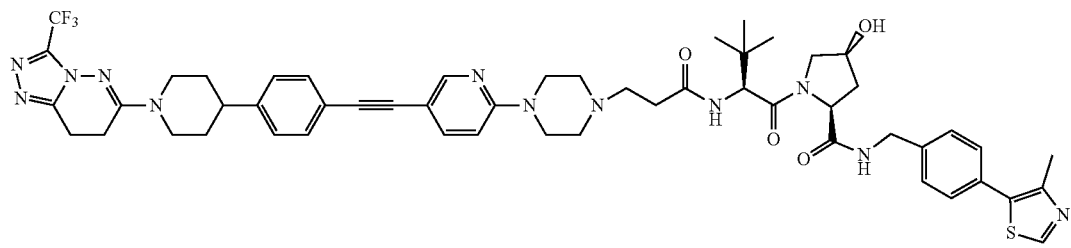<br>15 |
| 16 | 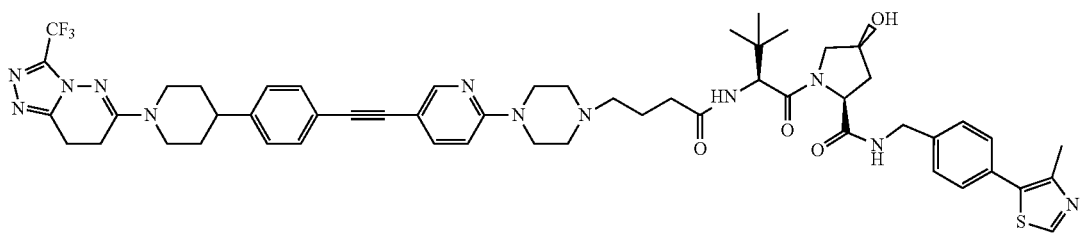<br>16 |

-continued

| Compound number | Structure |
|---|---|
| 17 | (structure 17) |
| 18 | (structure 18) |
| 19 | (structure 19) |
| 20 | (structure 20) |
| 21 | (structure 21) |

-continued

| Compound number | Structure |
|---|---|
| 22 | 22 |
| 23 | 23 |
| 24 | 24 |
| 25 | 25 |

-continued
| Compound number | Structure |
|---|---|
| 26 | 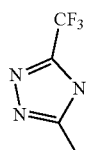 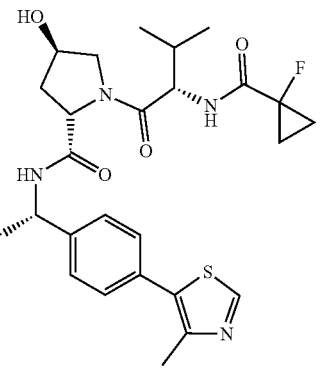 |
| 27 | 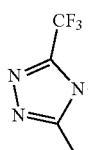 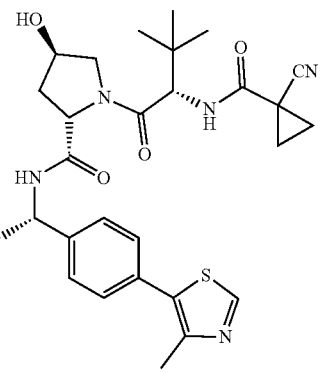 |
| 28 | 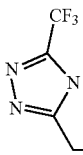 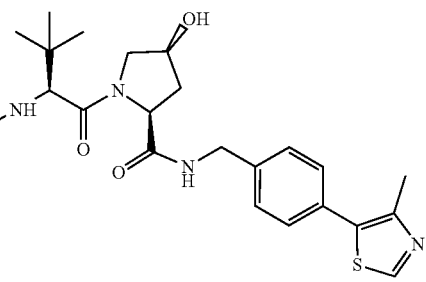 |
| 29 | 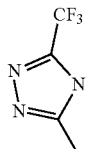 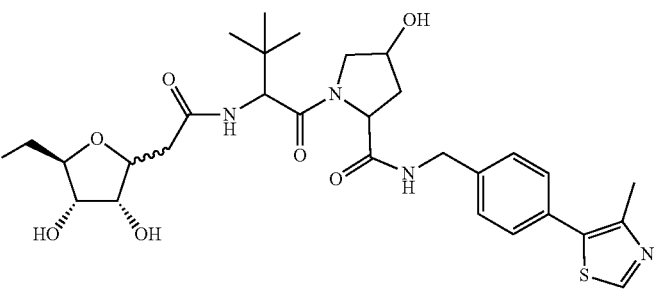 |

-continued
| Compound number | Structure |
|---|---|
| 30 | 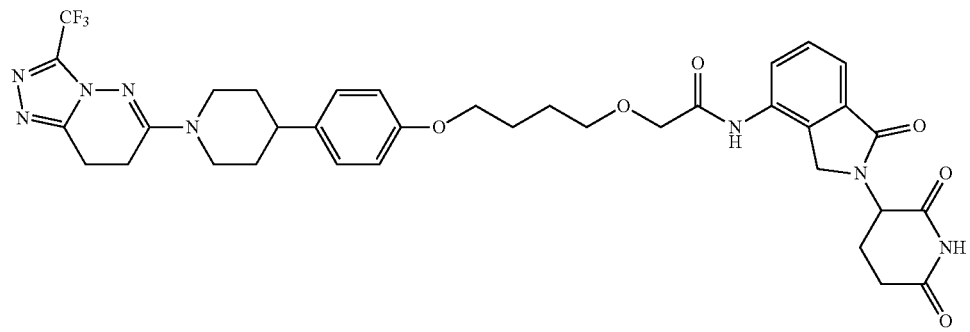<br>30 |
| 31 | 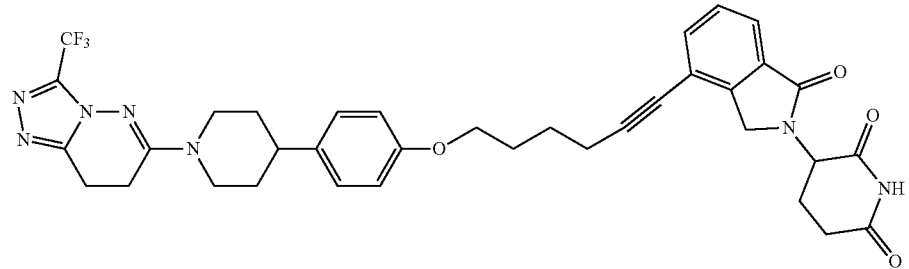<br>31 |
| 32 | 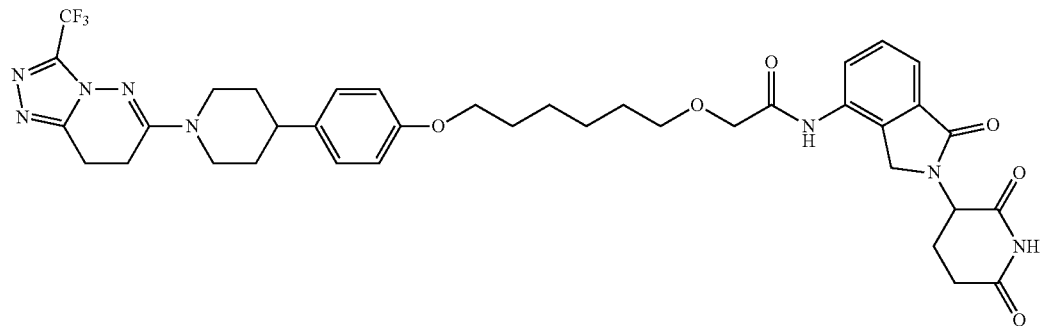<br>32 |
| 33 | 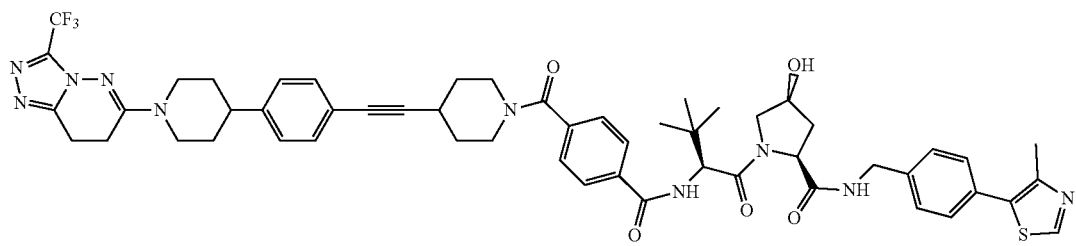<br>33 |

| Compound number | Structure |
| --- | --- |
| 34 | 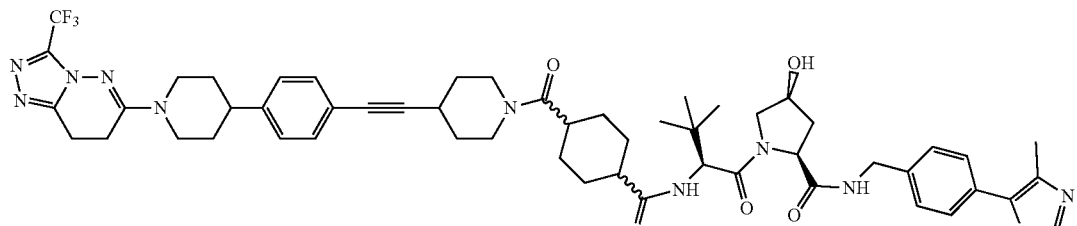 |
| 35 | 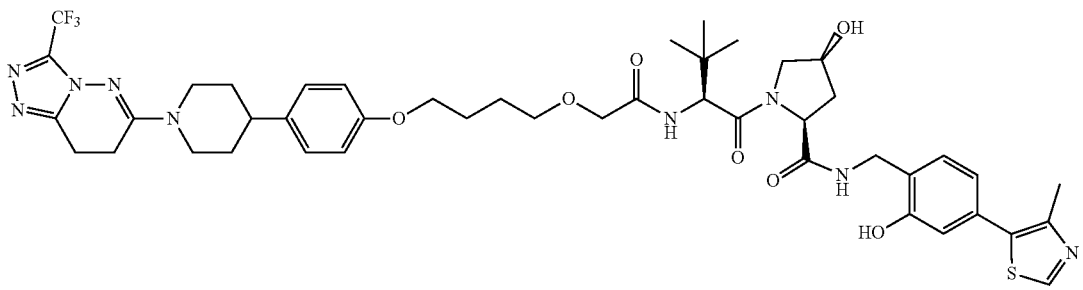 |
| 36 | 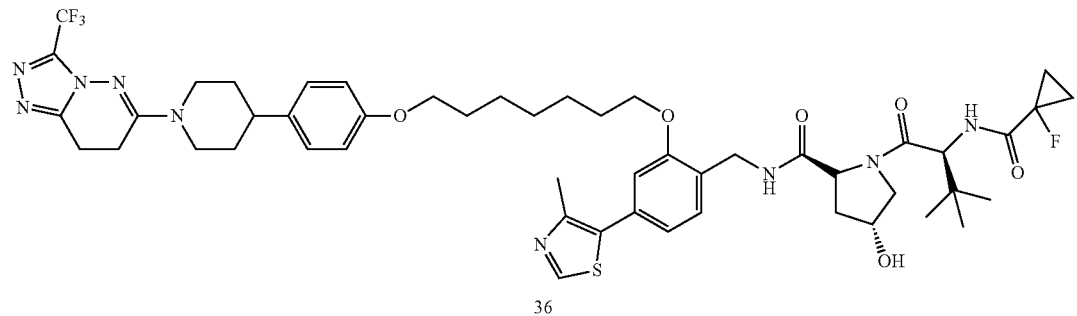 |
| 37 | 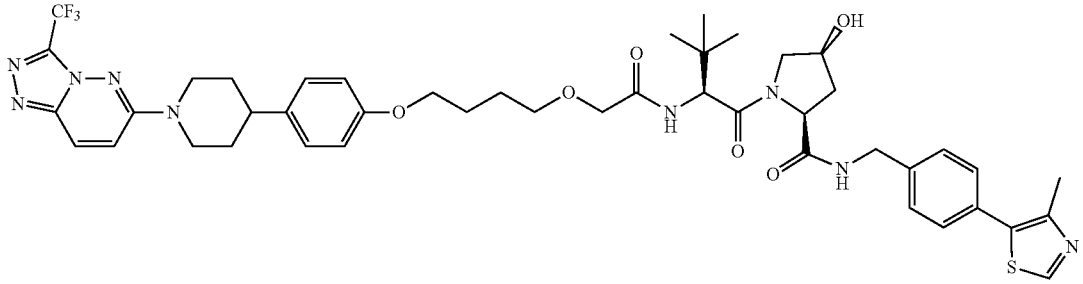 |

-continued
| Compound number | Structure |
|---|---|
| 38 | 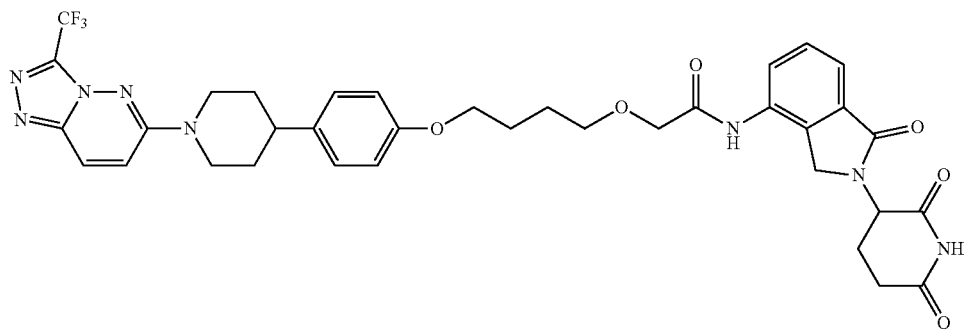<br>38 |
| 39 | 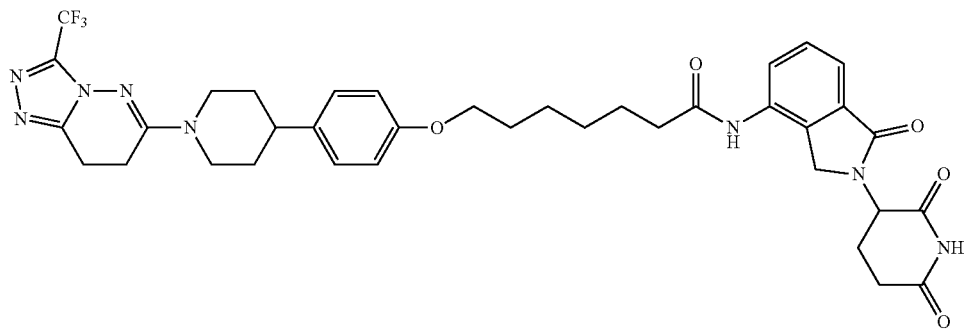<br>39 |
| 40 | 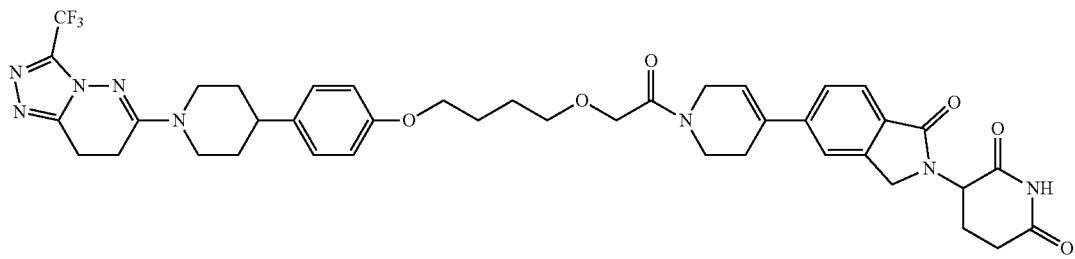<br>40 |
| 41 | 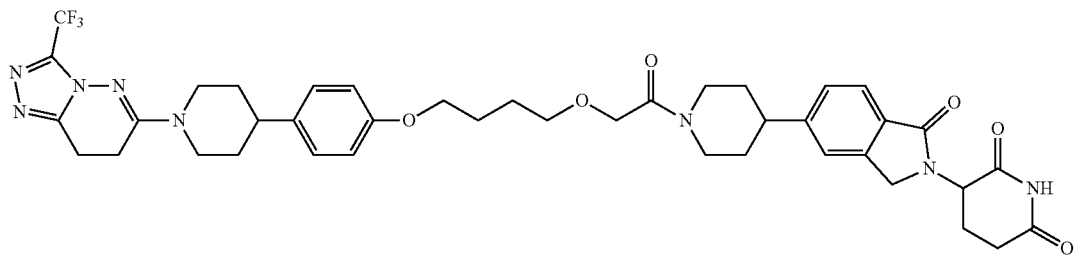<br>41 |

-continued
| Compound number | Structure |
|---|---|
| 42 | 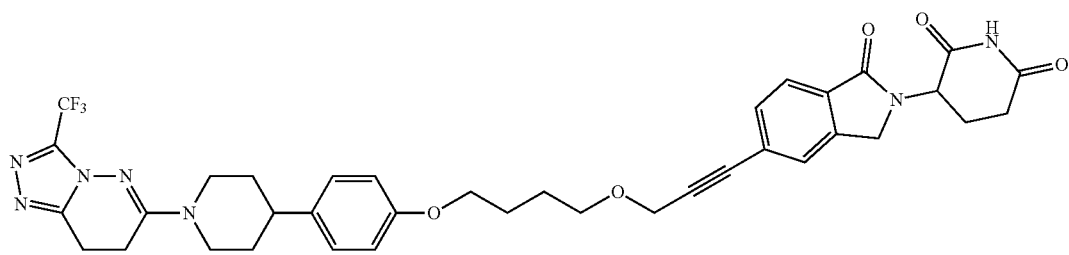<br>42 |
| 43 | 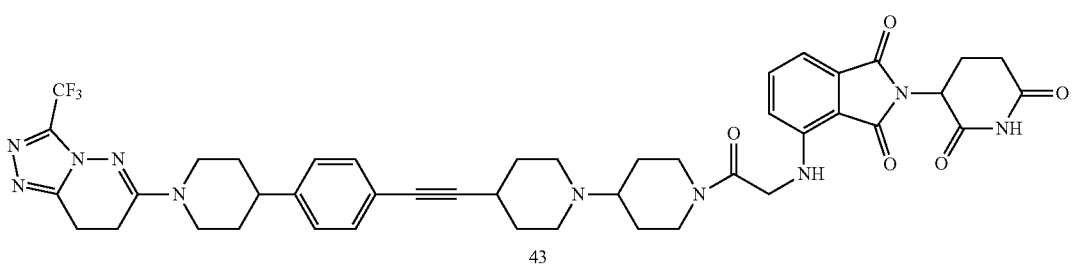 [SMILES: O=C1CCC(N2C(=O)c3cccc(NCC(=O)N4CCC(N5CCC(C#Cc6ccc(C7CCN(C8=Nn9c(nnc9C(F)(F)F)CC8)CC7)cc6)CC5)CC4)c3C2=O)C(=O)N1]<br>43 |
| 44 | 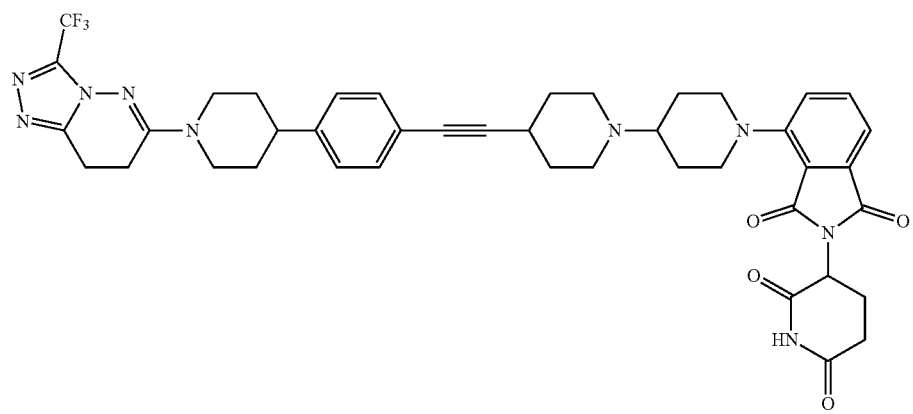<br>44 |
| 45 | 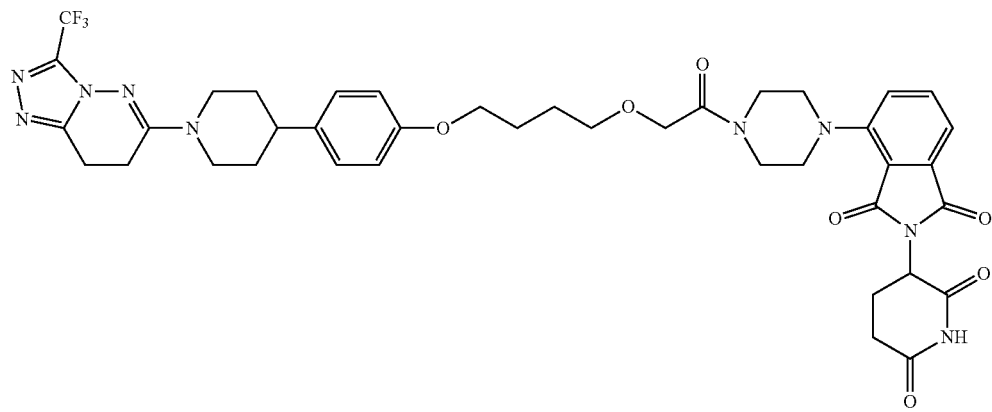<br>45 |

| Compound number | Structure |
|---|---|
| 46 | 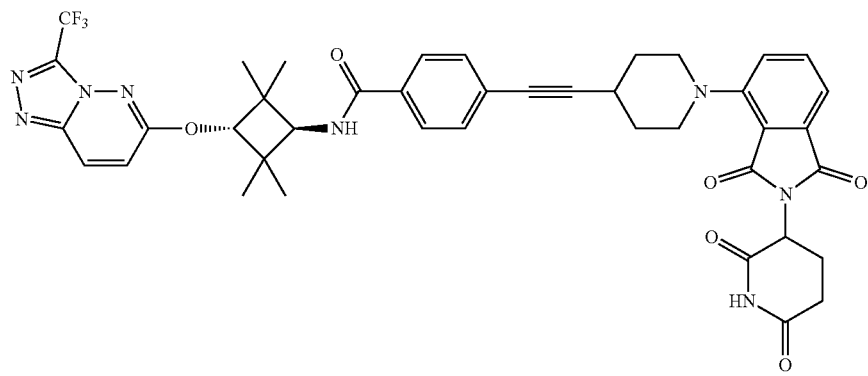  46 |
| 47 | 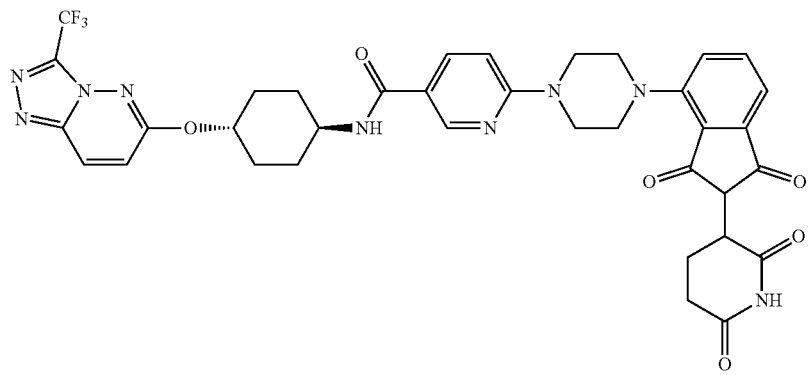  47 |
| 48 | 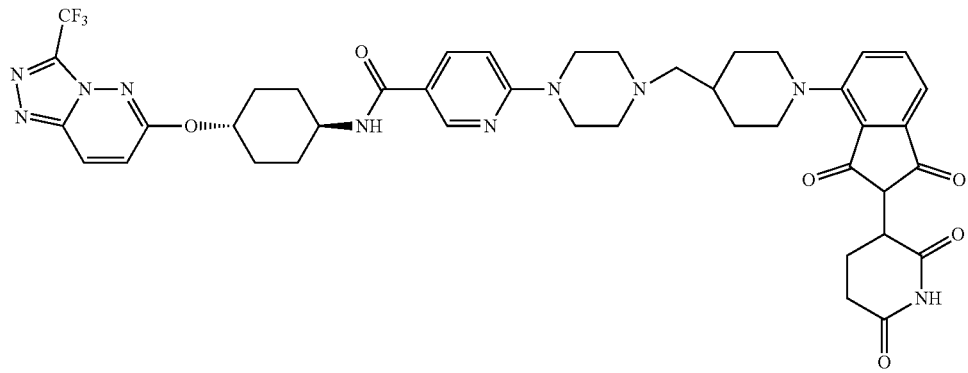  48 |

-continued
| Compound number | Structure |
|---|---|
| 49 | 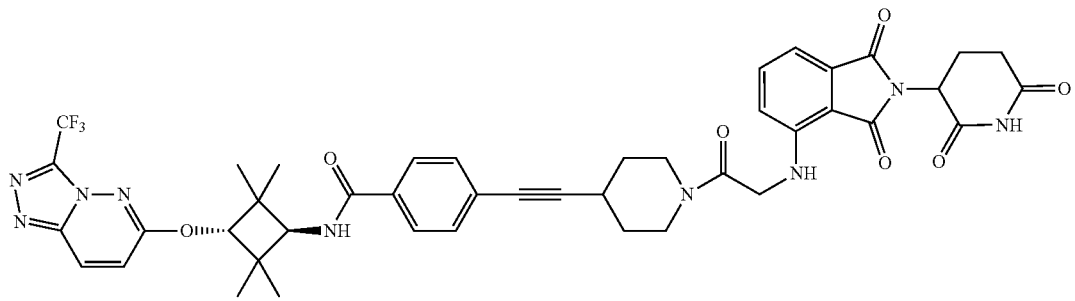<br>49 |
| 50 | 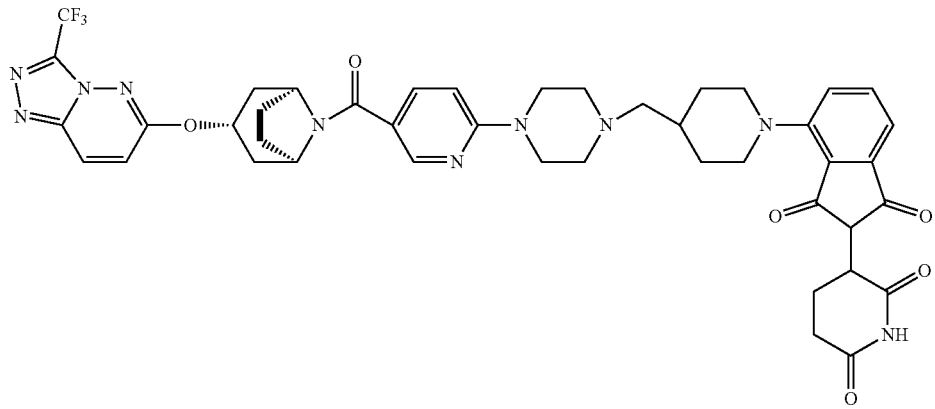<br>50 |
| 51 | 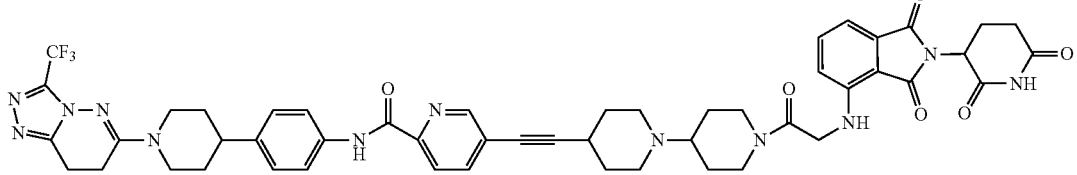<br>51 |
| 52 | 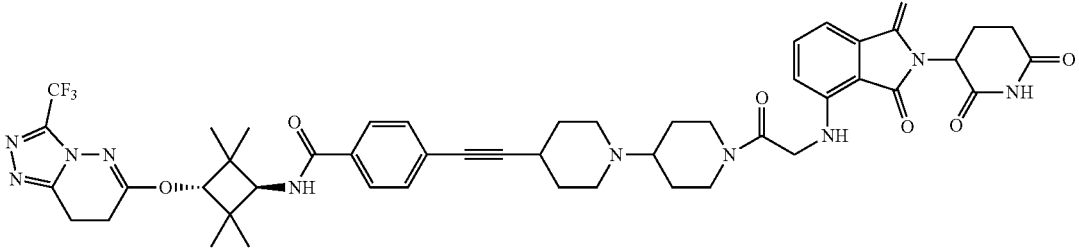<br>52 |

| Compound number | Structure |
|---|---|
| 53 | (structure 53) |

3. The method for treating prostate cancer as claimed in claim 2, wherein the prostate cancer is prostate cancer with full length androgen receptor and/or androgen receptor splice variant 7.

* * * * *